(12) United States Patent
Langenfeld et al.

(10) Patent No.: US 12,024,701 B2
(45) Date of Patent: Jul. 2, 2024

(54) SYSTEM AND METHOD FOR CREATING TISSUE

(71) Applicant: DEKA Products Limited Partnership, Manchester, NH (US)

(72) Inventors: Christopher C. Langenfeld, Nashua, NH (US); David D. B. Cannan, Manchester, NH (US); Dirk A. van der Merwe, Canterbury, NH (US); Dean Kamen, Bedford, NH (US); Jason A. Demers, Manchester, NH (US); Frederick Morgan, Bedford, NH (US); Timothy D. Moreau, Manchester, NH (US); Brian D. Tracey, Litchfield, NH (US); Matthew Ware, Merrimack, NH (US); Richard J. Lanigan, Concord, NH (US); Michael A. Baker, Manchester, NH (US); David Blumberg, Jr., Deerfield, NH (US); Richard E. Gautney, Manchester, NH (US); Derek G. Kane, Manchester, NH (US); Dane Fawkes, Amesbury, MA (US); Thomas J. Bollenbach, Canton, MA (US); Michael C. Tilley, Amherst, NH (US); Stuart A. Jacobson, Lexington, MA (US); John F. Mannisto, Bedford, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 118 days.

(21) Appl. No.: 17/465,133

(22) Filed: Sep. 2, 2021

(65) Prior Publication Data
US 2022/0041975 A1    Feb. 10, 2022

Related U.S. Application Data

(62) Division of application No. 15/805,790, filed on Nov. 7, 2017, now Pat. No. 11,299,705.
(Continued)

(51) Int. Cl.
*C12M 3/00* (2006.01)
*A01N 1/02* (2006.01)
(Continued)

(52) U.S. Cl.
CPC ............ *C12M 41/48* (2013.01); *A01N 1/0247* (2013.01); *A61L 27/3895* (2013.01); *B33Y 10/00* (2014.12);
(Continued)

(58) Field of Classification Search
CPC ........ B33Y 10/00; B33Y 70/00; C12M 21/08; C12M 41/48
See application file for complete search history.

(56) References Cited

U.S. PATENT DOCUMENTS

| 1,133,254 A | 3/1915 | Backus |
| 1,664,576 A | 4/1928 | Staples |

(Continued)

FOREIGN PATENT DOCUMENTS

| CA | 2685964 | 5/2011 |
| DE | 3605640 | 8/1987 |

(Continued)

OTHER PUBLICATIONS

Written Opinion PCT/US2004/035952, dated Apr. 30, 2006, 11 pages.
(Continued)

*Primary Examiner* — Nathan A Bowers
(74) *Attorney, Agent, or Firm* — Mark E. Tetreault

(57) ABSTRACT

A system and method for growing and maintaining biological material including producing a protein associated with
(Continued)

the tissue, selecting cells associated with the tissue, expanding the cells, creating at least one tissue bio-ink including the expanded cells, printing the at least one tissue bio-ink in at least one tissue growth medium mixture, growing the tissue from the printed at least one tissue bio-ink, and maintaining viability of the tissue.

4 Claims, 75 Drawing Sheets

Related U.S. Application Data

(60) Provisional application No. 62/534,984, filed on Jul. 20, 2017, provisional application No. 62/418,784, filed on Nov. 7, 2016.

(51) Int. Cl.

| | | |
|---|---|---|
| *A61L 27/38* | (2006.01) | |
| *B33Y 10/00* | (2015.01) | |
| *B33Y 30/00* | (2015.01) | |
| *B33Y 70/00* | (2020.01) | |
| *C12M 1/00* | (2006.01) | |
| *C12M 1/12* | (2006.01) | |
| *C12M 1/26* | (2006.01) | |
| *C12M 1/34* | (2006.01) | |
| *C12M 1/36* | (2006.01) | |
| *C12N 1/00* | (2006.01) | |
| *C12N 5/00* | (2006.01) | |

(52) U.S. Cl.
CPC ............. *B33Y 30/00* (2014.12); *B33Y 70/00* (2014.12); *C12M 21/08* (2013.01); *C12M 23/22* (2013.01); *C12M 23/38* (2013.01); *C12M 25/02* (2013.01); *C12M 27/18* (2013.01); *C12M 29/00* (2013.01); *C12M 33/00* (2013.01); *C12M 37/02* (2013.01); *C12M 41/12* (2013.01); *C12M 41/40* (2013.01); *C12M 41/46* (2013.01); *C12N 5/0018* (2013.01); *C12N 5/0062* (2013.01); *C12N 2533/00* (2013.01); *C12N 2533/50* (2013.01); *C12N 2533/90* (2013.01)

(56) References Cited

U.S. PATENT DOCUMENTS

| | | |
|---|---|---|
| 1,792,906 A | 2/1931 | Heilos |
| 2,313,551 A | 3/1943 | Hurlbut |
| 2,525,251 A | 10/1950 | Willard |
| 2,526,017 A | 10/1950 | Figg |
| 2,703,055 A | 3/1955 | Veth |
| 2,776,854 A | 1/1957 | Billstrom |
| 2,834,504 A | 5/1958 | Anniq |
| 2,902,253 A | 9/1959 | Page |
| 2,917,465 A | 12/1959 | Begley |
| 3,002,804 A | 10/1961 | Kilian |
| 3,339,956 A | 9/1967 | Bencene et al. |
| 3,449,864 A | 6/1969 | Claude et al. |
| 3,481,076 A | 12/1969 | Bedard |
| 3,540,694 A | 11/1970 | Cornelius |
| 3,570,486 A | 3/1971 | Engelsher et al. |
| 3,722,858 A | 3/1973 | Sugimoto et al. |
| 3,727,882 A | 4/1973 | Burris et al. |
| 3,814,548 A | 6/1974 | Rupp |
| 3,856,338 A | 12/1974 | Johnsson |
| 4,049,352 A | 9/1977 | Lardon et al. |
| 4,056,224 A | 11/1977 | Lolachi |
| 4,072,934 A | 2/1978 | Hiller et al. |
| 4,073,521 A | 2/1978 | Mena |
| 4,093,176 A | 6/1978 | Contastin |
| 4,161,264 A | 7/1979 | Johnson et al. |
| 4,212,589 A | 7/1980 | Bosio |
| 4,230,300 A | 10/1980 | Wiltse |
| 4,247,018 A | 1/1981 | Credle |
| 4,272,824 A | 6/1981 | Lewinger et al. |
| 4,427,415 A | 1/1984 | Cleveland |
| 4,431,425 A | 2/1984 | Thompson et al. |
| 4,468,219 A | 8/1984 | George et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,573,994 A | 3/1986 | Fischell et al. |
| 4,576,211 A | 3/1986 | Valentini et al. |
| 4,583,971 A | 4/1986 | Bocquet et al. |
| 4,606,734 A | 8/1986 | Larkin et al. |
| 4,634,430 A | 1/1987 | Polaschegg |
| 4,648,868 A | 3/1987 | Hardwick et al. |
| 4,650,339 A | 3/1987 | Chetcuti et al. |
| 4,662,540 A | 5/1987 | Schroter |
| 4,662,829 A | 5/1987 | Nehring |
| 4,667,927 A | 5/1987 | Oscarsson |
| 4,696,671 A | 9/1987 | Epstein et al. |
| 4,698,160 A | 10/1987 | Haraguchi |
| 4,718,447 A | 1/1988 | Marshall |
| 4,721,138 A | 1/1988 | Simonazzi |
| 4,778,451 A | 10/1988 | Kamen |
| 4,798,580 A | 1/1989 | Demeo et al. |
| 4,804,366 A | 2/1989 | Zdeb et al. |
| 4,807,660 A | 2/1989 | Aslanian |
| 4,808,161 A | 2/1989 | Kamen |
| 4,818,186 A | 4/1989 | Pastrone et al. |
| 4,825,444 A | 4/1989 | Johna et al. |
| 4,826,482 A | 5/1989 | Kamen |
| 4,828,543 A | 5/1989 | Weiss et al. |
| 4,833,922 A | 5/1989 | Frick et al. |
| 4,850,978 A | 7/1989 | Dudar et al. |
| 4,855,714 A | 8/1989 | Clarkson et al. |
| 4,925,444 A | 5/1990 | Orkin et al. |
| 4,927,198 A | 5/1990 | Fennell et al. |
| 4,976,162 A | 12/1990 | Kamen |
| 5,004,351 A | 4/1991 | Salaba et al. |
| 5,005,604 A | 4/1991 | Aslanian |
| 5,006,050 A | 4/1991 | Cooke et al. |
| 5,045,068 A | 9/1991 | Kawai et al. |
| 5,051,922 A | 9/1991 | Toral et al. |
| 5,059,365 A | 10/1991 | Hertzer et al. |
| 5,062,774 A | 11/1991 | Kramer et al. |
| 5,069,792 A | 12/1991 | Prince et al. |
| 5,088,515 A | 2/1992 | Kamen |
| 5,098,262 A | 3/1992 | Wecker et al. |
| 5,098,371 A | 3/1992 | Juji et al. |
| 5,106,366 A | 4/1992 | Steppe |
| 5,113,904 A | 5/1992 | Aslanian |
| 5,116,316 A | 5/1992 | Sertic et al. |
| 5,122,116 A | 6/1992 | Kriesel et al. |
| 5,146,414 A | 9/1992 | McKown et al. |
| 5,150,796 A | 9/1992 | Pierson |
| 5,156,053 A | 10/1992 | Shiraishi et al. |
| 5,156,186 A | 10/1992 | Manska |
| 5,167,837 A | 12/1992 | Snodgrass et al. |
| 5,178,182 A | 1/1993 | Kamen |
| 5,186,333 A | 2/1993 | Pierson et al. |
| 5,197,787 A | 3/1993 | Matsuda et al. |
| 5,255,072 A | 10/1993 | Mikasa et al. |
| 5,266,272 A | 11/1993 | Griner et al. |
| 5,267,956 A | 12/1993 | Beuchat |
| 5,272,646 A | 12/1993 | Farmer |
| 5,279,504 A | 1/1994 | Williams |
| 5,290,076 A | 3/1994 | Smith |
| 5,292,306 A | 3/1994 | Wynkoop et al. |
| 5,294,157 A | 3/1994 | Smith et al. |
| 5,302,093 A | 4/1994 | Owens et al. |
| 5,324,422 A | 6/1994 | Colleran et al. |
| 5,325,884 A | 7/1994 | Mirel et al. |
| 5,330,426 A | 7/1994 | Kriesel et al. |
| 5,336,053 A | 8/1994 | Wynkoop |
| 5,342,422 A | 8/1994 | Wimboeck |
| D350,823 S | 9/1994 | Lanigan |
| 5,350,357 A | 9/1994 | Kamen et al. |
| 5,351,686 A | 10/1994 | Steuer et al. |

(56) References Cited

U.S. PATENT DOCUMENTS

| | | |
|---|---|---|
| 5,355,890 A | 10/1994 | Aguirre et al. |
| 5,378,126 A | 1/1995 | Abrahamson et al. |
| 5,384,714 A | 1/1995 | Kidd |
| 5,385,540 A | 1/1995 | Abbott et al. |
| 5,401,059 A | 3/1995 | Ferrario |
| 5,408,420 A | 4/1995 | Slocum et al. |
| 5,411,472 A | 5/1995 | Steg, Jr. et al. |
| 5,421,823 A | 6/1995 | Kamen et al. |
| 5,423,738 A | 6/1995 | Robinson et al. |
| 5,428,527 A | 6/1995 | Niemi |
| 5,429,485 A | 7/1995 | Dodge |
| 5,431,626 A | 7/1995 | Bryant et al. |
| 5,438,510 A | 8/1995 | Bryant et al. |
| 5,439,355 A | 8/1995 | Jimison et al. |
| 5,463,228 A | 10/1995 | Krause |
| 5,466,220 A | 11/1995 | Brenneman |
| 5,474,683 A | 12/1995 | Bryant et al. |
| 5,478,337 A | 12/1995 | Okamoto et al. |
| 5,482,440 A | 1/1996 | Dennehey et al. |
| 5,496,273 A | 3/1996 | Pastrone et al. |
| 5,507,412 A | 4/1996 | Ebert et al. |
| 5,558,255 A | 9/1996 | Sancoff et al. |
| 5,569,181 A | 10/1996 | Heilman et al. |
| 5,575,310 A | 11/1996 | Kamen et al. |
| 5,578,012 A | 11/1996 | Kamen et al. |
| 5,579,244 A | 11/1996 | Brown |
| 5,584,671 A | 12/1996 | Schweitzer, Jr. et al. |
| 5,588,816 A | 12/1996 | Abbott et al. |
| 5,593,290 A | 1/1997 | Greisch et al. |
| 5,628,908 A | 5/1997 | Kamen et al. |
| 5,634,896 A | 6/1997 | Bryant et al. |
| 5,638,737 A | 6/1997 | Mattson et al. |
| 5,645,531 A | 7/1997 | Thompson et al. |
| 5,647,391 A | 7/1997 | Chan et al. |
| 5,649,810 A | 7/1997 | Schweitzer, Jr. et al. |
| 5,651,775 A | 7/1997 | Walker et al. |
| 5,653,533 A | 8/1997 | Green |
| 5,681,285 A | 10/1997 | Ford et al. |
| 5,713,865 A | 2/1998 | Manning et al. |
| 5,716,343 A | 2/1998 | Kriesel et al. |
| 5,755,683 A | 5/1998 | Houle et al. |
| 5,758,095 A | 5/1998 | Albaum et al. |
| 5,776,103 A | 7/1998 | Kriesel et al. |
| 5,795,328 A | 8/1998 | Barnitz et al. |
| 5,808,181 A | 9/1998 | Wamsiedler et al. |
| 5,816,779 A | 10/1998 | Lawless et al. |
| 5,823,026 A | 10/1998 | Finke |
| 5,837,905 A | 11/1998 | Strauss et al. |
| 5,868,162 A | 2/1999 | Dickerson, Jr. |
| 5,879,328 A | 3/1999 | Holmberg et al. |
| 5,883,299 A | 3/1999 | Green et al. |
| 5,935,105 A | 8/1999 | Manning et al. |
| 5,935,332 A | 8/1999 | Caucal |
| 5,938,634 A | 8/1999 | Packard |
| 5,965,821 A | 10/1999 | Grudzien |
| 5,989,423 A | 11/1999 | Kamen et al. |
| 6,022,483 A | 2/2000 | Aral |
| 6,041,801 A | 3/2000 | Gray et al. |
| 6,053,052 A | 4/2000 | Starostovic |
| 6,065,941 A | 5/2000 | Gray et al. |
| 6,070,761 A | 6/2000 | Bloom et al. |
| 6,103,528 A | 8/2000 | An et al. |
| 6,109,881 A | 8/2000 | Snodgrass et al. |
| 6,136,586 A | 10/2000 | Budowsky |
| 6,149,627 A | 11/2000 | Uber, III |
| 6,165,154 A | 12/2000 | Gray et al. |
| 6,210,361 B1 | 4/2001 | Kamen et al. |
| 6,214,231 B1 | 4/2001 | Cote et al. |
| 6,217,847 B1 | 4/2001 | Contag et al. |
| 6,218,182 B1 | 4/2001 | Naughton et al. |
| 6,223,130 B1 | 4/2001 | Gray et al. |
| 6,234,997 B1 | 5/2001 | Kamen et al. |
| 6,245,570 B1 | 6/2001 | Grimm et al. |
| 6,264,458 B1 | 7/2001 | Marcuz et al. |
| 6,302,653 B1 | 10/2001 | Bryant et al. |
| 6,321,597 B1 | 11/2001 | Demers et al. |
| 6,343,614 B1 | 2/2002 | Gray et al. |
| 6,364,857 B1 | 4/2002 | Gray et al. |
| 6,382,923 B1 | 5/2002 | Gray |
| 6,416,293 B1 | 7/2002 | Bouchard et al. |
| 6,464,667 B1 | 10/2002 | Kamen et al. |
| 6,485,263 B1 | 11/2002 | Bryant et al. |
| 6,503,062 B1 | 1/2003 | Gray et al. |
| 6,512,387 B1 | 1/2003 | Bohn |
| 6,520,747 B2 | 2/2003 | Gray et al. |
| 6,527,758 B2 | 3/2003 | Ko |
| 6,547,026 B2 | 4/2003 | Kamen et al. |
| 6,604,908 B1 | 8/2003 | Bryant et al. |
| 6,605,223 B2 | 8/2003 | Jorgensen et al. |
| 6,610,040 B1 | 8/2003 | Fowles et al. |
| 6,642,019 B1 | 11/2003 | Anderson et al. |
| 6,663,359 B2 | 12/2003 | Gray |
| 6,726,656 B2 | 4/2004 | Kamen et al. |
| 6,749,403 B2 | 6/2004 | Bryant et al. |
| 6,767,928 B1 | 7/2004 | Murphy et al. |
| 6,796,702 B2 | 9/2004 | Wire et al. |
| 6,808,369 B2 | 10/2004 | Gray et al. |
| 6,814,547 B2 | 11/2004 | Childers et al. |
| 6,877,713 B1 | 4/2005 | Gray et al. |
| 6,910,797 B2 | 6/2005 | Falcon |
| 6,929,751 B2 | 8/2005 | Bowman, Jr. et al. |
| 6,936,311 B2 | 8/2005 | Ringeisen et al. |
| 6,942,830 B2 | 9/2005 | Rolf et al. |
| 6,949,079 B1 | 9/2005 | Westberg et al. |
| 6,952,963 B2 | 10/2005 | Delnevo |
| 6,986,739 B2 | 1/2006 | Warren et al. |
| 6,993,406 B1 | 1/2006 | Cesarano, III et al. |
| 7,011,742 B2 | 3/2006 | Rosiello |
| 7,051,654 B2 | 5/2006 | Boland et al. |
| 7,083,719 B2 | 8/2006 | Bowman, Jr. et al. |
| 7,114,384 B1 | 10/2006 | Bates et al. |
| 7,174,282 B2 | 2/2007 | Hollister et al. |
| 7,214,210 B2 | 5/2007 | Kamen et al. |
| 7,278,776 B2 | 10/2007 | Helbing et al. |
| 7,354,190 B2 | 4/2008 | Demers et al. |
| 7,422,868 B2 | 9/2008 | Fan et al. |
| 7,445,441 B2 | 11/2008 | West et al. |
| 7,461,968 B2 | 12/2008 | Demers et al. |
| 7,507,169 B2 | 3/2009 | Kamen |
| 7,509,183 B2 | 3/2009 | Lin et al. |
| 7,544,179 B2 | 6/2009 | Distler et al. |
| 7,560,245 B2 | 7/2009 | Hattori et al. |
| D598,109 S | 8/2009 | Collins et al. |
| 7,604,987 B2 | 10/2009 | Hutmacher et al. |
| 7,615,373 B2 | 11/2009 | Simpson et al. |
| D606,197 S | 12/2009 | Collins et al. |
| D606,198 S | 12/2009 | Collins et al. |
| 7,625,198 B2 | 12/2009 | Lipson et al. |
| 7,632,078 B2 | 12/2009 | Demers et al. |
| 7,632,080 B2 | 12/2009 | Tracey et al. |
| 7,662,139 B2 | 2/2010 | Demers et al. |
| D612,336 S | 3/2010 | Bodwell et al. |
| D613,411 S | 4/2010 | Collins et al. |
| 7,726,362 B2 | 6/2010 | Demers et al. |
| 7,780,897 B2 | 8/2010 | Wicker et al. |
| D624,180 S | 9/2010 | Grant et al. |
| 7,794,141 B2 | 9/2010 | Perry et al. |
| 7,798,997 B2 | 9/2010 | Kamen et al. |
| 7,857,756 B2 | 12/2010 | Warren et al. |
| 7,874,718 B2 | 1/2011 | Demers et al. |
| D633,619 S | 3/2011 | Collins et al. |
| D636,077 S | 4/2011 | Dale et al. |
| D639,930 S | 6/2011 | Collins et al. |
| D640,372 S | 6/2011 | Grant et al. |
| 7,959,196 B2 | 6/2011 | Dale |
| 7,967,022 B2 | 6/2011 | Grant et al. |
| 7,967,138 B2 | 6/2011 | Ryan et al. |
| 7,993,050 B2 | 8/2011 | Demers et al. |
| D646,392 S | 10/2011 | Collins et al. |
| 8,042,563 B2 | 10/2011 | Wilt et al. |
| 8,143,055 B2 | 3/2012 | Forgacs et al. |
| D658,130 S | 4/2012 | Bodwell et al. |
| 8,158,102 B2 | 4/2012 | Demers et al. |
| 8,197,439 B2 | 6/2012 | Wang et al. |

(56) References Cited

U.S. PATENT DOCUMENTS

| | | |
|---|---|---|
| 8,197,743 B2 | 6/2012 | Wicker et al. |
| 8,198,086 B2 | 6/2012 | Koga et al. |
| 8,236,515 B2 | 8/2012 | Charm et al. |
| 8,241,905 B2 | 8/2012 | Forgacs et al. |
| 8,246,826 B2 | 8/2012 | Wilt et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,366,316 B2 | 2/2013 | Kamen et al. |
| 8,393,690 B2 | 3/2013 | Grant et al. |
| 8,425,471 B2 | 4/2013 | Grant et al. |
| 8,459,292 B2 | 6/2013 | Wilt et al. |
| 8,470,520 B2 | 6/2013 | Ott et al. |
| 8,485,800 B2 | 7/2013 | Lanigan et al. |
| 8,491,184 B2 | 7/2013 | Kamen et al. |
| 8,492,140 B2 | 7/2013 | Smith et al. |
| 8,499,780 B2 | 8/2013 | Wilt et al. |
| 8,507,263 B2 | 8/2013 | Asnaghi et al. |
| 8,545,698 B2 | 10/2013 | Wilt et al. |
| 8,562,834 B2 | 10/2013 | Kamen et al. |
| 8,579,620 B2 | 11/2013 | Wu |
| 8,585,377 B2 | 11/2013 | Kamen et al. |
| 8,586,345 B2 | 11/2013 | Simpson et al. |
| 8,639,484 B2 | 1/2014 | Sun et al. |
| 8,691,274 B2 | 4/2014 | Xu et al. |
| 8,691,974 B2 | 4/2014 | Gatenholm et al. |
| 8,708,950 B2 | 4/2014 | Scarpaci et al. |
| 8,709,793 B2 | 4/2014 | Taboas et al. |
| 8,721,879 B2 | 5/2014 | Van Der Merwe et al. |
| 8,721,884 B2 | 5/2014 | Wilt et al. |
| 8,728,807 B2 | 5/2014 | Forgacs et al. |
| 8,747,880 B2 | 6/2014 | Forgacs et al. |
| 8,771,508 B2 | 7/2014 | Grant et al. |
| 8,817,332 B2 | 8/2014 | Wu |
| 8,840,581 B2 | 9/2014 | Mcgill et al. |
| 8,852,932 B2 | 10/2014 | Forgacs et al. |
| 8,863,772 B2 | 10/2014 | Dale et al. |
| 8,870,549 B2 | 10/2014 | Tracey et al. |
| 8,888,470 B2 | 11/2014 | Demers et al. |
| 8,926,294 B2 | 1/2015 | Demers et al. |
| 8,931,880 B2 | 1/2015 | Murphy et al. |
| 8,968,232 B2 | 3/2015 | Kamen et al. |
| 8,985,133 B2 | 3/2015 | Grant et al. |
| 8,992,075 B2 | 3/2015 | Kamen et al. |
| 8,992,189 B2 | 3/2015 | Wilt et al. |
| 9,005,885 B2 | 4/2015 | Ott |
| 9,005,972 B2 | 4/2015 | Xu et al. |
| 9,011,754 B2 | 4/2015 | Leong et al. |
| 9,022,969 B2 | 5/2015 | Helmore et al. |
| 9,028,400 B2 | 5/2015 | Yadlowsky et al. |
| 9,028,691 B2 | 5/2015 | Grant et al. |
| 9,039,998 B2 | 5/2015 | Guillemot et al. |
| 9,078,971 B2 | 7/2015 | Scarpaci et al. |
| 9,115,708 B2 | 8/2015 | Van Der Merwe et al. |
| 9,121,403 B2 | 9/2015 | Lanigan et al. |
| 9,222,932 B2 | 12/2015 | Shepherd et al. |
| 9,227,339 B2 | 1/2016 | Murphy et al. |
| 9,242,027 B2 | 1/2016 | Bellan et al. |
| 9,242,031 B2 | 1/2016 | Bonassar et al. |
| 9,248,225 B2 | 2/2016 | Demers et al. |
| 9,248,233 B2 | 2/2016 | Kamen et al. |
| 9,272,082 B2 | 3/2016 | Demers et al. |
| 9,301,925 B2 | 4/2016 | Xu et al. |
| 9,302,037 B2 | 4/2016 | Wilt et al. |
| 9,303,245 B2 | 4/2016 | Rivron et al. |
| 9,315,043 B2 | 4/2016 | Murphy et al. |
| 9,358,332 B2 | 6/2016 | Mcgill et al. |
| 9,364,655 B2 | 6/2016 | Grant et al. |
| 9,366,781 B2 | 6/2016 | Scarpaci et al. |
| 9,442,105 B2 | 9/2016 | Shepherd et al. |
| 9,499,779 B2 | 11/2016 | Murphy et al. |
| 9,517,295 B2 | 12/2016 | Wilt et al. |
| 9,526,426 B1 | 12/2016 | Lim |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,556,415 B2 | 1/2017 | Forgacs et al. |
| 9,597,442 B2 | 3/2017 | Wilt |
| 9,603,985 B2 | 3/2017 | Wilt et al. |
| 9,604,858 B2 | 3/2017 | Kamen et al. |
| 9,649,418 B2 | 5/2017 | Demers et al. |
| 9,677,554 B2 | 6/2017 | Wilt et al. |
| 9,700,711 B2 | 7/2017 | Grant et al. |
| 9,717,834 B2 | 8/2017 | Wilt et al. |
| 9,719,964 B2 | 8/2017 | Blumberg, Jr. |
| 9,724,458 B2 | 8/2017 | Grant et al. |
| 9,765,916 B2 | 9/2017 | Cunningham |
| 9,795,728 B2 | 10/2017 | Grant et al. |
| 9,839,775 B2 | 12/2017 | Mcgill et al. |
| 9,839,776 B2 | 12/2017 | Helmore et al. |
| 9,951,768 B2 | 4/2018 | Grant et al. |
| 9,957,960 B2 | 5/2018 | Lanigan et al. |
| 9,981,079 B2 | 5/2018 | Scarpaci et al. |
| 9,987,407 B2 | 6/2018 | Grant et al. |
| 9,987,410 B2 | 6/2018 | Helmore et al. |
| 9,999,717 B2 | 6/2018 | Van Der Merwe et al. |
| 10,058,694 B2 | 8/2018 | Norris et al. |
| 10,060,867 B2 | 8/2018 | Kamen et al. |
| 10,077,766 B2 | 9/2018 | Demers et al. |
| 10,098,996 B2 | 10/2018 | Scarpaci et al. |
| 10,294,450 B2 | 5/2019 | Kamen et al. |
| 10,697,862 B2 | 6/2020 | Duchow |
| 2003/0052065 A1 | 3/2003 | Rosiello |
| 2003/0215945 A1 | 11/2003 | Atala |
| 2003/0229302 A1 | 12/2003 | Robinson et al. |
| 2004/0219668 A1 | 11/2004 | Frei et al. |
| 2004/0235142 A1 | 11/2004 | Schein et al. |
| 2004/0253365 A1 | 12/2004 | Warren et al. |
| 2005/0079620 A1 | 4/2005 | Eberhard et al. |
| 2005/0094485 A1 | 5/2005 | Demers et al. |
| 2005/0095141 A1 | 5/2005 | Lanigan et al. |
| 2005/0095152 A1 | 5/2005 | Dale |
| 2005/0095576 A1 | 5/2005 | Demers et al. |
| 2006/0105011 A1 | 5/2006 | Sun et al. |
| 2006/0141623 A1 | 6/2006 | Smith et al. |
| 2006/0195064 A1 | 8/2006 | Plahey et al. |
| 2006/0199260 A1 | 9/2006 | Zhang et al. |
| 2007/0216334 A1 | 9/2007 | Jones |
| 2007/0227270 A1 | 10/2007 | Mennenga et al. |
| 2007/0275363 A1 | 11/2007 | Bertram et al. |
| 2008/0058697 A1 | 3/2008 | Kamen et al. |
| 2008/0073610 A1 | 3/2008 | Manning et al. |
| 2008/0108968 A1 | 5/2008 | Demers et al. |
| 2008/0113331 A1 | 5/2008 | Demers et al. |
| 2008/0113426 A1 | 5/2008 | Smith et al. |
| 2008/0138223 A1 | 6/2008 | Lanigan et al. |
| 2008/0175719 A1 | 7/2008 | Tracey et al. |
| 2008/0192104 A1 | 8/2008 | Nye et al. |
| 2008/0240929 A1 | 10/2008 | Kamen et al. |
| 2008/0253911 A1 | 10/2008 | Demers et al. |
| 2008/0281533 A1 | 11/2008 | Galliot et al. |
| 2009/0035845 A1 | 2/2009 | Tan et al. |
| 2009/0035856 A1 | 2/2009 | Galliher et al. |
| 2009/0107335 A1 | 4/2009 | Wilt et al. |
| 2009/0128272 A1 | 5/2009 | Hills |
| 2009/0142836 A1 | 6/2009 | Wang et al. |
| 2009/0185920 A1 | 7/2009 | Lanigan et al. |
| 2009/0208466 A1 | 8/2009 | Yoo et al. |
| 2009/0208577 A1 | 8/2009 | Xu et al. |
| 2009/0215109 A1 | 8/2009 | Hennecke |
| 2010/0056975 A1 | 3/2010 | Dale et al. |
| 2010/0190254 A1 | 7/2010 | Chian et al. |
| 2011/0091926 A1 | 4/2011 | Frerich |
| 2011/0105877 A1 | 5/2011 | Wilt et al. |
| 2011/0136225 A1 | 6/2011 | Vunjak-Novakovic et al. |
| 2011/0165676 A1 | 7/2011 | Hopkins |
| 2011/0177590 A1 | 7/2011 | Clyne et al. |
| 2011/0306931 A1 | 12/2011 | Kamen et al. |
| 2011/0319868 A1 | 12/2011 | Hiles et al. |
| 2012/0022441 A1 | 1/2012 | Kelly et al. |
| 2012/0064050 A1 | 3/2012 | Calle et al. |
| 2012/0089238 A1 | 4/2012 | Kang et al. |
| 2012/0136477 A1 | 5/2012 | Merrow et al. |

(56) References Cited

U.S. PATENT DOCUMENTS

| | | |
|---|---|---|
| 2012/0209195 A1 | 8/2012 | Kamen et al. |
| 2012/0221025 A1 | 8/2012 | Simpson et al. |
| 2012/0250024 A1 | 10/2012 | Noda et al. |
| 2013/0143323 A1 | 6/2013 | Frost et al. |
| 2013/0144374 A1 | 6/2013 | Zilla et al. |
| 2013/0156744 A1 | 6/2013 | Taylor et al. |
| 2013/0164339 A1 | 6/2013 | Murphy et al. |
| 2013/0177972 A1 | 7/2013 | Green et al. |
| 2013/0190210 A1 | 7/2013 | Murphy et al. |
| 2013/0238257 A1 | 9/2013 | Rajamani et al. |
| 2013/0304020 A1 | 11/2013 | Wilt et al. |
| 2013/0304233 A1 | 11/2013 | Dean et al. |
| 2013/0344490 A1 | 12/2013 | Kim |
| 2013/0345794 A1 | 12/2013 | Khatiwala et al. |
| 2014/0012225 A1 | 1/2014 | Yoo et al. |
| 2014/0052285 A1 | 2/2014 | Butcher et al. |
| 2014/0074029 A1 | 3/2014 | Kamen et al. |
| 2014/0099709 A1 | 4/2014 | Presnell et al. |
| 2014/0102958 A1 | 4/2014 | Kamen et al. |
| 2014/0144909 A1 | 5/2014 | Bobritski |
| 2014/0199193 A1 | 7/2014 | Wilt et al. |
| 2014/0228970 A1 | 8/2014 | Boland |
| 2014/0274802 A1* | 9/2014 | Shepherd ............. C12N 5/0697 506/14 |
| 2014/0299544 A1 | 10/2014 | Wilt et al. |
| 2014/0330418 A1 | 11/2014 | Wu |
| 2014/0330421 A1 | 11/2014 | Wu |
| 2014/0377864 A1 | 12/2014 | Sumitran-Holgersson et al. |
| 2015/0004273 A1 | 1/2015 | Forgacs et al. |
| 2015/0014558 A1 | 1/2015 | Lanigan et al. |
| 2015/0017140 A1 | 1/2015 | Bhatia et al. |
| 2015/0037445 A1 | 2/2015 | Murphy et al. |
| 2015/0042366 A1 | 2/2015 | Wilt et al. |
| 2015/0050166 A1 | 2/2015 | Tracey et al. |
| 2015/0084956 A1 | 3/2015 | Wu |
| 2015/0088291 A1 | 3/2015 | Wu |
| 2015/0105891 A1 | 4/2015 | Golway et al. |
| 2015/0119994 A1 | 4/2015 | Kang et al. |
| 2015/0182560 A1 | 7/2015 | Calle et al. |
| 2015/0224226 A1 | 8/2015 | Bhatia et al. |
| 2015/0238656 A1 | 8/2015 | Orlando et al. |
| 2015/0282885 A1 | 10/2015 | King et al. |
| 2015/0307728 A1* | 10/2015 | Omenetto ............. A61K 33/24 428/209 |
| 2015/0342720 A1 | 12/2015 | Koç et al. |
| 2015/0344828 A1 | 12/2015 | Forgacs et al. |
| 2015/0351896 A1 | 12/2015 | D'Lima et al. |
| 2015/0375453 A1 | 12/2015 | Yost et al. |
| 2015/0376560 A1 | 12/2015 | Finlay et al. |
| 2016/0022903 A1 | 1/2016 | Kamen et al. |
| 2016/0024461 A1 | 1/2016 | Sun et al. |
| 2016/0025544 A1 | 1/2016 | Kamen et al. |
| 2016/0030658 A1 | 2/2016 | Van Der Merwe et al. |
| 2016/0040132 A1* | 2/2016 | Sears ................ G01N 33/5011 506/10 |
| 2016/0046832 A1 | 2/2016 | Wroblesky et al. |
| 2016/0058933 A1 | 3/2016 | Ballantyne et al. |
| 2016/0082173 A1 | 3/2016 | Coll et al. |
| 2016/0083681 A1 | 3/2016 | Tavana et al. |
| 2016/0101227 A1 | 4/2016 | Norris et al. |
| 2016/0136895 A1 | 5/2016 | Beyer et al. |
| 2016/0144093 A1 | 5/2016 | Demers et al. |
| 2016/0144114 A1 | 5/2016 | Kamen et al. |
| 2016/0175506 A1 | 6/2016 | Wilt et al. |
| 2016/0239025 A1 | 8/2016 | Van Der Merwe et al. |
| 2016/0245277 A1 | 8/2016 | Lanigan et al. |
| 2017/0000938 A1 | 1/2017 | Wilt et al. |
| 2017/0029765 A1* | 2/2017 | Vellinger ............. C12M 41/40 |
| 2017/0073631 A1 | 3/2017 | Miyauchi |
| 2017/0100533 A1 | 4/2017 | Wilt et al. |
| 2017/0128652 A1 | 5/2017 | Mcgill et al. |
| 2017/0130705 A1 | 5/2017 | Demers et al. |
| 2017/0143886 A1 | 5/2017 | Wilt et al. |
| 2017/0198252 A1 | 7/2017 | Mironov et al. |
| 2017/0268495 A1 | 9/2017 | Overson et al. |
| 2017/0296803 A1 | 10/2017 | Grant et al. |
| 2017/0319765 A1 | 11/2017 | Wilt et al. |
| 2017/0326282 A1 | 11/2017 | Wilt et al. |
| 2017/0342972 A1 | 11/2017 | Wilt et al. |
| 2017/0368252 A1 | 12/2017 | Grant et al. |
| 2017/0368827 A1 | 12/2017 | Koga et al. |
| 2017/0370799 A1 | 12/2017 | Jones et al. |
| 2018/0017474 A1 | 1/2018 | Langenfeld et al. |
| 2018/0055984 A1 | 3/2018 | Grant et al. |
| 2018/0079999 A1 | 3/2018 | Blanchard |
| 2018/0104466 A1 | 4/2018 | Mcgill et al. |
| 2018/0127705 A1 | 5/2018 | Langenfeld et al. |
| 2018/0230423 A1* | 8/2018 | O'Mahony ............. C12M 21/08 |
| 2018/0256803 A1 | 9/2018 | Helmore et al. |
| 2018/0273886 A1* | 9/2018 | Akiyama ............... G16H 50/20 |
| 2018/0296746 A1 | 10/2018 | Van Der Merwe et al. |
| 2019/0017010 A1 | 1/2019 | Tilley, Jr. et al. |
| 2019/0170672 A1 | 6/2019 | Blumberg, Jr. et al. |
| 2019/0218501 A1 | 7/2019 | Kamen et al. |
| 2019/0339181 A1 | 11/2019 | Langenfeld et al. |
| 2019/0367884 A1* | 12/2019 | Satchi-Fainaro .... C12N 5/0691 |
| 2020/0040291 A1* | 2/2020 | Hakimi ................. A61L 27/60 |
| 2020/0324469 A1 | 10/2020 | Zhang et al. |

FOREIGN PATENT DOCUMENTS

| | | |
|---|---|---|
| DE | 3627231 A1 | 2/1988 |
| DE | 1017205485 A1 | 10/2018 |
| EP | 0154191 A1 | 9/1985 |
| EP | 0335378 A2 | 10/1989 |
| EP | 2679669 A1 | 1/2014 |
| EP | 3190171 A1 | 7/2017 |
| FR | 2560049 A1 | 8/1985 |
| FR | 2717919 A1 | 9/1995 |
| GB | 2478801 A1 | 9/2011 |
| WO | 087006119 | 10/1987 |
| WO | 93012825 | 7/1993 |
| WO | 1994008549 A1 | 4/1994 |
| WO | 1994012235 A1 | 6/1994 |
| WO | 1994022566 A1 | 10/1994 |
| WO | 1995029455 A1 | 11/1995 |
| WO | 1996013790 A1 | 5/1996 |
| WO | 1996040328 A2 | 12/1996 |
| WO | 1997004712 A1 | 2/1997 |
| WO | 1999010028 A1 | 3/1999 |
| WO | 2001018396 A1 | 3/2001 |
| WO | 2003086509 A1 | 10/2003 |
| WO | 05042139 A1 | 5/2005 |
| WO | 05044337 A2 | 5/2005 |
| WO | 2005042139 A1 | 5/2005 |
| WO | 2005044435 A2 | 5/2005 |
| WO | 2005081970 A2 | 9/2005 |
| WO | 2006042301 A2 | 4/2006 |
| WO | 07009036 A2 | 1/2007 |
| WO | 2008106440 A3 | 4/2008 |
| WO | 08069759 A1 | 6/2008 |
| WO | 2009051669 A1 | 4/2009 |
| WO | 09094179 A2 | 7/2009 |
| WO | 09094182 A2 | 7/2009 |
| WO | 09094183 A1 | 7/2009 |
| WO | 09094184 A1 | 7/2009 |
| WO | 09094185 A2 | 7/2009 |
| WO | 09094186 A2 | 7/2009 |
| WO | 2009094183 A1 | 7/2009 |
| WO | 2009094184 A1 | 7/2009 |
| WO | 09154466 A1 | 12/2009 |
| WO | 16019078 A1 | 2/2010 |
| WO | 11097330 A2 | 8/2011 |
| WO | 11107599 A1 | 9/2011 |
| WO | 11116125 A1 | 9/2011 |
| WO | 2012006425 A2 | 1/2012 |
| WO | 12122105 A1 | 9/2012 |
| WO | 12162515 A2 | 11/2012 |
| WO | 2012162515 A2 | 11/2012 |
| WO | 13006399 A2 | 1/2013 |
| WO | 2013067359 A2 | 5/2013 |
| WO | 13096741 A2 | 6/2013 |
| WO | 13158508 A1 | 10/2013 |
| WO | 13192290 A1 | 12/2013 |

(56) References Cited

FOREIGN PATENT DOCUMENTS

| | | |
|---|---|---|
| WO | 14039427 A1 | 3/2014 |
| WO | 14085725 A1 | 6/2014 |
| WO | 14110590 A1 | 7/2014 |
| WO | 14151921 A1 | 9/2014 |
| WO | 14194180 A1 | 12/2014 |
| WO | 15054577 A1 | 4/2015 |
| WO | 15066705 A1 | 5/2015 |
| WO | 15104018 A1 | 7/2015 |
| WO | 15129881 A1 | 9/2015 |
| WO | 15138999 A1 | 9/2015 |
| WO | 15158700 A1 | 10/2015 |
| WO | 15168528 A1 | 11/2015 |
| WO | 15173020 A1 | 11/2015 |
| WO | 2015173020 A1 | 11/2015 |
| WO | 15183976 A2 | 12/2015 |
| WO | 15198025 A1 | 12/2015 |
| WO | 2015183976 A2 | 12/2015 |
| WO | 2015183981 A2 | 12/2015 |
| WO | 2015188154 A1 | 12/2015 |
| WO | 16012583 A1 | 1/2016 |
| WO | 16022830 A1 | 2/2016 |
| WO | 16036275 A1 | 3/2016 |
| WO | 2017062784 A1 | 4/2017 |
| WO | 2018013737 A1 | 1/2018 |
| WO | 18085832 A1 | 5/2018 |
| WO | 18226642 A1 | 12/2018 |

OTHER PUBLICATIONS

Written Opinion PCT/US2004/035970, dated Nov. 23, 2007, 10 pages.
Written Opinion PCT/US2004/036144, dated Apr. 30, 2006, 6 pages.
Written Opinion, PCT/US2017/060389, dated May 11, 2018, 9 pages.
Xu et al., "Monitoring Tissue Engineering Using Magnetic Resonance Imaging", Journal of Bioscience and Bioengineering 106:6, pp. 515-527, 2008.
Yeo et al., "N anosensors for Regenerative Medicine", Journal of Biomedical Nanotechnology, vol. 10, pp. 2722-2746, 2014.
Badrossamay et al., "Engineering hybrid polymer-protein super-aligned nanofibers via rotary jet spinning", Biomaterials 35, pp. 3188-3197, 2014.
Badrossamay et al., "Nanofiber Assembly by Rotary Jet-Spinning", Nano Lett. 10(6), pp. 2257-2261, Jun. 9, 2010.
Bajaj et al., "3D Biofabrication Strategies for Tissue Engineering and Regenerative Medicine", Annu Rev Biomed Eng. 16, pp. 247-276, Jul. 11, 2014.
Bauer, C. et al., Design of a permanent magnet with a mechanical sweep suitable for variabletemperature continuous-wave and pulsed EPR spectroscopy, Journal of Magnetic Resonance, Academic Press, Orlando, FL, US, 198:2, Jun. 1, 2009, pp. 222-227, Figs. 1, 2, Results and discussion, Magnet design.
Bhattacharjee et al., "Writing in the granular gel medium", Sci. Adv., pp. 1-6, Sep. 25, 2015.
Boland et al., "Tailoring Tissue Engineering Scaffolds Using Electrostatic Processing Techniques: A study of Poly(Glycolic Acid) Electrospinning", J. Macromol. Sci.—Pure Appl. Chem., A38(12), pp. 1231-1243, 2001.
Bose et al., "Bone tissue engineering using 3D printing", Materials Today, vol. 16:12, pp. 496-504, Dec. 2013.
Capulli et al., "JetValve: Rapid manufacturing ofbiohybrid scaffolds for biomimetic heart valve replacement", Biomaterials 133, pp. 229-241, 2017.
Cole, D.B., "An Integrated Heterodyne Interferometer with On-chip Detectors and Modulators", Dissertation, Submitted to Department of Electrical Engineering and Computer Science, MIT, 206 pp., 2015.
Danieli, Ernesto et al., Mobile Nuclear Magnetic Resonance, eMagRes, Jun. 15, 2012. Wiley & Sons, Ltd., ISBN: 978-0-470-03459-0, pp. 849-861, Closed Magnets, Figs 5, 8, 9.
Deravi et al., "Design and Fabrication of Fibrous N anomaterials Using Pull Spinning", Macro 1. Mater. Eng. 1600404, DD. 1-14, 2017.
Derby, B., "Printing and Prototyping of Tissues and Scaffolds", Science 338, pp. 921, 2012.
Dunn, et al., "Gemini Interfaces in Aqueous Lubrication with Hydrogels", Tribal Lett 54, pp. 59-66, 2014.
Edmond et al., "Prevention of Mis-Prescribing in the Elderly: A Potential Use for Micro-Computers," Proceedings of the s1h Annual Symposium on Computer Applications in Medical Care, Washington, DC, USA, Nov. 4-7, pp. 357-360, 1984.
Hohman et al., "Electrospinning and electrically forced jets. li. Applications", Physics of Fluids, vol. 13:8, Aug. 2001.
International Search Report, Int. App. #PCT/US2017/041791, dated Dec. 15, 2017.
Kreyenschulte, Dirk et al., Online monitoring of fermentation processes via non-invasive low-field NMR: online-NMR for Fermentation Processes, Biotechnology and Bioengineering, 112:9, Apr. 7, 2015, pp. 1810-1821, Materials and Methods, Results and Discussion, Figs. 1-3, 5-7.
Kunstar et al., "Label-free Raman monitoring of extracellular matrix formation in threedimensional polymeric scaffolds", J.R. Soc. Interface, Jul. 3, 2013.
Leak Testing Case Studies: Small Medical Device Leak Test Machine, http://tqc.co.uk/leak-testingsmall-medical-device-leak-test-machine.php, Jun. 29, 2017.
Li et al., "Recent advances in bioprinting techniques: approaches, applications and future projects", Journal of Translational Medicine 14:271, 15 pp., 2016.
Liu et al., "Rapid injection of fluorescent sensor into a cell by local mechanical stimulus using optical tweezers", Department of Micro-Nano systems Engineering, Nagoya University, 1 pp., Japan, 2014.
Manandhar et al., "Evaluation of dialysis adequacy in patients under hemodialysis and effectiveness of dialysers reuses", Nepal Med Coll J 11(2), pp. 107-112, 2009.
Marx, V., "Organs from the Lab", Nature, vol. 522, pp. 373-377, Jun. 18, 2015.
Mather et al., "Meeting the Needs of Monitoring in Tissue Engineering", Regenerative Medicine, vol. 2:2, pp. 145-160, Apr. 2007.
McCullen et al., "Nanofibrous composites for tissue engineering applications", Wires Nanomedicine and Nanobiotechnology, vol. 1, pp. 369-390, Jul./Aug. 2009.
Meyer, U., "The History of Tissue Engineering and Regenerative Medicine in Perspective", Fundamentals of Tissue Engineering and Regenerative Medicine, Meyer et al., eds., Springer, ISBN: 978-3-540-77754-0, pp. 5-12, 2009.
Moliver et al., "Decision Support for Medical Treatment: A TPM Prescription System on a Central Hospital computer", Proceedings of the 11 th Annual Symposium on Computer Applications in Medical Care, Washington, DC, USA, Nov. 1-4, pp. 246-254, 1987.
Murphy, S., "3D Bioprinting of Tissues and Organs", Nature Biotechnology, vol. 32:8, pp. 773-785, Aug. 2014.
Nam et al., "Imaging Strategies for Tissue Engineering Applications", Tissue Engineering: Part B, vol. 21:1, pp. 88-102, 2015.
Notification of Transmittal of the International Search Report and the Written Opinion of the International Searching Authority, International application# PCT/US2017/041776, dated Oct. 26, 2017.
Ntziachristos, V., "Fluorescence Molecular Imaging", Annu. Rev. Biomed. Eng. 2006.8, pp. 1-33, 2006.
Ogura et al., "Online Support Functions of Prescription Order System and Prescription Audit in an Integrated Hospital Information System", Med. Inform., vol. 13:3, pp. 161-169, 1988.
Ogura et al., One-line Prescription Order and Prescription Support in an Integrated Hospital Information System, Med. Inform, vol. 104, pp. 287-299, 1985.
PCT /US2017 /041776, Notification Concerning Transmittal of International Preliminary Report of Patentability (Chapter I of the Patent Cooperation Treaty), dated Jan. 24, 2019.
PCT /US2017 /041791, Notification Concerning Transmittal of International Preliminary Report of Patentability (Chapter I of the Patent Cooperation Treaty), dated Jan. 24, 2019.
PCT/US2017/019214, ISR and Written Opinion of the International Search Authority, dated Apr. 9, 2019.

(56) References Cited

OTHER PUBLICATIONS

Peeters et al., "Bioluminescence-mediated longitudinal monitoring of adipose-derived stem cells in a large mammal ex vivo organ culture", Scientific Reports, 5:13960, DD. 1-12, Sep. 9, 2015.

Persidis, A, "Tissue Engineering", Nature Biotechnology 17, pp. 508-510, 1999.

Phuc, Hung Dang et al., Design and Construction of Light Weight Portable NMR Halbach Magnet, International Journal of Smart Sensing and Intelligent Systems, Dec. 1, 2014, 7:4, pp. 1555-1578, URL: http://s2is.org/Issues/v7/n4/papers/paper6.pdf (retrieved on Jul. 25, 2016), IV. Prototype Design and Experimental Set Up, Figs. 14, 15.

Price et al., "Automated Decellularization of Intact, Human-Sized Lungs for Tissue Engineering", Tissue Engineering: Part C, vol. 21:1, 2015.

Price et al., "Development of a Decellularizied Lung Bioreactor System for Bioengineering the Lung: The Matrix Reloaded", Tissue Engineering: Part A, vol. 16:8, 2010.

So, P. TC., "Two-photon Fluorescence Light Microscopy", Encyclopedia of Life Sciences, pp. 1-5, 2002.

Stuart, M.P., et al., Successful Low-Cost Scaffold-Free Cartilage Tissue Engineering Using Human Cartilage Progenitor Cell Spheroids Formed by Micromolded Nonadhesive Hydro gel, Hindawi, Stem Cells Interntational, vol. 2017, Art. ID 7053454, 11 p.

Tokarev et al., "Touch- and Brush-Spinning ofNanofibers", Adv. Mater., pp. 1-7, 2015.

Twardowski, Z.J., "Dialyzer Reuse—Part II: Advantages and Disadvantages", Seminars in Dialysis, pp. 217-226, 2006.

Urbano et al., "Decellularized Lung Scaffolds for Bioengineered Organs", Med Sci tech 55:66-70, 2014.

Urbano, J. J. et al., Lung Scaffolds for Bioengineered Organ, XXIV Congresso Brasileiro de Engenharia Biomedica—CBEB 2014, DD. 2014-2016.

Vogel, Michael W. et al., Rotatable Small Permanent Magnet Array for Ultra-Low Field Nuclear Magnetic Resonance Instrumentation: A Concept Study, PLOS One 11:6, Jun. 6, 2016, pp. 1-24, Materials and Methods, Figs. 2, 6, SPMA design, Manual SPMA.

Weymann et al., "Perfusion-Decellularization of Porcine Lung and Trachea for Respiratory Bioengineering", Artificial Organs 39(12):1024-32, Dec. 2015.

Written Opinion of the International Searching Authority, PCT/US2016/056138, Int. filing date Oct. 7, 2016.

\* cited by examiner

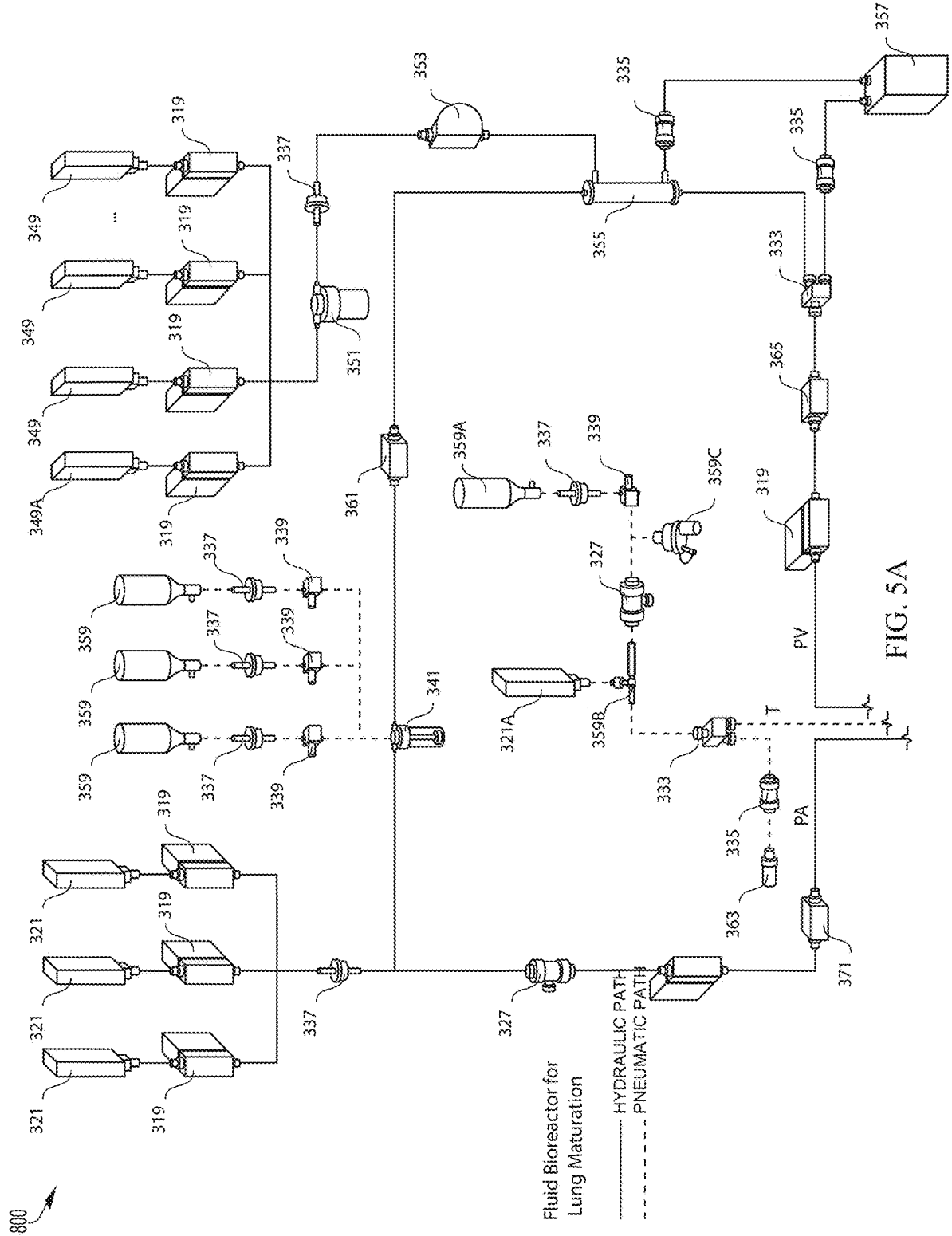

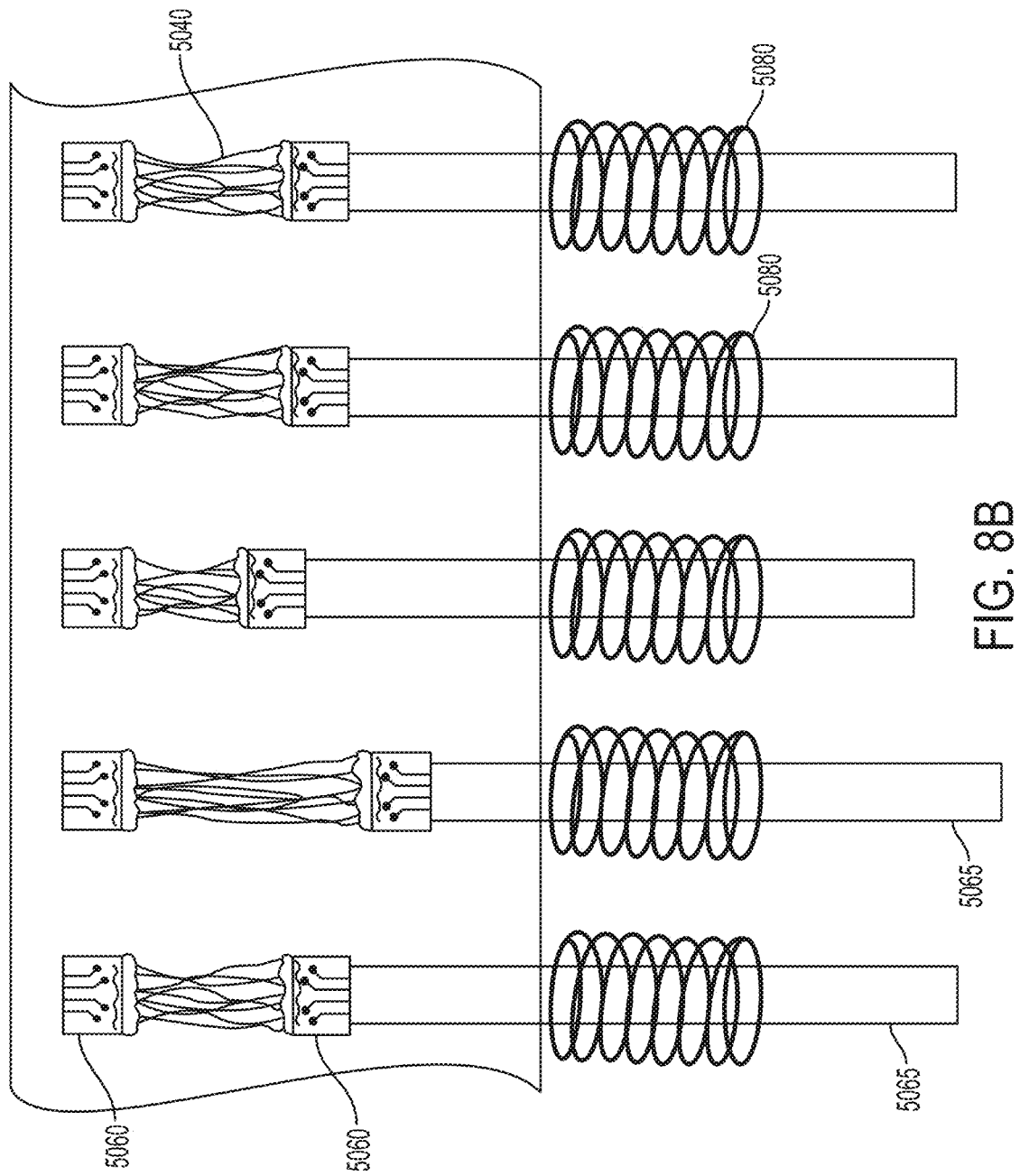

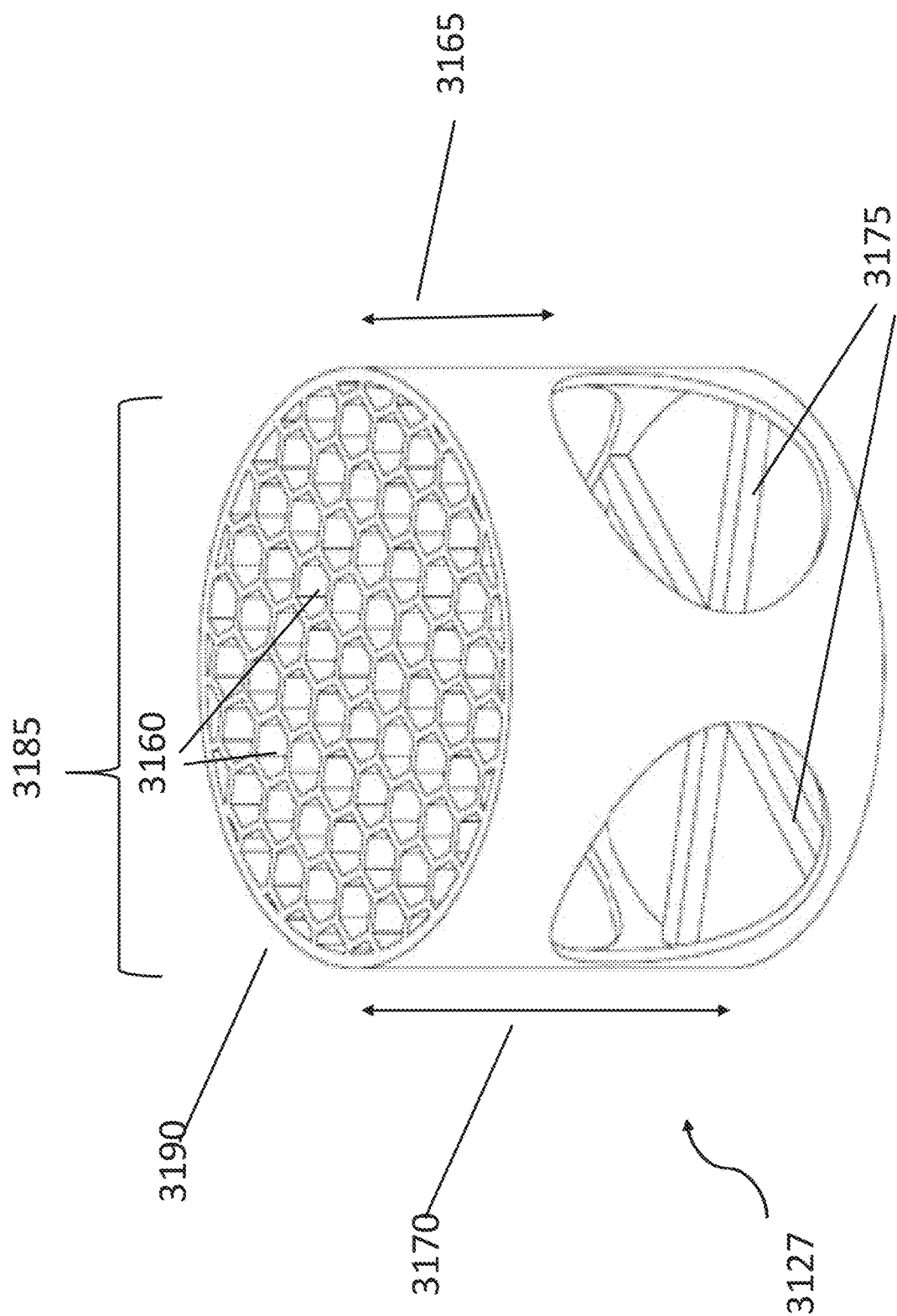

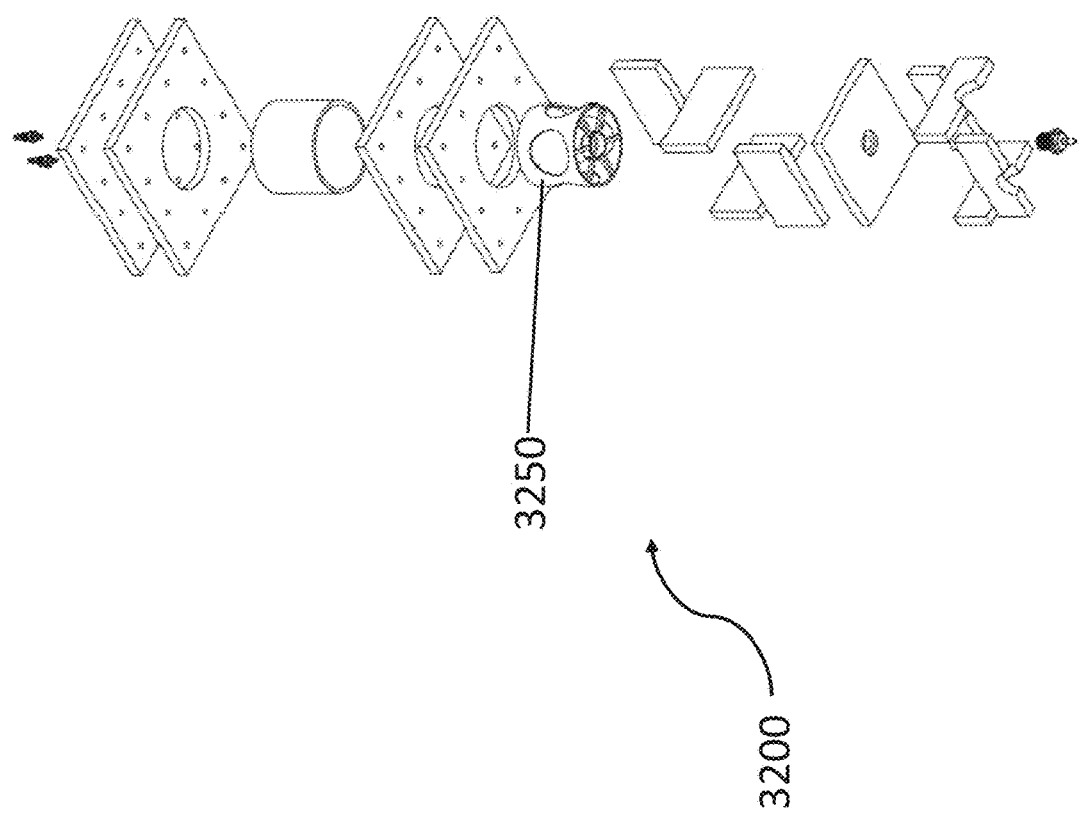

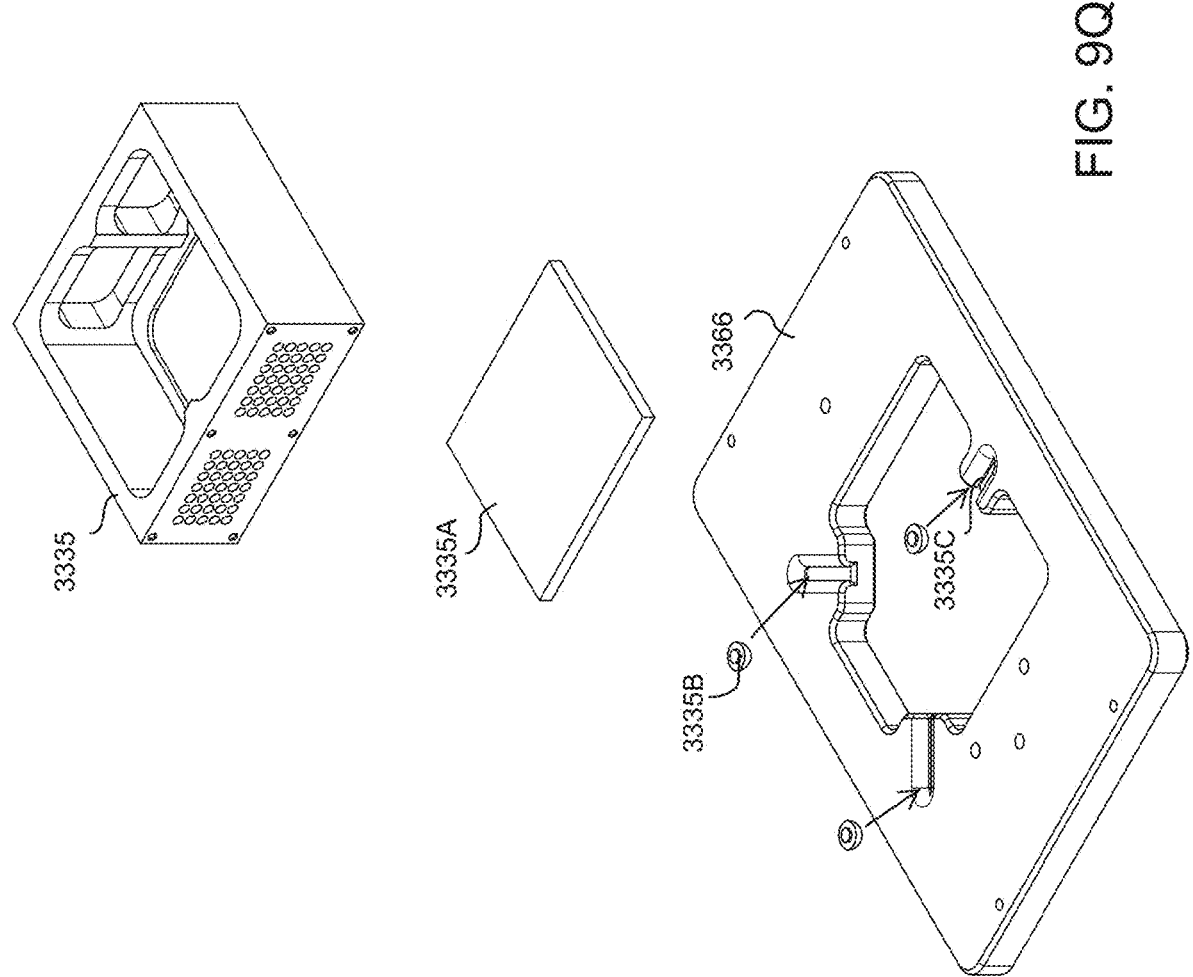

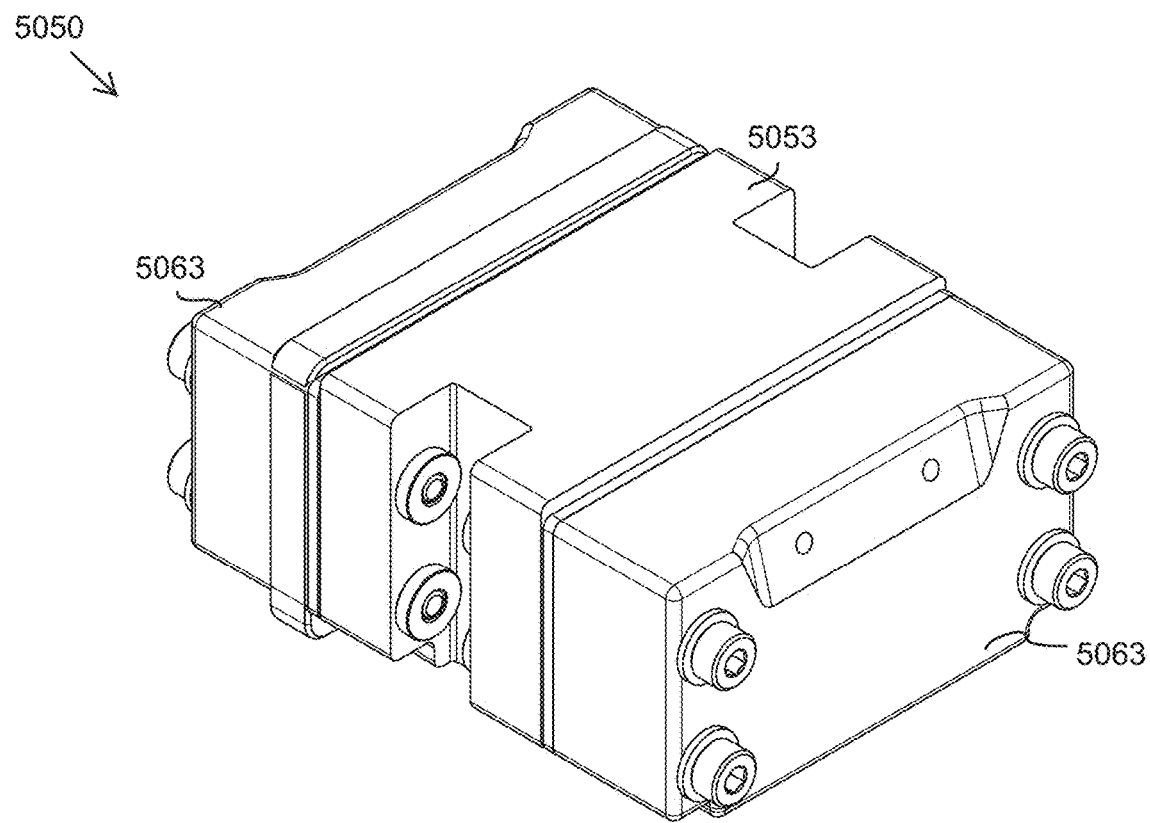
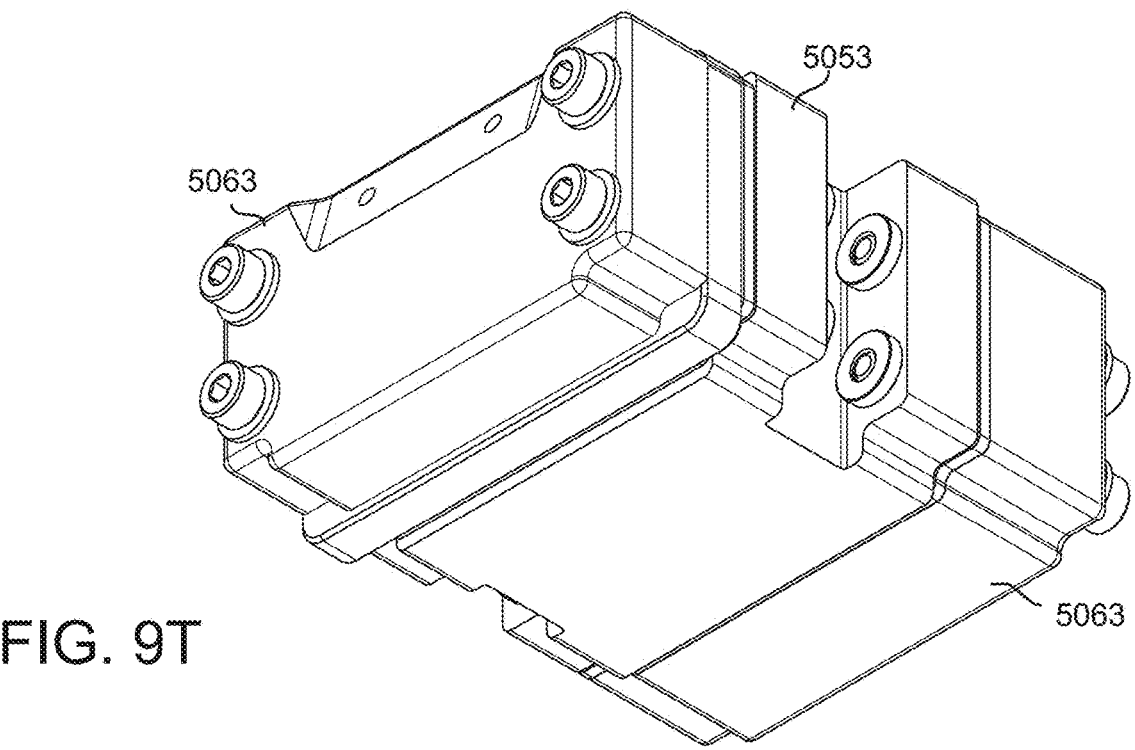
FIG. 9T

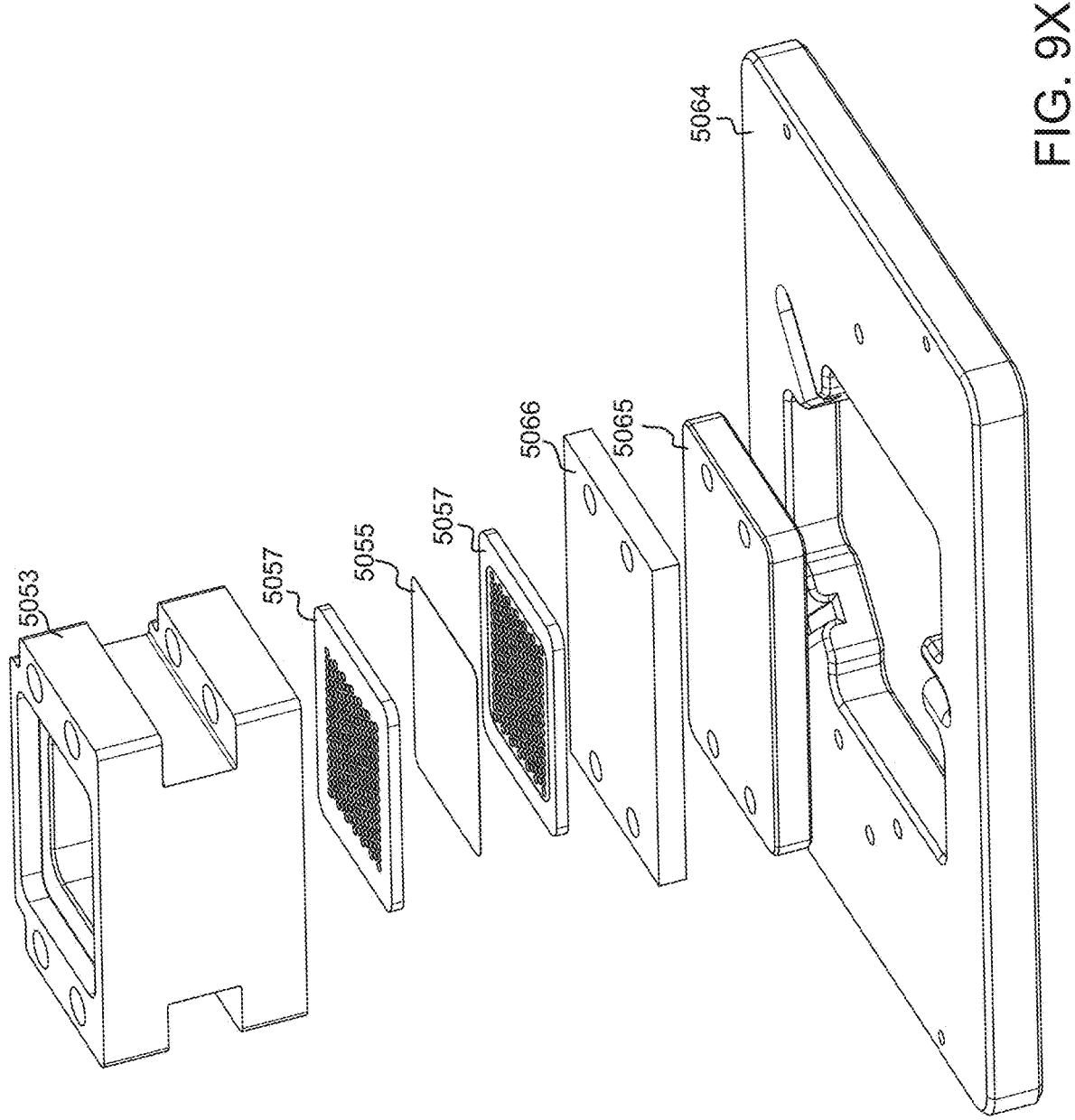

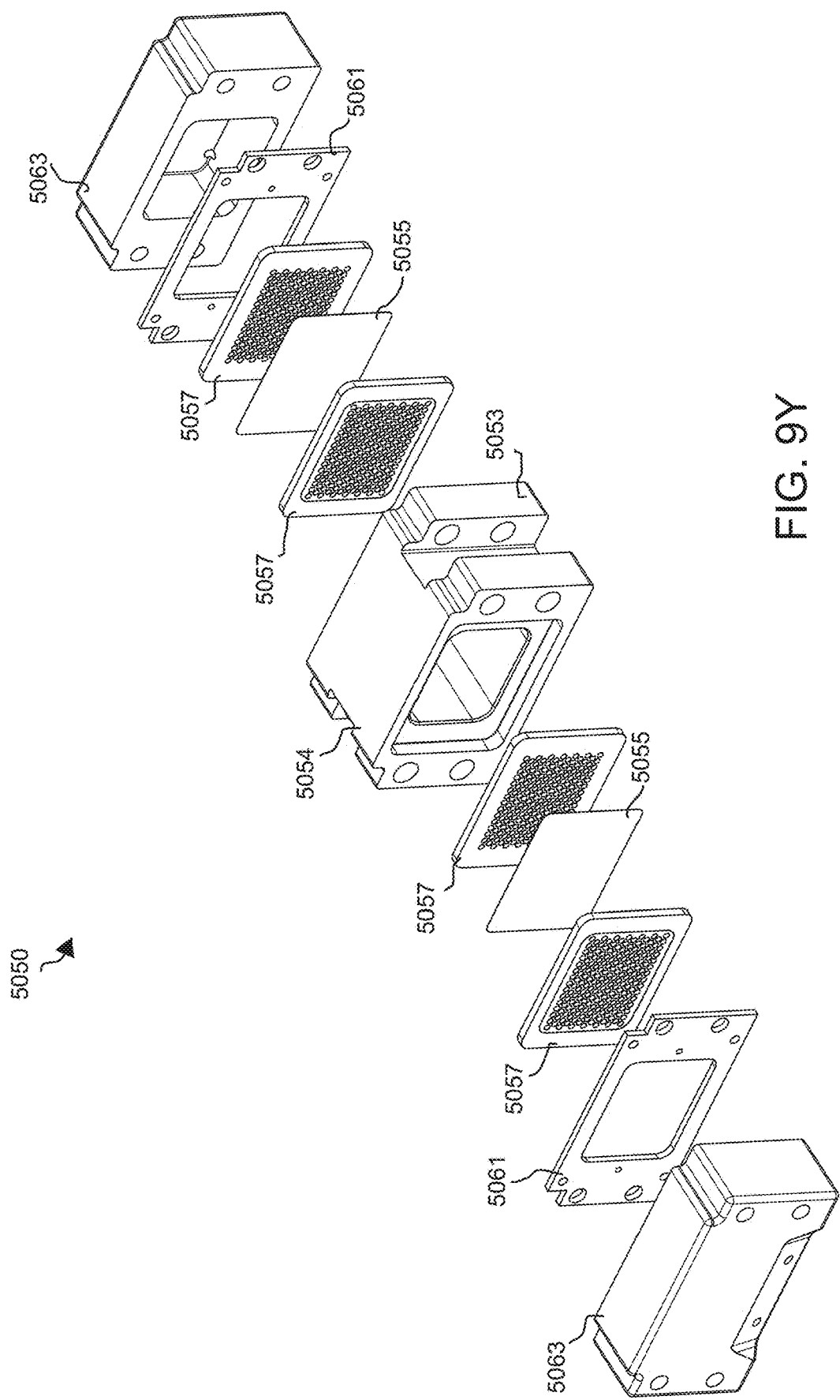

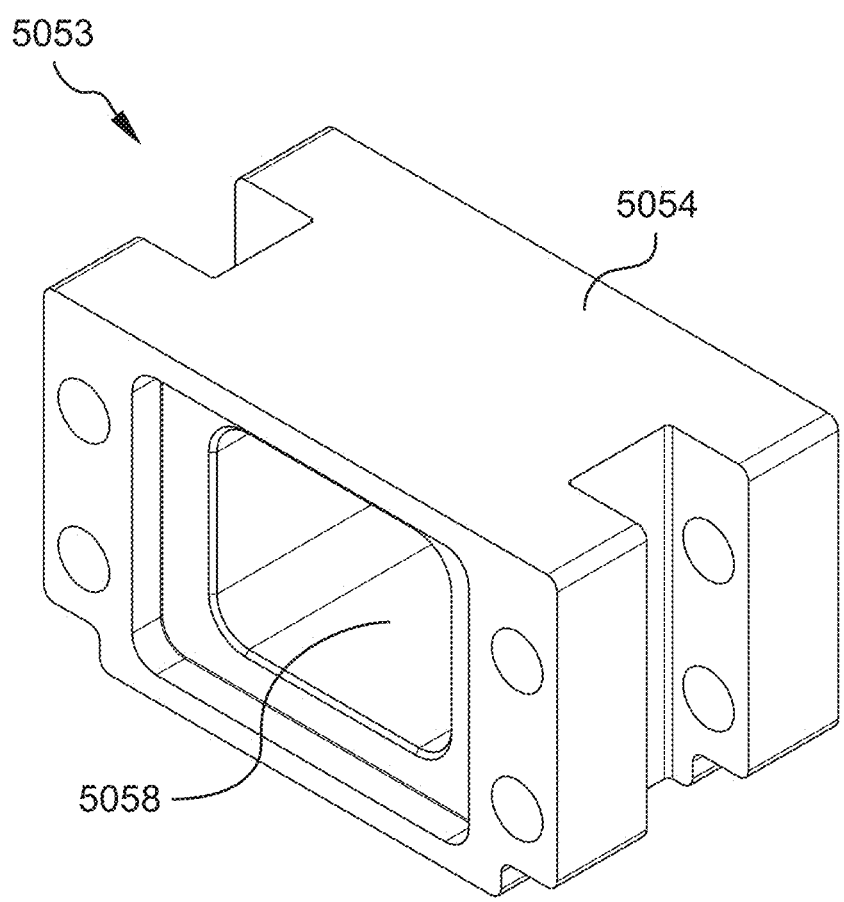
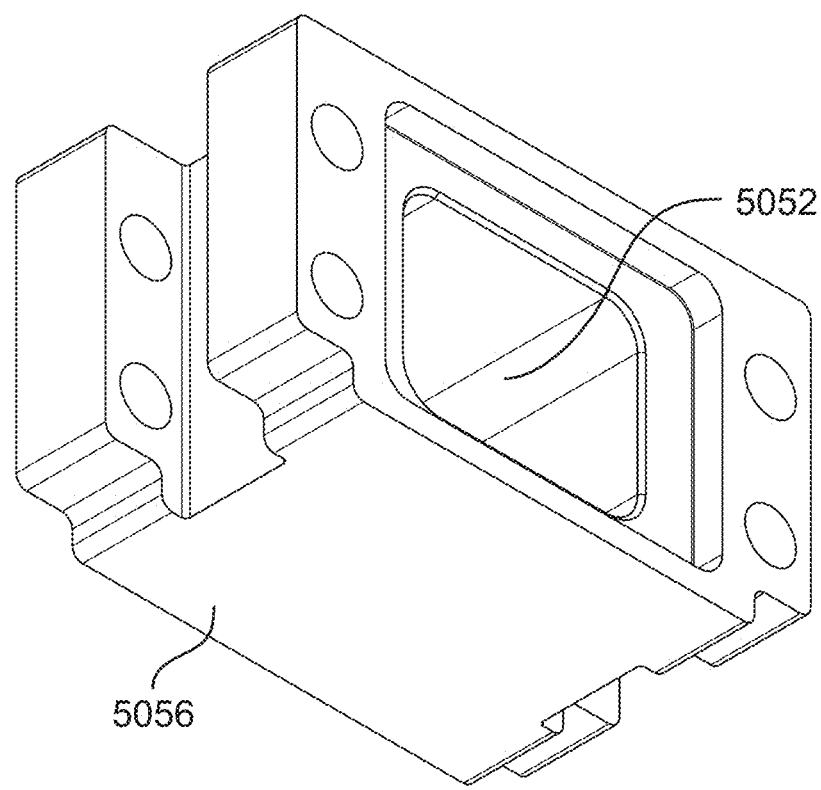
FIG. 9Z

SYSTEM AND METHOD FOR CREATING TISSUE

CROSS REFERENCE TO RELATED APPLICATIONS

This application is a divisional of U.S. patent application Ser. No. 15/805,790 filed Nov. 7, 2017, now U.S. Publication No. US-2018-0127705-A1, published May 10, 2018 entitled System and Method for Applying Creating Tissue, which claims the benefit of U.S. Provisional Patent Application Ser. No. 62/418,784 filed Nov. 7, 2016, entitled System and Method for Applying Creating Tissue, and U.S. Provisional Patent Application Ser. No. 62/534,984 filed Jul. 20, 2017, entitled Tissue Enclosure, which are incorporated herein by reference in their entirety.

BACKGROUND

The present teachings relate generally to tissue engineering, and more specifically to systems and methods to enable tissue creation.

The current approach to growing structures in a granular gel bioreactor is to supply a fluid or pneumatic pressure gradient on an upstream reservoir or plenum to encourage flow through the granular gel and any cells or structures suspended in the gel. The flowing material could include nutrients and could wash away waste products from the structures. It might be optimal if the structures could remain positionally static while the nutrients flow through them. However, depending on the granular gel concentration, pressure amplitudes used, and other factors, the structures may only remain positionally static at a pressure gradient too low to provide a feasible flow rate of material. If the movement of the structures is too high, the structures may compress to a point where the cellular viability or future functionality of the tissue is compromised.

In 2016, approximately 119,000 people were on a waiting list for an organ transplant, and yet only 33,606 transplants occurred, an 8.5% increase over 2015. This disparity continues to grow. Tissue engineering and regenerative medicine seek to address this shortage by creating viable cells, tissues, and organs for transplantation in a controlled setting such as a bioreactor. These cells, tissues, and organs could potentially replace animal and human subjects for drug development and testing. In order to accomplish this goal, tissue engineering has turned to 3D tissue printing. Tissue printing uses living cells and other biological materials as bio-ink to produce a 3D structure. There are three categories of printing technologies used in this field: inkjet-based bioprinting, pressure-assisted bioprinting, and laser-assisted bioprinting.

In order to maintain the viability of the printed tissue structure, a steady supply of nutrients must enter a bioreactor that can house the printed tissue while waste exits from it. The field of tissue engineering faces the challenge of monitoring tissue production, which is crucial to ensuring that cells are growing and differentiating properly while receiving the appropriate nutrients and signals. However, monitoring developing tissue presents a unique challenge: obtaining high resolution images of developing cells and tissue in a non-invasive manner.

Creating human tissue can involve problems such as achieving the necessary precision in a timely way to create the tissue, and maintaining the viability of the tissue while it awaits use. Currently tissue engineering is primarily a manual and empirical process without a great deal of reproducibility or quality assurance. What is needed is a combination of state-of-the-art engineering solutions applied to the biological problems of creating and maintaining tissue.

One such technology is three-dimensional printing that can be used to print living cells, scaffolds for living cells, and/or complete organs. However, three-dimensionally printing even simple living tissues can require substantial improvements over current three-dimensional printing technology. Further, what is needed is a repeatable process so that the results of tissue creation can be predictable. Therefore, what is needed is a complete, automated system for creating tissue and maintaining its viability.

SUMMARY

The method of the present teachings for growing tissue can include, but is not limited to including, producing a protein associated with the tissue, selecting cells associated with the tissue, expanding the cells, creating at least one tissue bio-ink including the expanded cells, printing the at least one tissue bio-ink in at least one tissue growth medium mixture, growing the tissue from the printed at least one tissue bio-ink, and maintaining viability of the tissue. The method can optionally include maintaining the tissue, and packaging the tissue for transport. Producing the protein can include forming a recombinant protein precursor based on viral vectors associated with the tissue and cell lines associated with the tissue, forming disassociated protein precursor cells based on subjecting the recombinant protein precursor to at least one disassociation reagent and stress, creating at least one protein bio-ink based on the disassociated protein precursor cells and a sterile gel, creating at least one printable protein bio-ink based on the at least one protein bio-ink and at least one protein support material, printing the at least one printable protein bio-ink in at least one protein growth medium mixture, and growing the at least one printable protein bio-ink into the protein. The stress can include mechanical stress and fluid stress. The at least one protein growth medium can include the sterile gel, a sterile basal medium, and a recombinant protein. Expanding the cells can include forming disassociated tissue precursor cells based on subjecting the selected cells to at least one disassociation reagent and stress, creating a growth medium associated with growing the disassociated tissue precursor cells, forming a tissue precursor recombinant protein mixture based on the protein associated with the tissue and indicators and support materials associated with the disassociated tissue precursor cells, forming a cell/medium mixture of the disassociated tissue precursor cells, the growth medium, and the tissue precursor recombinant protein mixture, and growing the expanded cells in a bioreactor loaded with the cell/medium mixture. At least one tissue bio-ink can include the protein, tissue growth indicators, tissue growth factors, tissue support materials, and tissue gel. At least one tissue growth medium mixture can include the protein, tissue gel, and basal medium.

The system of the present teachings for growing tissue can include a protein production process producing a protein associated with the tissue, a cell selection process selecting cells associated with the tissue, a cell expansion process expanding the cells, and a build process creating bio-ink based on the expanded cells and the protein, the build process printing the bio-ink in a growth medium mixture, the bio-ink growing into the tissue.

The organ life support system to maintain and reproduce tissue and/or cells, can include, but is not limited to including, at least one incoming chamber configured to receive an incoming fluid, at least one corresponding effluent chamber configured to allow a fluid outflow from the system, the at least one corresponding effluent chamber further maintained at a pressure different from the at least one incoming chamber, at least one filtration zone, disposed between each of the at least one incoming chambers and the at least one corresponding effluent chamber, and a gel layer to contain tissue and/or cells.

The method of the present teachings for automatically growing tissue can include, but is not limited to including, selecting cells associated with the tissue, expanding the cells, creating at least one tissue bio-ink including the expanded cells, printing the at least one tissue bio-ink in at least one tissue growth medium mixture, growing the tissue from the printed at least one tissue bio-ink in the at least one tissue growth medium mixture, and maintaining viability of the tissue. The method can optionally include producing a protein associated with the tissue.

The method of the present teachings for regrowing at least one axon of a nervous system and for restoring lost connections in the nervous system can include, but is not limited to including, providing, in a tissue enclosure, mechanical loading for axonal stretch growth of the at least one axon in at least one tissue-engineered nerve graft. The step of providing mechanical loading can include, but is not limited to including, attaching at least one integrative neuron, including the at least one axon, of the at least one tissue-engineered nerve graft to at least one sled within the bioreactor system. The at least one integrative neuron can include a first end and a second end. The first end can attach with a first set of the at least one sled, and the second end can attach with a second set of the at least one sled. The step of providing mechanical loading can include drawing apart the attached first set and the attached second set with a pre-selected force, and maintaining, by a plurality of load cells attached to at least one of the first set and the second set, the pre-selected force within a pre-selected limit. The plurality of load cells can communicate with electromagnetically driven shafts that can engage with at least one of the first set and the second set. The pre-selected force can be maintained electromagnetically. The method for regrowing an axon can include adjusting current signals sent to the electromechanically driven shafts when the at least one tissue-engineered nerve graft reaches maturity. The method can optionally include detecting indicators of potential damage during stretching based on information collected by sensors operably coupled with the tissue enclosure. The sensors can optionally include at least one optical sensor and a microelectrode. The method can optionally include stimulating the at least one integrative neuron, and augmenting a rate of growth and minimizing breakage of the at least one axon based on an amount of nutrients provided in the tissue enclosure, growth factors and supplements provided, and an amount of waste products evacuated from the tissue enclosure.

The bioreactor system of the present teachings for axonal stretch growth of tissues can include, but is not limited to including, a plurality of sleds. Each of the plurality of sleds can be operably coupled with a movable shaft. A first set of the plurality of sleds can be engaged with a first end of a bundle of neurons, and a second set of the plurality of sleds can be engaged with a second end of the plurality of sleds. The system can include a plurality of load cells attached to the plurality of sleds, at least one sensor sensing movement of at least one of the plurality of sleds, and a bundle of neurons engaged on one end with a first set of the plurality of sleds. The bundle of neurons can be engaged on a second end with a second set of the plurality of sleds. The system can include a controller monitoring the at least one sensor. The controller can control the at least one sensor, the controller can control at least one environmental parameter in the bioreactor system, and the controller can command a pre-selected force to be applied to the bundle of neurons. The controller can monitor the pre-selected force, and maintain the pre-selected force within a pre-selected limit. The movable shaft can optionally be electromagnetically driven. The movement of the movable shaft can optionally be controlled by varying a current to the electromagnet.

The organ life support system for maintaining tissue of the present teachings can include, but is not limited to including, at least one incoming chamber receiving an incoming fluid, and at least one effluent chamber allowing a fluid outflow from the system. The at least one effluent chamber can be maintained at a pressure different from the at least one incoming chamber. The organ life support system can include at least one filtration zone disposed between each of the at least one incoming chambers and the at least one effluent chambers, and a medium/tissue chamber housing the tissue and growth media. The medium/tissue chamber can receive the incoming fluid from the at least one incoming chamber through the at least one filtration zone, and the medium/tissue chamber can enable fluid flow to at least one effluent chamber through the at least one filtration zone. The pressure within at least one effluent chamber is optionally lower than the pressure within the at least one incoming chamber. The difference in pressures can optionally be maintained by at least one pump. The at least one incoming chamber and the medium/tissue chamber can optionally be separated by one of the at least one filtration zones, and the medium/tissue chamber and the at least one effluent chamber can optionally be separated by one of the at least one filtration zones. The system can optionally include observation windows and sensors disposed within the at least one incoming chamber and the at least one effluent chamber. The at least one filtration zone can optionally include a membrane filter. The at least one pump can optionally include a fluid pressure pump and/or a fluid vacuum pump.

The tissue enclosure of the present teachings enabling creation, maintenance, and monitoring of tissue can include, but is not limited to including, a core including a cavity. The core can include at least one monitoring area and at least one opening into the cavity. One of the at least one openings can receive the tissue, and the core can accommodate at least one material ingress and at least one material egress. The tissue enclosure can include at least one filter assembly operably coupled with the core. The tissue can be confined within the cavity by the at least one filter assembly, the life of the tissue can be maintained at least by fluid flowing through the cavity between the at least one material ingress and the at least one material egress, and the tissue can be monitored through the at least one monitoring area. The tissue enclosure can optionally include at least one plenum operably coupled with the at least one filter assembly. The at least one plenum can enable the application of pressure to the fluid and to the tissue. The tissue enclosure can optionally include at least one heater that can maintain the temperature of the tissue, and at least one medium surrounding the tissue. The at least one medium can optionally include a gel. A multi-dimensional printer can optionally print the tissue into the cavity. The at least one filter assembly can optionally include at least one filter, at least one filter support operably coupled with the at least one filter and at least one filter frame operably coupling the at least one filter and the at least one filter support with the at least one plenum. The tissue enclosure can optionally include a tissue enclosure top removably enclosing the tissue within the core. The at least one monitoring area can optionally include a transparent window.

The tissue enclosure of the present teachings enabling creation, maintenance, and monitoring of tissue can include, but is not limited to including, a core including a cavity. The core can include at least one monitoring area and at least one opening into the cavity. The tissue enclosure can include at least one filter assembly operably coupled with the core. The tissue enclosure can include at least one plenum swapably coupled with the at least one filter assembly during the maintenance of the tissue. The at least one plenum can enable maintenance of the tissue by enabling the application of pressure to the material and the tissue. The tissue can be printed into the cavity through the at least one opening. The tissue can be maintained within the cavity by the at least one filter assembly. The tissue can be monitored through the at least one monitoring area. The core can optionally accommodate at least one material ingress and at least one material egress. The tissue enclosure can optionally include at least one medium surrounding the tissue. The at least one medium can optionally include a gel. A multi-dimensional printer can optionally print the tissue into the cavity. The at least one filter assembly can optionally include at least one filter, at least one filter support operably coupled with the at least one filter, and at least one filter frame operably coupling the at least one filter and the at least one filter support with the at least one plenum or the at least one block-off plate. The tissue enclosure can optionally include at least one mounting feature operably coupled with the core, and a tissue enclosure mounting plate. The mounting plate can optionally include receiving features enabling kinematic mounting of the core at the at least one mounting feature. The at least one monitoring area can optionally include a transparent window. The system can optionally include at least one block-off plate swapably coupled with the at least one filter during the creation of the tissue. The at least one block-off plate can be mounted on a side of the cavity opposing the at least one opening.

The system of the present teachings for maintaining viability of tissue can include, but is not limited to including, a tissue enclosure loaded with a print medium, and a pressure pump pumping at least one fluid through at least one fluid inlet in the print medium. The fluid can provide nutrition to the tissue, and the tissue can create effluent based on the fluid. The system can include a vacuum pump evacuating the effluent though at least one fluid outlet in the tissue enclosure. The system can optionally include at least one window in the tissue enclosure enabling monitoring the tissue and the print medium.

The tissue enclosure of the present teachings enabling creation and maintenance of tissue can include, but is not limited to including, an incoming chamber containing media and tissue. The incoming chamber can admit a first material, and can emit a second material in response to a differential pressure within the tissue enclosure. The tissue enclosure can include a filtration zone operably coupled with the incoming chamber. The filtration zone can subject the first material, the second material, the media, and the tissue to at least one filter having a pore size based at least on the first material, the second material, the media, and the tissue. The filtration zone can emit filtered contents based at least on the first material, the second material, the media, the tissue, and the pore size. The tissue enclosure can include an effluent chamber operably coupled with the filtration zone. The effluent chamber can admit the filtered contents, and can manage the filtered contents. The differential pressure can optionally result from atmospheric pressure being applied perpendicularly to the media and the tissue, and a vacuum pump being applied to the effluent chamber. The media can optionally include a gel. The tissue can optionally include live human tissue. The first material can optionally include nutrition for the tissue. The second material can optionally include waste generated by the tissue. The filtered contents can optionally result from recycling the filtered contents to the incoming chamber. Managing the filtered contents can optionally include discarding the filtered contents. Managing the filtered contents can optionally include monitoring the filtered contents. The filtration zone can optionally include at least one filter sandwiched between at least one supporting mesh and at least one sealing frame.

The tissue enclosure of the present teachings enabling creation and maintenance of tissue can include, but is not limited to including, an incoming chamber including media and tissue. The incoming chamber can admit a first material, and can emit a second material in response to a differential pressure within the tissue enclosure. The tissue enclosure can include a filtration zone operably coupled with the incoming chamber. The filtration zone can subject the first material, the second material, the media, and the tissue to at least one filter having a pore size based at least on the first material, the second material, the media, and the tissue. The filtration zone can emit filtered contents based at least on the first material, the second material, the media, the tissue and the pore size. The tissue enclosure can include an effluent chamber operably coupled with the filtration zone. The effluent chamber can admit and manage the filtered contents. The tissue enclosure can include at least one fluid outlet that can enable departure of fluid from the effluent chamber, and at least one vacuum outlet enabling a vacuum to be applied to the effluent chamber. The vacuum can form, along with atmospheric pressure perpendicularly forcing contents of the incoming chamber, the pressure differential between the effluent chamber and the incoming chamber. The tissue enclosure can optionally include a support structure including a plurality of tunnels disposed in a first orientation, and a plurality of ribs disposed in a second orientation. The support structure can optionally operably couple with the filtration zone, and can optionally funnel the filtered contents from the filtration zone to the effluent chamber.

A tissue enclosure of the present teachings enabling creation and maintenance of tissue can include, but is not limited to including, an incoming chamber containing incoming chamber contents. The contents can include the tissue, media, and a first material. The incoming chamber can emit a second material in response to a differential pressure within the tissue enclosure, and the incoming chamber can include a pressure inlet enabling pressure to be applied to the incoming chamber contents. The tissue enclosure can include a filtration zone operably coupled with the incoming chamber. The filtration zone can subject the first material, the second material, the media and the tissue to at least one filter having a pore size based on the first material, the second material, the media and the tissue. The filtration zone can emit filtered contents based on the first material, the second material, the media, the tissue and the pore size. The tissue enclosure can include an effluent chamber operably coupled with the filtration zone. The effluent chamber can admit and manage the filtered contents. The tissue enclosure can include at least one fluid outlet enabling departure of fluid from the effluent chamber, and at least one vacuum outlet enabling a vacuum to be applied to the effluent chamber. The vacuum can form, along with atmospheric pressure perpendicularly forcing contents of the incoming chamber, the pressure differential between the effluent chamber and the incoming chamber. The tissue enclosure can include at least one waste outlet enabling emission of waste from the effluent chamber. The tissue enclosure can optionally include a support structure including a tunnel disposed in a first orientation, and a plurality of ribs disposed in a second orientation. The support structure can operably couple with the filtration zone, and can include a plurality of tunnel structures feeding the filtered contents from the effluent chamber into the tunnel. The support structure can funnel the filtered contents from the filtration zone through the tunnel to the waste outlet.

The tissue enclosure of the present teachings enabling creation, maintenance, and monitoring of tissue can include, but is not limited to including, an incoming chamber admitting a first material. The incoming chamber can emit the first material in response to a differential pressure within the tissue enclosure. The tissue enclosure can include a core including a cavity. The core can include, but is not limited to including, at least one monitoring area and at least one opening into the cavity. The core can accommodate at least one material ingress and at least one material egress, and can include the tissue, media, and metabolism products from the tissue. The tissue enclosure can include at least one first filtration zone operably positioned between the incoming chamber and the core. The filtration zone can subject the first material to at least one filter having a first pore size based at least on the first material, and can emit first filtered contents to the core based at least on the first material and the first pore size. The tissue enclosure can include at least one second filtration zone operably coupled with the core. The at least one second filtration zone can subject the first filtered material, the media, the tissue, and the metabolism products to at least one filter having a second pore size based at least on the first filtered material, the media, the tissue, and the metabolism products. The filtration zone can emit second filtered contents based at least on the first filtered material, the media, the tissue, the metabolism products, and the second pore size. The tissue enclosure can include an effluent chamber that can admit the second filtered contents, and can manage the filtered contents. The tissue can enter the cavity through the at least one opening, the tissue can be confined within the cavity by the at least one first filtration zone and the at least one second filtration zone, the life of the tissue can be maintained by the first material entering the cavity through the at least one material ingress and by the metabolism products exiting the cavity through the at least one material egress, and the tissue can be monitored through the at least one monitoring area. The at least one opening can optionally enable printing of the tissue. The at least one monitoring area can optionally include a transparent window that can be disposed opposite the at least one opening. The tissue enclosure can optionally include at least one mount button accommodating kinematic mounting of the tissue enclosure upon a tissue enclosure holder having corresponding mount wells.

The system of the present teachings for automatically growing tissue can include, but is not limited to including, a cell expansion subsystem that can create at least one type of cell. The at least one type of cell can be based on the tissue. The system can include an ink mixing subsystem that can combine the at least one type of cell with components to create a bio-ink. The system can include a life support enclosure that can include means for feeding the tissue, means for removing waste from the tissue, and means for transporting the tissue. The system can include a build subsystem that can print the bio-ink in the life support enclosure. The printed bio-ink can form the tissue, and the life support enclosure can house the tissue. The system components can optionally include protein and gel. The system can optionally include a protein production subsystem that can create the protein.

The system of the present teachings for automatically growing tissue can include, but is not limited to including, a controller providing commands to the system, and a growth medium subsystem responding to the commands. The growth medium subsystem can produce growth medium. The system can include a build subsystem that can respond to the commands. The build subsystem can receive, at least, cells associated with the tissue and the growth medium, and the build subsystem can create the tissue based at least on the cells and the growth medium. The system can include a growth subsystem that can respond to the commands. The growth subsystem can grow the created tissue into a pre-selected mature tissue. The system can include a maintenance subsystem that can respond to the commands. The maintenance subsystem can maintain the viability of the pre-selected mature tissue. The system can include a tissue pack subsystem that can transport the viable mature tissue to a patient. The growth medium can optionally include indicators, support materials, gel, protein, and basal medium. The build subsystem can optionally create the protein. The protein can optionally include commercially-available protein. The build subsystem can optionally include a bio-ink subsystem responding to the commands. The bio-ink subsystem can receive cells, the indicators, growth medium, and the support materials, and can create a bio-ink. The build subsystem can optionally include a printer subsystem that can respond to the commands. The printer subsystem can receive the bio-ink, and can print the bio-ink. The build subsystem can optionally include a bioreactor subsystem that can respond to the commands. The bioreactor subsystem can receive the printed bio-ink, and the growth medium from the growth medium subsystem, and can provide the tissue to the maintenance subsystem. The maintenance subsystem can include a solid tissue subsystem that can respond to the commands. The solid tissue subsystem can receive the tissue from the build subsystem, and can transmit viability and nutrition status of the tissue. The maintenance subsystem can include a fluid bioreactor subsystem that can respond to the commands. The fluid bioreactor subsystem can receive the viable tissue from the solid tissue subsystem, and can incubate the viable tissue received from the solid tissue subsystem, along with at least in the growth medium received from the growth medium subsystem, supplements, diluent, and basal media. The fluid bioreactor subsystem can provide viable incubated tissue. The maintenance subsystem can include a packaged tissue subsystem that can enable the transport of the viable incubated tissue. The growth medium subsystem can include a disassociated cell subsystem that can respond to the commands. The disassociated cell subsystem can create disassociated cells based at least on incoming cells, viral vectors, and commercial protein, and can provide the disassociated cells to the build subsystem. The growth medium subsystem can include a print medium subsystem that can respond to the commands. The print medium subsystem can create the growth medium based at least on the indicators, support materials, carbomer, the basal media, and the protein. The growth medium subsystem can include a protein subsystem that can respond to the commands. The protein subsystem can receive the protein from the build subsystem and can supply the protein to the print medium subsystem. The controller can include a feedback controller controlling the flow and composition of fluid to and through the tissue. The feedback controller can communicate through the commands formatted according to a communications protocol. The feedback controller can receive sensed information from at least one sensor, and can base the commands at least on the sensed information. The system can optionally include a dialysis/recirculation subsystem that can cleanse the fluid after the fluid has passed through the tissue, and can return the fluid to the tissue.

The system of the present teachings for incubating an organ can include, but is not limited to including, an organ scaffold that can host the organ, and a tube that can operably couple with the organ scaffold. The tube can provide a conduit between a fluid source and the organ scaffold. The system can include a chamber that can house the organ scaffold. The chamber can include at least one inlet and at least one outlet. The at least one inlet can receive fluids, and the fluids can maintain viability of the organ. The at least one outlet can evacuate wastes from metabolism of the organ. The system can optionally include at least one pump that can operably couple with the at least one inlet. The at least one pump can pump fluids into the chamber through the at least one inlet. The at least one pump can enable pressure to be applied to the fluids and the wastes, and can enable the movement of the fluids and the wastes through the chamber. The organ scaffold can optionally include a fluid cavity that can enable the receiving of fluids into and the emitting of fluids from the interior of the organ scaffold. The fluid cavity can include an inner surface and an outer surface. The inner surface can provide a boundary for the received fluids. The organ scaffold can include a compliant wrapper that can operably couple with the outer surface. The compliant wrapper can enable inflation and deflation of the fluid cavity. The organ scaffold can include at least one layer of fiber that can be disposed upon the compliant wrapper. The at least one layer of fiber can be disposed in the shape of the organ. The organ scaffold can include a plurality of cells that can be disposed upon the at least one layer of fiber. The plurality of cells can be associated with the biology of the organ.

The system of the present teachings for monitoring activity in tissue can include, but is not limited to including, at least one resonator including a thermally sensitive material. The thermally sensitive material can have absorption properties, and the absorption properties can be adjustable based at least on heat attained. The at least one resonator can include at least one inductive component and at least one capacitive component. The system can include at least one illuminator that can illuminate the resonator. The at least one illuminator can enable the at least one resonator to absorb energy and convert the energy into heat. The system can include at least one receiver monitoring the frequency of the illuminated at least one resonator as the tissue changes. The at least one illuminator can optionally periodically illuminate the at least one resonator. The at least one illuminator can optionally continuously illuminate the at least one resonator, reversing polarity periodically during the continuous illumination. The at least one inductive component can optionally store energy, the at least one inductive component can optionally discharge the stored energy when the polarity is reversed, and the discharged energy can optionally be stored in the at least one capacitive component. The periodic storing and discharging of energy can convert the energy into heat. The system can optionally include at least one diode that can convert the energy absorbed by the resonator into a control pulse or a DC voltage or both. A plurality of the at least one diode can create various voltage gradients across the tissue, and the various voltage gradients can mimic bioelectrical potentials in the tissue.

The method of the present teachings for monitoring activity of tissue can include, but is not limited to including, printing the tissue within a tissue enclosure, and printing at least one sensing element within the tissue. The at least one sensing element can enable sensing of low energy signals produced by the tissue. The method can include printing at least one structure within the tissue enclosure. The at least one structure can surround the tissue, and the at least one structure can isolate the signals generated by the tissue.

The method of the present teachings for electrospinning biological material can include, but is not limited to including, energizing a needle with a pre-selected voltage, and pumping the biological material into the needle. The pumping and the energizing can force the biological material into an energized droplet stream. The method can include transmitting an RF signal of a pre-selected phase angle across an array of antennas. The array of antennas can each be associated with at least one resonator. The antennas and resonators can have a pre-selected geometry, and the array of antennas can substantially surround the energized droplet stream. The method can include creating a voltage gradient by adjusting the phase angle of the RF signal. The voltage gradient and the pre-selected geometry can create a torque on the energized droplet stream. The torque can move the droplet stream to a pre-selected position on a surface. The pre-selected voltage can optionally be greater than 10 kV. The method can optionally include pumping the biological material into a reservoir, and pumping the biological material from the needle into a nozzle. The nozzle can direct the energized droplet stream, and the energized droplet stream can have a diameter of approximately 10 µm. The surface can optionally include a collector plate and/or tissue.

BRIEF DESCRIPTION OF THE DRAWINGS

The present teachings will be more readily understood by reference to the following description, taken with the accompanying drawings, in which:

FIGS. 5A-5E are schematic block diagrams of the lung bioreactor of the present teachings;

FIGS. 5A-5E are schematic block diagrams of the lung bioreactor of the present teachings;

FIGS. 7K-1, 7K-2, and 7K-3 are cross sections of the mixing cassette as in FIGS. 7H-7K;

FIG. 8B is a pictorial representation of the nerve growth system of the present teachings;

FIG. 9G is a perspective schematic view of the support structure of the second configuration of the bioreactor of the present teachings;

FIG. 9K is a schematic perspective exploded view of the third configuration of the bioreactor of the present teachings;

FIGS. 9O, 9P, and 9Q are schematic perspective exploded views of the fourth configuration of the bioreactor of the present teachings;

FIG. 9T is an schematic perspective of the sixth configuration of the tissue enclosure of the present teachings;

FIG. 9X is a schematic perspective exploded view of the sixth configuration tissue enclosure in printing mode;

FIG. 9Y is a schematic perspective of the sixth configuration of the tissue enclosure of the present teachings in life support mode;

FIG. 9Z is a schematic perspective of the core of the sixth configuration of the tissue enclosure of the present teachings;

FIG. 9AA is a schematic perspective diagram of the exploded bladder bioreactor of FIG. 9AA-1;

FIG. 9AA-1 is a schematic exploded perspective diagram of a bladder bioreactor of the present teachings;

FIG. 9BB is a schematic block diagram of a system employing the bladder bioreactor of FIG. 9AA;

DETAILED DESCRIPTION

A configuration of a system of the present teachings for creating tissue is discussed in detail herein. Throughout the following description, references to fasteners can include any type of fastening mechanism including, but not limited to, glue, bolts, screws, nails, and hook-and-eye devices.

Figure 1:
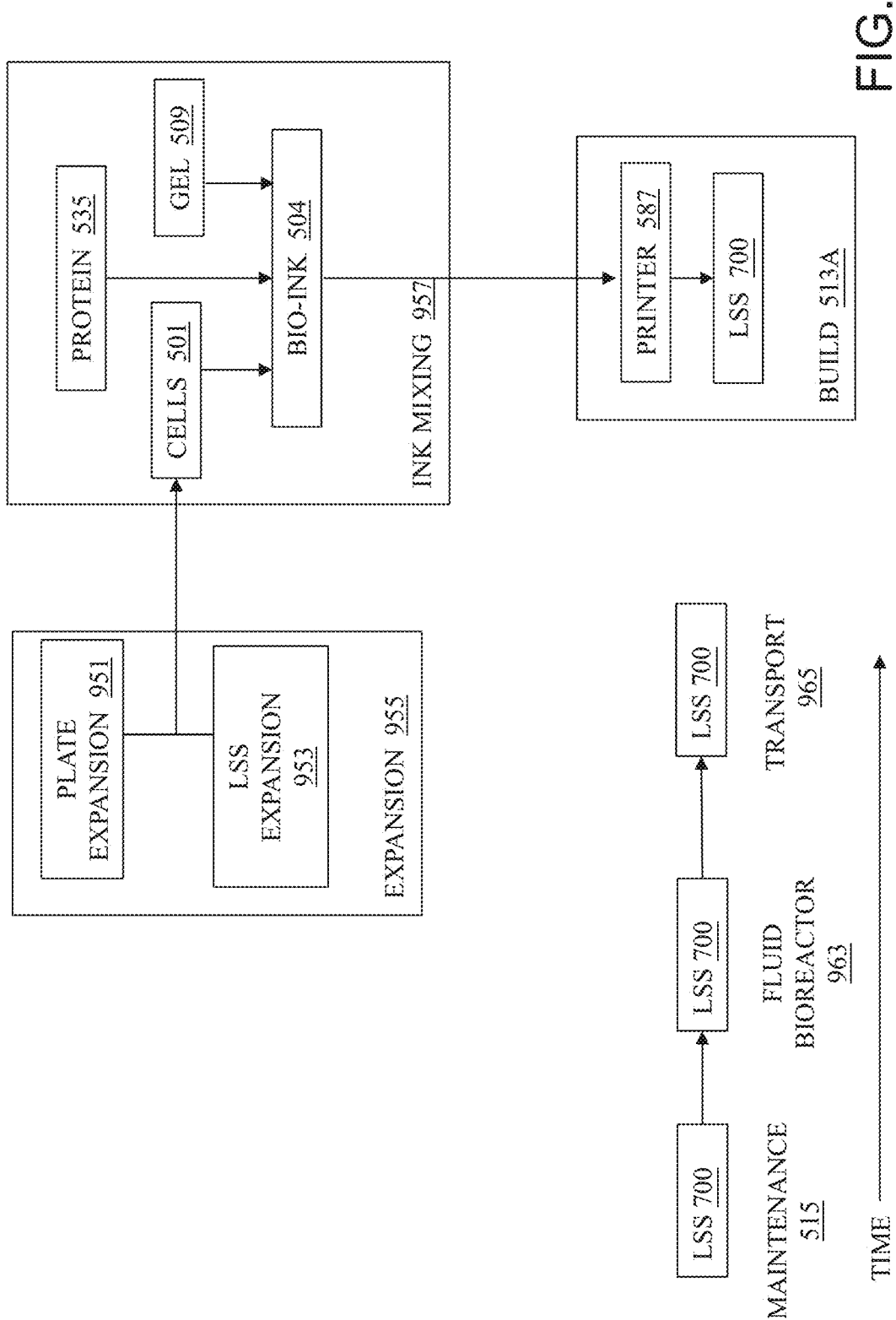
FIG. 1 is a schematic block diagram of the tissue engineering environment of the present teachings.

Referring now to FIG. 1, tissue engineering environment 500A can expand cells, create biological and support mixtures for printing and growing the cells into tissue, print the mixtures as tissue into a life support enclosure, maintain the viability of the tissue in the life support enclosure, and transport the mature, viable tissue in the life support enclosure. Tissue engineering environment 500A can include partial and/or complete automation in which each phase of tissue creation and phase transitions can be directed by a controller that can receive feedback on the status of the process and the viability of the tissue. The life support enclosure can include features that can enable tissue creation, maintenance, and transport without moving the tissue from one enclosure to another. Cell expansion 955 can create the cells necessary to create the desired tissue. Cell expansion 955 can rely on, for example, plate expansion 951 or expansion 953 in a life support system (LSS) of the present teachings, to create cells 501. Ink mixing 957 can include creating bio-ink 504 based on one, or some, or all of cells 501, protein 535, and gel 509. Protein 535 can be grown within tissue engineering environment 500A or can be commercially acquired, for example. Build 513A can include printing the tissue using printer 587 from bio-ink 504 into LSS 700. After the tissue is printed into LSS 700, maintenance subsystem 515 can maintain the viability of the tissue in the LSS 700. Over time, as the tissue ages, waste products can be produced, and the tissue can require nutrition. LSS 700 can include fluid bioreactor 963 that can enable fluid transfer across the tissue to provide nutrition and remove wastes. When the tissue in LSS 700 matures, transport 965 can move LSS 700, including the tissue, to a final destination, such as, for example, a transplant recipient.

Figure 1A:
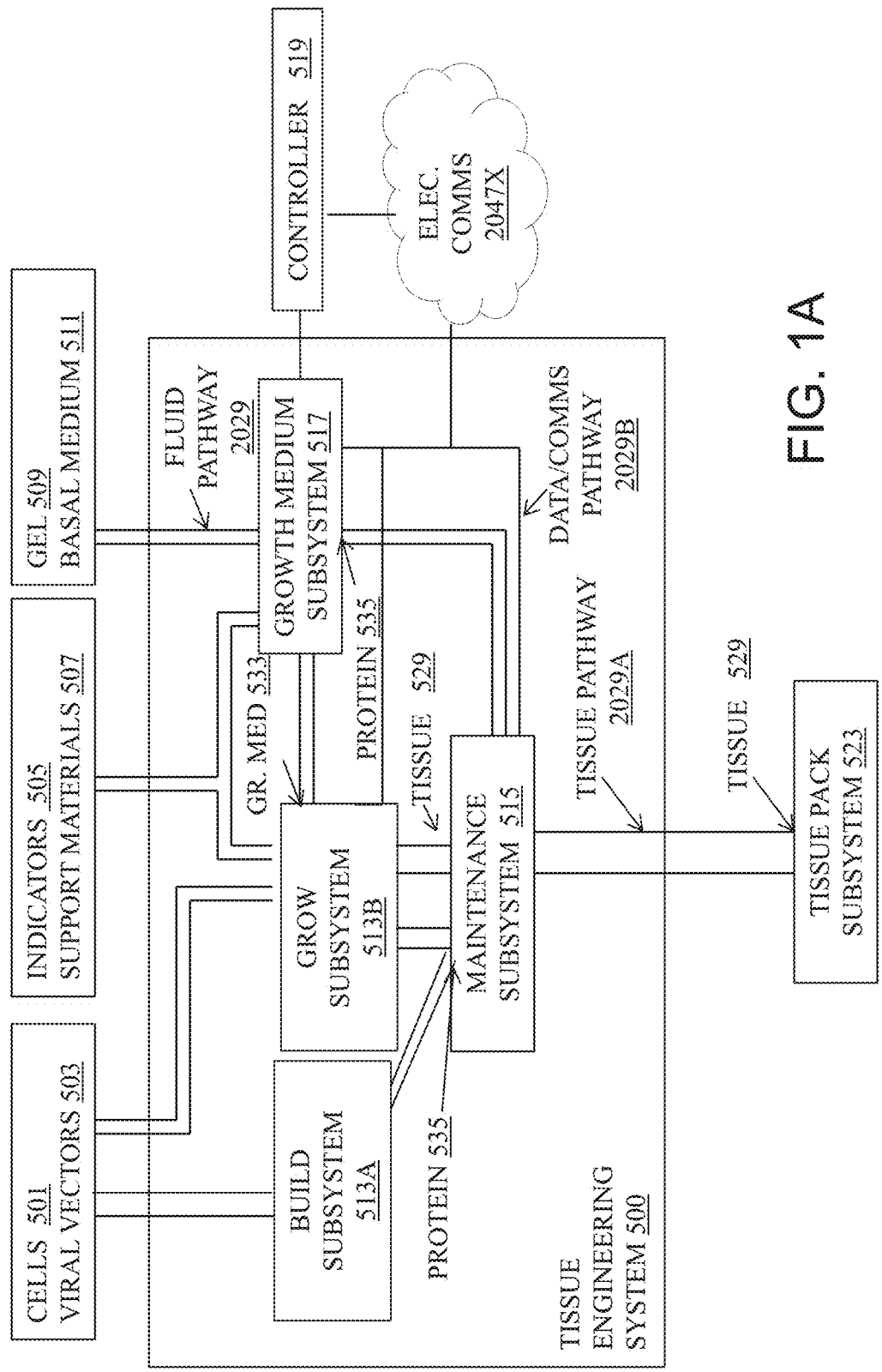
FIG. 1A is a schematic block diagram of the tissue engineering system of the present teachings.

Referring now to FIG. 1A, tissue engineering system 500 can create tissue 529 from individual cells 501 and/or patient biopsy, and can maintain created tissue 529 until, for example, tissue 529 is needed for transplantation. System 500 can include, but is not limited to including, growth medium subsystem 517, build subsystem 513A and grow subsystem 513B, maintenance subsystem 515, and controller 519. Growth medium subsystem 517 can receive, for example, but not limited to, growth medium indicators 505, growth medium support materials 507, medium 509, protein producing cells 535, and basal medium 511, through a first of fluid pathways 2029. Some of the components that can be received by growth medium subsystem 517 can be chosen to grow a particular kind of cell and/or organized group of cells—tissue 529—and can create growth medium 533. Growth medium 533 can be characterized optically. Tissue 529 can grow in and be maintained in a sterile carbomer granular gel preparation that can include photonic markers. Build subsystem 513A and grow subsystem 513B can receive a combination of the components through a second of fluid pathways 2029. The combination of components can depend on a desired resultant tissue 529, including, for example, but not limited to, output from the growth medium subsystem 517. Maintenance subsystem 515 can nurture expanded cells, protein producing cells 535, and tissue 529 received through a first of tissue pathways 2029A until they are needed by other parts of system 500 or as transplants, for example. Controller 519 can include subcontrollers for various parts of system 500 that can manage the interactions among the components of system 500 through signals sent over data/communications pathways 2029.

Figure 1B:
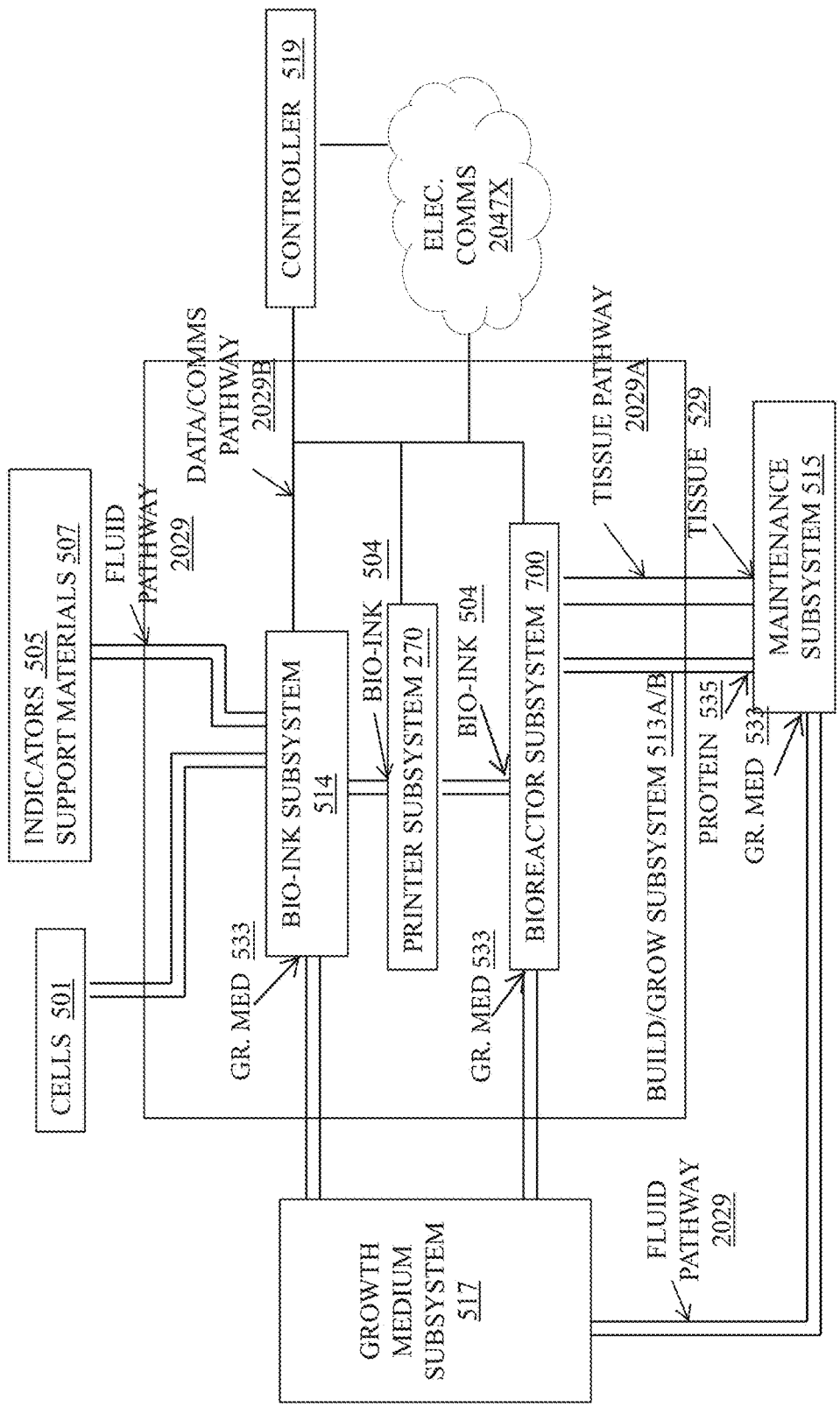
FIG. 1B is a schematic block diagram of the build or grow subsystem of the present teachings.

Referring now to FIG. 1B, build subsystem 513A and grow subsystem 513B can create an environment for growth of, for example, but not limited to, tissue 529 and protein producing cells 535. Build subsystem 513A and grow subsystem 513B can include, but are not limited to including, bio-ink subsystem 514, and bioreactor subsystem 700. Build subsystem 513A can include printer subsystem 270 which can print bio-ink 504 into bioreactor subsystem 700. Cells 501, indicators 505, support materials 507, and growth media 533 can be supplied to bio-ink subsystem 514. Bio-ink subsystem 514 can create bio-ink 504 that can be used to print desired biological material to bioreactor subsystem 700. Bio-inks 504 can be mixed together according to a recipe that can enable growth and maintenance of tissue 529 and can reduce the number of print heads necessary. Bio-inks 504 can include, but are not limited to including, cells, carbomer, markers, and dots, for example. Bioreactor subsystem 700 can incubate printed bio-ink 504 in growth media 533 that is chosen based on bio-ink 504 and desired biological structures such as, but not limited to, tissue 529 and protein producing cells 535. Controller 519 can direct fluid and tissue flow through data/communications pathways among subsystems. Electronic communications 2047X can include wired and wireless means.

Figure 1C:
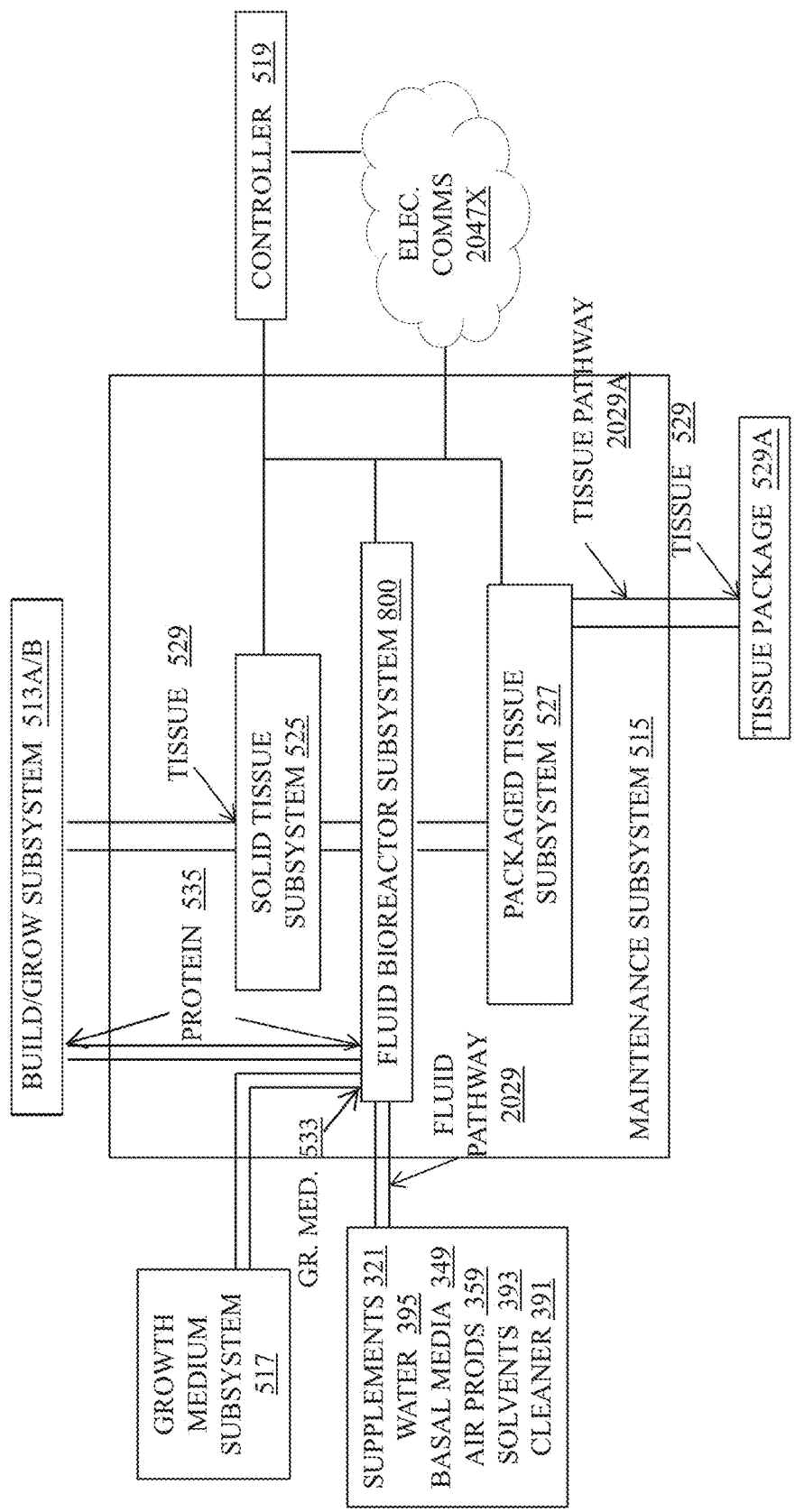
FIG. 1C is a schematic block diagram of the maintenance subsystem of the present teachings.

Referring now to FIG. 1C, maintenance subsystem 515 can ensure that biological material created by build subsystem 513A can remain viable until it is used in, for example, but not limited to, a transplant. Maintenance subsystem 515 can include, but is not limited to including, solid tissue subsystem 525, fluid bioreactor subsystem 800, and packaged tissue subsystem 527. An exemplary fluid bioreactor subsystem 800 is described in U.S. patent application Ser. No. 15/288,900, entitled FLUID PUMPING AND BIOREACTOR SYSTEM, ('900). Build subsystem 513A can provide biological material, for example, but not limited to, tissue 529 to solid tissue subsystem 525 that can transfer viable tissue 529 to fluid bioreactor subsystem 800. Fluid bioreactor subsystem 800 can maintain viability of biological material such as, for example, but not limited to, tissue 529 and protein producing cells 535 until the biological material is needed by supplying, for example, but not limited to, supplements 321, diluent 395, basal media 349, air products 359, solvents 393, cleaner 391, and growth media 533 to the biological material in quantities that can maintain viability of the biological material. Controller 519 can adjust the amounts and rates of delivery of substances to the biological material according to a pre-defined recipe, and can control draining/recycling of waste material. When tissue 529 is required, packaged tissue subsystem 527 can store tissue 529 for portability in tissue package 529A. When protein producing cells 535 is required, it can be provided to build subsystem 513A. Tissue package 529A can include, but is not limited to include, a material coated with a hydrophobic material. Transferring protein producing cells 535 and tissue 529 between physical enclosures, if necessary, can include insuring sterility in the environment surrounding the biological material being transferred.

Figure 1D:
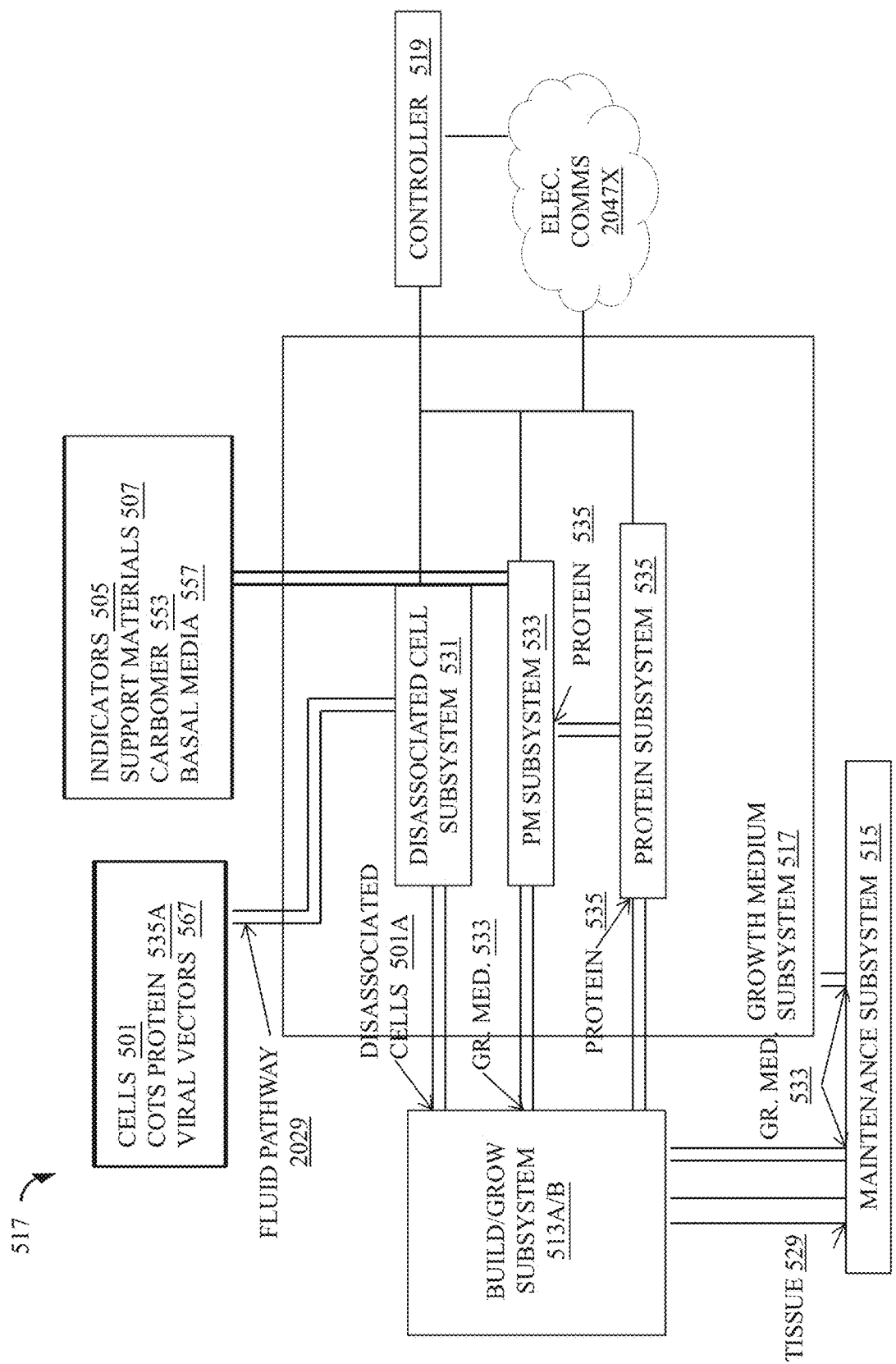
FIG. 1D is a schematic block diagram of the growth medium subsystem of the present teachings.

Referring now to FIG. 1D, growth medium subsystem 517 can enable creation of specific growth media for a given biological material outcome. Growth medium subsystem 517 can include, but is not limited to including, disassociated cell subsystem 531, print medium subsystem 533, and protein subsystem 535. Growth media 533 can be developed based upon the desired biological material. Growth media 533 can include, for example, but not limited to, basal media 557, carbomer powder 553, indicators 505, support materials 507, and proteins 535. Disassociated cell subsystem 531 can create disassociated cells 501A from, for example, but not limited to, supplied cells 501, commercial protein producing cells 535A, and viral vectors 567. Supplied cells 501 can include, but are not limited to including, patient biopsy cells 541 (FIG. 2A) from which can be created patient stem cells 543 (FIG. 2A) which can then become differentiated stem cells 545 (FIG. 2A) or immortalized cell lines 547 (FIG. 2A) isolated patient cell lines 549 (FIG. 2A), for example. Commercially-available or otherwise procured viral vectors 567 and immortalized cell lines 571 can be combined by transduction to produce protein producing cell lines 569. Growth media 533 can be supplied to build subsystem 513A to promote growth of the desired biological material, and to maintenance subsystem 515 to maintain tissue 529 that results from the growth of the desired biological material. Disassociated cell subsystem 531 can isolate cells according to the desired biological material outcome and the source of the cells. Disassociated cell subsystem 531 can disassociate the cells based on the source of the cells, for example, cells resulting from a biopsy can require disassociation. Cells can be disassociated using, for example, a reagent such as trypsin to wash the cells and then isolate the cells using standard techniques A flow cytometer can be used to sort disassociated cells, and the sorted cells can be suspended in a solution and mixed with, for example, gel, media, and proteins.

Figure 1E:
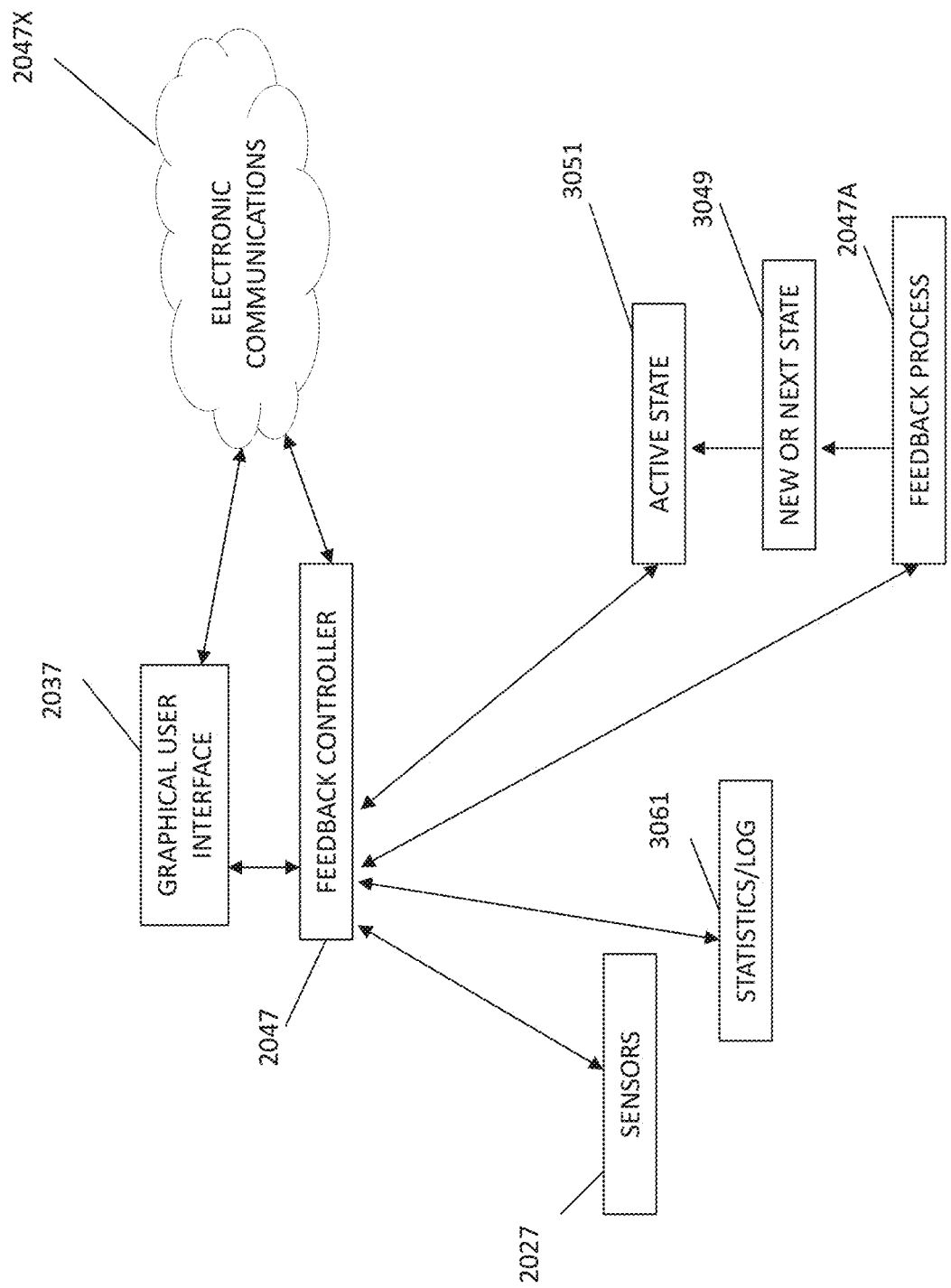
FIG. 1E is a schematic block diagram of the feedback controller of the present teachings.

Referring now to FIG. 1E, controller 519 can coordinate the activities of build subsystem 513A, maintenance subsystem 515, and growth media subsystem 517 so that together they can achieve the given biological material outcome. Controller 519 can include feedback controller 2047 that can control the flow of cells and fluid to and through biological material such as, for example, but not limited to, protein producing cells 535, and tissue 529. The cells and fluid flow through fluid pathways 2029 (FIG. 1A) and tissue pathways 2029A (FIG. 1A) to/from build subsystem 513A, growth media subsystem 517, and maintenance subsystem 515. Feedback controller 2047 can control the path and amount of fluid/tissue through system 500. Feedback controller 2047 can communicate with other parts of system 500 through, for example, but not limited to, an CANbus interface using a protocol such as, for example, but not limited to, the CAN protocol (referred to herein as CANbus interface), and can receive information about other parts of system 500 from, for example, sensors 2027. Sensors 2027 can include, but are not limited to including, temperature, pressure, conductivity, leak detection, air-in-line, and flow rate. Feedback controller 2047 can, for example, calibrate pressure sensors through messages routed over the CANbus interface, update pressure readings, and display flow diagram valve pressures. Feedback controller 2047 can execute step-by-step tissue creation according to, for example, but not limited to, feedback process 2047A, and in addition, feedback controller 2047 can accept override commands from, for example, but not limited to, graphical user interface (GUI) 2037.

Continuing to refer to FIG. 1E, feedback controller 2047 can communicate with, for example, but not limited to, sensors 2027, GUI 2037, and feedback process 2047A either directly or through electronic communications 2047X. Some configurations can include 2-way communications between feedback process 2047A and feedback controller 2047, as well as 2-way communications between GUI 2037 and feedback controller 2047. In some configurations, feedback controller 2047 can read and modify feedback process 2047A either statically or dynamically. Further, feedback controller 2047 can receive information from GUI 2037, such as, for example, recipe override information, and can supply information to GUI 2037 as the system proceeds through biological material creation processes. Some configurations can include 2-way communications between GUI 2037 and feedback process 2047A. In some configurations, GUI 2037 can read and modify feedback process 2047A when, for example, a step, precondition, pressure, port, flow rate, mode, and/or duration is entered into GUI 2037 that differs from feedback process 2047A. Some configurations can include 1-way communications between feedback process 2047A and feedback controller 2047 in which feedback controller 2047 can read, but not modify, feedback process 2047A. Some configurations can include 2-way communications among all of feedback process 2047A, GUI 2037, and feedback controller 2047. In some configurations, feedback controller 2047 can direct fluid flow based on both feedback process 2047A and GUI 2037 by receiving information from feedback process 2047A and/or GUI 2037, reconciling conflicting commands dynamically, opening/closing valves, and starting/stopping pumps based on the reconciled commands. In some configurations, feedback controller 2047 can dynamically update GUI 2037 while receiving commands from GUI 2037. In some configurations feedback process 2047A can be isolated from changes attempted through GUI 2037, and can be isolated from modifications attempted by feedback controller 2047.

Continuing to still further refer primarily to FIG. 1E, feedback controller 2047 can log data, for example pressure data. To maintain the size of log 3061, feedback controller 2047 can trim excessive old first elements off log 3061 while adding new data to the end of log 3061. Feedback controller 2047 can decide dynamically or statically which elements to trim. Feedback controller 2047 can also adjust the logging sample rate, for example, based on the amount of memory available. Errors, email information, valve status, pump configuration, pump status, control status, reservoir status, preconditions, recipe step status, priming status, GUI selections, logging status, solution status, override status, enclosure status, recipe load status, hardware status, and system state can be logged. Feedback controller 2047 can recognize states 3051/3049 that can guide execution of feedback process 2047A (FIG. 31A). Feedback controller 2047 can connect to hardware using, for example, a process that can include, but is not limited to including, if the CANbus interface is disconnected, feedback controller 2047 can connect the CANbus interface, start control of the system, and read the hardware configuration before a search for devices is initiated. Feedback controller 2047 can update hardware status by, for example, but not limited to, getting/showing the status of any of the pumps in the system. Feedback controller 2047 can also reset hardware. Feedback controller 2047 can initialize pause times and start time of feedback process 2047A. The steps of feedback process 2047A can each include a duration. In some configurations, starting and ending times of each step can be determined based on the start time of feedback process 2047A. Each step can have preconditions that can be checked and fulfilled before the step of feedback process 2047A is executed. If feedback process 2047A is restarted, or if another feedback process 2047A is loaded, feedback controller 2047 can perform housekeeping such as, for example, setting an appropriate active state 3051. To pause and resume feedback process 2047A, preconditions can be checked for next step 3049. Automatic changes of state 3049/3051 and other processing of states 3049/3051 can be blocked while in a paused state. Feedback controller 2047 can stop any of the devices in the system before proceeding to next step 3049 in feedback process 2047A, as a part of feedback process 2047A, as a part of an error condition, and as part of a manual override. Feedback controller 2047 can update the progress of each step of feedback process 2047A. Feedback controller 2047 can receive information from sensors 2027 that can update feedback process 2047A based on the current conditions sensed in system 500 (FIG. 1A). For example, if tissue 529 is found to need specific ingredients in growth medium 533, the specific ingredients may be introduced into system 500 until sensors 2027 determine that tissue 529 needs other different attention. Feedback process 2047A can begin with an initial "recipe" that can be continually updated based on the information received from, for example, but not limited to, sensors 2027 and GUI 2037.

Figure 2A:
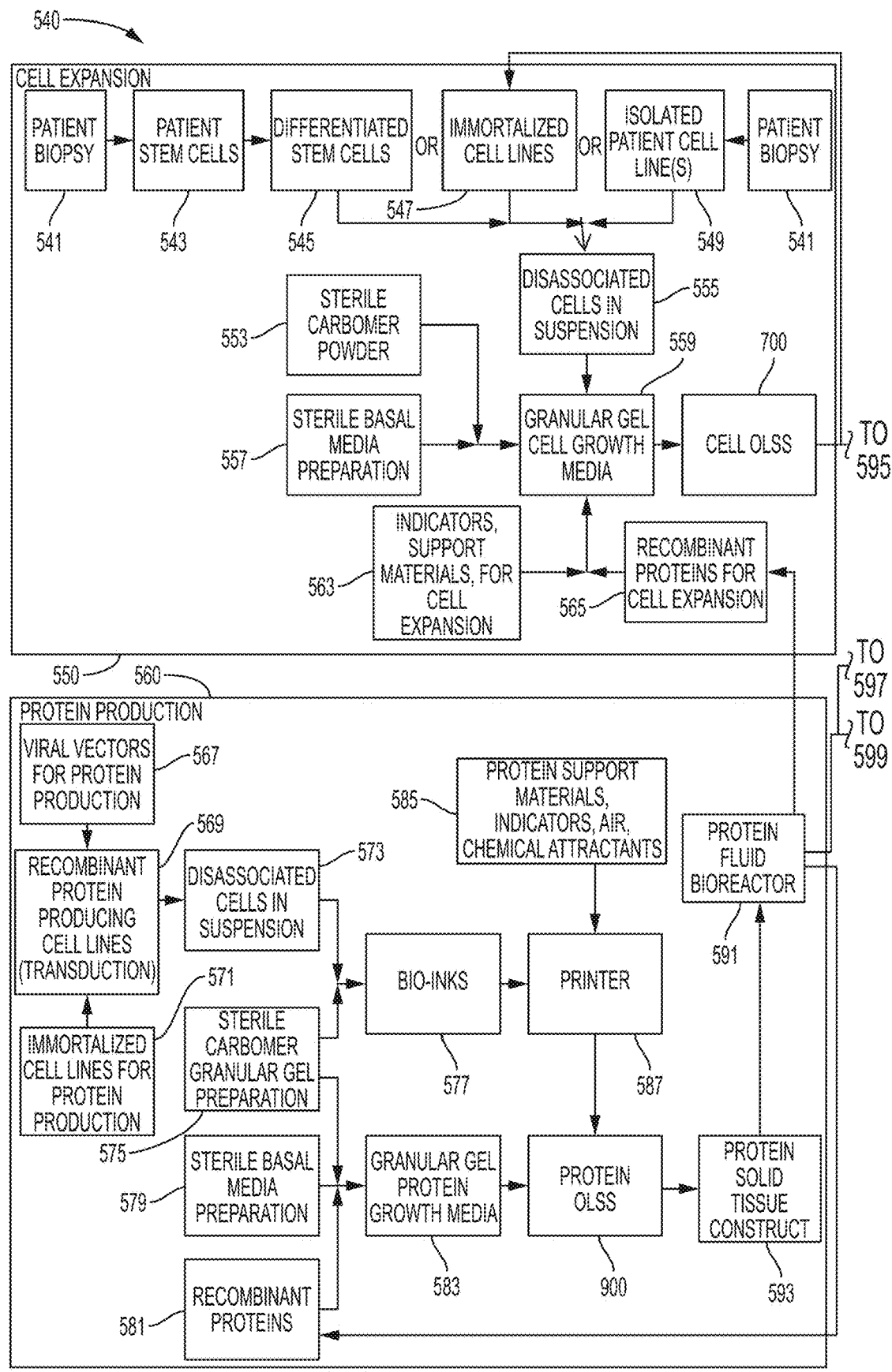
FIGS. 2A-2C are schematic block diagrams of an alternate configuration of the tissue engineering system of the present teachings.
Figure 2B:
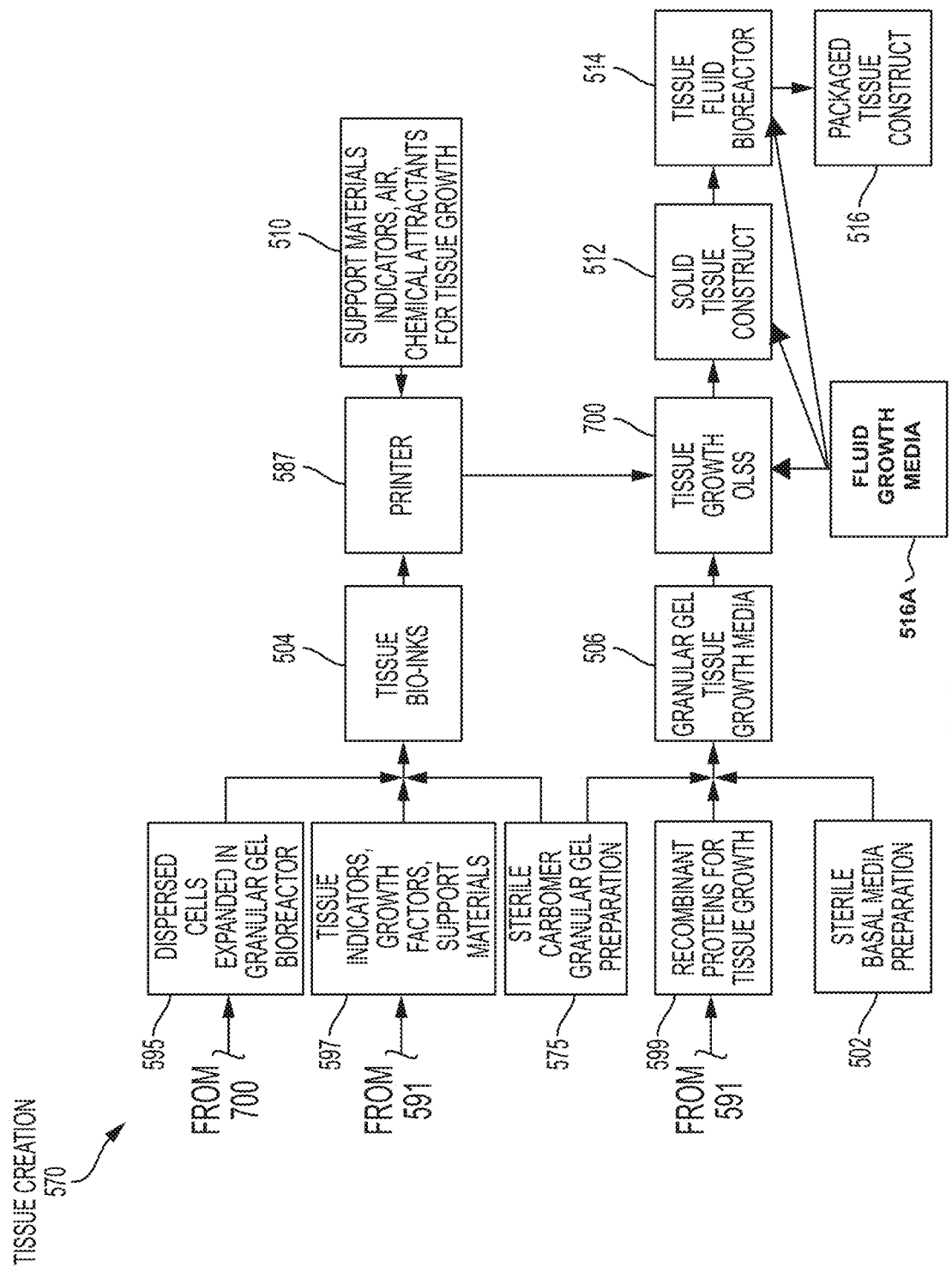

Referring now to FIGS. 2A and 2B, system 540 is an alternate configuration of system 500 (FIG. 1A). System 540 can produce and maintain protein producing cells 535 and tissue 529. System 540 can include cell expansion subsystem 550, protein production subsystem 560, and tissue creation subsystem 570. Cell expansion subsystem 550 can create cells that are specific for creating a certain type of tissue. There can be multiple configurations of cell expansion 550 each expanding a type of cell necessary for a specific tissue. Alternatively, there can be multiple types of cells resulting from one configuration of cell expansion subsystem 550. Cell expansion subsystem 550 can grow cells in a medium in three dimensions at high density. System 540 can include processes that can combine specific growth factors and media, diffuse media, and enable cell expansion. System 540 can include a process that can enable continued viability of cells before, during, and after cell expansion, and can enable removal of the gel by changing the ionic strength in system 540. System 540 can include photonic markers with the media. Cell expansion subsystem 550 can monitor the characteristics of cells in real time. To produce protein, disassociated cells in suspension 573 and sterile carbomer granular gel preparation 575 can combine to produce bio-ink 577 that can be printed, along with protein support materials 585 (along with, for example, but not limited to, indicators, air, and chemical attractants), by printer 587 into protein LSS 900 and incubated therein. Sterile carbomer granular gel preparation 575 can combine with sterile basal media preparation 579 and recombinant proteins 581 to produce granular gel protein growth media 583 which can be supplied to protein LSS 900 to maintain viability of the protein growing therein.

Figure 2C:
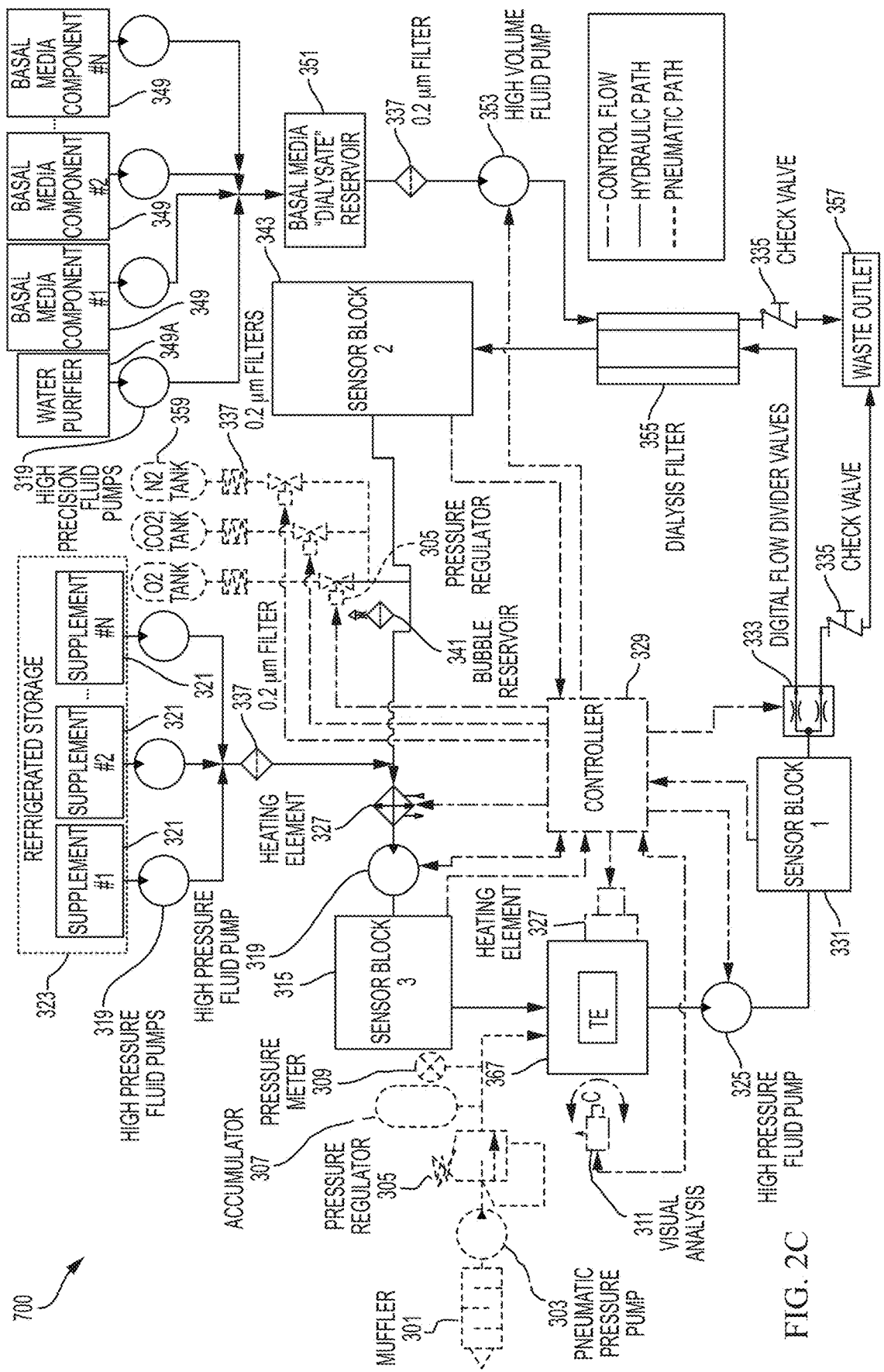
Figure 2D:
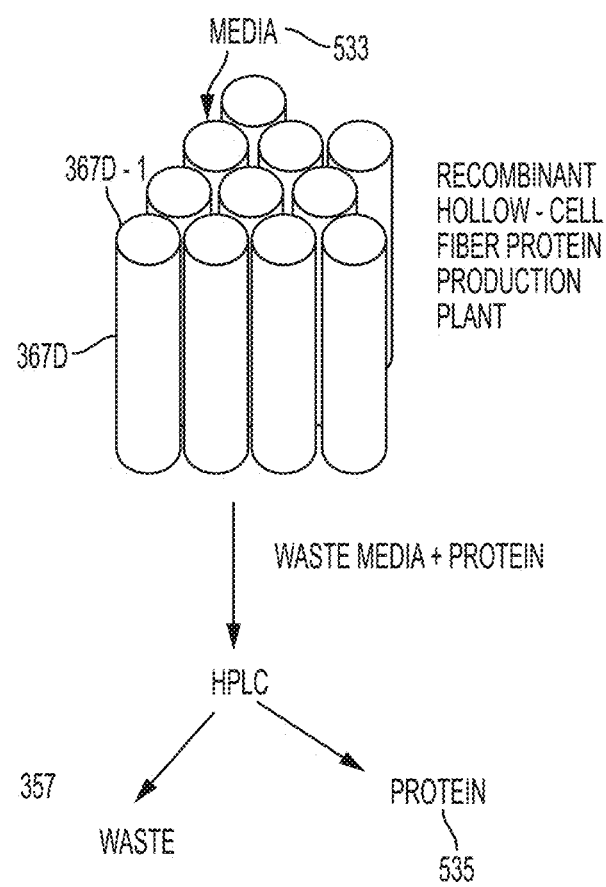
FIG. 2D is a pictorial representation of another alternate configuration of the tissue engineering system of the present teachings.

Referring now primarily to FIG. 2D, protein production subsystem 560 can produce protein producing cells 535 necessary for a particular cell expansion and for particular tissue growth, as well as to stock and distribute for use external to system 540. Protein production subsystem 560 can enable a batch-like process of protein production and/or a continuous process of protein production by, for example, washing medium through a hollow fiber-shaped bioreactor 367D. The walls of the hollow bioreactor and cells thereon can be continually replenished with growth media and be continuously monitored. Protein production system 560 can include a series of tubes that can form a hollow fiber system formed by the protein producing cells. Protein production system 560 can include mechanisms to detach cells from surfaces where they might have attached during growth, for example, but not limited to a centrifuge-like structure and specific enzymes, systems that can maintain characteristics of the cells such as, for example, but not limited to, the pH and the temperature. Visual analysis 311 (FIG. 2C) can include sorting cells using, for example, Raman spectroscopy, florescence-activated near infrared, and a cytometer. The kind of cell, its viability, identity, and purity can be determined and recorded. An organ life support system (OLSS) can include a granular gel bioreactor that can include a suspension of recombinant protein expressing cells. A fluid bioreactor can include plumbed, previously fabricated, recombinant protein expressing tissue construct. Selection of an OLSS or a fluid bioreactor can depend upon relative protein expression rates of suspended constructs versus tissue constructs for a given cell type and protein, and the application such as, for example, but not limited to, large organs, cancer screening, drug screening, small organs, cell expansion, and protein production. Physical construction of the bioreactor can depend upon the expected size of the contents during tissue growth. The bioreactor can include durable, possibly metal, parts, and/or disposable parts. Large organs can possibly require a relatively large durable bioreactor, for example, a bioreactor that can hold 10 liters of fluid and can measure 8 inches on a side. Drug screens can possibly require a relatively small disposable bioreactor, for example, a bioreactor that can hold 0.1 liter that can include a tube or ball of cells and can measure 10×10 cm, 0.1 cm thick. In some configurations, a vertically-oriented bioreactor can accommodate large organs, for example, and a horizontally-oriented bioreactor can accommodate small tissues, for example. Because the OLSS and the fluid bioreactor may be one and the same, they may be referred to herein collectively as a bioreactor.

Continuing to still further refer to FIGS. 2A and 2B, components of system 540 can be modular and can be specifically designed for an application. The bioreactor can include a cavity that can accommodate a few milliliters to thousands of liters of fluid, depending upon the application. The orientation, shape, filter material, number of filters, mesh, air/fluid pressure, dialysis recirculation, reusability, and desired flow rates can vary with the type and size of the bioreactor. Each bioreactor can include, but is not limited to including, at least one inlet for fluid (liquid and/or gaseous), at least one chamber for holding the granular gel media and imbedded cells or the previously fabricated tissue construct with plumbing for fluid flow or cells on a scaffold. The bioreactor can include at least one filter, for example, but not limited to, etched plastic or hydrogel, at least one support for holding the filter in place, at least one effluent chamber, and at least one outlet port. The number, size, construction, materials, and location of the filters in the bioreactor can be based upon the application and the desired density of cells, and can be determined based on metabolite usage, visual sensors, and impedance measurement, for example. Smaller horizontal flow bioreactors can include transparent components that can accommodate viewing of the interior of the bioreactor with, for example, at least one microscope. The bioreactor can include sterilizable materials and/or disposable materials.

Referring now to FIG. 2A, a protein production process enabled by protein production subsystem 560 can include selecting viral vectors 567 based on the desired protein. Multiple proteins can be produced simultaneously using cell lines that are physically separated until they are printed. The protein process can include transducing immortalized cell lines 571 with viral vectors 567 to produce recombinant protein producing cell lines 569, adding a disassociation reagent to produce disassociated cells in suspension 573, and applying a stress to mix protein producing cells 569 with granular gel 575 to produce bio-ink 577. The stress can be, for example, but not limited to, mechanical or sheer stress. The protein process can include mixing support material according to the desired protein and loading bio-ink 577 into printer 587. Mixing the support material can include mixing granular gel 575, basal media 579, and recombinant proteins 581 to produce growth media 583 specific for protein growth, and neutralizing growth media 583. The protein process can include printing bio-inks 577 into protein OLSS 900 where growth media 583 have been placed. Bio-inks 577 can be printed into any shape. The protein process can include providing a flow of, for example, nutrients through protein OLSS 900, and testing the outgoing effluent to determine how much protein is being produced. The protein process can include harvesting and purifying the protein, and maintaining the viability of the protein in solid tissue construct 593 in protein fluid bioreactor 591.

Continuing to refer to FIG. 2A, cell expansion subsystem 550 can include a cell process for cell expansion. The cell process can include adding a disassociation reagent to cell lines to form disassociated cells in suspension 555. Cells from patient biopsy 541, for example, can be sorted according to the desired tissue, or all the cells can be placed in cell growth media 559 that can be tailored to allow a specific type of cell to thrive. The cell process can include mixing sterile power 553 with basal media 557 and neutralizing the mixture to provide gel for cell growth media 559. The process can include mixing indicators 563, proteins for cell expansion 565, the gel, and disassociated cells in suspension 555 to form cell growth media 559. The process can include placing or printing the mixture into cell OLSS 700, growing the cells, and determining when to terminate the cell growth stage when a pre-selected number of cells has been reached. The process can include isolating the grown cells from the growth media, for example, by crashing the media. Crashing the media can include adding enough salt to change the balance of ions and disrupt the polymer chains of the gel. Cells can be harvested from the crashed media and can be resuspended in another medium, for example, for transport. The process can include removing some of the cells, thus allowing more space for cells to grow.

Referring now to FIG. 2B, a tissue growth process that can be associated with tissue creation subsystem 570 can include, but is not limited to including, mixing cells 595, indicators 597, and gel 575 to create tissue bio-inks 504. The tissue growth process can include selecting proteins based on the desired tissue, the stage of the cells, and the desired activity of the cells. Multiple proteins can be used to seed a single tissue growth OLSS 700; which protein is delivered at what time can be controlled. The mixture in tissue OLSS can be chemically optimized based on the desired tissue. The tissue growth process can include creating tissue growth media 506 based on gel 575, recombinant proteins for tissue growth 599, and basal media 502. Tissue grown media 506 can be prepared in a batch, and can be maintained in a pre-selected temperature range, for example, 37° C.±1° C. Recombinant proteins for tissue growth 599 can be added to the batch at a later time, for example, after neutralization. The tissue growth process can include loading growth media 506 into tissue growth OLSS 700 before printing begins, and printing tissue bio-inks 504 with printer 587, continually correcting the mixture based on information provided by sensors. Correction can be based on, for example, pH balance, oxygen level, and flow rate. The tissue growth process can include determining when the tissue is complete and optionally moving solid tissue construct 512 to tissue fluid bioreactor 514 to ripen the tissue and maintain its viability through use of fluid growth media 516A. If an organ is being grown, the tissue growth process is complete when automatically-determined tests indicate that the organ fulfills its function. Further, tissue that can be used to test treatment protocols can be grown, for example, tumors can be grown to test cancer treatment protocols.

Referring now to FIG. 2C, OLSS tissue generator system 700 can provide an environment that can create and maintain biological materials in, for example, but not limited to, a carbomer-like material. In general, various types of materials can be pumped into system 700, their status can be tested before entering OLSS 367, and the status of the products exiting OLSS 367 can be tested. The progress of the biological material within OLSS 367 can be monitored throughout the growth and maintenance cycles to correct any imbalances and to determine the status of the biological materials. System 700 can determine by these various tests when the biological material has reached its progress goals. In some configurations, the biological material can grow in an environment that can include a carbomer-based product. A family member of carbomer-based products can be chosen to include in the biological material environment based on variations in physical properties such as, for example, but not limited to, neutralized viscosities and pH ranges, that can provide characteristics needed for specific tissue outcomes. Sodium hydroxide can be used to neutralize the gel, or a neutral carbomer product can be used. In some configurations, the carbomer-based product can be combined with basal medium such as, for example, but not limited to, salts, amino acids, simple sugars, and buffers, and can be neutralized by sodium hydroxide to produce a gel. Basal medium can be required to maintain cell viability. An optimal ratio of basal medium to carbomer can allow the cells to remain in suspension in the gel. The biological material can be fed by pumping and/or vacuuming growth medium 533 (FIG. 1A) through gel, and by, for example, diffusion.

Continuing to refer to FIG. 2C, controller 329 can direct an agitation device (not shown) to agitate bioreactor 367 to enhance diffusion. Other methods of enhancing diffusion can be used. The order of adding materials can be adjusted to enhance diffusion/dispersion, and can be adjusted to avoid undesirable levels of cells stress. Waste products can be cleaned from bioreactor 367 according to, for example, but not limited to, the system described in U.S. patent application Ser. No. 14/732,571 entitled Medical Treatment System and Methods Using a Plurality of Fluid Lines, filed Jun. 5, 2015, incorporated by reference herein in its entirety. In some configurations, fluids can be pumped through bioreactor 367 from "top" to "bottom" of bioreactor 367, i.e. making use of the force of gravity to assist whatever pressure/vacuum is applied to force the fluids through the gel. In some configurations, if bioreactor 367 includes multiple faces, pressure can be applied to several of the faces of bioreactor 367 to regulate flow rate of the fluid through bioreactor 367. The shape of bioreactor 367 can depend upon, for example, but not limited to, the geometry of tissue 529 and the desired flow rate of fluids through bioreactor 367. With respect to the materials destined for OLSS 367, refrigerated storage 323 can prolong the life of at least one supplement 321 until needed in OLSS 367. In some configurations, controller 329 can continually monitor state of, for example, but not limited to, the contents of OLSS 367, effluent, dialyzed media, inlet media, inline pressure, valve states, pump states, regulator states, detector output, and heating elements at the highest feasible accuracy and sampling rate. In some configurations, controller 329 can adjust pumps, valves, regulators, and heating elements to maintain homeostasis or fractionate sample. In some configurations, controller 329 can perform logging during the protein production and purification process. In some configurations, controller 329 can log media formulations and lot numbers and tie the media formulations and lot numbers to specific products and/or batches. In some configurations, controller 329 can enable in-process and post-process analysis for integration of quality by design (QbD) and process analytical technologies (PAT). In some configurations, controller 329 can activate high pressure fluid pumps 319 that can pump at least one supplement 323 according to a recipe chosen based on the desired tissue outcome.

Continuing to refer to FIG. 2C, high pressure fluid pumps 319 can include, but are not limited to including, peristaltic pumps such as, for example, those described in U.S. patent application Ser. No. 14/853,300 entitled Apparatus and Method for Infusing Fluid Through a Tube by Appropriately Heating the Tube, filed on Sep. 14, 2015, ('300), incorporated by reference herein in its entirety. High pressure fluid pumps 319 can include an air sensor, flow estimation, and under-fill detection. Diluent 349A and at least one basal media component 349 are pumped, using high precision fluid pumps 319, into basal media reservoir 351, the contents of which can be pumped, using high volume fluid pump 353, into dialysis filter 355 to assist in the process of cleansing the output from OLSS 367, some of which can result in waste bound for waste outlet 357. In some configurations, dialysis can be optional, for example, in drug screen configurations. Diluent 349A can be purified as needed by, for example, but not limited to, a purification system that can include reverse osmosis and bactericidal ultraviolet lamp technologies, such as, but not limited to, a Milli-Q® Integral system or any system that can supply highly-purified water meeting pre-defined conductivity and resistivity goals. Diluent 349A can be supplied in storage tanks. Basal media 349 can include, but are not limited to including, inorganic salts and pH buffers. Inorganic salts can include, but are not limited to including, sodium ion, potassium ion, calcium ion, magnesium sulfate, and sodium dihydrogen phosphate monohydrate. pH buffers can include, but are not limited to including, organic zwitterionic buffering agents and sodium bicarbonate. High precision fluid pump 319 can include pumps such as, for example, those described in '300, depending on volume and precision needs. In some configurations, high volume fluid pump 353 can include about ½ inch inner diameter tubing rotating peristaltic pump. In some configurations, accumulator 307 can provide a pneumatic reservoir for fluid overflow that can withstand at least approximately 40 psi, and can include, but is not limited to including, a Parker #AD016B25T9A1 diaphragm accumulator.

Continuing to refer to FIG. 2C, pneumatic pressure pump 303 can fill and drain accumulator 307 based on the readings of pressure regulator 305 and pressure meter 309. Pneumatic pressure pump 303 can include an air pump than can include a tank and a regulator, for example, but not limited to, a Parker PTS2 diaphragm pump, or any kind of air pump that can provide the pressure necessary to propel fluids through the gel in OLSS 367. Pressure can be controlled by air and/or pressure pump 303. In some configurations, pressure meter 309 can include an Ashcroft PPT-2, for example. The pneumatic reservoir can accommodate at least one liter in volume. Pressure regulator 305 can include, but is not limited to including, a volume booster, field reversibility, low air consumption, a relatively wide supply pressure range, and a relatively low supply pressure sensitivity, for example an Omega IP211/EP211, described in U.S. patent application Ser. No. 14/967,093 entitled Modular Valve Apparatus and System, filed Dec. 11, 2015, incorporated by reference herein in its entirety. Fluid pumps can include, but are not limited to including, those described in U.S. patent application Ser. No. 14/627,287 entitled Syringe Pump Having a Pressure Sensor Assembly, filed on Feb. 20, 2015, incorporated by reference herein in its entirety.

Continuing to refer to FIG. 2C, filters 337 can include, but are not limited to including, polydisc aqueous solution in-line filters that can have WHATMAN® filters that can include polyethersulfone membranes with low protein binding and that can be free of surfactants. Filters 337 can include radiation sterilization and a pre-filter that can remove heavy particles. Filters 337 can include GE Healthcare Life Sciences 6724-5002 air filters. In some configurations, filters 337 can include a 0.2 μm pore size. In some configurations, if fluid is sterilely maintained, filters 337 may not be necessary. Muffler 301 can be used to reduce the audible footprint of OLSS tissue generator 700. Muffler 301 can include, but is not limited to including, flame resistance and 35-42 dB noise reduction, for example, McMaster-Carr #1629T11. In some configurations, OLSS 367 can include at least one membrane filter that can include, but is not limited to including, 0.65-1.2 micron pore size, approximately 90 mm diameter, and maximum pore density. The membrane filter can include, but is not limited to including, STERLITECH® filter PES089025.

Figure 3A:
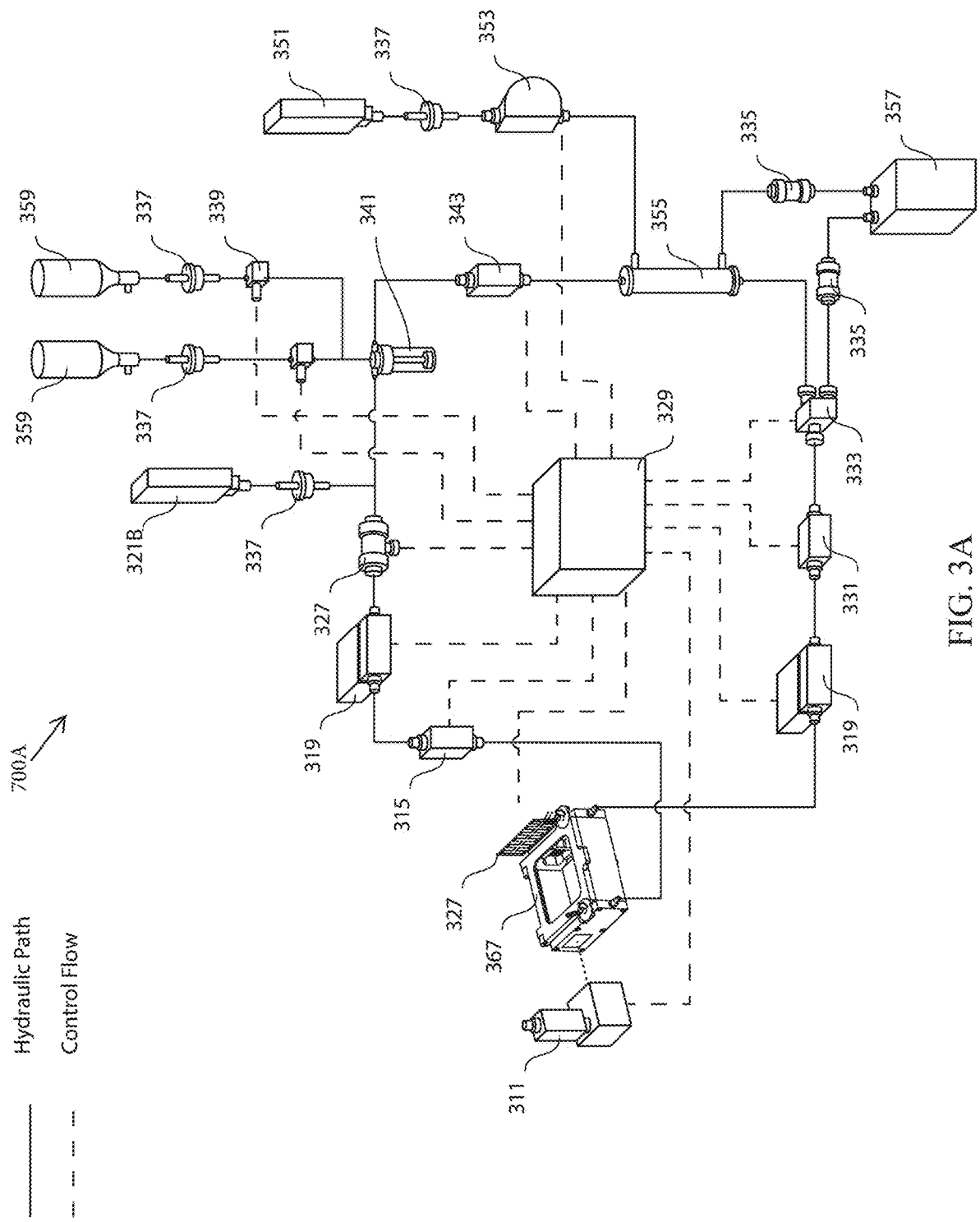
FIGS. 3A and 3B are schematic block diagrams of the assay bioreactor of the present teachings.
Figure 3B:
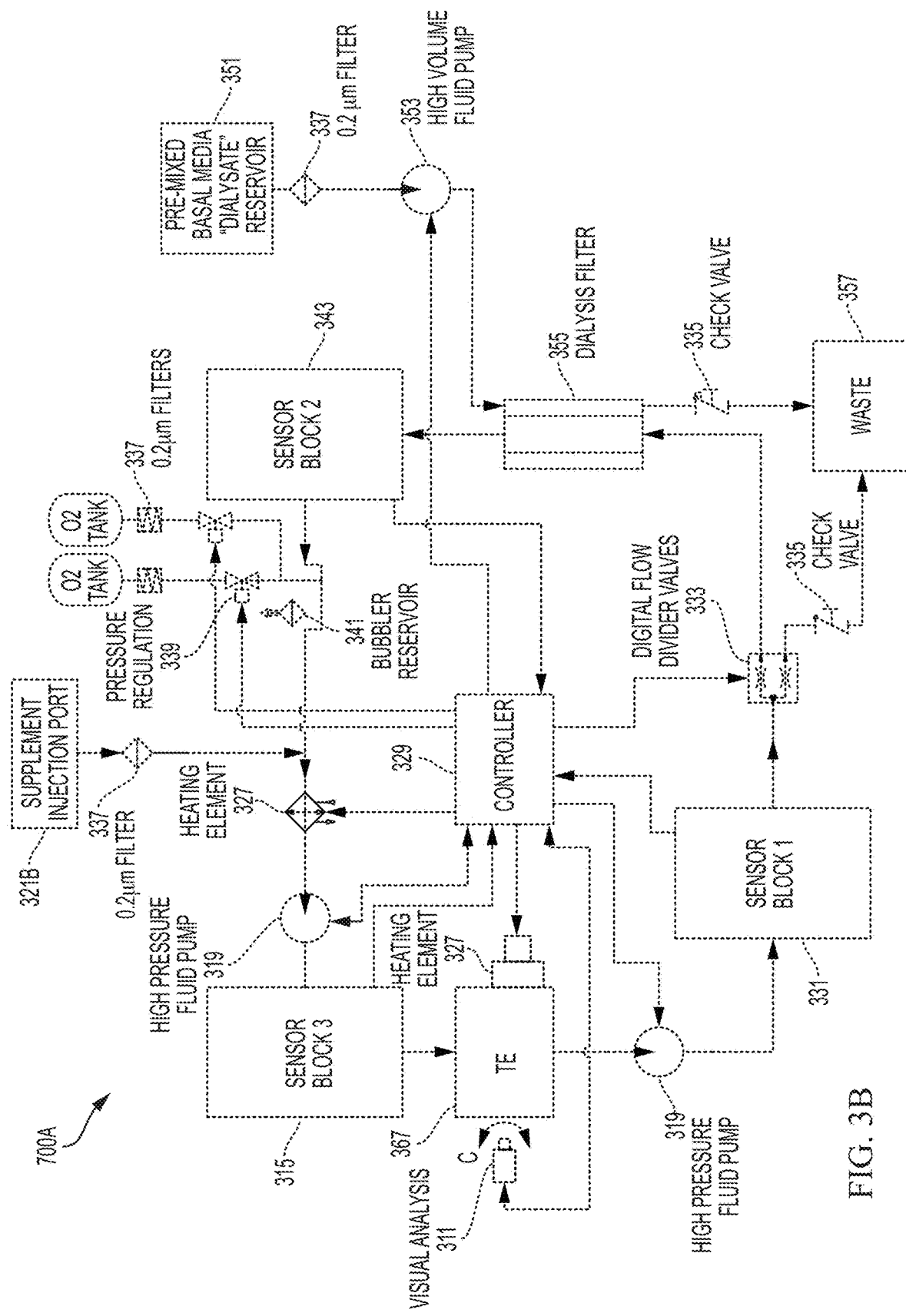

Referring now to primarily FIGS. 3A and 3B, tissue fluid bioreactor 514 (FIG. 2B) can include, but is not limited to including, assay bioreactor system 700A. Assay bioreactor system 700A can accommodate the creation of small arrays of tissue that can be exposed to drugs and then disposed of. Assay bioreactor system 700A can be used to produce any type of cell, and controller 329 can continually test and control the quality of the cells. Assay bioreactor 700A can provide an environment that can create and maintain biological materials in, for example, but not limited to, a carbomer-like material. In general, various types of materials can be pumped into system 700A, their status can be tested before entering OLSS 367, and the status of the products exiting OLSS 367 can be tested. The progress of the biological material within OLSS 367 can be monitored throughout the growth and maintenance cycles to correct any imbalances and to determine the status of the biological materials. System 700A can determine by these various tests when the biological material has reached its progress goals. In some configurations, the biological material can grow in an environment that can include a carbomer-based product. A family member of carbomer-based products can be chosen to include in the biological material environment based on variations in physical properties such as, for example, but not limited to, neutralized viscosities and pH ranges, that can provide characteristics needed for specific tissue outcomes. Basal medium can be required to maintain cell viability.

Continuing to refer to FIGS. 3A and 3B, controller 329 can control the adding of materials through injection port 321B and filter 337, for example, but not limited to, a 0.2 μm filter. Waste products can be cleaned from bioreactor 367. In some configurations, controller 329 can continually monitor state of, for example, but not limited to, the contents of OLSS 367, effluent, dialyzed media, inlet media, and other characteristics of system 700A. In some configurations, controller 329 can adjust pumps 319/353, valves 335, regulators 305, flow dividers 333, visual analysis 311, and heating elements 327 to maintain homeostasis or fractionate sample. In some configurations, controller 329 can perform logging during the protein production and purification process. In some configurations, controller 329 can log media formulations and lot numbers and tie the media formulations and lot numbers to specific products and/or batches. In some configurations, controller 329 can enable in-process and post-process analysis for integration of quality by design (QbD) and process analytical technologies (PAT). In some configurations, controller 329 can activate high pressure fluid pumps 319 that can pump fluid through system 700A.

Continuing to refer to FIGS. 3A and 3B, pre-mixed basal media dialysate 351 can be pumped, using high volume fluid pump 353, into dialysate reservoir 351, the contents of which can be pumped, using high volume fluid pump 353, into dialysis filter 355 to assist in the process of cleansing the output from OLSS 367, some of which can result in waste bound for waste outlet 357. In some configurations, dialysis can be optional, for example, in drug screen configurations. Basal media 349 can include, but are not limited to including, inorganic salts and pH buffers. Inorganic salts can include, but are not limited to including, sodium ion, potassium ion, calcium ion, magnesium sulfate, and sodium dihydrogen phosphate monohydrate. pH buffers can include, but are not limited to including, organic zwitterionic buffering agents and sodium bicarbonate. Pressure can be controlled by controller 329. In some configurations, filters 337 can include a 0.2 μm pore size. In some configurations, if fluid is sterilely maintained, filters 337 may not be necessary. Fluid passing through sensor block 331 can travel to waste reservoir 357 or dialysis filter 355, depending upon the contents of the fluid. Flow divider valve 333 makes the bifurcation of the fluid flow possible.

Figure 4A:
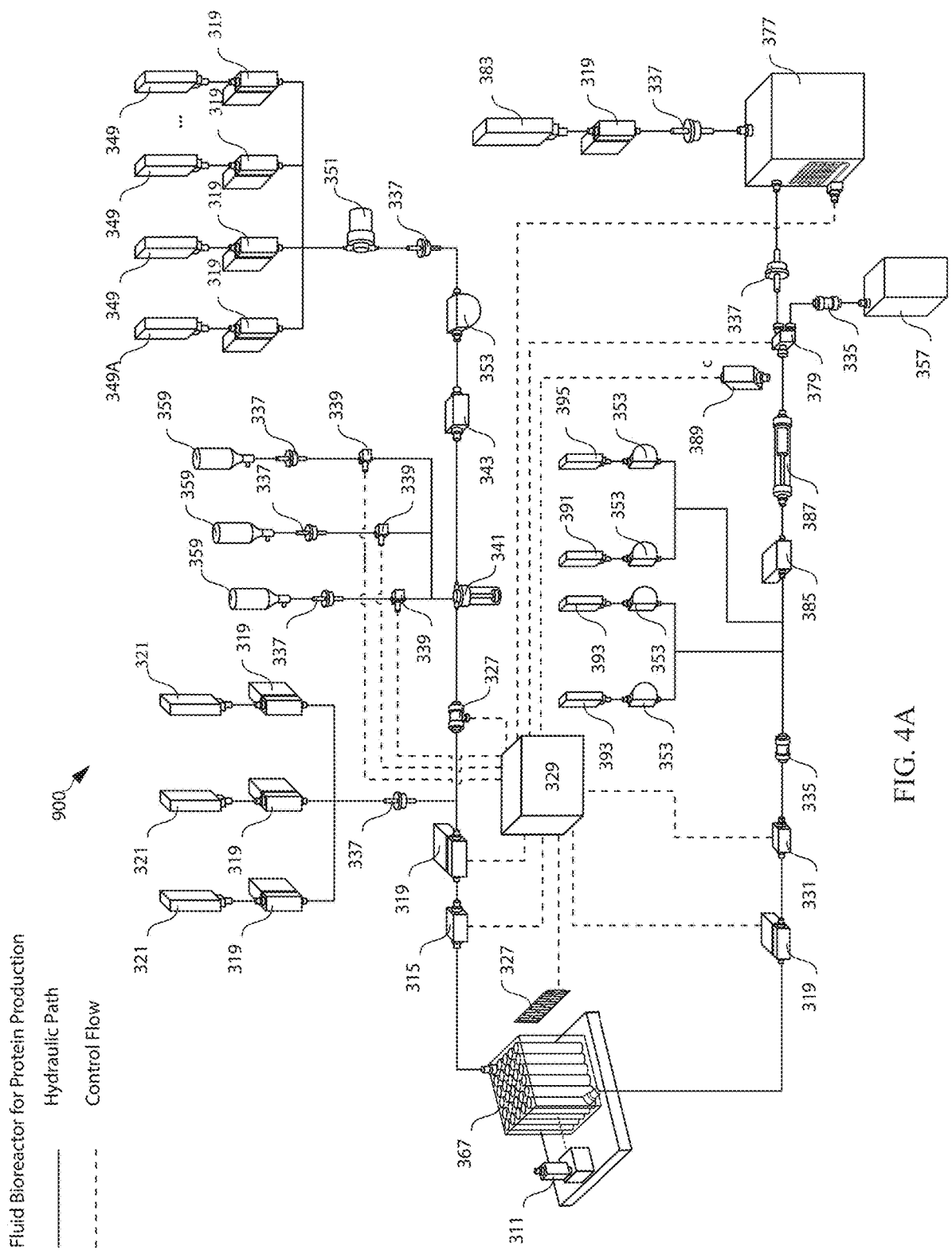
FIGS. 4A and 4B are schematic block diagrams of the protein bioreactor of the present teachings.
Figure 4B:
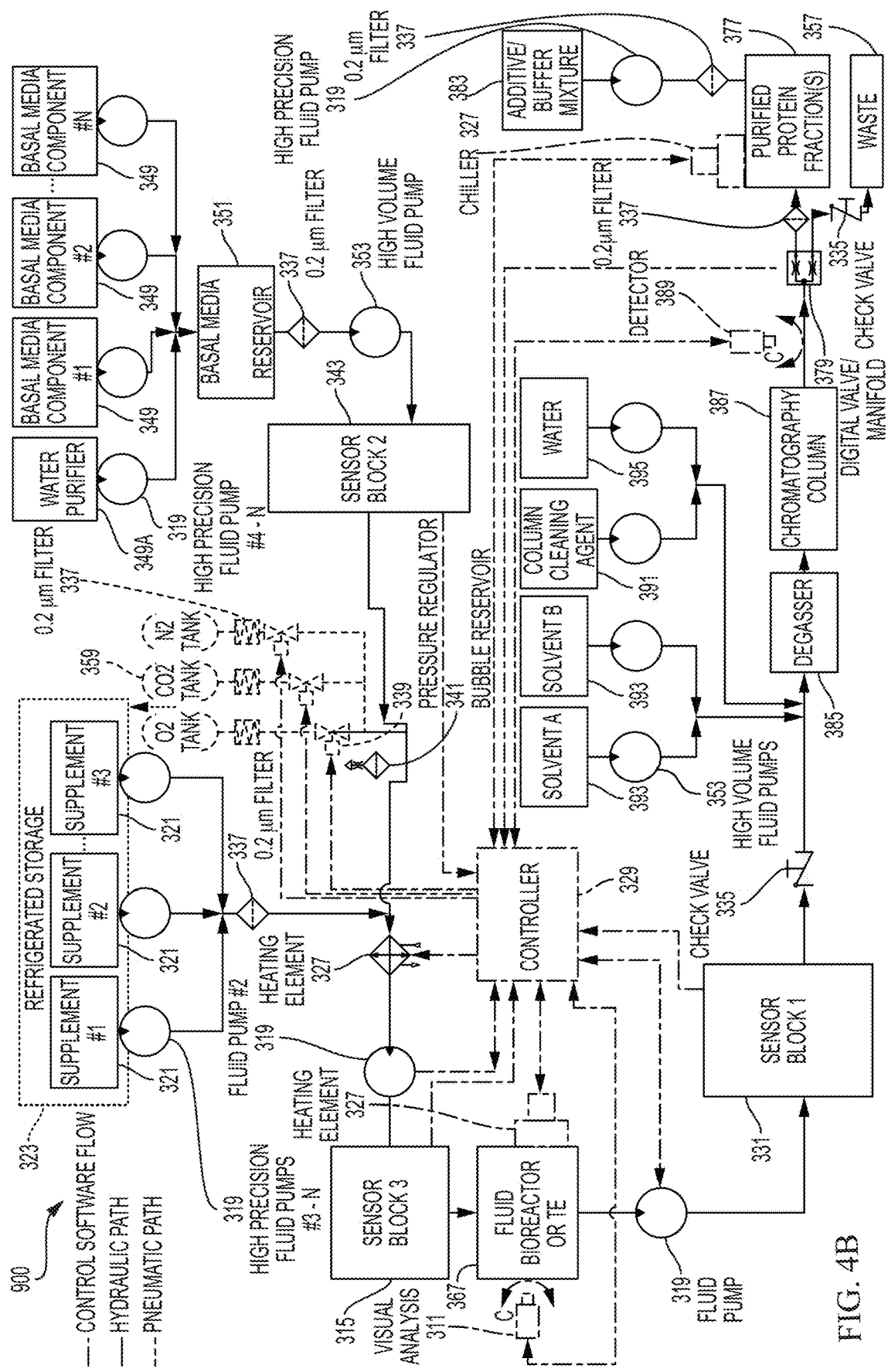
Figure 5B:
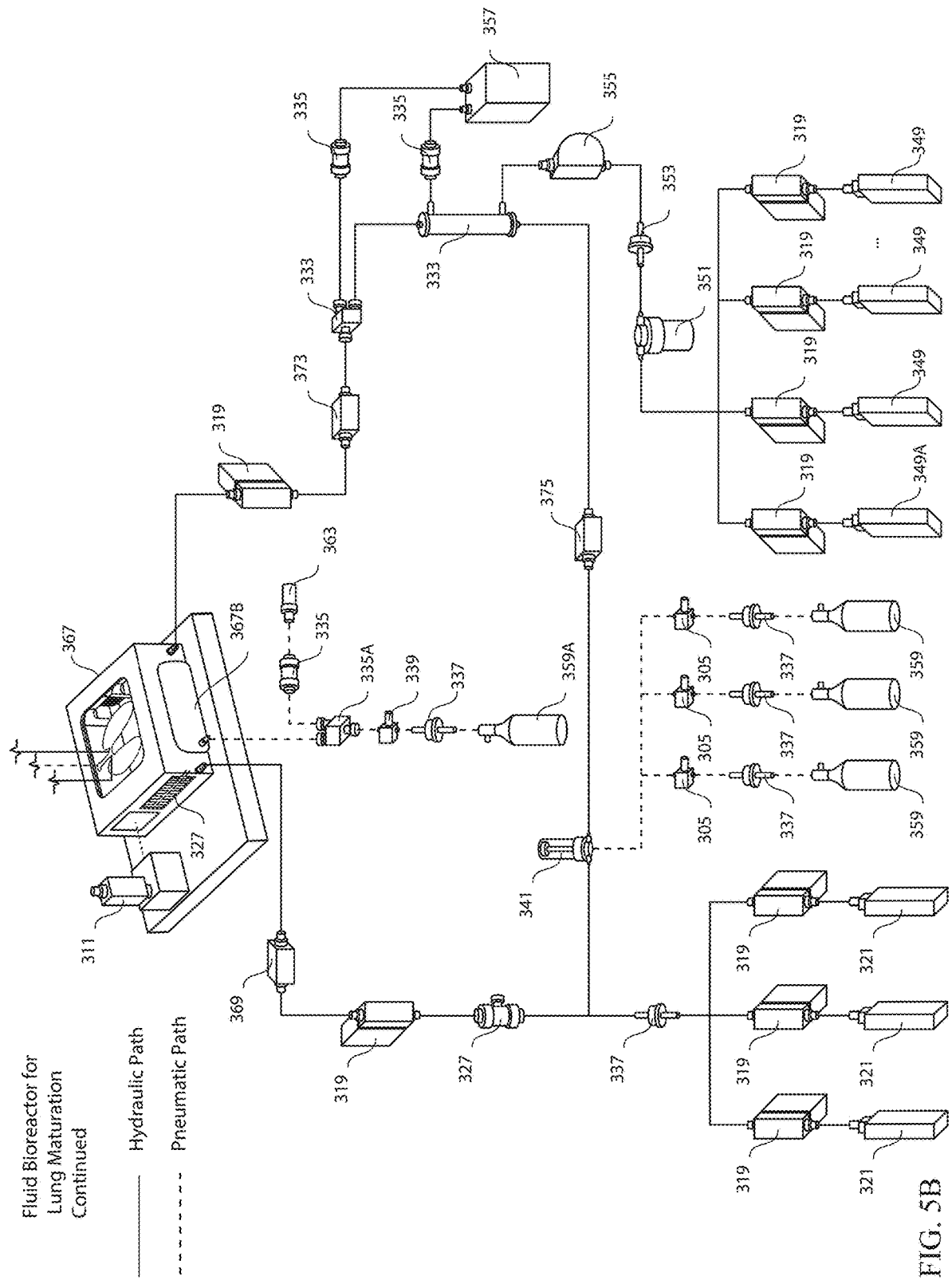
Figure 5C:
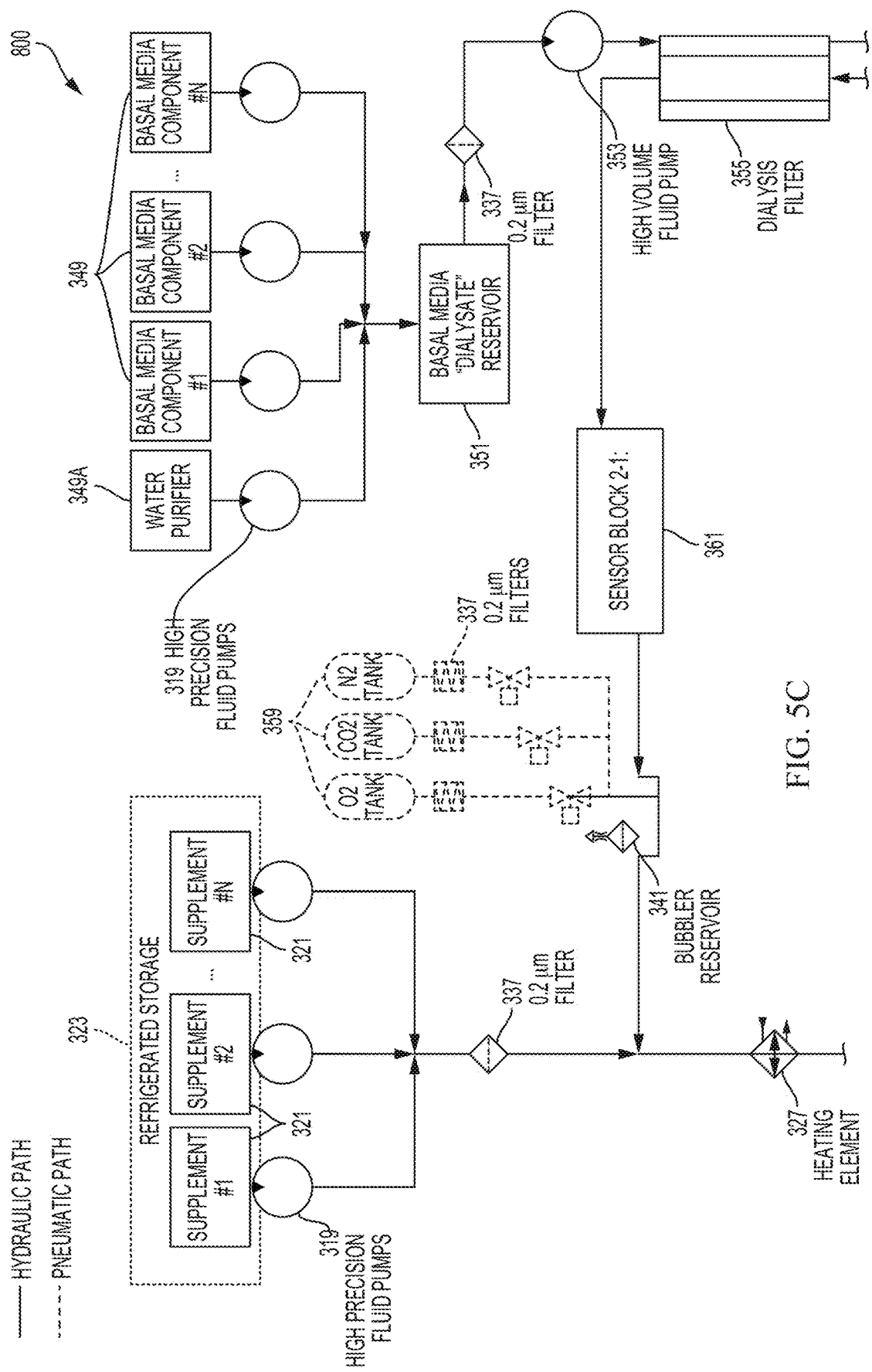
Figure 5D:
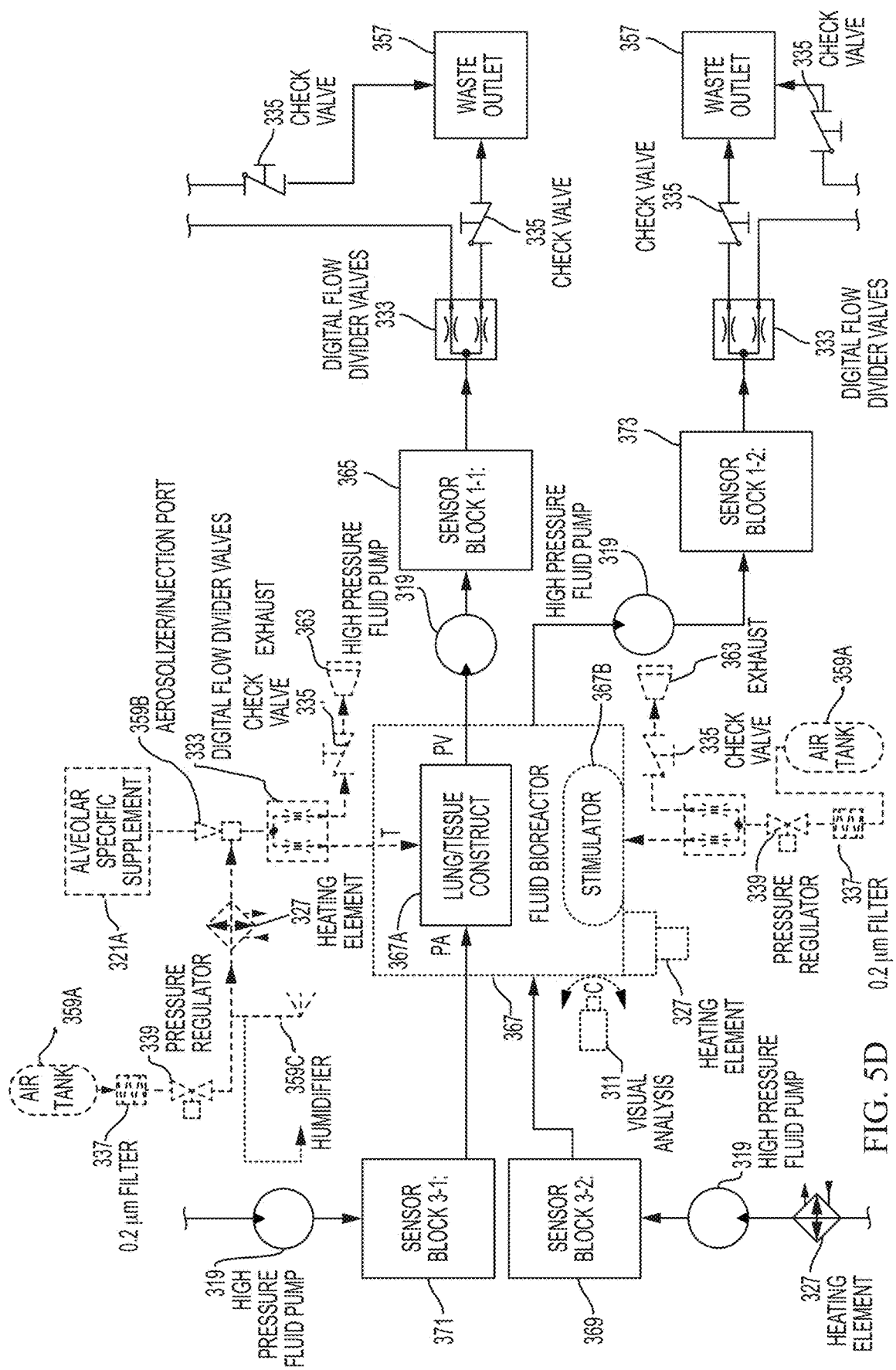
Figure 5E:
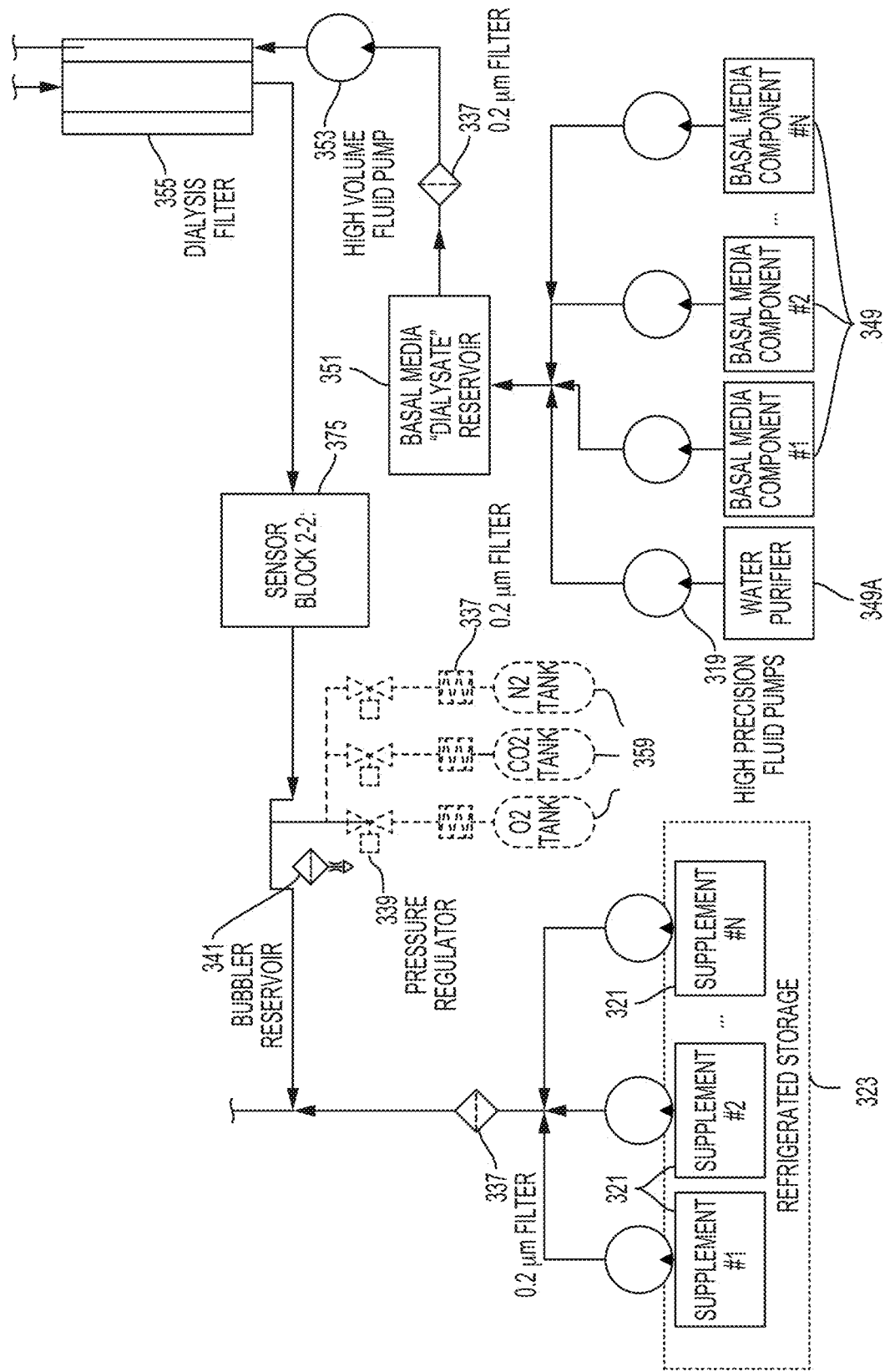

Referring now to primarily FIGS. 4A and 4B, tissue fluid bioreactor 514 (FIG. 2B) can include, but is not limited to including, protein production bioreactor system 900. Controller 329 in protein production bioreactor 900 can coordinate the delivery of supplements 321 through high precision fluid pumps 319, heating elements 327, and sensor block 315 to bioreactor 367. Temperature controls such as, for example, heating/chilling elements 327 can include, but are not limited to including, electric-resistive elements and in-line temperature control elements that can control temperature to, for example, approximately 37°±1° C. to maintain warmth and ~4°±2° C. to maintain protein stability. Sensor blocks 315 can include modular, in-line devices that may not contact the fluid path directly. Sensor blocks 315 can include, but are not limited to including, relatively high accuracy, real-time, sterilizable devices. Controller 329 can coordinate the delivery of diluent 349A and basal media 349 through high precision fluid pumps 319 to basal media reservoir 351. Sensor block 331 can include, but is not limited to including, at least one temperature sensor, at least one in-line pressure sensor, at least one carbon dioxide pressure sensor, at least one membrane protein pH sensor. The number and content of basal media 349 and supplements 321 can be a function of the desired of purified protein fractions 377. Contents of basal media reservoir 351 can proceed through high volume fluid pump 353 to sensor block 343 where the characteristics of the contents of basal media reservoir 351 are provided to controller 329. Sensor block 343 can include, but is not limited to including, at least one lactate sensor, at least one glucose sensor, at least one glutamine sensor, at least one glutamate sensor, at least one sodium ion sensor, at least one potassium ion sensor, at least one calcium ion sensor, at least one osmolarity sensor, and at least one protein concentration sensor. Controller 329 can coordinate, through pressure regulator 339, which, if any, air products 359 can be used to aerate using a bubbler such as, for example, but not limited to, Micro Sparger BBI-43530005, in bubbler reservoir 341, the contents of basal media reservoir 351. In some configurations, bubbles can be removed from air products 359. Air products 359 can be filtered by, for example, but not limited to, a McMaster-Carr 9841K93 air filter. Air products 359 can include, but are not limited to including, oxygen ($O_2$), carbon dioxide ($CO_2$), and nitrogen ($N_2$). Oxygen can enable cellular metabolism, carbon dioxide can control pH levels, and nitrogen can displace oxygen and carbon dioxide. Any combination of air products 359 can be used in system 900, depending upon the application. In some configurations, air products 359 can include medical grade and oil-free oxygen and carbon dioxide. In some configurations, ambient air can be used in place of separate air products 359. The aerated reservoir contents can be combined with supplements 321, temperature controlled by heating element 327, and pumped, by fluid pump 325, through sensor block 315 into bioreactor 367.

Continuing to refer to FIGS. 4A and 4B, protein production bioreactor 900 can include at least one visual analysis device 311 that can monitor the progress of protein production in bioreactor 367. Visual analysis device 311 can include, but is not limited to including, a device that can perform Raman spectroscopy. The information from, for example, but not limited to, at least one visual analysis device 311 and temperature controls 327 is analyzed by controller 329 to determine cell viability, cell differentiation, extracellular matrix production, tissue cohesiveness, and print location status. Spontaneous emissions caused by cellular activity in which low counts of photons can be emitted can occur in all frequency ranges of the optical spectrum. Spontaneous emissions can occur at low energy levels so that detection can require a photomultiplier and/or a noise detector for example, in the infrared range. Ultraviolet emissions can indicate DNA activity, and since there are few naturally-occurring ultraviolet emissions, the signal to noise ratio can increase in the presence of DNA activity. The biological material can be energized, and sensors can detect the radiation emitted after the material is energized, in particular, sensors can detect the decay of photons after, for example, the biological material has been illuminated with, for example a device that does not damage the biological materials. Infrared emission and specific emission/absorption spectra can indicate various kinds of activity in the bioreactor. In some configurations, optical tags such as, for example, photons, optical sensors, and fiber optics, can be included in the bio-ink and can be printed in the bioreactor along with the biological material. The photons can be used in tomographic studies of the biological material. In some configurations, the biological material can be surrounded with quantum dots and/or dyes that can be activated through exposure to certain frequencies, for example, an RF frequency. Raman spectroscopy can be used within the biological material through tunnel penetration, and can be printed to surround the biological material. Particles, such as, for example, but not limited to, Smarticles® particles, printed in the bioreactor can be used to detect live activity and to eliminate contaminants. Doppler techniques can be used to provide flow field information within growth media 533 (FIG. 2D).

Continuing to refer to FIGS. 4A and 4B, from this detected and gathered information it can be possible to determine when the protein production process has completed. At that time, controller 329 pumps, through fluid pump 319 and sensor block 331, the contents of bioreactor 367 through processing to isolate the desired of purified protein fractions 377. Sensor block 331 can include, but is not limited to including, at least one temperature sensor, at least one in-line pressure sensor, at least one oxygen pressure sensor, at least one carbon dioxide pressure sensor, at least one lactate sensor, at least one membrane protein pH sensor, at least one glucose sensor, at least one glutamine sensor, at least one glutamate sensor, at least one sodium ion sensor, at least one potassium ion sensor, at least one calcium ion sensor, at least one osmolarity sensor, and at least one protein concentration sensor. Sensor block 331 can detect flow, and can measure the normal range of waste production. High change can be attributed to bacterial growth. Viability can be directly measured by measuring metabolism, which can be indirectly measured both within the biological material and in the environment.

Continuing to refer to FIGS. 4A and 4B, the process can include mixing into the fluid stream that includes the contents of bioreactor 367, for example, but not limited to, at least one solvent 393, and/or column clean agent 391, and/or diluent 395. Solvents can include, but are not limited to including, protein-dependent materials that can detach protein from chromatography column 387. Column cleaning agent 391 can include a protein-dependent, column-dependent chemical that can remove the residue from chromatography column 387. Diluent 395 can include, but is not limited to including, sterile water. Removal of the residue can make chromatography column 387 reusable. The mixture can flow through degasser 385 into chromatography column 387 and then past detector 389/digital valve manifold 379 that can sort purified protein fractions 377 from waste 357. Degasser 385 can include, but is not limited to including, devices like those described in U.S. patent application Ser. No. 14/723,237 entitled Control Systems and Methods for Blood or Fluid Handling Medical Devices, filed on May 27, 2105, ('237), incorporated by reference herein in its entirety. Chromatography column 387 can be selected based on the volume of media to be purified and the physical properties of the desired biological material. Types of possible chromatography columns 387 can include, but are not limited to including, size exclusion, reversed phase (hydrophobic), ionic, and affinity, for example, but not limited to, ligands, metal, antibody pairs. Detector 389 can include, but is not limited to including, ultraviolet, visual, photo diode array, refractive index, evaporative light scattering, mass spectrometer, multi-angle light-scattering, conductivity, fluorescence, chemiluminescence, optical rotation, and electrochemical or other sensor designed to differentiate between the protein of interest and other waste materials. Additive buffer mixture 383 can be pumped, by high precision fluid pump 319, into purified protein fractions 377 that can be temperature controlled by chiller 327. Flow can be restricted to one direction in many of the fluid paths by check valves 335, and many of the fluid paths can include filters. Bioreactor 367 can accommodate a gel medium. High precision fluid pumps 319, high volume fluid pumps 353, and fluid pumps 325 can accommodate pumping at a force that maintains the viability of the cells. Chromatography can be replaced with mass spectroscopy, depending upon the desired protein. Weight, a series of ridges, and/or a centrifuge can be used to sort out proteins.

Referring now to FIGS. 5A-5E, tissue fluid bioreactor 514 (FIG. 7B) can include, but is not limited to including, lung bioreactor system 800. Lung bioreactor system 800 can provide a version of tissue fluid bioreactor 514 (FIG. 2B) that can accommodate the maintenance a lung can require to remain viable. Lung bioreactor system 800 can include, but is not limited to including, fluid paths to supply specific fluids to, for example, the pulmonary vein, pulmonary artery, and trachea of the lung tissue grown in tissue growth OLSS 700 (FIG. 2C). In some configurations, a first set of supplements 321 and media/diluent 349/349A can enter lung/tissue construct 367A through sensor block 3-1 371 and the pulmonary artery, and a second set of supplements 321 and media/diluent 349/349A can enter bioreactor 367 through sensor block 3-2 369. Air 359 can be included in the mix supplied to bioreactor 367, and can include, for example, a controlled mix of oxygen, carbon dioxide, and nitrogen, that can be passed through bubbler 341 to, for example, control the pH and metabolic processes of the cells. In some configurations, bioreactor 367 can be constructed of titanium or other non-reactive metal, or a plastic that can be injection molded. Bioreactor 367 can include filters such as, for example, but not limited to, DVPP, PVDF, RTPP, polycarbonate, and other etched, hydrophilic plastic. In some configurations, the range of the pore size can be 0.65 μm to 1.2 μm. A vacuum or suction can be created in bioreactor 367 to draw nutrients through and remove waste.

Continuing to refer to FIGS. 5A-5E, mirror-imaged components such as, for example, sensor block 1-1 365 and sensor block 1-2 373 can provide equivalent functionality to the mirrored components described herein throughout system 800. Sensor block 3-1 371 and sensor block 3-2 369 can monitor the contents and flow rates of supplements 321 as they enter fluid bioreactor 367. Lung bioreactor 800 can include stimulation 367B in fluid bioreactor 367 that can mimic diaphragm/lung interaction. Lung bioreactor 800 can maintain the viability of a grown lung through continued use of quality by design techniques including constant monitoring of the health of the lung and closed loop control. Supplements 321 can include, but are not limited to including, metabolites, vitamins, growth factors, other signaling factors, potential solutes, surfactants, and potential Additives/Buffers. Metabolites can include, but are not limited to including, glucose, dextrose, pyruvate, fatty acids, amino acids, organic acids, lipoproteins, and I-inositol. Vitamins can include, but are not limited to including, biotin, choline chloride, D-calcium pantothenate, folic acid, nicotinamide, pyridoxal hydrochloride, riboflavin, and thiamine hydrochloride. Growth factors can include, but are not limited to including, HGH, FGF, ECGF, VEGF, and insulin. Signaling factors can include, but are not limited to including, MST1, MST2, YAP, TAZ, HAS, A1AT, Transferrin, T3, and T4. Surfactants can include, but are not limited to including, Pluronic F-127. Potential additives/buffers can include, but are not limited to including, protease inhibitors, cryoprotectants such as, for example, glycerol, anti-microbial agents, metal chelators, reducing agents, and stabilizing agents.

Continuing to refer to FIGS. 5A-5E, sensor block 2-1 361 and sensor block 2-2 375 can monitor the dialysis process through dialysis filter 355. Dialysis filter 355 can include GE healthcare life sciences 6724-5002, for example, can filter molecules smaller than 1 kDa, and can maintain molecules larger than ~5 kDa. In some configurations, high volume fluid pumps 353 can pump at a flow rate of ~0.1-91/min. Sensor block 1-1 365 and sensor block 1-2 373 can monitor the output of fluid bioreactor 367 that can be compared to the common metrics in sensor block 2-1 361/sensor block 3-1 371 and sensor block 2-2 375/sensor block 3-2 369 to determine how to adjust the dialysis system/dialysate formulation. Sensor block 1-1 365 and sensor block 1-2 373 can provide information sufficient to activate flow divider valves 333, separating waste from recycled output from bioreactor 367. The recycled output can be combined with additional nutrients and provided to dialysis filter 355, and ultimately back to bioreactor 367. The sensor blocks can sense, for example, but not limited to, glucose, photon detection, temperature, in-line pressure, partial pressures of oxygen and carbon dioxide, conductivity, pH, lactose, ammonium, glutamine, glutamate, sodium, potassium, calcium, osmolarity, protein concentration, sensor failures, electrical failures, communication failures, raman spectroscopy, visual fields, autofluorescence, dyes, optical tracks, x-ray diffraction, tomography, and proteins/excreted factors. Air to the trachea can be adjusted by, for example, but not limited to, heating element 327, humidifier 359C, and pressure regulator 339, and specific supplements can be dispensed by, for example, but not limited to, alveolar specific supplement dispenser 321A through aerosolizer/injection port 359B. Dialysis materials can be pumped into basal media reservoir 351 by high precision fluid pumps 319, and pumped into dialysis filter 355 by high volume fluid pumps 353. Dialysis materials can include, but are not limited to including, diluent 349A and various basal media components 349. Lung bioreactor system 800 can include filters 337 at various points in the flow, for example, between supplements 321 and bioreactor 367. The fluid pressure range can be approximately −11 psi to 14 psi, and may be outside of this range depending upon filters 337. The pressure can be varied, or a constant pressure can be maintained to maintain a desired flow rate. The flow rate can naturally change over time as the number of cells changes. Stimulator 367B can be managed by a combination of air supply 359A and pressure regulator 339. To maintain the appropriate pressure to activate stimulator 367B, check valve 335 can release any excess gas through exhaust 363. Materials that can maintain the viability of a lung can include materials that process through the lung and materials that form the medium surrounding the lung. The interaction with the lung and these materials produces recyclable materials and waste products, both of which are handled by the dialysis and waste processes in lung bioreactor system 800.

Continuing to refer to FIGS. 5A-5E, in some configurations, between around 5 and 40 different cell types can be used in tissue creation. Cells can be continually mixed into the gel/medium combination, and supplements can be added in, to prepare for printing. Managing cell loss and cell differentiation can require that printing occur as the bio-inks become ready. In some configurations, gel-touching components of the system, for example, the bioreactor and the printer, can be coated with, for example, a hydrophobic coating, to manage gel adhesion to the bioreactor and therefore cell loss due to gel adhesion. In some configurations, a rotor system that is designed to reduce cell damage can be used to mix the cells into the gel/medium/supplement combination. Bio-inks can include, but are not limited to including, various cell types, growth factors, media, specialized bio-ink media, supplements, surfactants, optionally other biological support material, for example, but not limited to, collagen, fibronectin, laminin, fibrin, and vitronectin. Bio-inks can be limited to, for example, growth media that can feed cells and tissues that have been previously printed. In some configurations, attractants can be included in the feeding bio-ink to motivate cell growth in a particular direction. In some configurations, creating a specific tissue geometry can include injecting air into a group of cells. In some configurations, hydrogel, oil, optical paths, conductive paths, and inductive heating/chilling can be printed into the environment of the cells at specific locations. For example, inductive heating/chilling can maintain, at a cellular level, the temperature of the cells at about 37° C. In some configurations, oxygen can be mixed with basal medium to encourage cell growth. In some configurations, a layer of bio-ink can be printed, then fluids including growth media can flow through the bioreactor, then another layer of bio-ink can be printed. In some configurations, bio-ink printing and fluid transfer in the bioreactor can happen simultaneously. In some configurations, a vacuum can be used to maintain fluid flow. In some configurations, a vacuum/pressure combination can be used to maintain fluid flow. In some configurations, pressure can be applied in one area of the bioreactor and a vacuum can be drawn in another area of the bioreactor. For example, pressure can be applied to the printing surface while a vacuum can be drawn along the surface opposite the printing surface. Any kind of printer can be used including, but not limited to, extrusion, ink jet, and laser.

Continuing to still further refer to FIGS. 5A-5E, the amount of time it takes to print cells and other tiny materials can be reduced by simultaneously printing of parts of the tissue, for example, in sheets, and placing the sheets in the bioreactor, in the proper order, as they are completed. Photolithography can be used to print high precision structures, for example, on a permeable membrane. Arrays of print tools, such as needles, can be used to print the bio-ink. The arrays can include any number of print tools, for example, 100,000. A controller (not shown) can manage the selective activation of the nozzles to print any desired shape. In some configurations, printing of a lung can include, but is not limited to including, printing the vasculature, printing the support cells, printing the alveoli, printing the pneumatic tubing, and printing the outer shell of the lung. Delicate control and angular movement of the print heads can be advantageous to printing the lung. In some configurations, as some of the layers are printed, the gel can be selectively crashed to achieve a specific geometry. Support materials can include, but are not limited to including, fugitive inks such as, for example, but not limited to, bio-inks that transition from a rigid structure to another form when the temperature of the structure is changed rapidly. Support materials can include spacers that can force empty regions in the tissue. Grown tissues can be physically transferred from a growth bioreactor to a fluid bioreactor, or the growth bioreactor and the fluid bioreactor can be one and the same. An external change of pressure can be used to simulate lung action when the desired biological material is a lung. The flow rate of fluid through the system can be controlled to control the interstitial air in the tissue. An air pathway in the tissue can be used to add additional treatments to the tissue. The health of the tissue can be monitored by monitoring gas transfer. Any tissue can be grown in bioreactor 367, including, but not limited to, liver, heart, kidney, nerves, and pancreas. The lung process discussed herein refers to an exemplary organ, the process described herein for which can be used to grow other tissues.

Figure 6A:
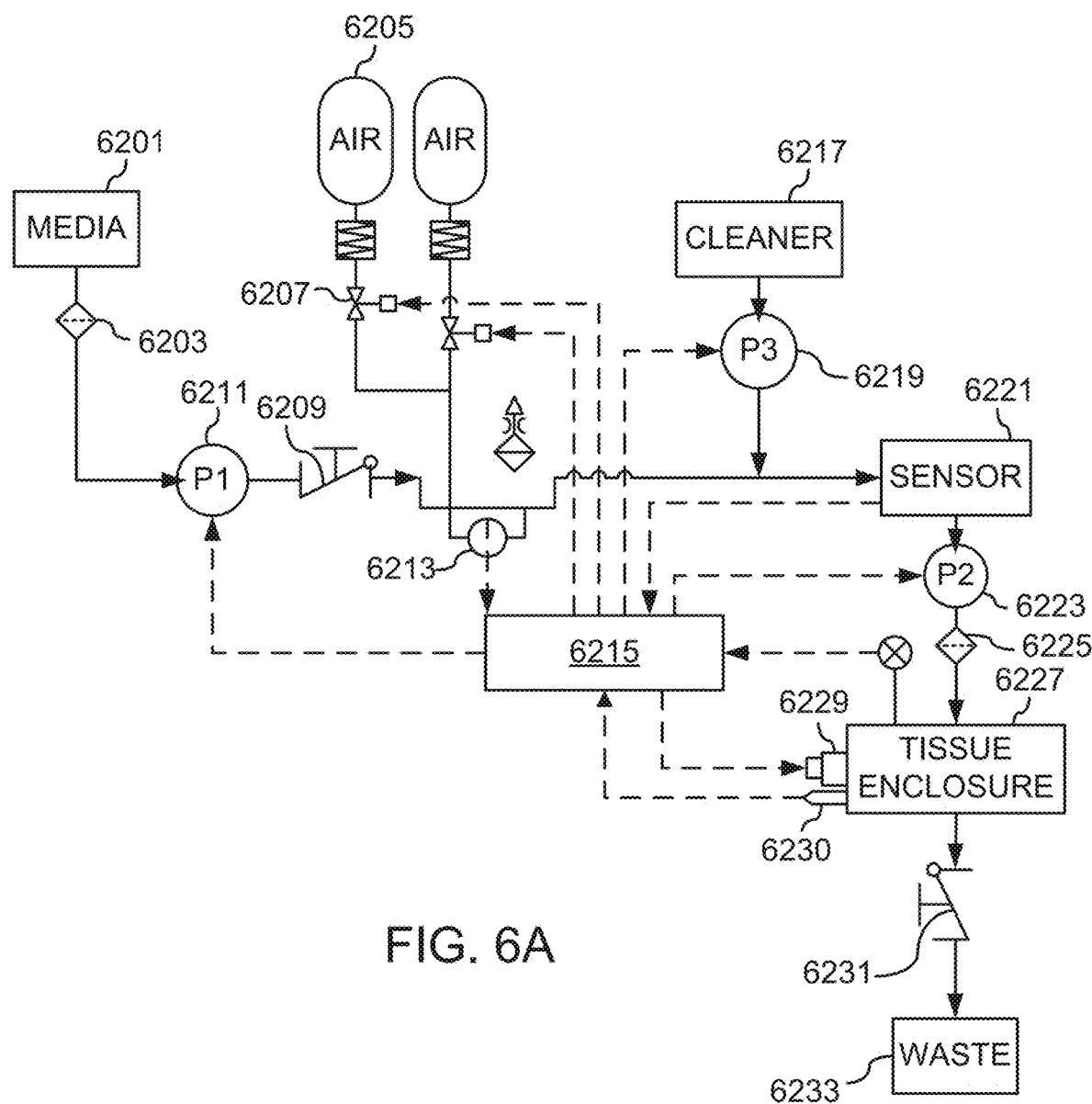
FIG. 6A is a schematic block diagram of an exemplary system for growing tissue of the present teachings.

Referring now to FIG. 6A, an exemplary system for growing tissue can include controls 6215 that can enable fluid pump #1 6211 to pump pre-mixed growth media 6201 through filter 6203 and into a fluid stream when check valve 6209 is open. Controls 6215 can enable valves 6207 (carbon dioxide and/or oxygen valves) to admit air 6205 (carbon dioxide and/or oxygen, for example) into the fluid stream, through fluid level sensor 6213 and oxygen/carbon dioxide/pH sensor 6221. Controls 6215 can direct fluid pump 6223 to draw the fluid stream through sensor 6221 and pressure gauge 6225 into tissue enclosure 6227 that can include the tissue that is being grown. Controls 6215 can monitor tissue enclosure 6227 by processing data from resistance temperature detector 6230 and pressure gauge 6225, both associated with tissue enclosure 6227. Controls 6215 can adjust the temperature of tissue enclosure 6227 by controlling heater bank 6229. As the fluid stream including air and growth media passes through tissue enclosure 6227, wastes can be removed and can flow to waste tank 6233 when check valve 6231 is properly positioned. Controls 6215 can control the pH of the tissue in tissue enclosure 6227 by directing syringe pump 6219 to draw sodium hydroxide 6217 into a fluid stream and through tissue enclosure 6227 as described herein.

Figure 6B:
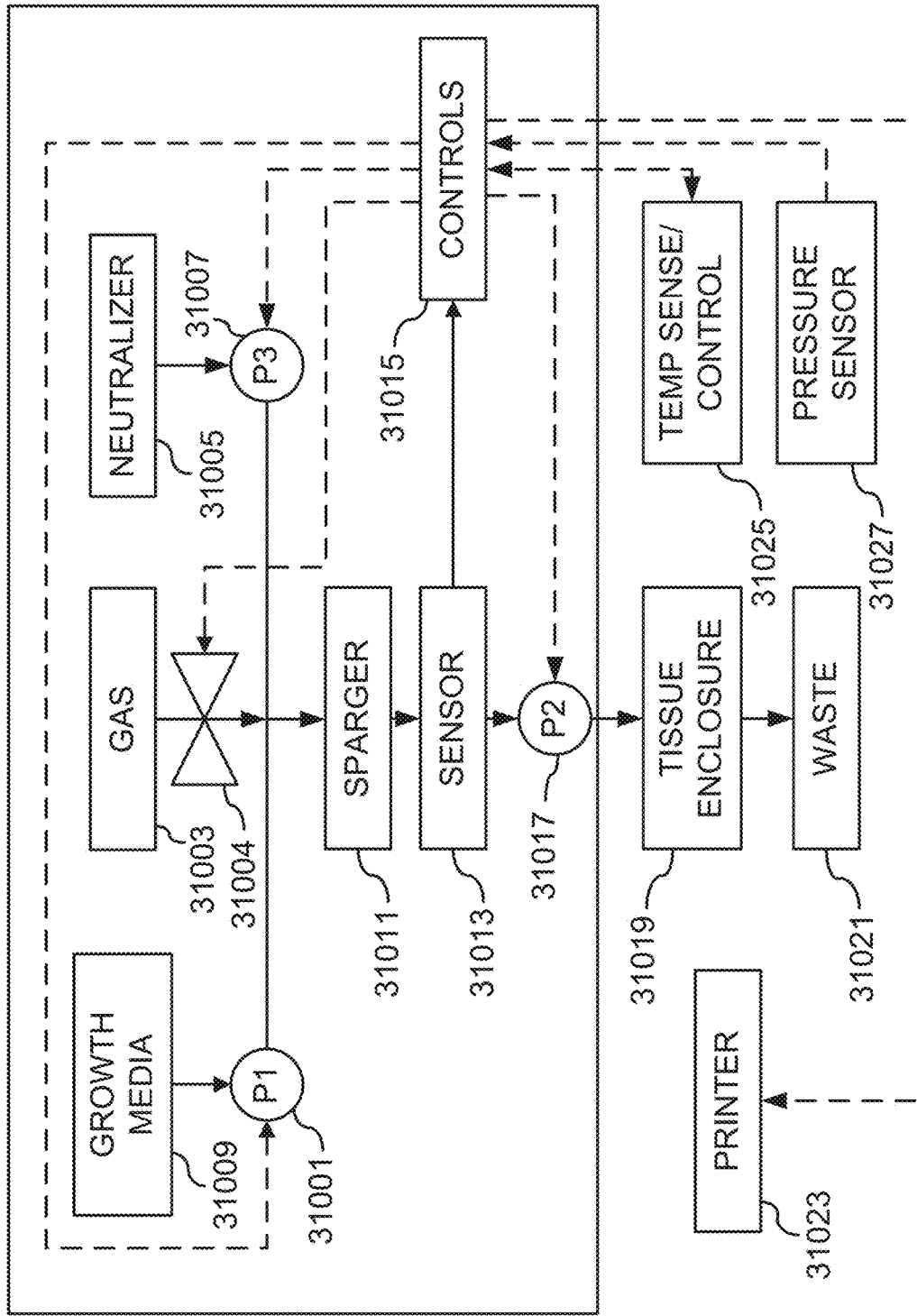
FIG. 6B is a schematic block diagram of another exemplary system for growing tissue of the present teachings.
Figure 6C:
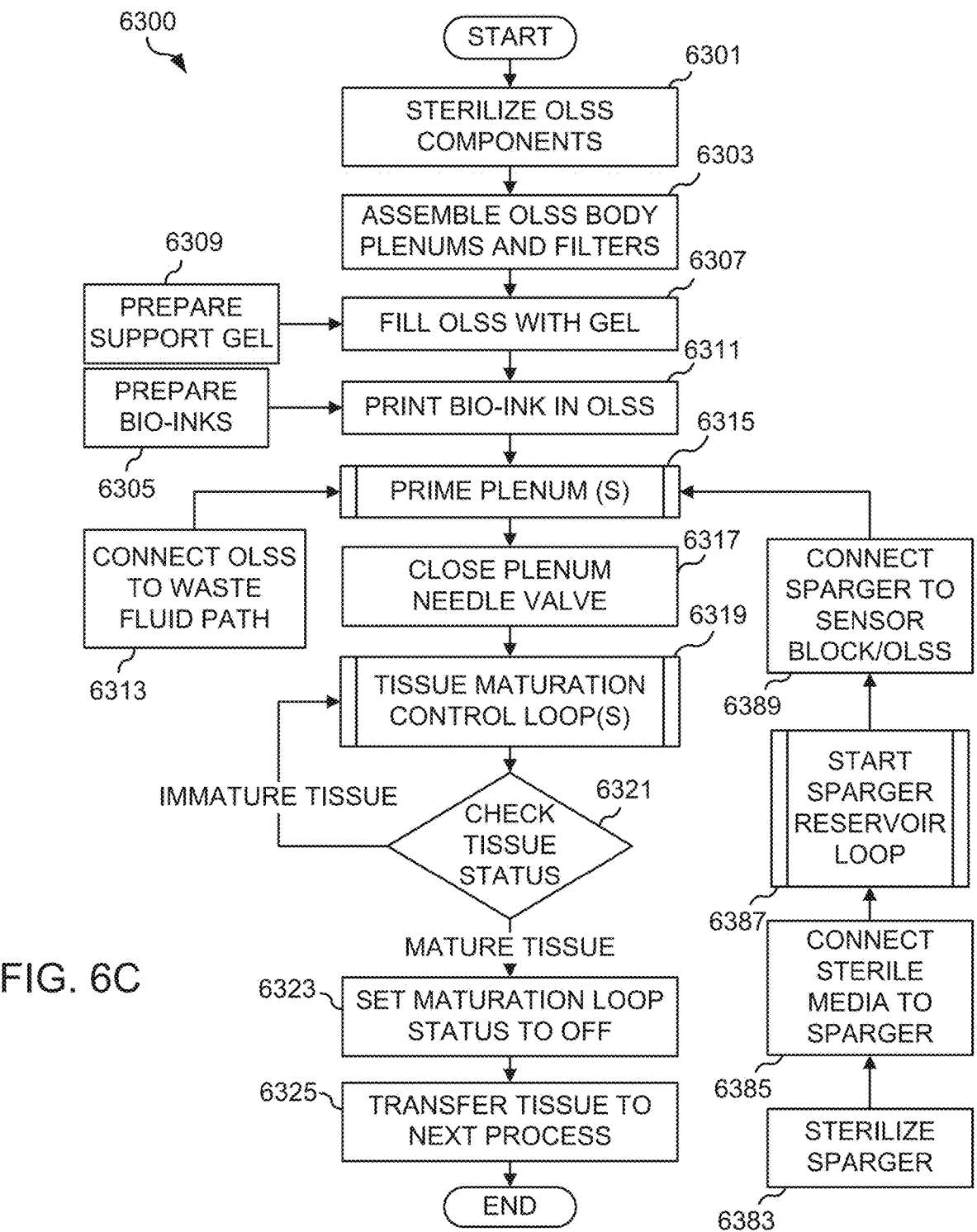
FIGS. 6C-6E are flowcharts of a method of the present teachings for growing tissue.
Figure 6D:
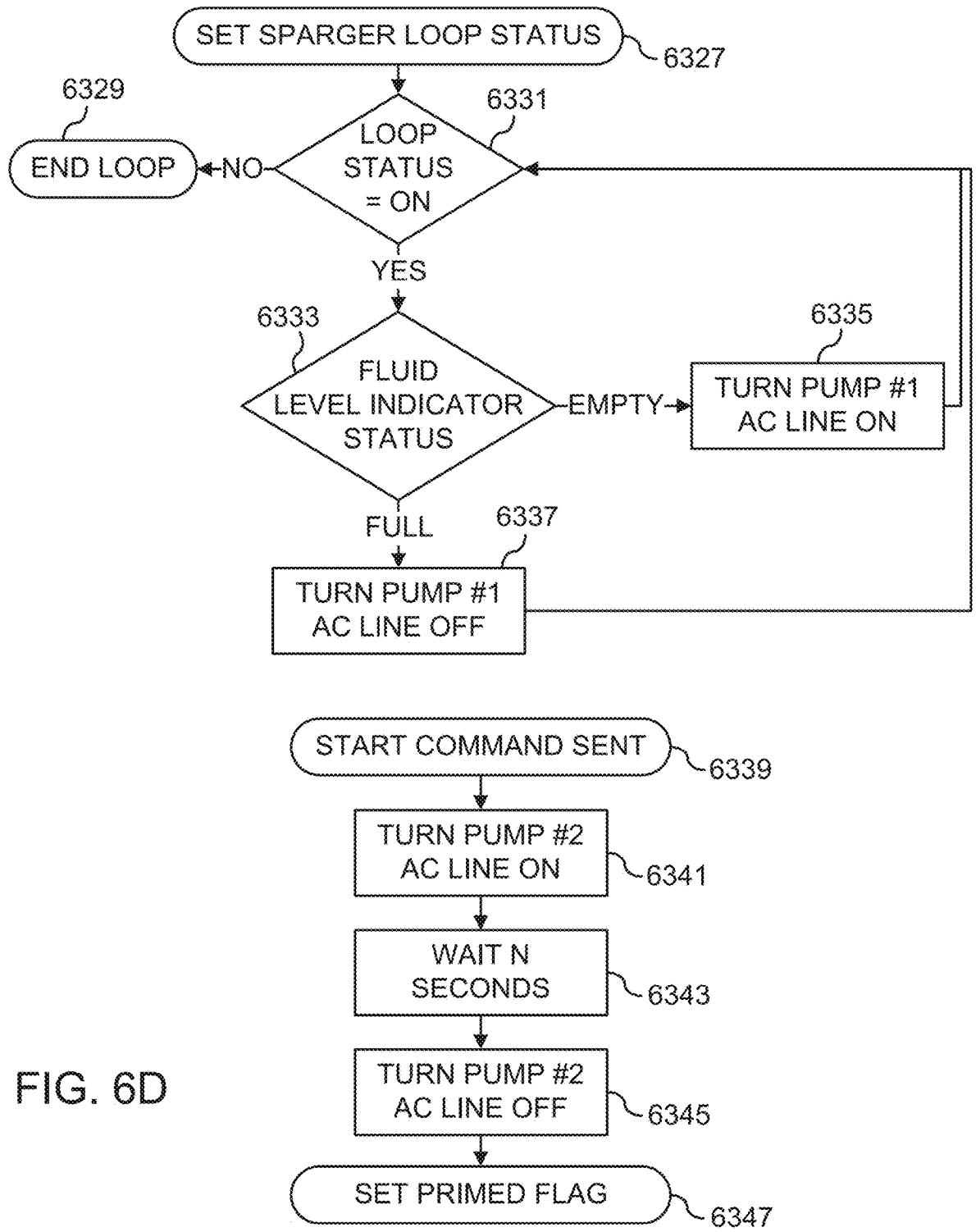
Figure 6E:
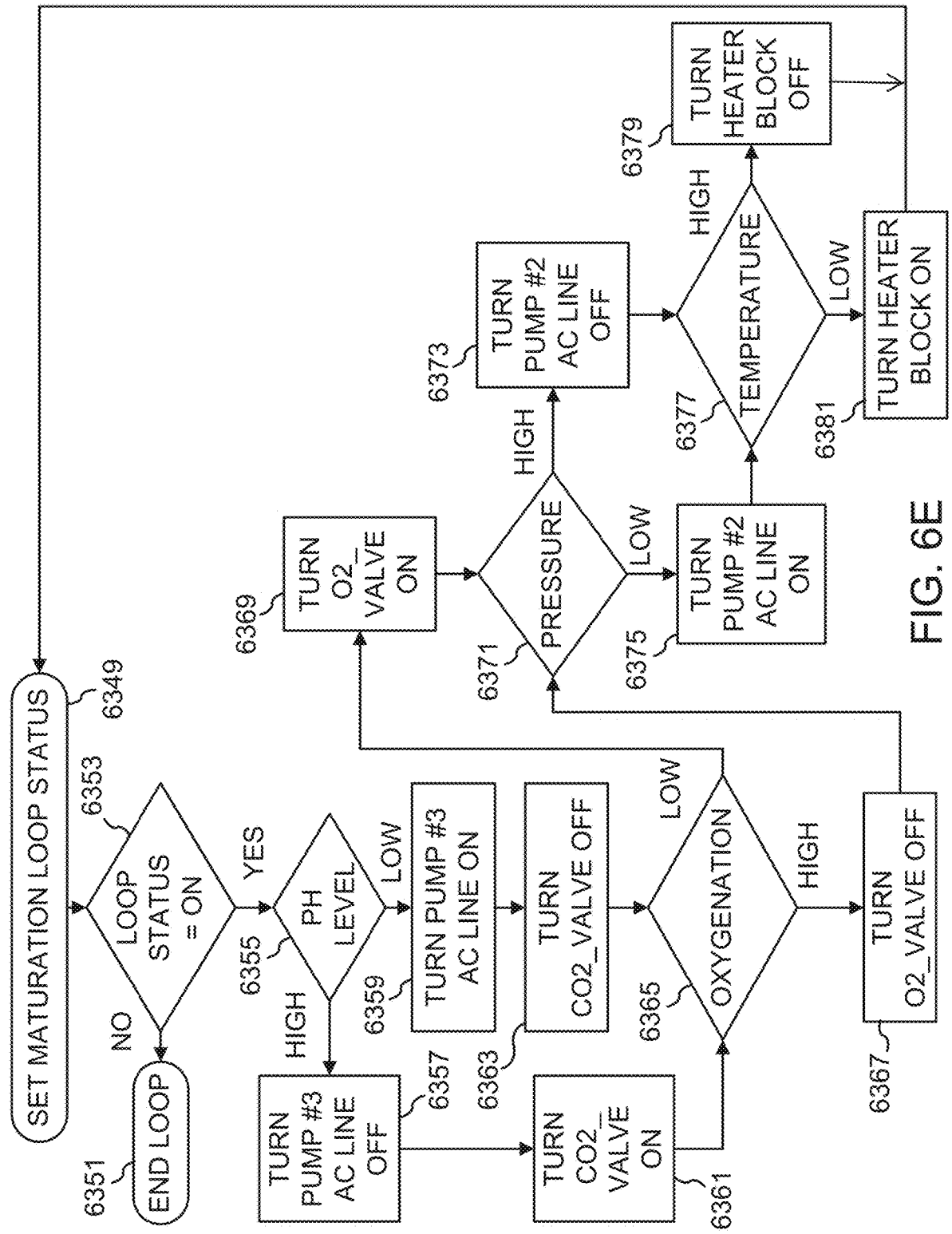

Referring now to FIGS. 6B-6E, exemplary system and method 6300 (FIG. 6C) for growing tissue can include sterilizing 6301 (FIG. 6C) components of bioreactor 31019 (FIG. 6B), assembling 6303 (FIG. 6C) plena and filters of tissue enclosure 31019 (FIG. 6B), preparing 6309 (FIG. 6C) a tissue supporting medium such as a gel, and filling 6307 (FIG. 6C) bioreactor 31019 (FIG. 6B) with the tissue supporting medium. Method 6300 (FIG. 6C) can include preparing 6305 (FIG. 6C) bio-inks, printing 6311 (FIG. 6C), using printer 31023 (FIG. 6B), into tissue enclosure 31019 (FIG. 6B) and connecting 6313 (FIG. 6C) tissue enclosure 31019 (FIG. 6B) to waste 31021 (FIG. 6B). Method 6300 (FIG. 6C) can include sterilizing 6383 (FIG. 6C) sparger 31011 (FIG. 6B), connecting 6385 (FIG. 6C) growth media 31009 (FIG. 6B) to sparger 31011 (FIG. 6B), executing 6387 (FIG. 6C) a sparger reservoir loop, and connecting 6389 (FIG. 6C) sparger 31011 (FIG. 6B) to sensor 31013 (FIG. 6B) and ultimately tissue enclosure 31019 (FIG. 6B). The sparger reservoir loop can include setting 6327 (FIG. 6C) a loop status, and, if 6331 (FIG. 6C) the loop status is set, and if 6333 (FIG. 6C) the level of the fluid in sparger 31011 (FIG. 6B) is empty, enable pump 31001 (FIG. 6B), controlled by signals from controls 31015 (FIG. 6B) through control flow line 31006 (FIG. 6B), to pump growth media 31009 (FIG. 6B) into fluid flow 31008. If 6331 (FIG. 6C) the loop status is set, and if 6333 (FIG. 6C) the level of the fluid in sparger 31011 (FIG. 6B) is not empty, disable pump 31001 (FIG. 6B), controlled by signals from controls 31015 (FIG. 6B) through control flow line 31006 (FIG. 6B), to discontinue pumping growth media 31009 (FIG. 6B) into fluid flow 31008 (FIG. 6B). If 6331 (FIG. 6C) the loop status is reset, ending 6329 (FIG. 6C) the sparger reservoir loop. Method 6300 (FIG. 6C) can include priming 6315 the plena of tissue enclosure 31019 (FIG. 6B). Priming the plena can include sending 6339 (FIG. 6C) as start command, enabling 6341 (FIG. 6C) pump 31017 (FIG. 6B), controlled by signals from controls 31015 (FIG. 6B), waiting 6343 (FIG. 6C) a pre-selected amount of time, disabling 6345 (FIG. 6C) pump 31017 (FIG. 6B), and setting 6347 (FIG. 6C) a primed flag. Method 6300 (FIG. 6C) can include closing 6317 (FIG. 6C) a needle valve in the plenum and executing 6319 (FIG. 6C) a tissue maturation control loop. The tissue maturation control loop can include setting 6349 (FIG. 6E) a loop status. If 6353 (FIG. 6E) the loop status is reset, the tissue maturation control loop can include ending 6351 the loop. If 6353 (FIG. 6E) the loop status is set, and if 6355 (FIG. 6E) the pH level is high, disabling 6357 (FIG. 6E) pump 31007 (FIG. 6B), thereby cutting off the entry of neutralizer 31005 (FIG. 6B) into fluid stream 31008 (FIG. 6B), and opening 6361 (FIG. 6E) gas valve 31004 (FIG. 6B) by controls 31015 (FIG. 6B). If 6353 (FIG. 6E) the loop status is set, and if 6355 (FIG. 6E) the pH level is low, the tissue maturation control loop can include enabling 6359 (FIG. 6E) pump 31007 (FIG. 6B), thereby drawing neutralizer 31005 (FIG. 6B) into fluid stream 31008 (FIG. 6B), and closing 6363 (FIG. 6E) gas valve 31004 (FIG. 6B) by controls 31015 (FIG. 6B). If 6365 (FIG. 6E) oxygenation is high, the tissue maturation control loop can include closing 6367 (FIG. 6E) gas valve 31004 (FIG. 6B), disabling the entry of gas 31003 (FIG. 6B) into fluid stream 31008 (FIG. 6B). If 6365 (FIG. 6E) oxygenation is low, the tissue maturation control loop can include opening 6369 (FIG. 6E) gas valve 31004 (FIG. 6B). If 6371 (FIG. 6E) the pressure, determined by pressure sensor 31027 (FIG. 6B), in tissue enclosure 31019 (FIG. 6B) is high, the tissue maturation control loop can include disabling 6373 (FIG. 6E) pump 31007 (FIG. 6B). If 6371 (FIG. 6E) pressure is low, the tissue maturation control loop can include enabling 6375 (FIG. 6E) pump 31007 (FIG. 6B). If 6377 (FIG. 6E) the temperature in tissue enclosure 31019 (FIG. 6B) is high, the tissue maturation control loop can include managing 6379 (FIG. 6E) temperature control 31025 (FIG. 6B) to reduce the temperature in tissue enclosure 31019 (FIG. 6B) and testing loop status. If 6377 (FIG. 6E) the temperature in tissue enclosure 31019 (FIG. 6B) is low, the tissue maturation control loop can include managing 6381 (FIG. 6E) temperature control 31025 (FIG. 6B) to increase the temperature in tissue enclosure 31019 (FIG. 6B) and testing loop status. If 6321 the tissue is not mature, method 6300 can include executing 6319 the tissue maturation control loop. If 6321 the tissue is mature, method 6300 can include resetting 6323 the loop maturation status and transferring 6325 the tissue to the next stage in its processing.

Figure 7A:
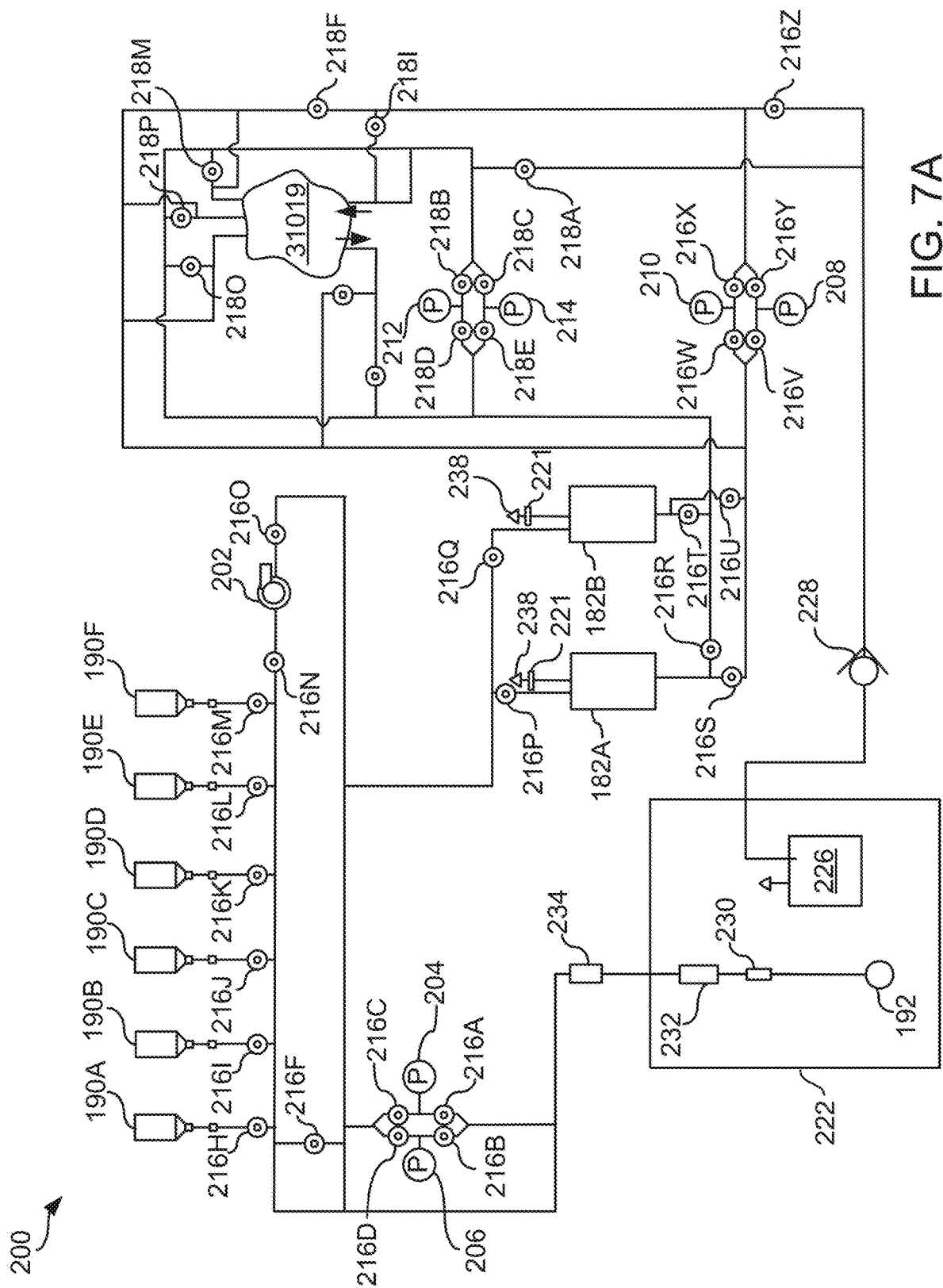
FIGS. 7A and 7B are schematic block diagrams of second and third configurations of the tissue maturation system of the present teachings.
Figure 7B:
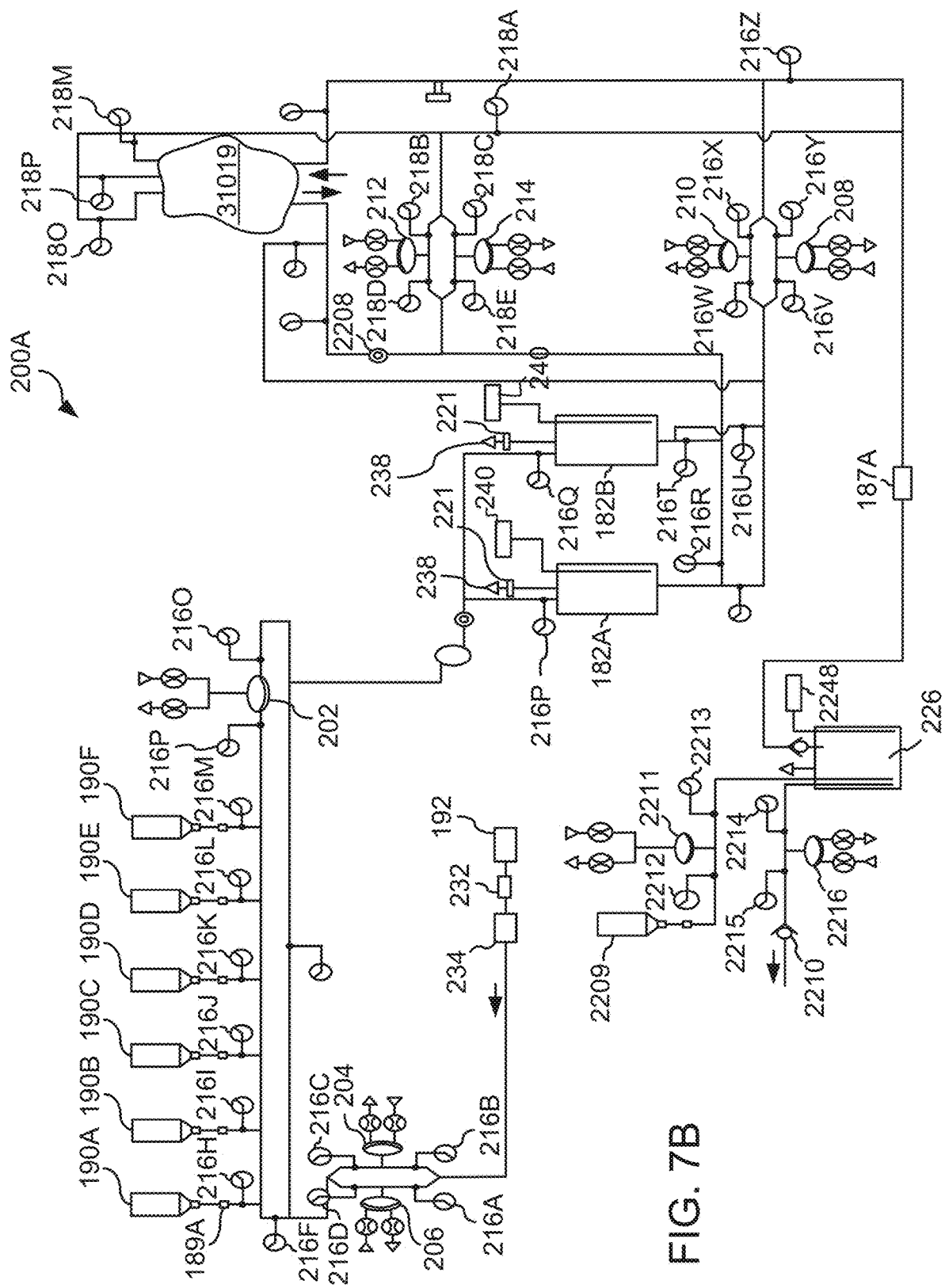
Figure 7C:
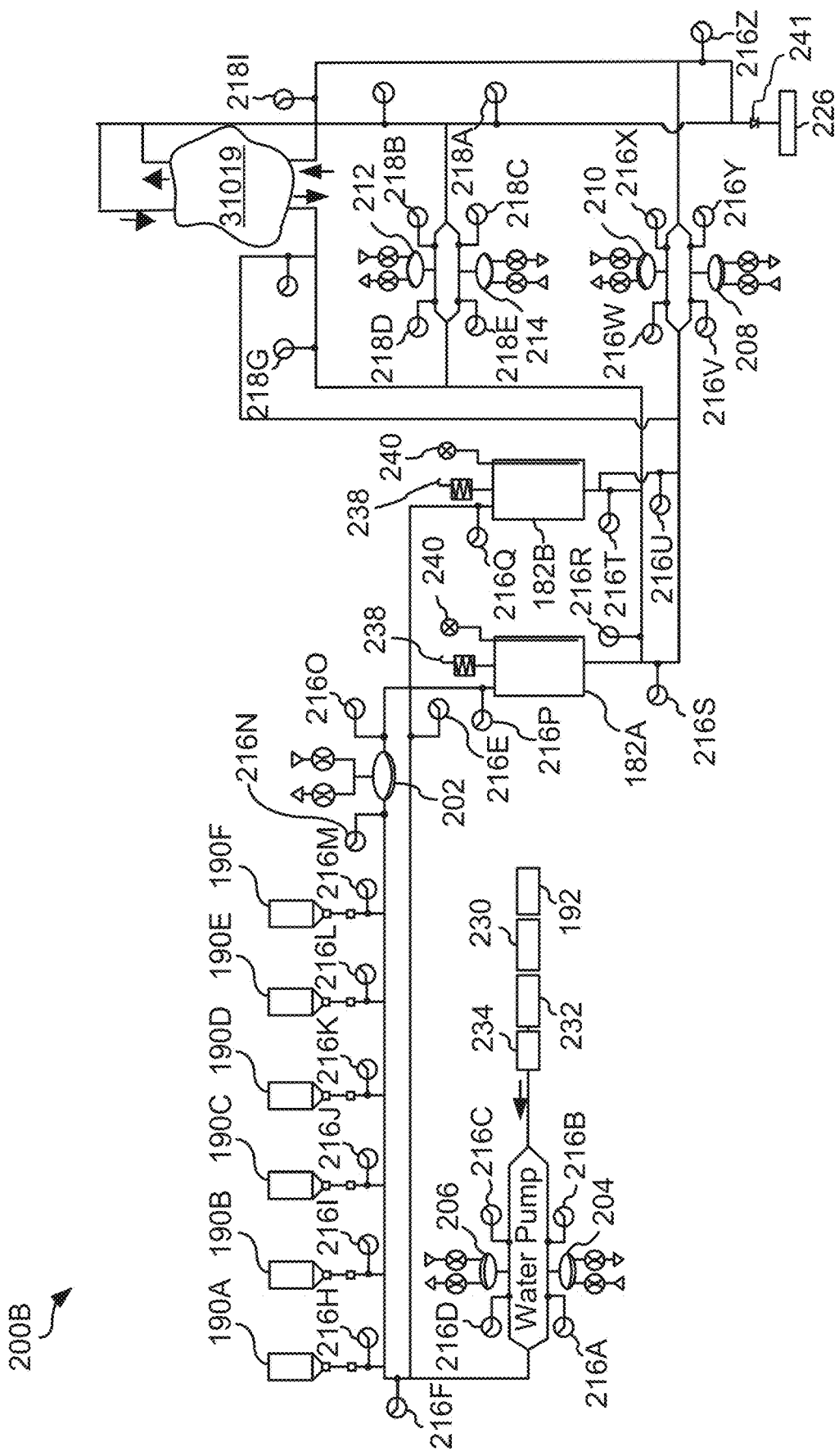
FIGS. 7C-7G are schematic block diagrams of exemplary configurations of the tissue maturation system of the present teachings.

Referring now to FIGS. 7A and 7B, a second and third configuration of tissue maturation system 800 (FIG. 5A) can include fluid circuit 200 (FIG. 7A) and fluid circuit 200A (FIG. 7B). Fluid circuit 200 can include, but is not limited to including, tissue enclosure 31019, fluid pumps 202, 204, 206, 208, 210, 212, 214, and valves 216A-D, 216F, 216H-Z and 218A-F, 218I, 218M, and 218O-P. By operating fluid pumps 202, 204, 206, 208, 210, 212, 214 and valves 216A-D, 216F, 216H-Z and 218A-F, 218I, 218M, and 218O-P cooperatively, fluid may be pumped throughout fluid circuit 200. In some configurations, fluid may be drawn into fluid circuit 200 via pumps 204 and 206. Pump 202 can draw fluid primarily from any of source 190A-F and/or pumps 204 and 206 can draw fluid primarily from diluent source 192. Though six sources 190A-F are shown, any number of sources 190A-F may be in communication with fluid circuit 200. In some configurations, one or more of sources 190A-F may be vented to the atmosphere. A filter between the atmosphere and at least one of the one or more sources 190A-F may be included. In some configurations, one or more source 190A-F may be associated with filter 189A between the one or more source 190A-F and valve 216H-216M. Filters 189A may be any suitable variety of filters in some configurations, for example, but not limited to, a 0.2 micron filter. In some configurations, one or more sources 190A-F may be compliant. Fluid circuit 200 may be disposable and may be replaced after each use, or may be replaced after a defined number of uses. Alternatively, fluid circuit 200 may require cleaning and/or sterilization after each use and/or after a predefined period of time/number of uses. Components in partitioned portion 222 can include drain reservoir 226 to accommodate waste fluid from fluid circuit 200. One or more one way valve or check valve 228 can be included to help discourage or stop waste fluid from back flowing into fluid circuit 200.

Continuing to refer to FIGS. 7A and 7B, a number of components may be included between diluent source 192 and the rest of fluid circuit 200 and fluid circuit 200A. Regulator 232 can regulate the pressure of diluent entering fluid circuit 200/200A. In some configurations, the pressure value which regulator 232 regulates to may be between 5-18 psi (e.g. 7 psi), though the pressure value may differ in other configurations. Deaerator 230 can remove air from incoming diluent 192. Filter 234 can protect against potential contaminants entering fluid circuit 200/200A from diluent 192. Filter 234 can decrease the likelihood of backwards contamination. Filter 234 can isolate deaerator 230 from the rest of fluid circuit 200/200A allowing deaerator 230 to be in a non-sterile portion of fluid circuit 200/200A. Pumps 202, 204, and 206 may mix fluid to create various admixtures or may deliver fluid directly from source 190A-F or diluent source 192 to storage reservoirs 182A, 182B. Admixtures may include fluid or solution diluted to a desired concentration and/or various "cocktails" consisting of a variety of different components. Pumps 202, 204, and 206 may draw fluid from any source 190A-F and/or diluent source 192 in a predefined ratio and deliver this fluid to storage reservoirs 182A, 182B. The predefined ratio may be chosen to create the desired fluid admixture. Storage reservoirs 182A, 182B may include vents 238 that can prevent pressure build up within the storage reservoirs 182A, 182B. In some configurations vent filter 221 such as a 0.2 micron filter may be included in vent 238 between the interior of storage reservoirs 182A, 182B and a vent reservoir, for example, but not limited to, the atmosphere.

Continuing to refer primarily to FIG. 7A, when storage reservoirs 182A, 182B contain a desired admixture or fluid, the fluid may be pumped to/from enclosure 31019 or, for example, the tissue within enclosure 31019. In some configurations, filters may be included. In some configurations, fluid circuit 200 can include pumps 208, 210, 212, and 214 which may be used to control the transfer of fluid to/from enclosure 31019 and to/from the enclosed tissue. Pumps 208, 210, 212, and 214 may be used to pump fluid to waste reservoir 226 when, for example, the fluid is considered used or spent. Pumps 202, 204, 206, 208, 210, 212, 214 may be any of a variety of pumps. In some configurations, pumps 204, 206, 208, 210, 212, 214 may be, but are not limited to being, any of or a combination of the following: centrifugal pumps, positive displacement pumps, peristaltic pumps, diaphragm pumps, vane pumps, and metering pumps. Valves 216A-D, 216F, 216H-Z and 218A-F, 218I, 218M, and 218O-P may be any of or a combination of a variety of valve types including but not limited to the following: solenoid valves, variable valves, and rotary valves, ball valves, pinch valves, bi-stable valves and membrane valves. In some configurations, each or at least one of valves 216A-D, 216F, 216H-Z and 218A-F, 218I, 218M, and 218O-P may include a combination of valves which may be of different types. For example, each or at least one of valves 216A-D, 216F, 216H-Z and 218A-F, 218I, 218M, and 218O-P may include a pneumatic valve that can control a fluid valve. In some configurations, the pneumatic valve may be a bi-stable pressure control valve that can supply pressure to a membrane type "volcano valve" to open/close the "volcano valve". In some configurations at least some valves, fluid pathways, and pumps may be incorporated into a fluid handling cassette or set including a plurality of fluid handling cassettes.

Referring again to FIGS. 7A and 7B, any fluid entering the fluid system can be filtered. Filter 234 (FIG. 7A) can be, but is not limited to being, a 0.2 μm filter. Incoming fluid may also be subjected to multiple filters or redundant filtration, deaeration in deaerator 230, and/or subjected to regulator 232 which may ensure fluid is at a desired pressure. Any number of storage reservoirs 182A/182B can be included in systems 200/200A (FIGS. 7A/7B). Storage reservoirs 182A/182B may include one or more port to which a fluid line may be connected. Each of storage reservoirs 182A/182B may be in fluid communication with a cassette. Storage reservoirs 182A/182B may, for example, receive fluid from a mixing cassette such as those described in '900. Storage reservoirs 182A/182B can include ports for air vents 238. Air vents 238 may allow air to escape or enter storage reservoirs 182A/182B as the level of fluid in storage reservoirs 182A/182B changes. Level sensor 240 (FIG. 7B) can measure the level of fluid in storage reservoirs 182A/182B. Level sensor 240 (FIG. 7B) and air vents 238 may help ensure no pressure build up occurs within storage reservoirs 182A/182B. Air vents 238 can optionally include filters 221. Filters 221 may be a 0.2 micron filter. Operationally, systems 200/200A (FIGS. 7A/7B) can circulate specific fluids through tissues within tissue enclosure 31019 according to an automatic process, a manual process, or a combination of both. A recipe including, for example, but not limited to, ingredients and valve positions as a function of, for example, time, can be constructed that can facilitate an automatic process which can be overridden manually.

Referring now to FIG. 7B, a waste control system can control waste 226 that results from, for example, biological activity, to avoid environmental contamination. Waste 226 can be filtered, diluted, and expelled from the waste control system. The level of waste 226 can be monitored by level sensor 2248, and incoming waste 226 can be filtered by filter 187A. Pump 2211 can draw fluid 2209 through valves 2212/2213, and fluid 2209 can dilute waste 226. Pump 2216 can draw fluid through valves 2214/2215 to move fluid 2209 and/or waste 226 out of the waste control system through check valve 2210. Waste exhaust can be vented to the environment.

Figure 7D:
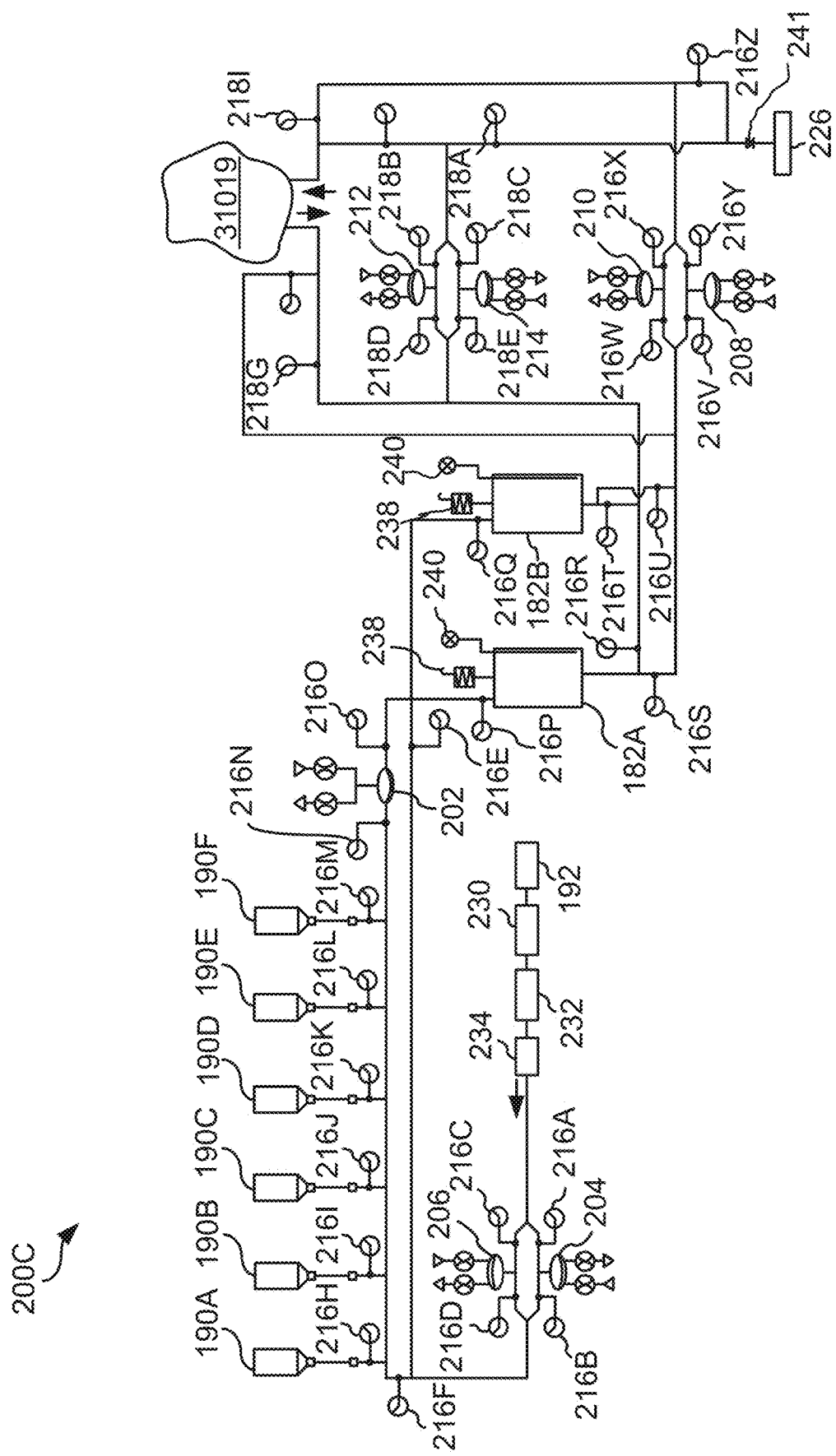
Figure 7E:
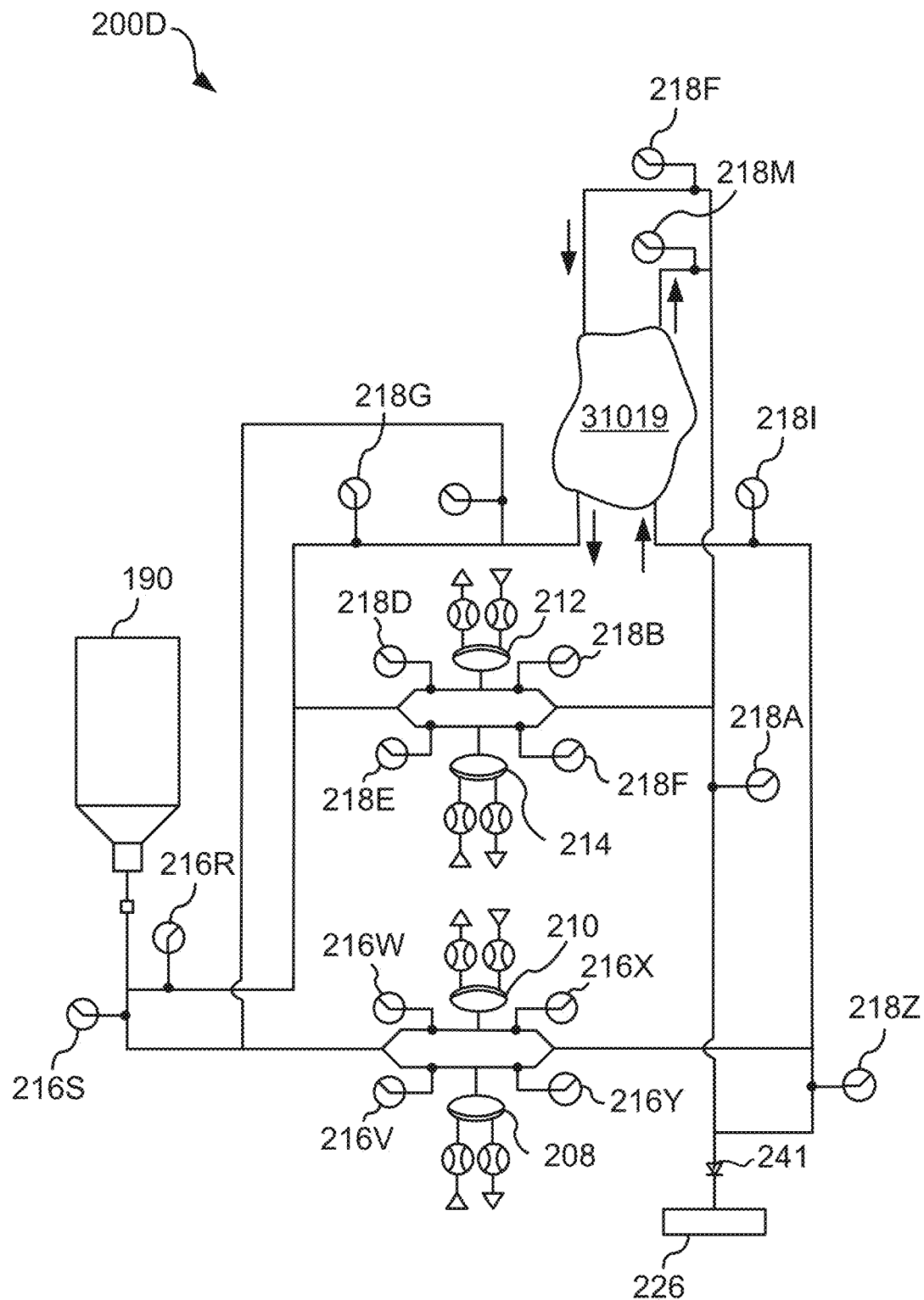
Figure 7F:
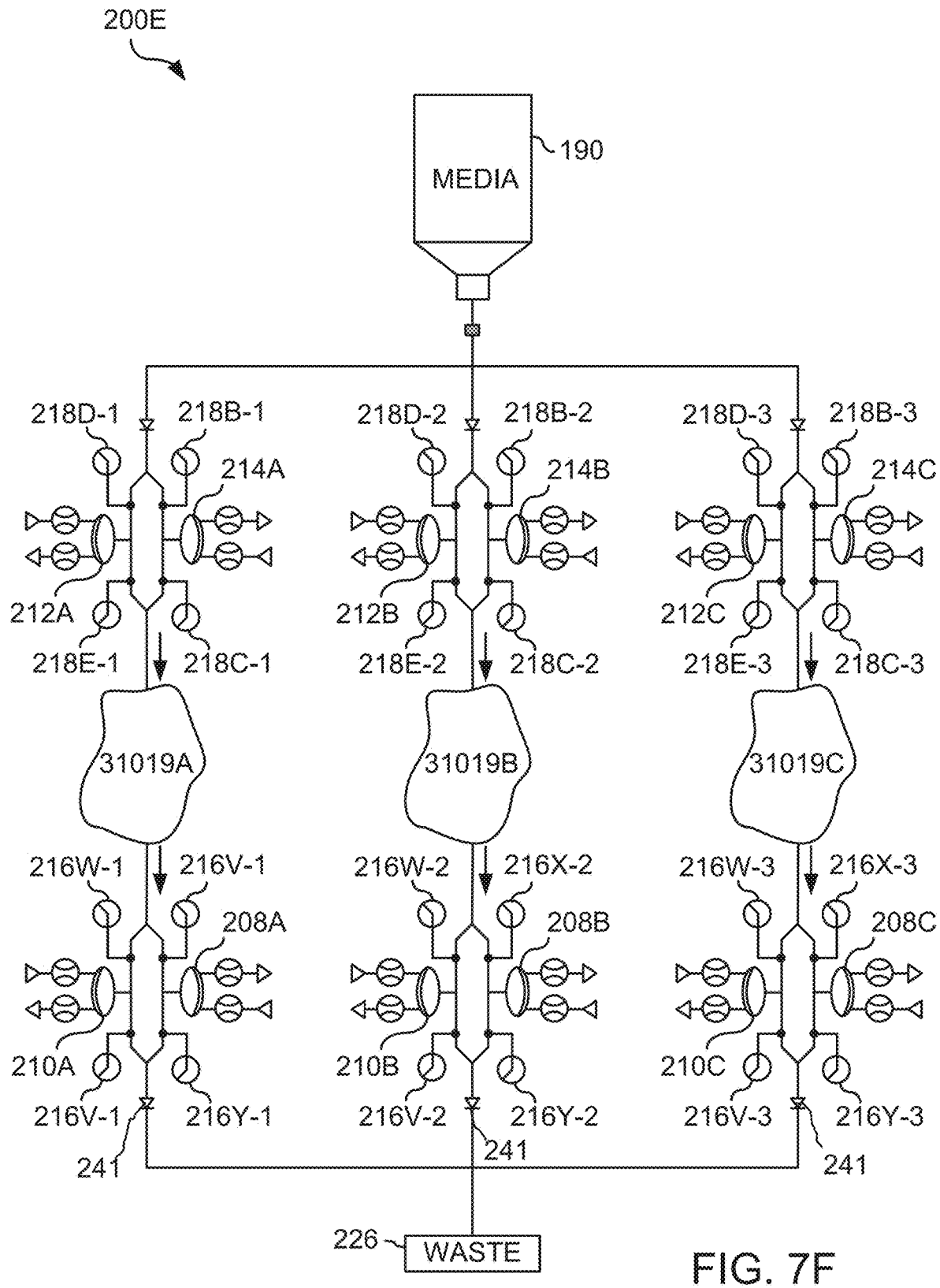

Referring now to FIGS. 7C-7G, exemplary configurations of tissue maturation systems can address particular types of tissue and timing requirements. For example, system 200B (FIG. 7C) can include valves, pumps, and inlet/outlet means to support blood vessel development. System 200B (FIG. 7C) can include a diluent pump including diaphragm valves 216D/216C/216A/216B operably coupled with pumping chambers 204/206 that can draw diluent 192, for example, deionized water, into the fluid circuit. Diluent 192 can travel through deaerator 230, pressure regulator 232, and filter 234 before entering the diluent pump. Pumping chambers 204/206 can accommodate up to a pre-selected amount of diluent 192, for example, but not limited to, 50 ml. Pumping chamber pods can be adjusted to optimize accuracy/flow rate based on desired mixing ratios. Any number of solutions 190A-190F can be brought into systems 200B (FIG. 7C)/200C (FIG. 7D) through diaphragm valves 216H-216M, if they are set to admit the solutions with which they are associated. Mixing pumping chamber 202 (FIG. 7C), operably coupled with diaphragm valves 216N/216O (FIG. 7C), can mix solutions 190A-190F (FIG. 7C) or a subset, along with diluent 192 if valve 216F is set to accommodate the flow of diluent 192. The number of solutions 190A-190F can increase or decrease based at least on the needs of the growing tissue. Some of the solution inlets can be blocked if not needed. The mixed solution can be admitted to either of storage reservoirs 182A/182B depending on the direction received by diaphragm valves 216P/216Q, and the solution can continue to travel to tissue enclosure 31019 depending on the direction received by diaphragm valves 216S/216U. Pump chambers 212/214 (FIG. 7C), operably coupled with diaphragm valves 218D/218B/218E/218C (FIG. 7C), can cooperate (under the direction of a controller (not shown)) with pump chambers 208/210 (FIG. 7C), operably coupled with diaphragm valves 216W/216X/216V/216Y and valves 218G/218I/218A to move fluid through tissue enclosure 31019, either new or recycled fluid, and on to waste 226, through check valve 241, when the fluid is spent. Tissue enclosure 31019, storage reservoirs 182A/182B, and solution containers can be constructed of compliant material, and/or can be open to the atmosphere, and/or can be vented. System 200C (FIG. 7D) can grow a tissue that does not require blood vessel accommodation. System 200D (FIG. 2D) can admit solution 190 (FIG. 2D) through diaphragm valves 218F/218M into vessels within tissue enclosure 31019. System 200D (FIG. 2D) can include a simplified configuration compared to, for example, system 200B (FIG. 7C) in that single solution 190 (FIG. 2D) does not require either a mixing pump or a diluent pump. The contents of solution 190 can include a single component or multiple components. Solution 190 can be diluted. System 200E (FIG. 7F) can include any number of tissue enclosures 31019A/31019B/31019C (FIG. 7F) fed by solution/media 190. Spent fluid from all tissue enclosures 31019A/31019B/31019C (FIG. 7F) can flow into waste container 226 through, for example, individual check valves 241. Pump chambers 212A-C/214A-C (FIG. 7F), operably coupled with diaphragm valves 218D-1-3/218B-1-3/218E-1-3/218C-1-3 (FIG. 7F), can draw fluid from solution 190 into tissue enclosures 31019A/31019B/31019C (FIG. 7F). Pump chambers 210A-C/208A-C (FIG. 7F), operably coupled with diaphragm valves 216W-1-3/216X-1-3/216Y-1-3/

216V-1-3 (FIG. 7F), can draw fluid from 190 into tissue enclosures 31019A/31019B/31019C (FIG. 7F) into waste containers 226.

Figure 7G:
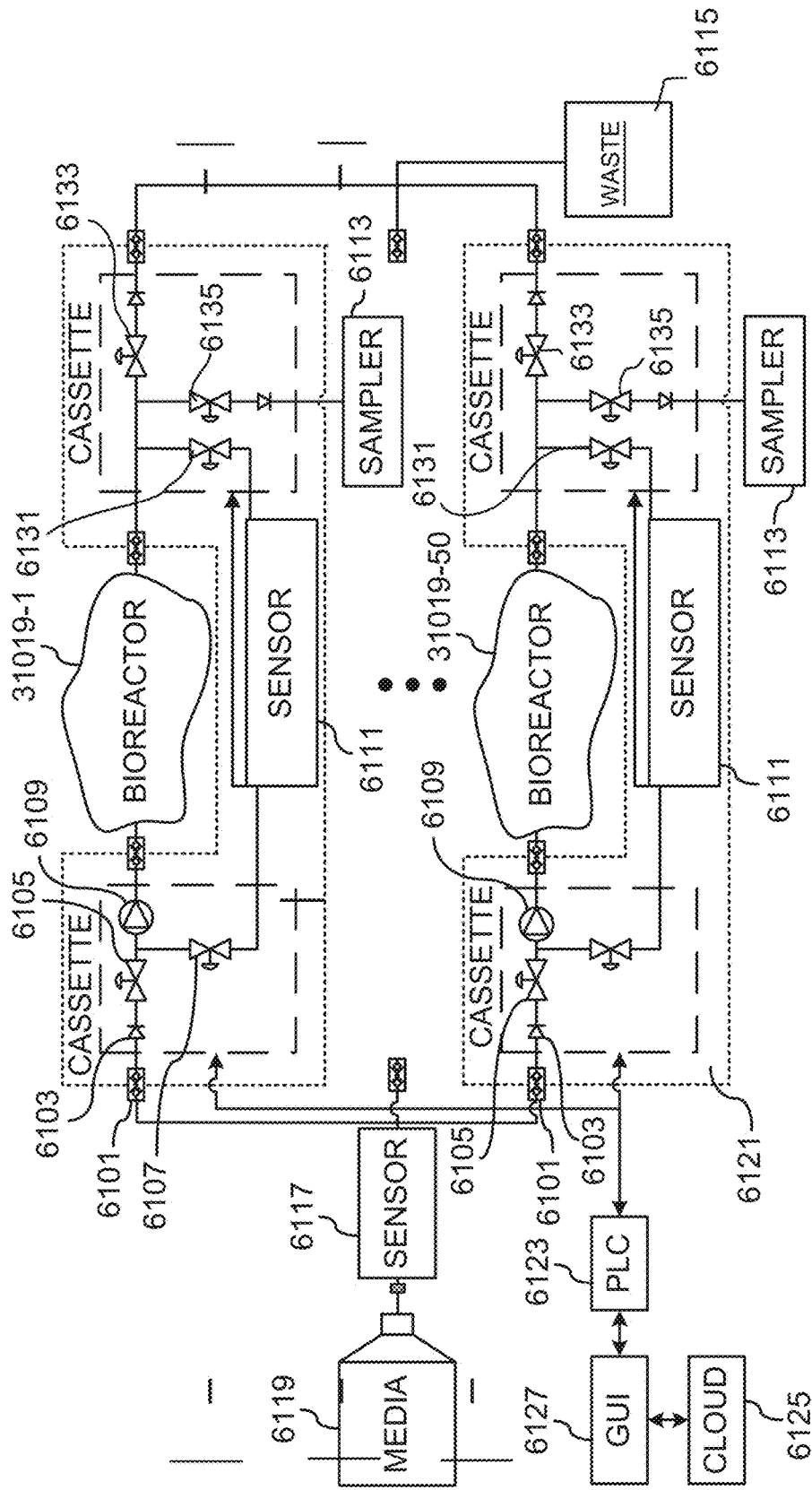

Referring now primarily to FIG. 7G, in another configuration such as system 200E (FIG. 7F), system 200F can manage multiple culture conditions for, for example, but not limited to, fifty tissue enclosures. In some configurations, system 200F can continually replenish culture media 6119, collect media samples by sampler 6113, remove used media from multiple tissue enclosures 31019-1 through 31019-50 without cross-contamination, and non-invasively sense and control media 6119. In some configurations, system 200F can include single-use, low-cost components and durable components located outside of the sterile boundary of system 200F. In some configurations, the single-use components can be configured based on flow, pressure, and the desired sensor suite. In some configurations, system 200F can store between 10 and 100 liters of fresh media 6119, can manage with control system 6123 up to 50 tissue enclosures, and can deliver media 6119 at a pre-selected flow rate such as, for example, but not limited to, 1-600 mL/min±0.1%. In some configurations, user control can be received through GUI 6127, and control 6123 can provide user feedback. In some configurations, data collected by, for example, but not limited to, sensors 6111 and 6117 and sampler 6113 can be stored in remote storage 6125, for example, or can be stored locally. In some configurations, system 200F can deliver a volume of media 6119 of between about 10 and 500 mL, can accommodate an oxygen range of about 0-20% and a carbon dioxide range of about 0-5%, can accommodate a variation of oxygen and carbon dioxide around a setpoint of better than ±0.1%, and can accommodate a temperature of about 37±0.5° C. System 200F can integrate various types of tissue enclosures. System 200F can include pump cassette 6121, including, in some configurations, diaphragm valves 6105/6107 and pumps 6109, and sensor block 6111 as a single unit that can be gamma sterilized. Pump cassette 6121 can include pneumatic valves that can direct flow during media exchange, media recirculation, and sampling. Cross-contamination between individual tissue enclosure sections during media exchange can be avoided by the use of check valves 6103. Tissue enclosures 31019-1 through 31019-50 can be independent from one another so that a tissue enclosure can be added or removed through sterile connectors 6101 while maintaining the sterility of system 200F. In some configurations, tissue enclosure 31019-1 through 31019-50 can accommodate a media circulating flow rate of 1-100±0.1 mL/min, a reversible flow, an oxygen range of 0-20%, a carbon dioxide range of 0-5%, oxygen and carbon dioxide variations around setpoint of better than ±0.1%, temperature of 37±0.5° C., glucose of 0.5-1±0.1 g/L, and pH of 7.2±0.1. System 200F can include waste container 6115 that can receive spent fluid from all tissue enclosures 31019-1 through 31019-50. Valves 6131 can control the flow of fluid into a loop that includes bioreactors 31019-1/50 and samplers 6113 through sensors 6111. Valves 6135 can control the flow of fluid from bioreactors 31019-1/50 to samplers 6113, and valves 6133 can control the flow of fluid from bioreactors 31019-1/50, sensors 6111, and samplers 6113 to waste 6115.

Continuing to refer to FIG. 7G, media and cells can be printed into a multiwell plate sized to conform to any of tissue enclosures 31019-1/31019-50 and others described herein, making it possible to incubate cells in the multiwell plate within the growth environment of any of tissue enclosures 31019-1/31019-50 and other described herein. The multiwell plate can include, but is not limited to including, construction materials that can enable visualization of the contents of each well, and construction materials that can enable optimal heat transfer and sample recovery. Multiwell plates can include, but are not limited to including, commercially available plates such as ThermoFisher Scientific ARMADILLO® PCR plate. A permeable support such as, for example, but not limited to a Corning TRANSWELL® permeable support, can be placed within the printed cells and media to enable anchorage and study of the cells. Permeable supports can include various types of membrane materials such as, for example, but not limited to, polycarbonate, polyester, and polytetrafluoroethylene. In some configurations, permeable supports can include translucent membranes having various pore sizes, for example, 0.4-0.8 µm. In some configurations, permeable supports can include treatment for cell attachment, and can include clear inserts enabling cell visibility and assessment under certain experiment configurations and liquid media can be introduced from the top can be kept separate from the culture media by way of a semi-permeable membrane that can allow for feeding by diffusion across the membrane. Development of a tumoroid or other small tissue can include printing a very thin layer of a culture medium in the bottom of a multiwell plate, placing a permeable support on top of the thin layer, and printing liquid media onto the permeable support, the liquid media being separated from the culture medium by way of the permeable support. Feeding of the tissue can occur by diffusion across the permeable support.

Referring now to FIGS. 7H-7K, mixing cassette 282A can move liquids from sources 190A, 190B, and diluent 192 to be mixed and provided to reservoir 182A and/or discarded as waste 226. Any of systems 200, 200A, 200B, 200C, 200D, 200E, and 200F can be operably coupled with mixing cassette 282A by supplying up to three source fluid inputs and two fluid outputs. Mixing cassette 282A can include a cassette body that can include a rigid member that can include a hard plastic or other hard material. The cassette body may be manufactured in any number of suitable manners such as molding, machining, etc. The cassette body may be, for example, but not limited to, a generally planar structure from which a number of walls and a perimeter wall project. The walls can project at an angle that can be substantially perpendicular from the plane of the cassette body. Mixing cassette 282A can also include a number of valve seats that can project away from the cassette body, for example, similar to walls. Each valve seat may be surrounded by walls which can define a valve well. The walls of cassette 282A may extend proud of the valve seats. Mixing cassette 282A can include a cassette sheeting or membrane. Cassette sheeting can include generally planar pieces of material. Cassette sheeting may include, for example, but not limited to, substantially impermeable and flexible material, for example a flexible plastic or elastomeric material. Cassette sheeting may be attached to each side of the cassette body at a perimeter wall, and can overlay the walls of mixing cassette 282A. Cassette sheeting may be positioned on mixing cassette 282A and attached to mixing cassette 282A e.g., by heat bonding, adhesive, ultrasonic welding or other means. Cassette sheeting can include a flexible polymer film made from, for example, polyvinyl chloride (PVC), that is cast, extruded or otherwise formed. Alternatively, cassette sheeting may be formed as a laminate of two or more layers of poly-cyclohexylene dimethylene cyclohexanedicarboxylate (PCCE) and/or ultra low density polyethylene (ULDPE), held together, for example, by a coextrudable adhesive (CXA). Urethane may also be used. The thickness of cassette sheeting may be any suitable thickness, and in some configurations, in the range of approximately 0.002 to 0.020 inches thick. In one configuration, the thickness may be in the range of approximately 0.012 to 0.016 inches thick, and in one configuration, can be approximately 0.014 inches thick.

Continuing to refer to FIGS. 7H-7K, mixing cassette 282A can include pumping chambers, incoming and outgoing ports, valves, and fluid paths between valves and pumps that can allow the fluid circuit to be relatively simple and compact. Pumping and directing of fluid through fluid handling cassette 282A can be driven, e.g., pneumatically as described in, for example, U.S. Pat. No. 5,350,357, filed Mar. 3, 1993, and entitled PERITONEAL DIALYSIS SYSTEMS EMPLOYING A LIQUID DISTRIBUTION AND PUMPING CASSETTE THAT EMULATES GRAVITY FLOW, which is hereby incorporated by reference herein in its entirety or as described in U.S. patent application Ser. No. 11/787,212, U.S. Pat. No. 8,292,594, filed Apr. 13, 2007, issued Oct. 23, 2012, entitled "Fluid Pumping Systems, Devices and Methods," (E78) incorporated herein by reference in its entirety. Mixing cassette 282A may be in fluid communication with up to two of fluid sources 190A/190B via up to two fluid lines. In some configurations, one or both of solution ports 286A/288A may be connected to source lines 190A/190B. In some configurations, one or more port may be blocked or sealed and not used. In some configurations, one or both solution ports 286A/288A may include a spike port for attachment of a vial or other source. In some configurations, a vial of source fluid may, for example, be spiked directly onto one of solution ports 286A/288A and source lines may not be necessary. Solution ports 286A/288A may include other fittings such as luer locks or similar fittings to which source lines may be attached. In some configurations, solution ports 286A/288A may be augmented and/or replaced by vent ports that can allow pressure build up in a source in communication with solution ports 286A/288A to be relieved. Mixing cassette 282A may draw in fluid via solution ports 286A/288A. This fluid may then be expelled from cassette 282A through tank port 290B to fluid reservoirs 182A. In some configurations, fluid may be drawn in from select sources in predetermined ratios to create a fluid mixture. The mixture may, in some configurations, be created within mixing cassette 282A or may be created by pumping the constituent fluids of the mixture to fluid reservoir 182A and allowing the constituent fluids to mix within storage reservoir 182A. A fluid mixture may, for example, be an admixture "cocktail" of the contents of different sources 190A/190B that can be in communication with mixing cassette 282A. Additionally, a fluid mixture may be created via mixing cassette 282A by drawing in fluid from a concentrated fluid source as well a diluent source. Mixing may occur within mixing cassette 282A or after pumping of these fluids to fluid reservoir 182A. To achieve a desired concentration of the concentrate in the diluted mixture, fluid may be pumped from the concentrate source and diluent source in a predetermined ratio.

Continuing to refer to FIGS. 7H-7K, in some configurations, mixing cassette 282A can be in fluid communication with a diluent source such as water source 192 (e.g. reverse osmosis, deionized, or distilled water). Solution ports 286A/288A can be connected to concentrates or additional diluent sources via a vial spike or source lines. When pressure is applied to each side of the cassette body, cassette sheeting may be forced against the walls of the cassette body. The pressure can, for example, form fluidically sealed chambers and pathways in mixing cassette 282A. Cassette sheeting may be, but is not limited to being, prevented from being forced against each of the valve seats because the walls may be, for example, proud of the valve seats. Positive pressure (pressure may be exerted mechanically or by a control fluid pneumatically, hydraulically, etc.) applied to cassette sheeting over the valve seat may displace cassette sheeting into contact with the valve seat. Negative pressure may displace cassette sheeting away from the valve seat. One or more pieces of cassette sheeting may optionally include one or more preformed region. Preformed regions may be, but are not limited to being, depression-like features in the cassette sheeting that can generally conform to the contours of various portions of mixing cassette 282A. Preformed regions may be added to the cassette sheeting during manufacture. Cassette sheeting may be, for example, generally formed as a flat member and preformed regions may later be thermoformed. In some configurations, preformed regions can correspond to pump chambers 332/336 of mixing cassette 282A. The dome-like preformed shapes can, for example, conform to depressions in pump chambers 332/336 of mixing cassette 282A. The dome-like shape of preformed portions may be constructed, for example, by heating and forming cassette sheeting over a vacuum form mold. The vacuum form mold can press a sheet of cassette sheeting against mixing cassette 282A and bond them together.

Continuing to refer primarily to FIGS. 7H-7K, when mixing cassette 282A is assembled, each of pump chambers 332/336 can be, for example, defined in part by cassette sheeting. Each of pump chambers 332/336 can be, for example, defined in part by the walls extending from the cassette body to create depressions in pump chambers 332/336. Application of pressure to cassette sheeting over pump chambers 332/336 may cause the volume of pump chambers 332/336 to vary. Negative pressure can draw cassette sheeting away from the cassette body and can increase the volume of pump chambers 332/336. If, in communication with a fluid source such as, for example, but not limited to, one or more of sources 190A/190B and/or storage reservoir 182A, fluid may be drawn into one or more of pump chambers 332/336 when negative pressure is applied, executing a fill pump stroke. Positive pressure can force cassette sheeting toward the cassette body and decrease the volume of one or more of pump chambers 332/336. When one or more of pump chambers 332/336 contains fluid, the application of positive pressure may cause the fluid to be expelled from one or more of pump chambers 332/336, executing a deliver pump stroke. Pressure may be applied in any of a variety of ways (e.g. mechanically or by a control fluid pneumatically, hydraulically, etc.). In configurations where cassette sheeting includes preformed regions, preformed regions may displace to conduct pumping action without requiring significant (or any) stretching of cassette sheeting, even when a region of cassette sheeting is at a maximum excursion point (e.g. when an associated pump chamber 332/336 is at minimum or maximum volume). In some configurations, cassette sheeting (also referred to as flexible sheeting) may be bonded to the walls of mixing cassette 282A. For example, cassette sheeting may be bonded to the walls that form various pathways or buses within mixing cassette 282A and can cover at least one pump chamber 332/336. At least one piece of cassette sheeting may be formed of a rigid sheet of material that is bonded or otherwise made integral with mixing cassette 282A. Thus, at least one piece of cassette sheeting need not necessarily be, or include, a flexible member. Similarly, cassette sheeting need not be flexible over its entire surface, but instead may include one or more flexible portions to permit pump and/or valve operation, and one or more rigid portions, e.g., to close fluid buses of mixing cassette 282A. In some configurations, mixing cassette 282A can include fluid buses or pathways that can be otherwise sealed or fully enclosed within mixing cassette 282A without cassette sheeting. Each of pump chambers 332/336 may be a variable volume chamber which may be defined in part by cassette sheeting which may act as a displaceable diaphragm. Pressure applied to one or more pump chambers 332/336 may cause fluid to be drawn into or forced out of one or more pump chambers 332/336. Mixing cassette 282A may include, but is not limited to including a number of fluid valves 7.4, 8.1-8.4, 10.1, and 11.1 (e.g. volcano valves) which may be independently opened and closed to make and break fluid communication with fluid pathways 324, 327A, 327B, 328A, 328B, 337B, 338A, and 340. Each of fluid valves 7.4, 8.1-8.4, 10.1, and 11.1 in mixing cassette 282A may be associated with the valve seats. Cassette sheeting may be forced against or pulled away from the valve seats associated with valves 7.4, 8.1-8.4, 10.1, and 11.1 to respectively close or open valves 7.4, 8.1-8.4, 10.1, and 11.1. Valves 7.4, 8.1-8.4, 10.1, and 11.1 can be opened and closed to direct fluid flow when fluid is pumped via one or more of pump chambers 332/336. Fluid in a valve well may, for example, flow through valve 11.1 to a flow path on the opposing side of mixing cassette 282A if the sheeting is not pressed against the valve seat of valve 12.1. Cassette sheeting may create a fluid tight seal for fluid pathways 324, 327A, 327B, 328A, 328B, 337B, 338A, 340 such that fluid in fluid pathways 324, 327A, 327B, 328A, 328B, 337B, 338A, 340 can be confined within each of fluid pathways 324, 327A, 327B, 328A, 328B, 337B, 338A, 340. Mixing cassette 282A may also include a number of fluid ports 290A, 290B, 284A, 286A, 288A. Each of ports 290A, 290B, 284A, 286A, 288A may be connected to fluid lines, or conduits leading to fluid sources 190A/190B/192 or reservoir 182A. Operation of pump chambers 332/336, and valves 7.4, 8.1-8.4, 10.1, and 11.1 may allow fluid to be pumped into or out of mixing cassette 282A through one or more of ports 290A, 290B, 284A, 286A, 288A. Closing all of valves 7.4, 8.1-8.4, 10.1, and 11.1 that are not associated with a desired of fluid pathways 324, 327A, 327B, 328A, 328B, 337B, 338A, 340 to one or more of ports 290A, 290B, 284A, 286A, 288A may allow one or more pump chambers 332/336 to be in exclusive communication with the desired ports 290A, 290B, 284A, 286A, 288A. Depending on how valves 7.4, 8.1-8.4, 10.1, and 11.1 are actuated in relation to the actuation of pump chambers 332/336, fluid may be pumped either in a first direction, or in a second direction. That is, one or more of pump chambers 332/336 may transfer fluid into and out of one or more ports 290A, 290B, 284A, 286A, 288A of mixing cassette 282A such that one or more ports 290A, 290B, 284A, 286A, 288A may behave as inlets and outlets.

Figure 7H:
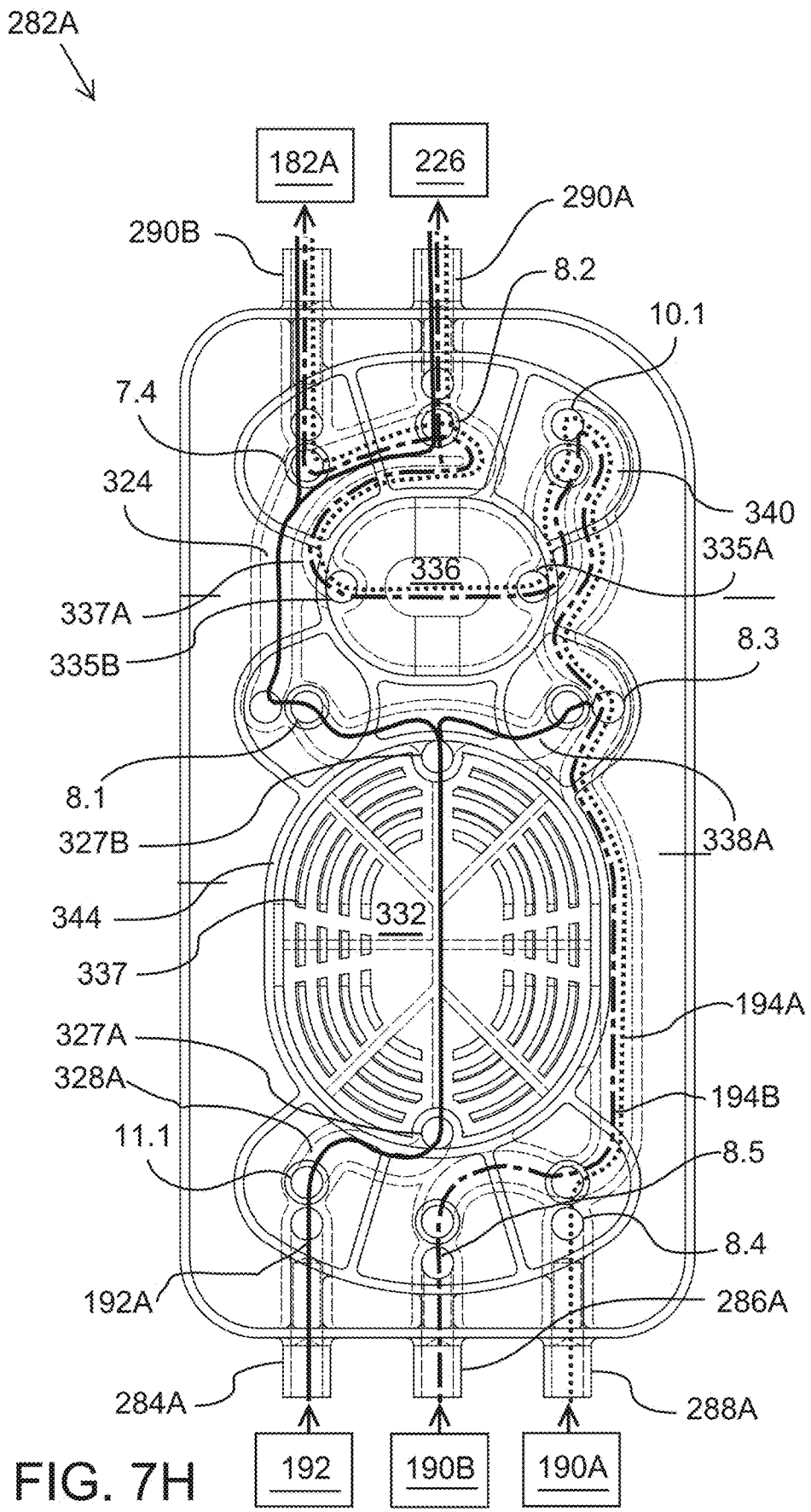
FIGS. 7H-7K are schematic diagrams of the single unit mix cassette of the present teachings.

Continuing to refer primarily to FIG. 7H, among the fluid pathways of mixing cassette 282A may be solution bus 324. Solution bus 324 may be a common bus for solution drawn into mixing cassette 282A through solution ports 286A/288A. Additional ports including, though not limited to, first line port 284A may be included in mixing cassette 282A. These ports may be connected to various fluid lines leading to fluid sources 190A/190B, diluent 192, and reservoir 182A. The diluent may, for example, include purified water in some configurations. Among the fluid pathways of mixing cassette 282A may be first reservoir inlet path 340. First reservoir inlet path 340 may allow fluid to be transferred from first and second ports 286A, 288A through inlet path 340 to pump chamber 336 and through ports 290A/290B. Central bus 338A (though it may be included anywhere on the cassette 282A and not necessarily near the cassette 282A center) may also be included among the flow pathways. Central bus 338A can allow mixing cassette 282A to "wash" pump chamber 336 and other areas of mixing cassette 282A between solutions 190A/190B, or can enable faster pumping of solutions 190A/190B using pump chamber 332, with diluent 192. Mixing cassette 282A may include diluent pump chamber 332 and solution pump chamber 336. In some configurations, mixing cassette 282A may be configured such that either of pump chambers 332, 336 may be placed in fluid communication with any of ports 290A, 290B, 284A, 286A, 288A. While in fluid communication with a desired of ports 290A, 290B, 284A, 286A, 288A, negative pressure may be applied to cassette sheeting (not shown) over one or more pump chambers 332, 336 to fill one or more pump chambers 332, 336 with fluid from fluid source 190A/190B or reservoirs 182A/B (FIG. 7A) connected to one or more of ports 290A, 290B, 284A, 286A, 288A. Positive pressure may be applied to expel fluid within one or more of pump chambers 332, 336 to one or more fluid lines connected to one or more of ports 290A, 290B, 284A, 286A, 288A. Each of pump chambers 332, 336 may be placed in communication with one another. Thus, the flow of fluid from any of ports 290A, 290B, 284A, 286A, 288A through mixing cassette 282A may be controlled by any of pump chambers 332, 336. Only one of pump chambers 332, 336 need be operable to draw fluid into itself. Other of pump chambers 332, 336 may be left inoperable and closed off to flow by closing the appropriate valves.

Referring now to FIGS. 7H-7K, mixing cassette 282A can include chambers 332/336, spacers 4337 (FIG. 7K-3), walls 344 (FIG. 7K-2), valve wells, and ports. Fill and deliver strokes may be performed in a manner which mimics a physiological characteristic or condition of a biological specimen. For example, the fill and deliver strokes may be synchronized in a manner which generates a pulsatile flow of the fluid(s) being pumped. The rate at which fill strokes and deliver strokes are performed may allow for the pulse rate of the flow to be adjusted. Such adjustment may allow a cassette to mimic physiological perfusion of a biological specimen. The pressure used to execute fill and delivery strokes may also be varied. This pressure may be set to a value which causes the pressure of the pumped fluid to mimic physiological perfusion pressures. Fluid pathways for mixing cassette 282A can include diluent path 192A transporting diluent 192 through port 284A, valve 11.1, pump chamber 332, central bus 338A, valve 8.1, solution line bus 324, valves 7.4 and/or 8.2, ports 290A/290B and out to reservoir 182A and/or waste 226. Diluent 192 can also travel from central bus 338A through valve 8.3, reservoir path 340, valve 10.1, pump chamber 336, valves 8.2 and/or 7.4, ports 290A/290B, and out to reservoir 182A and/or waste 226, when fluid paths are washed and/or diluent 192 is added to solutions 190A/190B. Fluid pathways for mixing cassette 282A can include solution path 194A that can transfer solution 190A through port 288A, valves 8.4 and 8.3, reservoir path 340, valve 10.1, pump chamber 336, valves 8.2 and/or 7.1, ports 290A/290B, and out to reservoir 182A and/or waste 226. Fluid pathways for mixing cassette 282A can include solution path 194B that can transfer solution 190B through port 286A, valve 8.5, reservoir path 340, valve 10.1, pump chamber 336, valves 8.2 and/or 7.1, ports 290A/290B, and out to reservoir 182A and/or waste 226. Solutions 190A/190B can be mixed in pump chamber 336.

Continuing to refer to FIGS. 7H-7K, the fluid pathways described herein for placing pump chambers 332, 336 in communication with specific ports 290A, 290B, 284A, 286A, 288A are merely exemplary. More than one pathway can be established by opening and closing of valves of mixing cassette 282A to place one or more of chambers 332, 336 in communication with a desired of ports 290A, 290B, 284A, 286A, 288A. Multiple of chambers 332, 336 may be placed in communication with the same of ports 290A, 290B, 284A, 286A, 288A at the same time. By opening certain valves, all of chambers 332, 336 may, for example, be operated to deliver fluid to first reservoir port 286A. In some configurations, a first line may be connected to a diluent source. Each of solution ports 290A/290B may be connected to a variety of sources 190A/190B which can contain a concentrate or number of concentrates. If the concentrate in source 190A/190B requires reconstitution, one or more of chambers 332, 336 may be placed in communication with first line port 284A and filled with diluent. The diluent may then be expelled from one or more of pump chambers 332, 336 to source 190A/190B through one or more of ports 290A/290B associated with source 190A/190B. In some configurations, one or more of chambers 332, 336 may be operated to pump the partially reconstituted concentrate back and forth between one or more of chambers 332, 336, and source 190A/190B. In some configurations, reconstitution may be performed similar to as described in U.S. Pat. No. 6,726,656, filed Oct. 8, 2002, and entitled System For Controlling Flow Through a Line During Intravenous Drug Delivery, which is incorporated by reference herein in its entirety.

Still further referring primarily to FIGS. 7H-7K, in some configurations, diluent 192 may be pumped via pump chamber 332 from first line port 284A through mixing cassette 282A to one or more of reservoir ports 286A, 288A. Diluent 192 may then proceed through a reservoir inlet line to one or more storage reservoirs 182A. Concentrate fluid from a desired of sources 190A/190B may be pumped via mixing chamber 336 from solution bus 324 to reservoir port 290B. With the concentration of the concentrate in source 190A/190B known, the ratio of diluent to concentrate pumped may be altered such that the fluid mixture delivered to one or more storage reservoirs 182A is at a desired concentration. In some configurations, the ratio of diluent to concentrate may, for example, be one full mixing chamber 336 delivered for every ten full deliveries from pump chamber 332. If a full delivery of pump chamber 332 is five times the volume of a full delivery of solution pump chamber 336, the ratio would be 50:1. For finer control of the ratio, partial deliveries of any of chambers 332, 336 may also be performed. In some configurations, partial deliveries may be done by calculating the volume of fluid transferred between one or more of chambers 332, 336 and one or more of sources 190A/190B and reservoir port 182A as the pump stroke is in progress. When the desired volume of fluid has been pumped, the stroke may be terminated. Such displaced volume accounting as a stroke is in progress may be conducted as described in U.S. patent application Ser. No. 14/732,564, filed Jun. 5, 2015, and entitled Medical Treatment System and Method Using a Plurality of Fluid Lines, which is incorporated by reference herein in its entirety. In some configurations, dilution may be performed within mixing cassette 282A. Two fluids, e.g. a diluent and a concentrated source fluid may be mixed similarly to as described in U.S. Pat. No. 7,461,968, filed Oct. 30, 2003, and entitled System, Device, and Method for Mixing Liquids, which is incorporated by reference herein in its entirety.

Figure 7I:
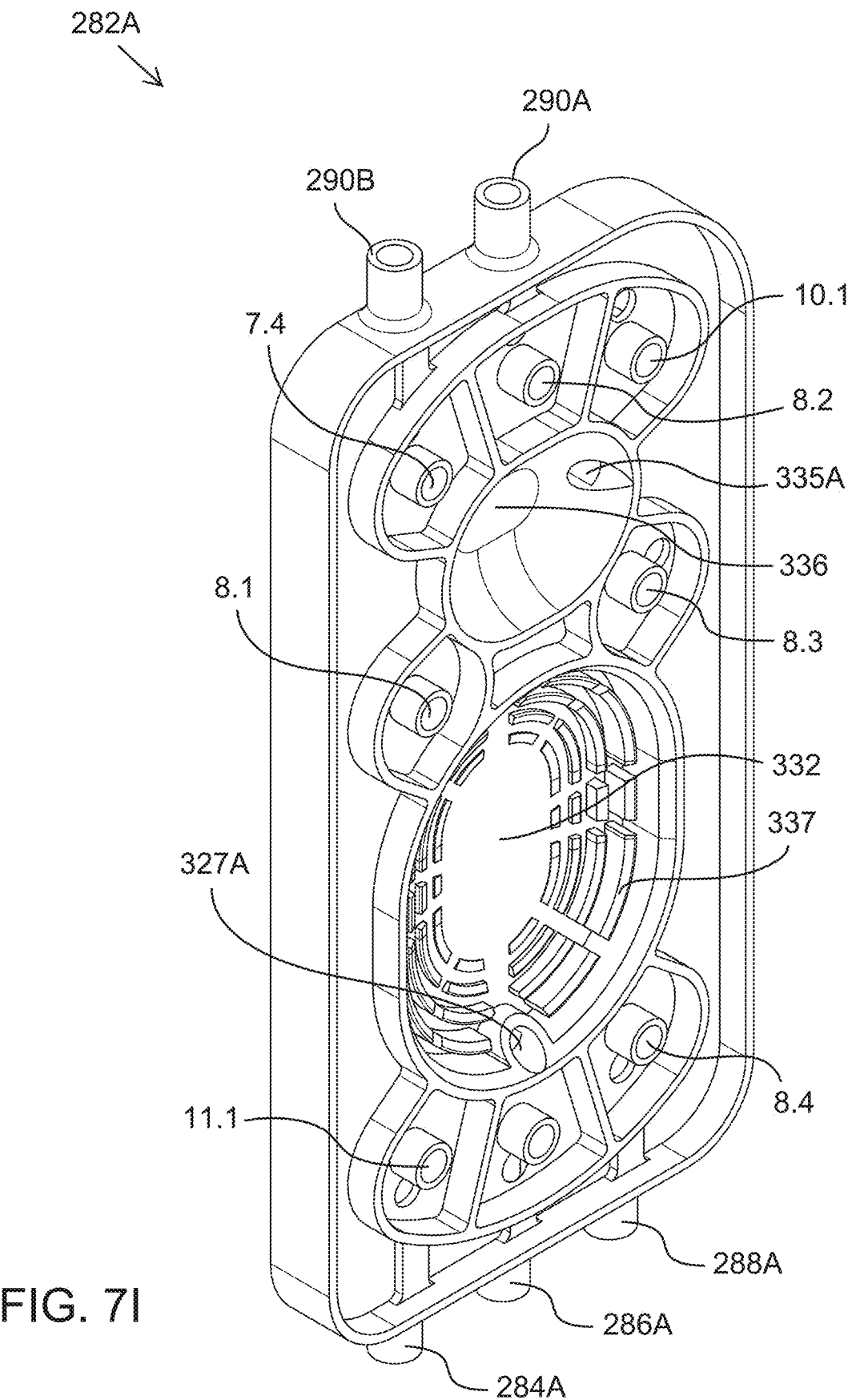
Figures 7J, 7K:
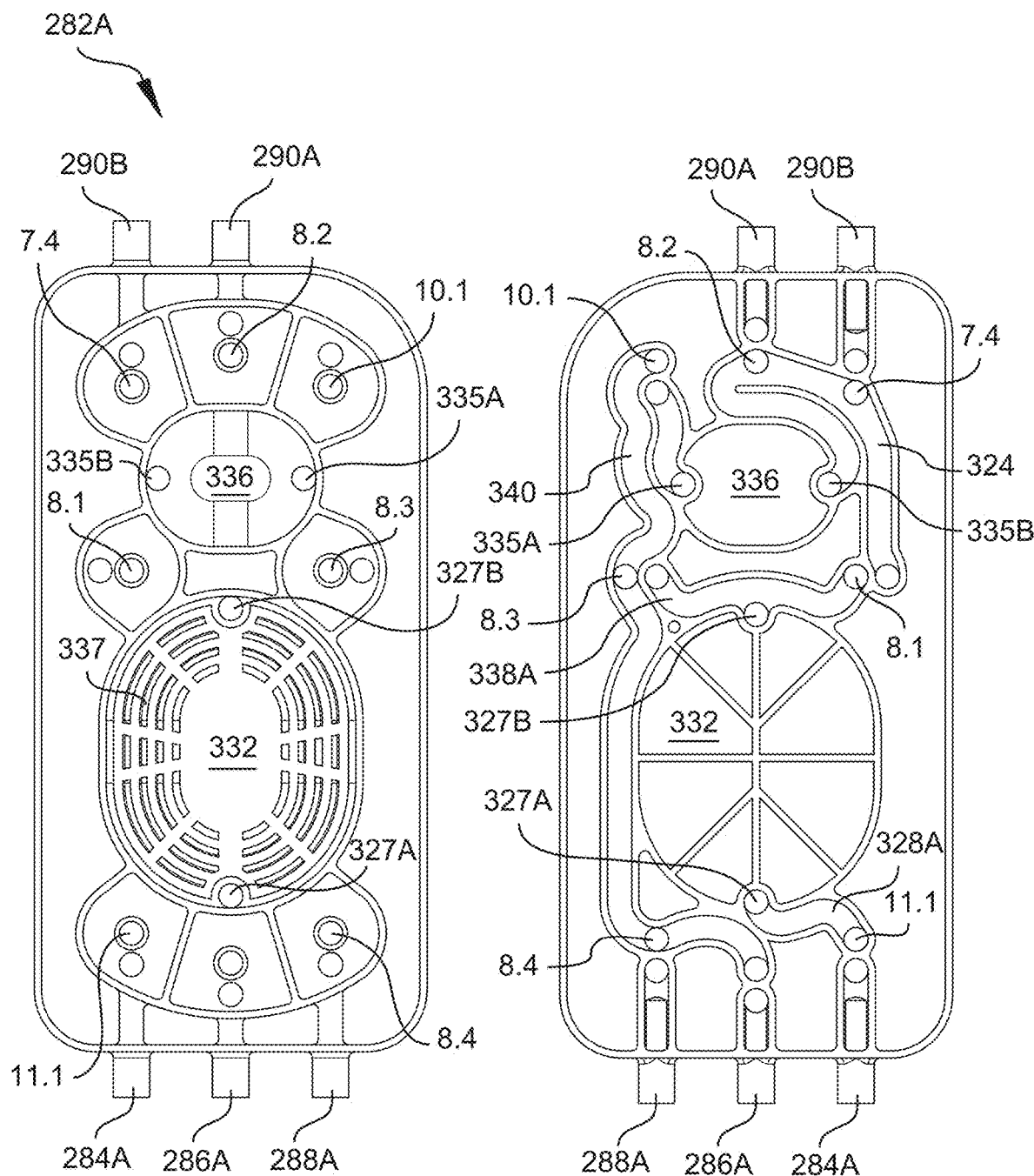
Figures 1, 7K:
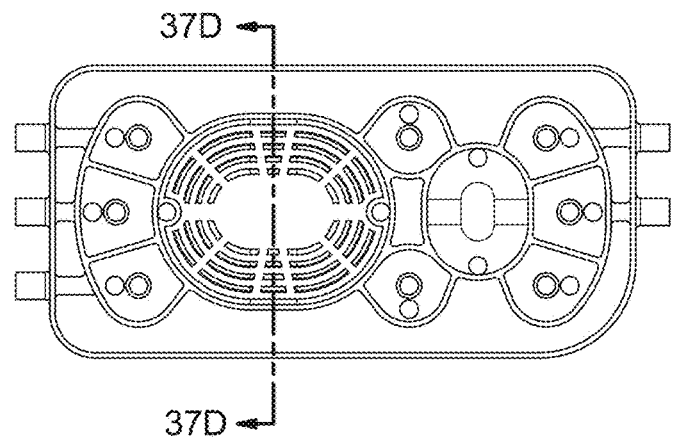
Figures 2, 7K:
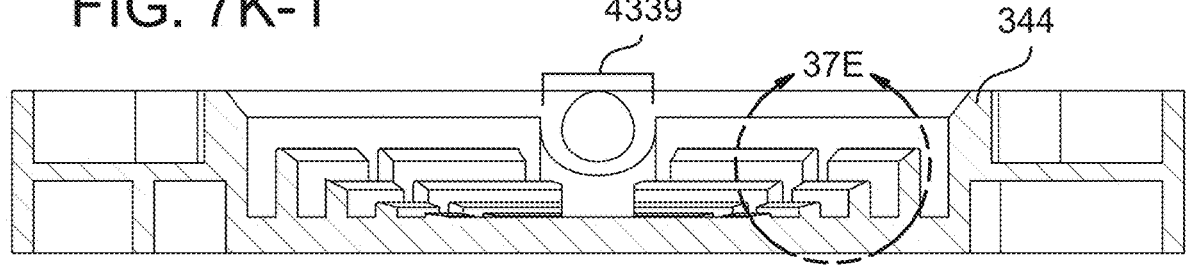
Figures 3, 7K:
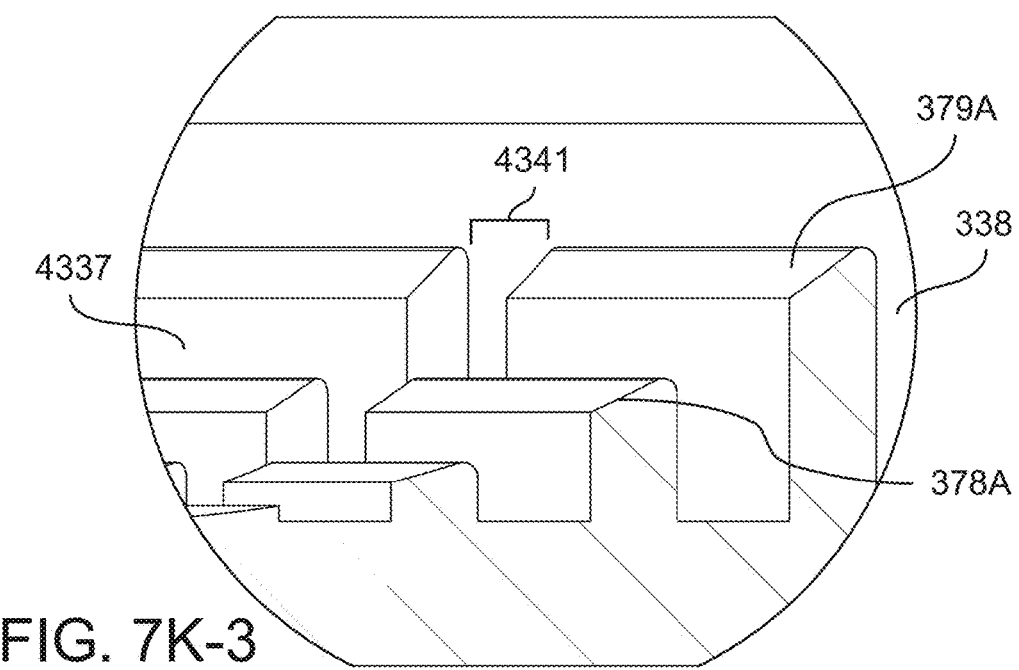

Continuing to still further refer to FIGS. 7H-7K, mixing cassette 282A can include one or more chambers. Each of chambers 332, 336, may be identical or may differ from one another. For example, chamber 336 can have a different design from pump chamber 332. Chamber 336 may be a small volume chamber, e.g. 5-20 ml or in some configurations 10 ml in volume when fully filled. Chamber 332 may or may not be of equal volume and may be larger in volume than chamber 336 when fully filled. In some configurations, chamber 332 may be about 3.5-7 times (e.g. 5 times) larger in volume when fully filled than chamber 336. In some configurations, chamber 332 may be about 40-50 ml (e.g. 50 ml) in volume when fully filled. Each of chambers 332, 336 may be of different or identical geometry. For example, chamber 336 may have a generally circular footprint while chamber 332 can be, for example, but not limited to, ovoid, elliptical, oblong, and stadium shaped. In some configurations, chamber 336 may be at least partially formed as a generally hemispherical or spherical cap like depression in mixing cassette 282A. Chamber 332 may be defined at least partially by flat-bottomed depressions in mixing cassette 282A. One or more of chambers 332, 336 may include spacers 4337 (FIG. 7K-3). For example, chamber 332 may include spacers 4337 (FIG. 7K-3) while chamber 336 can be devoid of spacers 4337 (FIG. 7K-3). Spacers 4337 (FIG. 7K-3) may be similar to those described in U.S. Pat. No. 6,302,653, filed Jul. 20, 1999, and entitled METHODS AND SYSTEMS FOR DETECTING THE PRESENCE OF A GAS IN A PUMP AND PREVENTING A GAS FROM BEING PUMPED FROM A PUMP, and, U.S. patent application Ser. No. 13/667,696, filed Nov. 2, 2012, and entitled MEDICAL TREATMENT SYSTEM AND METHODS USING A PLURALITY OF FLUID LINES, both of which are incorporated herein by reference in their entireties.

Referring now to FIGS. 7K-1 through 7K-3, each chamber 332, 336 (FIG. 7H) may have pressure applied in a different manner such as, for example, but not limited to, mechanically, with a control fluid, or with different control fluids. In some configurations, pressure may be applied to chambers 332, 336 (FIG. 7H) in a different manner than it is applied to sheeting over valve seats 347 (FIG. 7I). For example, the pressure may be applied to chambers 332, 336 (FIG. 7H) with a control fluid while sheeting may be mechanically pressed against valve seats 347 (FIG. 7I). Cross sectional views of an example mixing cassette 282A (FIG. 7J) taken at lines 37D-37D (FIG. 7K-1) are shown. In some configurations, depressions in chambers 332, 336 (FIG. 7H) may be defined by chamber depression faces 338 (FIG. 7K-3). Spacers 4337 (FIG. 7K-3) may be omitted from at least one chamber 332, 336 (FIG. 7H) of mixing cassette 282A (FIG. 7K). Chamber 336 (FIG. 7H), for example, may be defined by a relatively featureless or bald depression face 338 (FIG. 7K-3).

Referring now primarily to FIG. 7K-3 (which is an enlarged view of region 37E in FIG. 7K-2), depression face 338 (FIG. 7K-1) of chamber 332 (FIG. 7H) can include spacers 4337 which can project away from depression face 338. Spacers 4337 may extend, for example, but not limited to, in a manner substantially perpendicular from depression face 338 or in a manner parallel to walls 344 (FIG. 7K-2) of mixing cassette 282A (FIG. 7H). Spacers 4337 can be spaced, for example, but not limited to, an equal distance apart from one another. The height of spacers 4337 may be equal or may progressively increase or decrease in size within chambers 332, 336 (FIG. 7H). In one configuration, spacers 4337 can be arranged in a kind of "stadium seating" arrangement such that spacers 4337 can be arranged in a concentric elliptical pattern with ends of spacers 4337 increasing in height from one portion of depression face 338 to another to form a semi-elliptical domed shaped region. Spacers 4337 may have, for example, but not limited to, top face 379A that is, for example, but not limited to, flat or sloped. Edges 378A of top face 379A may be, for example, but not limited to, beveled, rounded, or chamfered. Top face 379A of each spacer 4337 may serve as a contact face for cassette sheeting when cassette sheeting travels into chamber 332 (FIG. 7H). Spacers 4337 may at least partially define the shape or curvature of cassette sheeting at an excursion into chamber 332 (FIG. 7H).

Continuing to refer primarily to FIG. 7K-3, by preventing contact of cassette sheeting with depression face 338, spacers 4337 can provide a dead space (or trap volume or tidal volume) which can trap an undesired fluid such as air or other gas in chamber 332 (FIG. 7H) during pumping. The trap volume may aid in inhibiting undesired fluid from being pumped out of chamber 332 (FIG. 7H) unless desired. Also, spacers 4337 can prevent cassette sheeting from sticking to depression faces 338. In addition, spacers 4337 can prevent cassette sheeting from contacting chamber inlet/outlets 335A, 335B, 327A, 327B (FIG. 7H). Spacers 4337 may also be arranged so as to allow undesired fluid to move toward a location of chamber 332 (FIG. 7H) where it may be easily discharged to, for example, but not limited to, waste port 290A (FIG. 7H) or other location. Discharging fluid may be accomplished, for example, by providing fluidic communication between spacers 4337 such that fluid may pass between spacers 4337 near depression face 338. When spacers 4337 are positioned in a "stadium seating" arrangement, "aisles" or breaks 4339 (FIG. 7K-2), 4341 in the elliptical pattern, for example, can be included. Density of the fluids may be leveraged to aid in moving fluid toward a discharge point. For example, mixing cassette 282A (FIG. 7H) may be used in a prescribed orientation. Aisles 4339 (FIG. 7K-2), 4341 and the discharge point (e.g. one of ports 327A, 327B, 335A, 335B (FIG. 7H)) may be arranged such that the undesired fluid may sink or rise to the discharge point based density properties. If, for example, the undesired fluid is air, the air may automatically rise toward the highest point in chamber 332. Aisles 4339 (FIG. 7K-2), 4341 may be positioned to facilitate this and the discharge point may be disposed at or near that location. In some configurations, cassette sheeting may have spacer elements or other features, such as, for example, but not limited to, ribs, bumps, tabs, grooves, and channels, in addition to, or in place of spacers 4337.

Figure 7L:
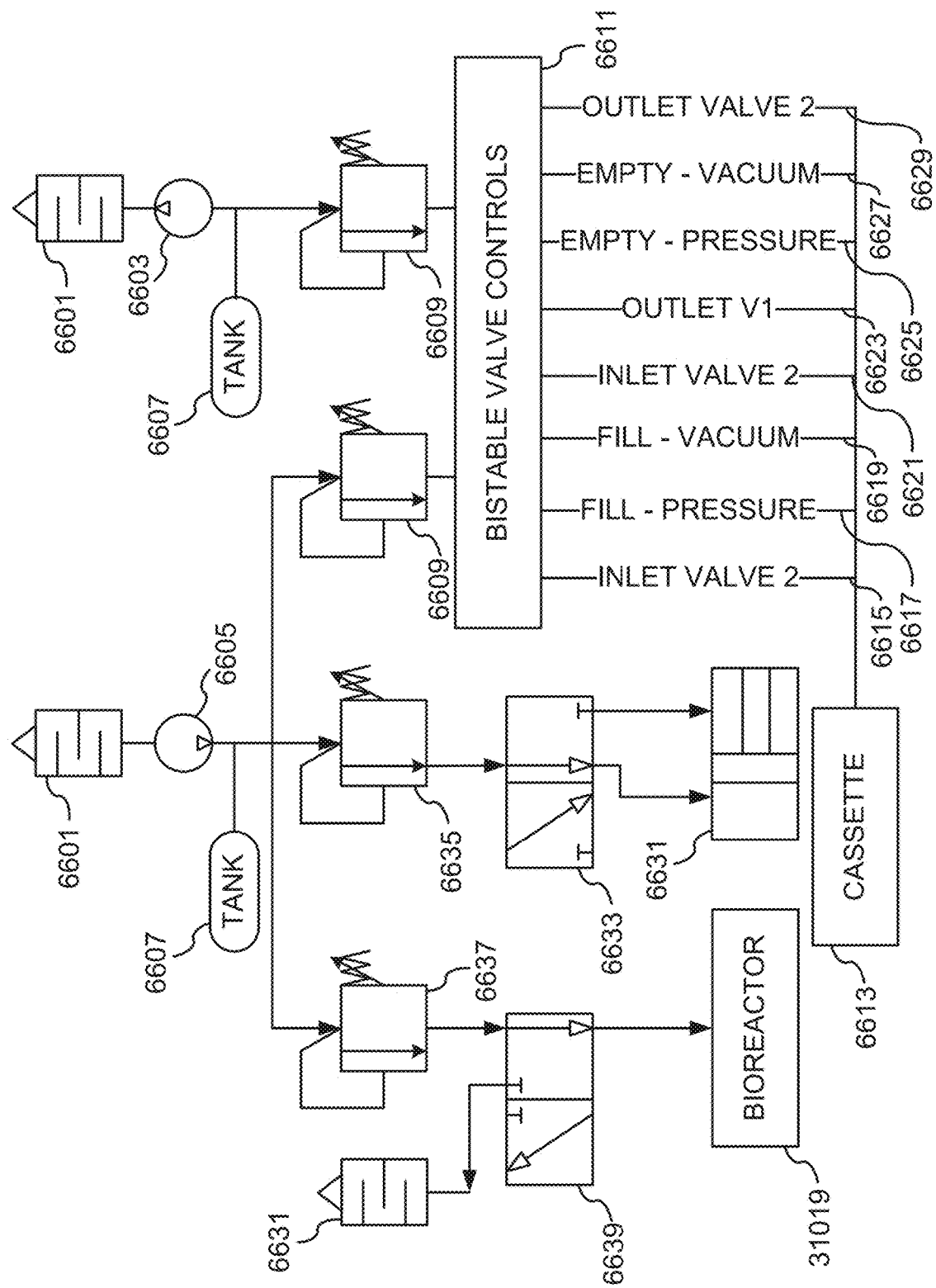
FIG. 7L is a schematic block diagram of a tissue exerciser system of the present teachings.

Referring now to FIG. 7L, an exerciser system can be used to simulate various activities that a tissue structure could experience, and can be used to stimulate the tissue structure. Media can flow into and out of pumping cassette 6613 and bioreactor 31019. When the path between cassette 6613 and bioreactor 31019 is occluded, hydrostatic force, applied to the tissue structure within bioreactor 31019, can exercise the tissue structure. Vacuum pump 6603, for example, a 5 psi vacuum pump, can act in conjunction with air compressor 6605, for example, a 120 psi air compressor, to activate valves that are onboard cassette 6613 and that are under the control of bistable valve controls 6611. Tank 6607 can retain excess vacuum as it exits cassette 6613 during evacuation caused by vacuum pump 6603. Evacuated air can flow to the atmosphere, and the noise of flow can be reduced by muffler 6601. Regulators 6609 can prevent excessive positive and negative pressures on valve controls 6611. Cassette 6613 can include first inlet valve 6615, second inlet valve 6621, first outlet valve 6623, and second outlet valve 6629 that can accommodate moving fluid to/from bioreactor 6613 and to/from media storage. Air cylinder 6631 can occlude the path between cassette 6613 and bioreactor 31019 when 3-port, 2-position valve 6633 is in the first position, moving air from air compressor 6605 through regulator 6635 to the upper chamber of the air cylinder. Exerciser valve 6639 can provide the hydrostatic pressure, for example, 73 psi, necessary to stimulate the tissue structure within bioreactor 31019. Exerciser valve 6639 can include three ports and two positions. The first port can provide an input air channel from air compressor 6605 through regulator 6637 to exerciser 6639. The second port can provide an output air channel from exerciser 6639 to bioreactor 31019. The third port can provide an output air channel for excess air from exerciser 6639 to the ambient environment through muffler 6601. Valves can control fill and empty pressures 6617/6625, and fill and empty vacuums 6619/6627. In prior art configurations, the process for growing tissue can include receiving a biopsy, expanding the cells from the biopsy, and fabricating materials such as cells, collagen bio-ink, and an acellular scaffold. The method can further include preparing a scaffold by placing bio-ink on the outside of scaffold, allowing time for the bio-ink to infiltrate the scaffold, and filling the media bag. The method can include exercising the scaffold by moving the scaffold to a tissue enclosure and placing the tissue enclosure in a standard incubator for seven days, giving the tissue enclosure 73 psi pulses using hydrostatic pressure. The method can include incubating the scaffold by moving the scaffold and surrogates to a shaker flask tin in a low oxygen incubator and allowing about five weeks of incubation in the shaker flask which has a shelf life of about five days. The method can include release testing and transporting the tissue, and resetting the system by re-sterilizing the tissue enclosure for the next scaffold, increasing the risk of contamination risk. An improved process for growing tissue can include, but is not limited to including, receiving a biopsy, expanding the cells in the biopsy, fabricating materials as described herein, and seeding the scaffold with the expanded cells. The method can include exercising the scaffold by transferring the scaffold to a disposable tissue enclosure and transferring the disposable tissue enclosure to a tissue enclosure rack. The method can include incubating the scaffold in the tissue enclosure rack and awaiting an automatic switch to low oxygen no-pulse mode when the tissue is ready. The method can include release testing and transporting the grown cells using a tubing sealer and a cassette sealer to turn tissue enclosure section of the disposable components into a shipping container, and shipping the grown tissue without delay. The method can include resetting the system by disposing of the remainder of disposable components. The tissue enclosure rack is ready for the next scaffold immediately. The improved process can lower labor requirements, require less time to move scaffolds and less time to analyze scaffold surrogates, and requires no time to re-sterilizing. The improved process allows fewer opportunities for human error/contamination, and has lower space and scalability cost requirements. There no time wasted in the improved process waiting for release tests.

Figure 7M:
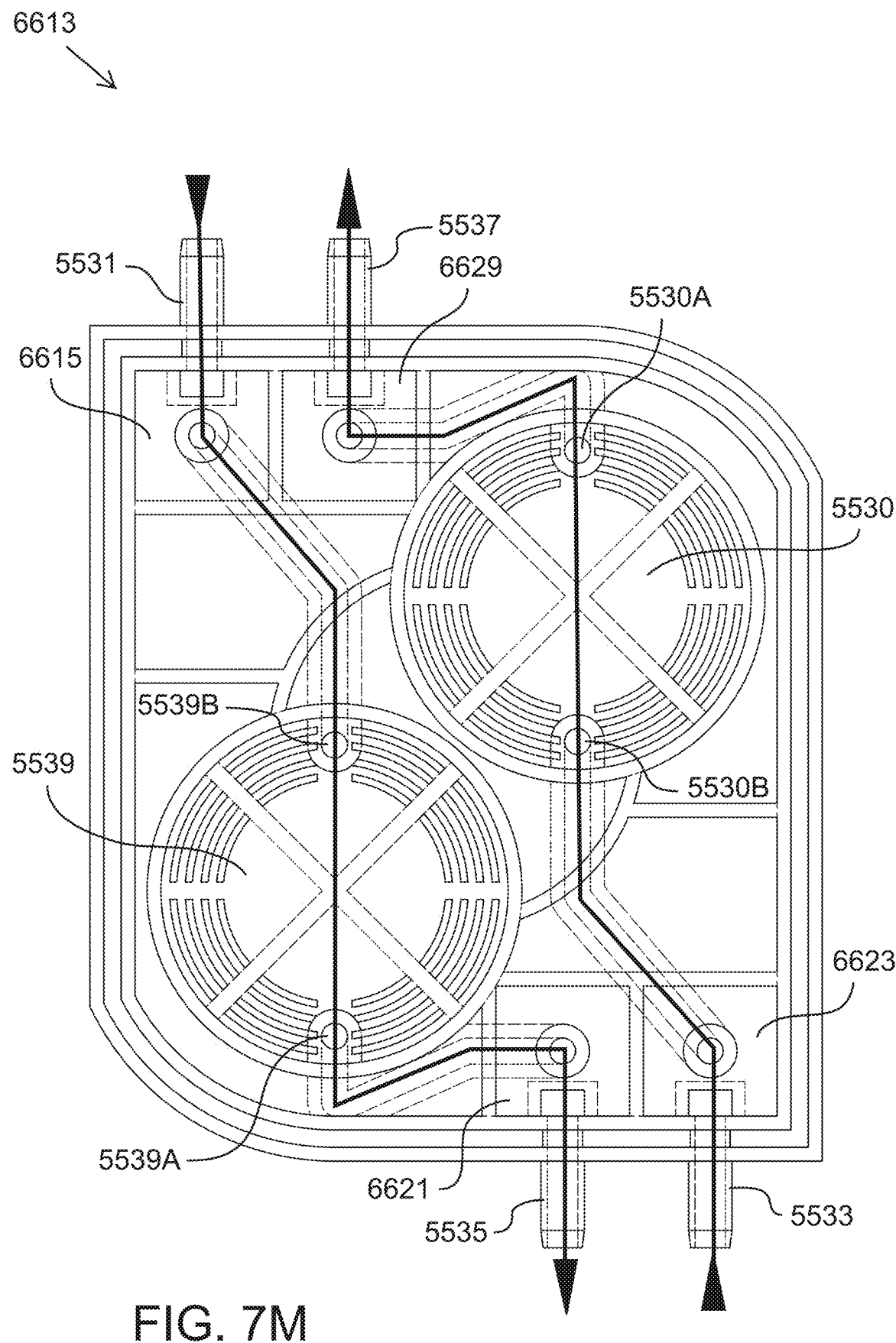
FIG. 7M is a schematic diagram of the pumping cassette of the present teachings.

Referring now to FIG. 7M, pump cassette 6613 can include first inlet valve 6615 that can receive fluid from media storage through first media port 5531. Fluid can travel through first inlet valve 6615 through first inlet pumping chamber valve 5539B and enter inlet pumping chamber

5539. A membrane across inlet pumping chamber 5539 can allow fluid to be received into inlet pumping chamber 5539, and can be depressed to expel fluid from inlet pumping chamber 5539 through second inlet pumping chamber valve 5539A and second inlet valve 6621 to first bioreactor port 5535. First outlet valve 6623 can receive fluid from tissue enclosure 31019 through second bioreactor port 5533. Fluid can travel through first outlet valve 6623 and first outlet pumping chamber valve 5530B and enter outlet pumping chamber 5530. A membrane across outlet pumping chamber 5530 can allow fluid to be received into outlet pumping chamber 5530, and can be depressed to expel fluid from outlet pumping chamber 5530 through second outlet pumping chamber valve 5530A and second outlet valve 6629 to second media port 5537. The valves can be controlled by bistable valve controls 6616 (FIG. 7K). Pump cassette 6613 can be sterilized by, for example, but not limited to, an Ethylene Oxide (EtO) sterilization process.

Figure 8A:
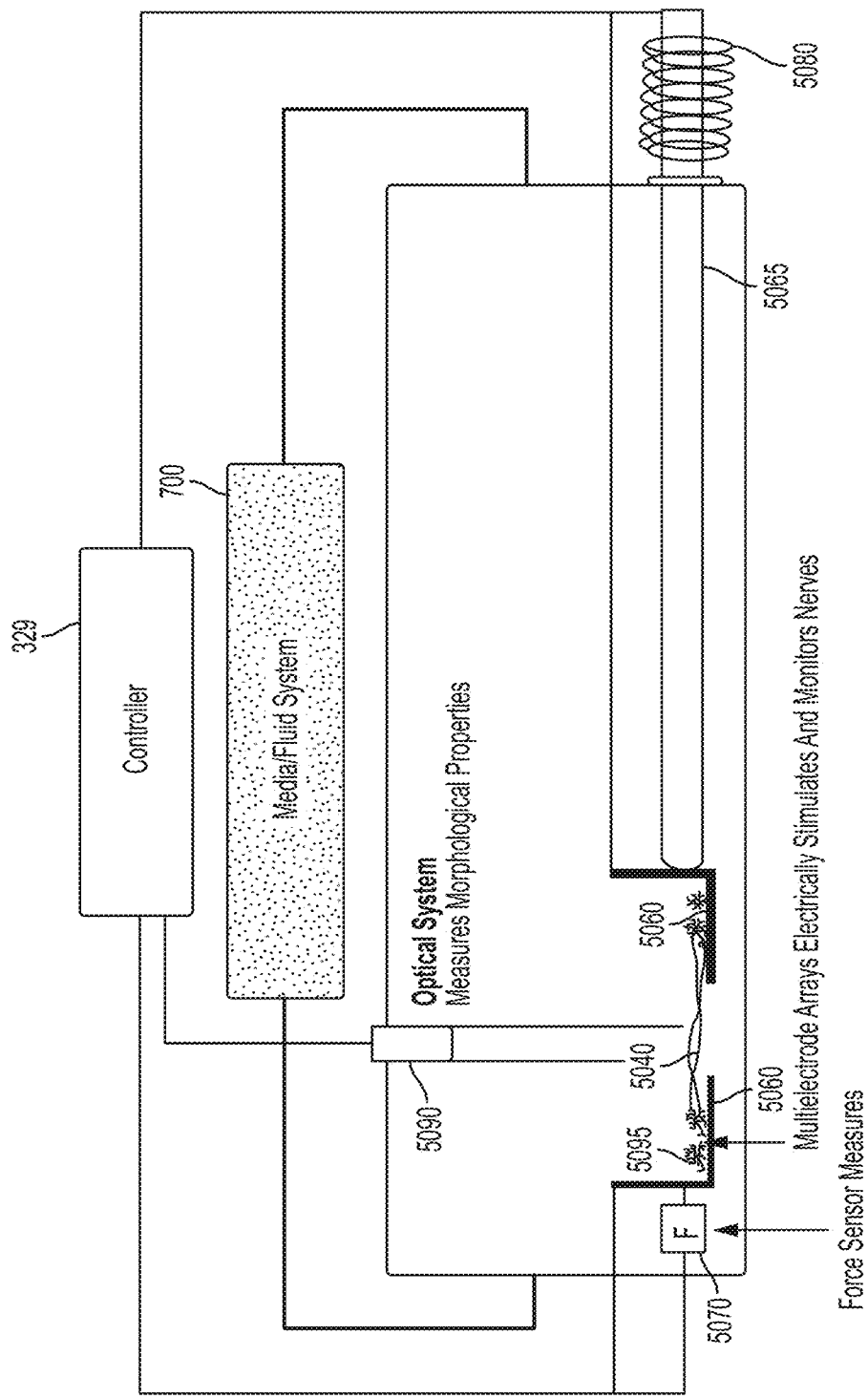
FIG. 8A is a schematic block diagram of the nerve growth system of the present teachings.

Referring now to FIGS. 8A and 8B, the nervous system has an extremely limited capacity to regrow axons and restore lost connections. System 500 (FIG. 1A) can include accommodations for growing transplantable nerve tracks, including, but not limited to, stimulation and monitoring mechanisms. System 500 (FIG. 1A) can create tissue-engineering nerve grafts by providing the microenvironment and mechanical loading that can enable axonal stretch growth in the tissue-engineered nerve grafts. Sleds 5060 can include monitoring and stimulation mechanisms. System 500 (FIG. 1A) can direct loading and stimulation based on the received information about the status of nerve populations 5040. At least one sled 5060 can be positioned in build subsystem 513 (FIG. 1A) and nerve populations 5040 can be attached to sleds 5060. Attachment can occur when nerve populations 5040 are printed according to system 500 (FIG. 1A). Controller 329 can direct sleds 5060 to draw apart to stretch nerve populations 5040. Sleds 5060 can include electromagnetically driven shafts 5065 to control movement of sleds 5060. Controller 329 can direct sleds 5060 to move shafts 5065 to reach a pre-selected stretch growth rate without tearing nerve populations 5040. Load cells 5070 attached to sleds 5060 can monitor the force exerted on each nerve population 5040 and can adjust the current to electromagnet 5080 to stretch nerve populations 5040 at a desired rate. Monitoring devices such as, for example, but not limited to, optical sensors 5090 and multielectrode arrays 5095, can monitor nerve populations 5040, evaluate when nerve populations 5040 have reached maturity, detect any indicators of potential damage during stretching, and stimulate nerve populations 5040. The extracellular concentration of nutrients, metabolic wastes, and ions can be controlled by system 500 (FIG. 1A) to promote nerve viability, growth, and excitability. Data from the monitoring devices of the present teachings can be continuously evaluated, and actuators can be automatically controlled to achieve the maximum stretch growth rate while minimizing the risk of breaking and/or disconnecting nerve populations 5040.

Figure 9A:
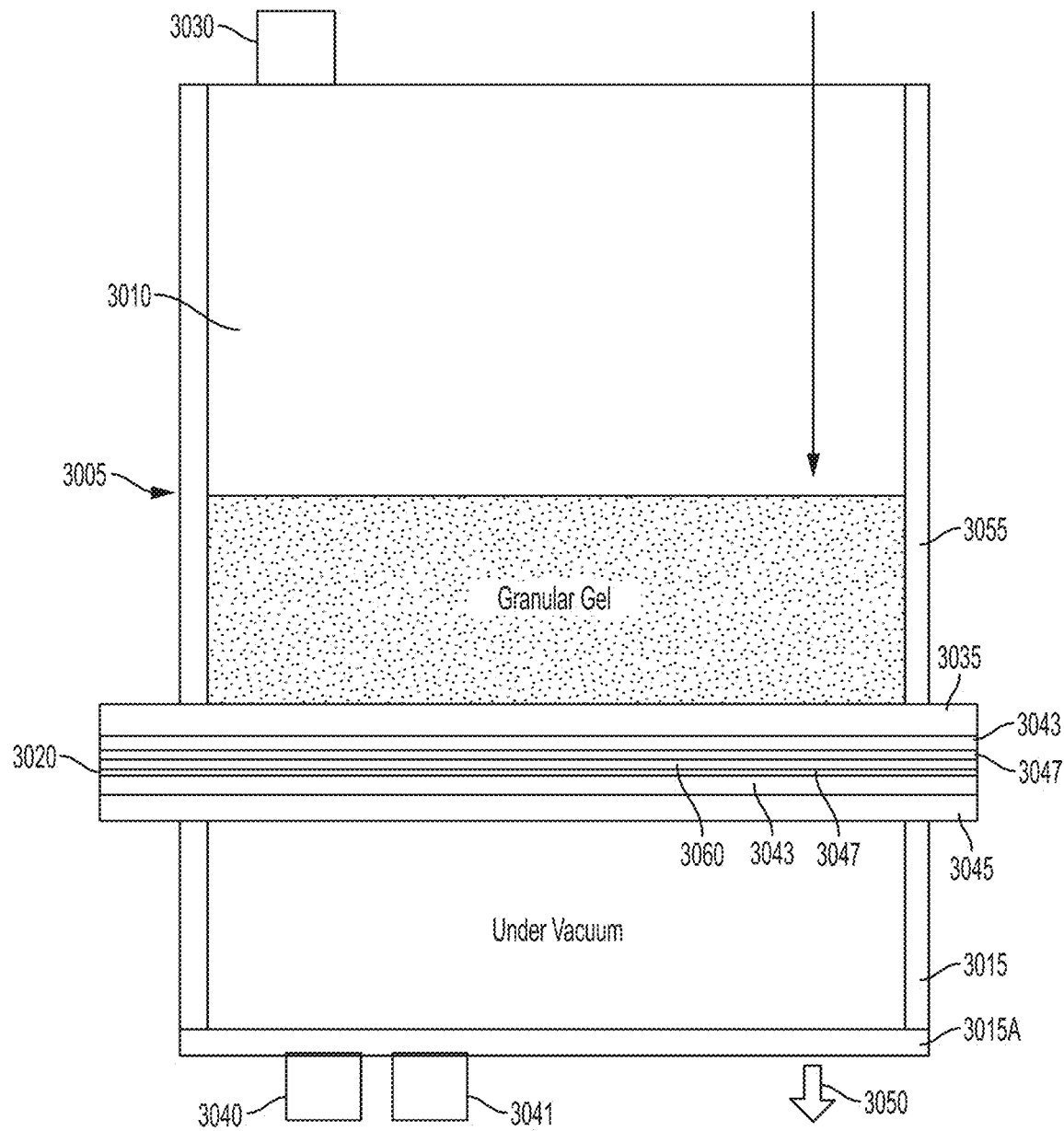
FIG. 9A is a pictorial representation of the first configuration of the bioreactor of the present teachings.
Figure 9B:
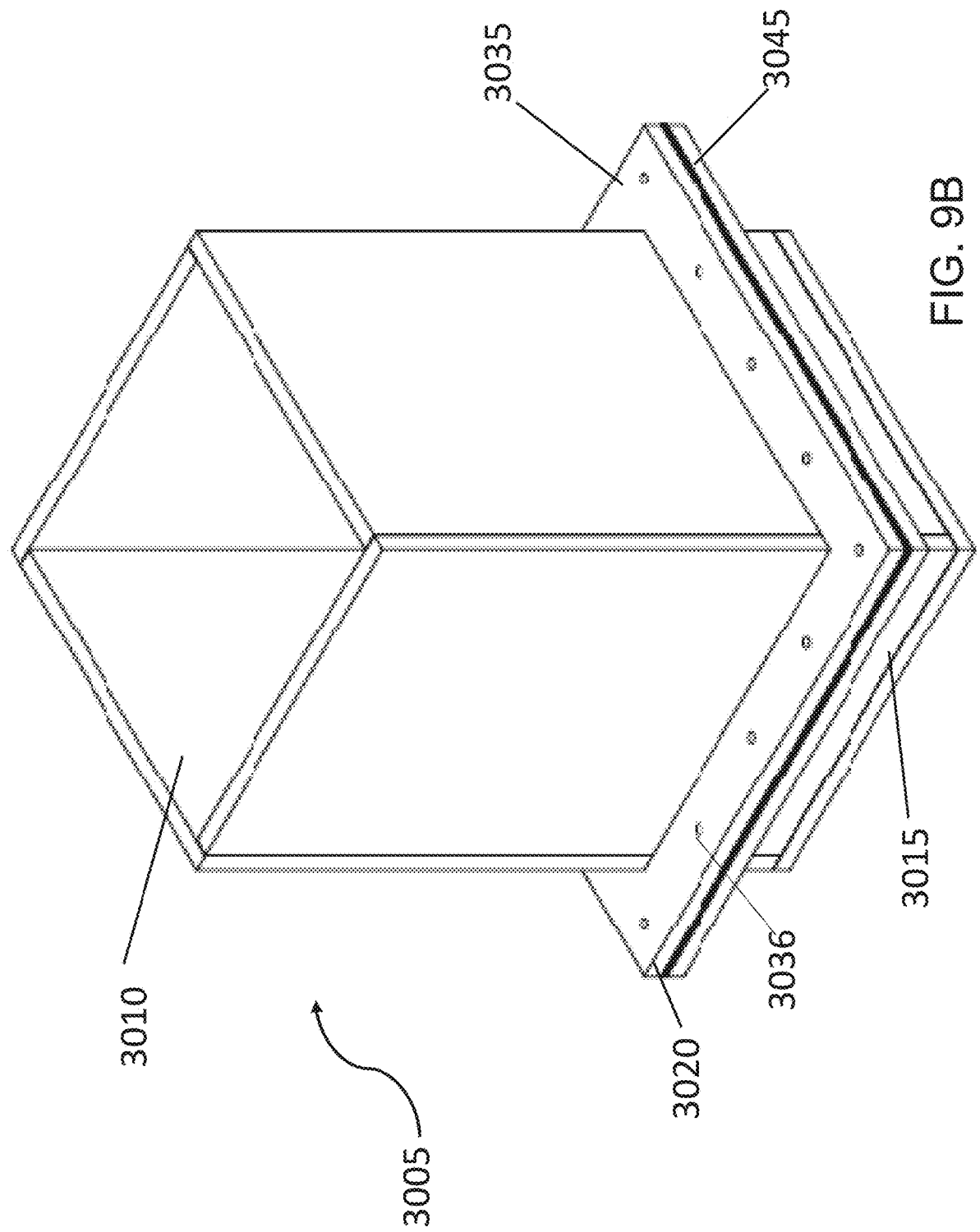
FIG. 9B is a perspective schematic view of the first configuration of the bioreactor of the present teachings.
Figure 9C:
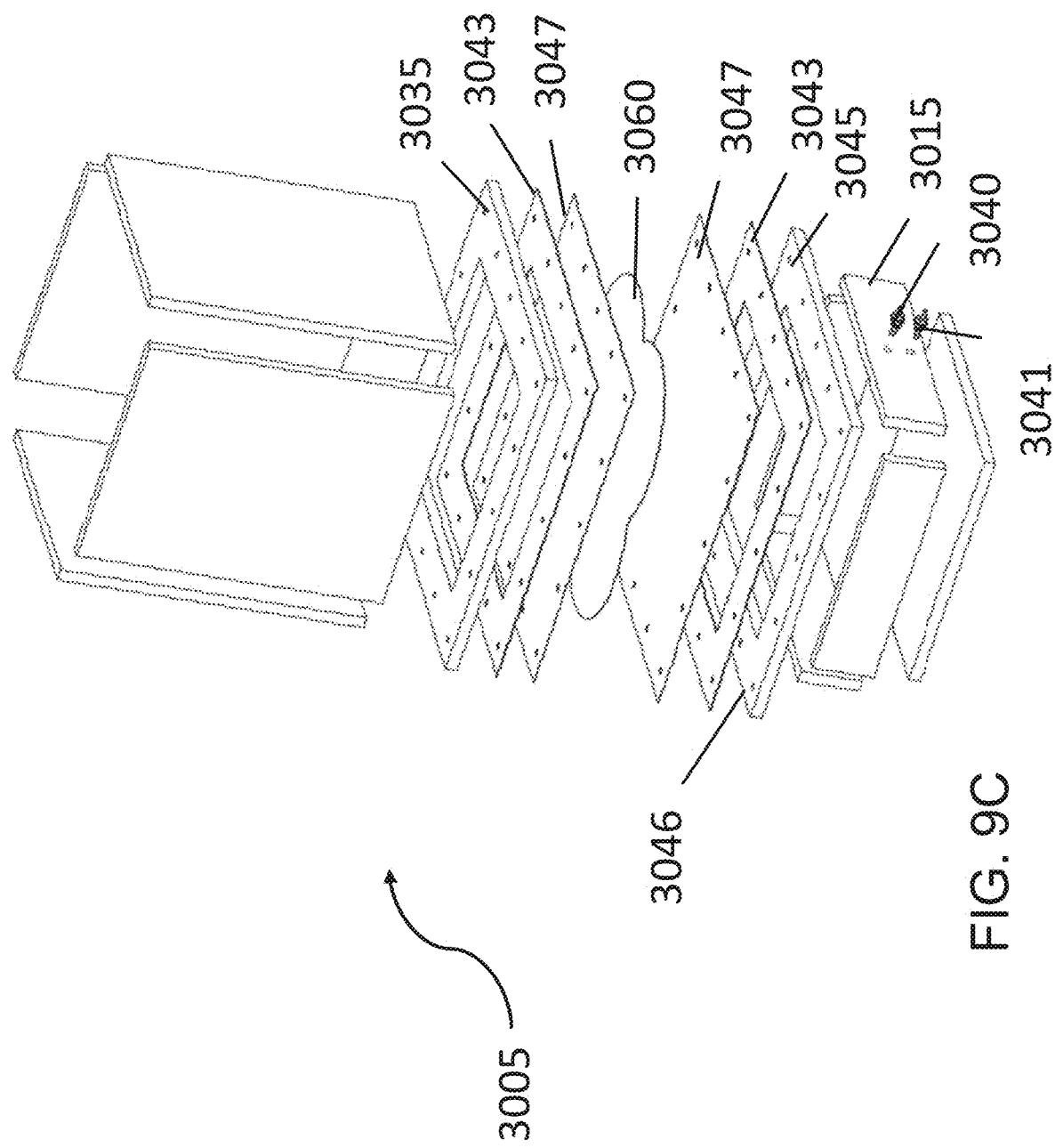
FIG. 9C is a schematic perspective exploded view of the first configuration of the bioreactor of the present teachings.

Referring to FIGS. 9A-9C, first configuration tissue enclosure 3005 can include, but is not limited to including, at least two sections—an incoming chamber 3010 and an effluent chamber 3015—that can enable substantially vertical flow through first configuration tissue enclosure 3005. The two chambers can be further separated by a filtration zone 3020, and can be surrounded by container structure 3015A. Incoming chamber 3010 can include a container including a biologically inert material, such as, but not limited to, a metal or a non-metal including an engineering plastic. In some configurations, incoming chamber 3010 can comprise at least one fluid inlet 3030 (FIG. 9A) configured to serve as an entrance of fluid into incoming chamber 3010. In some configurations, incoming chamber 3010 can be open to the atmosphere and to incoming fluid. Incoming chamber 3010 can interface with effluent chamber 3015 through filtration zone 3020 disposed there between. An engagement means can connect incoming chamber 3010 to filtration zone 3055 (FIG. 9A), and effluent chamber 3015 to filtration zone 3055. The engagement means can include, but is not limited to including, first flange 3035 disposed inseparably with the incoming chamber 3010. First flange 3035 can further comprise a plurality of holes 3036 (FIG. 9B).

Continuing to refer to FIGS. 9A-9C, effluent chamber 3015 can be constructed from a biologically inert material, such as but not limited to a metal, or a non-metal including an engineering plastic. Effluent chamber 3015 can further comprise at least one fluid outlet 3040 wherefrom fluid in effluent chamber 3015 can exit. In some embodiments, effluent chamber 3015 can include a vacuum outlet 3041 (FIG. 9A). Effluent chamber 3015 can further include a complementing engagement means to interact with incoming chamber 3010 through filtration zone 3020 disposed there between. Complementing engagement means in the present configuration can include a second flange 3045 operably coupled with effluent chamber 3015. Complementing flange 3045 can further comprise a plurality of holes 3046 (FIG. 9B) to achieve above mentioned engagement.

Continuing to refer to FIGS. 9A-9C, a pressure differential can be created between incoming chamber 3010 and effluent chamber 3015. Vacuum outlet 3041 provided on effluent chamber 3015 can be used to create the pressure differential. One of the many ways of creating the pressure difference can include opening the incoming chamber 3010 to the atmosphere while maintaining effluent chamber 3015 at a negative pressure.

Continuing to refer to FIGS. 9A-9C, a water swellable polymer in a semi-solid form, therefore termed as a gel throughout this description, can partially or completely occupy a portion of incoming chamber 3010. The portion of incoming chamber 3010 that can comprise the gel can be termed as gel layer 3055 of incoming chamber 3010. Gel layer 3055 can maintain cells or tissues in a particular shape in a controlled and hygienic environment. Gel layer 3055 and all its constituents, such as but not limited to, tissues or cells and their excreta and soaked fluid, and disassociation agents, can be supported by filtration zone 3020.

Continuing to refer to FIGS. 9A-9C, filtration zone 3020 can comprise at least one filter 3060 (FIG. 9A) of a pre-selected pore size, for example, but not limited to 1.2 microns. A pre-selected number of filters 3060 (FIG. 9A) can be sandwiched between a supporting mesh 3047 (FIG. 9A) that can be disposed parallel to filters 3060 (FIG. 9A). Sealing frames 3043 (FIG. 9A) can be parallel to and surround supporting mesh 3047. Filtration zone 3020 can include a five layered assembly, comprising, but not limited to, sealing frame 3043 (FIG. 9A), supporting mesh 3047 (FIG. 9A)—filter 3060 (FIG. 9A)—supporting mesh 3047 (FIG. 9A)—sealing frame 3043 (FIG. 9A). Supporting mesh 3047 (FIG. 9A), filter 3060 (FIG. 9A), and sealing frame 3043 (FIG. 9A) can comprise a plurality of holes that can be consonant with a pre-defined pitch and size of first flange plurality of holes 3036 (FIG. 9B) provided on first flange 3035 and second flange plurality of holes 3046 (FIG. 9C) provided on second flange 3045. Filtration zone 3020 can be disposed between incoming chamber 3010 and effluent chamber 3015 by providing fasteners through the plurality of holes, or in any other manner. Differential pressure between incoming chamber 3010 and effluent chamber 3015, can cause fluid, monomers and/or molecules to flow from incoming chamber 3010 through gel layer 3055 and through filtration zone 3020 to effluent chamber 3015, and possibly out 3050.

Figure 9D:
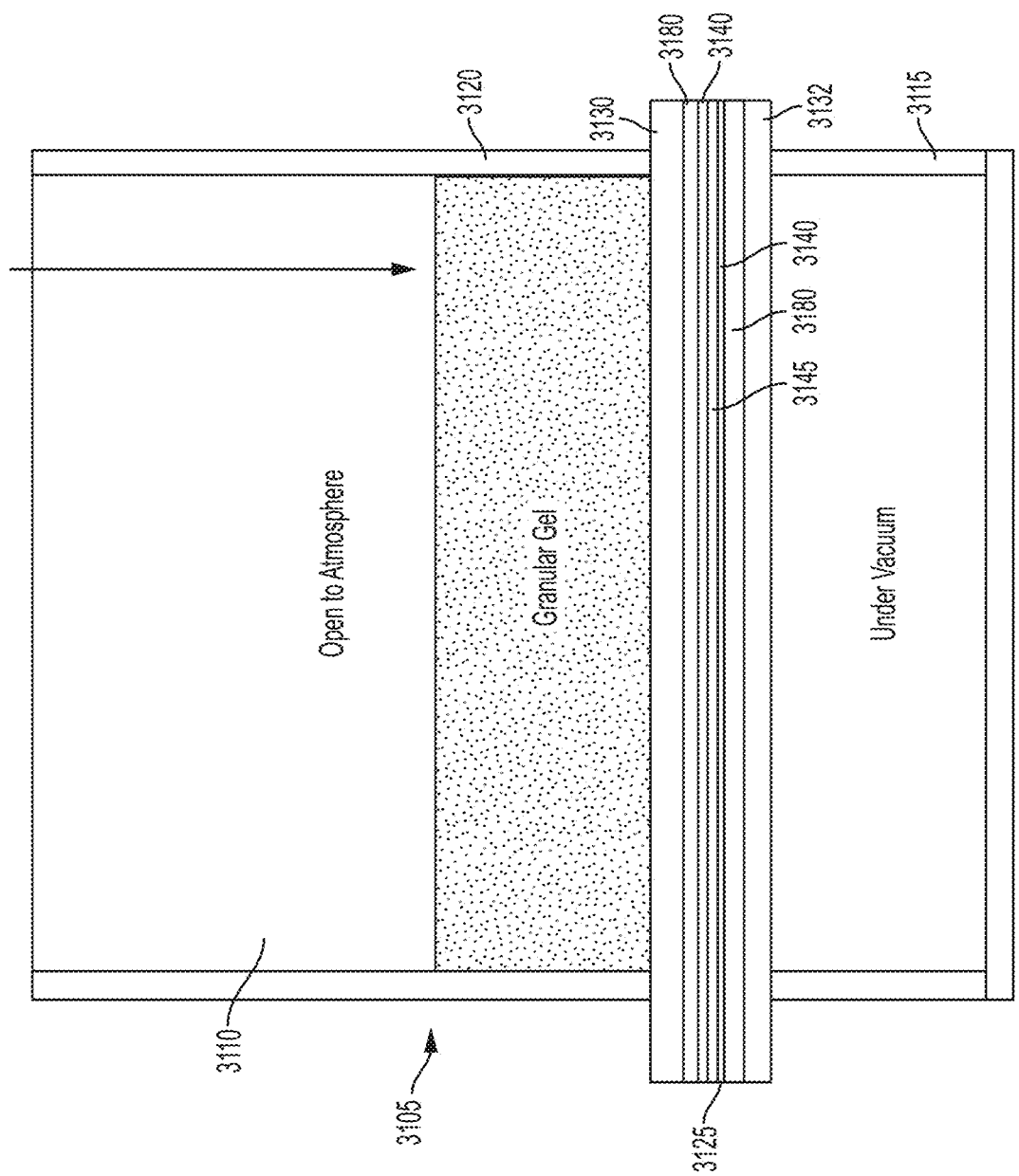
FIG. 9D is a pictorial representation of the second configuration of the bioreactor of the present teachings.
Figure 9E:
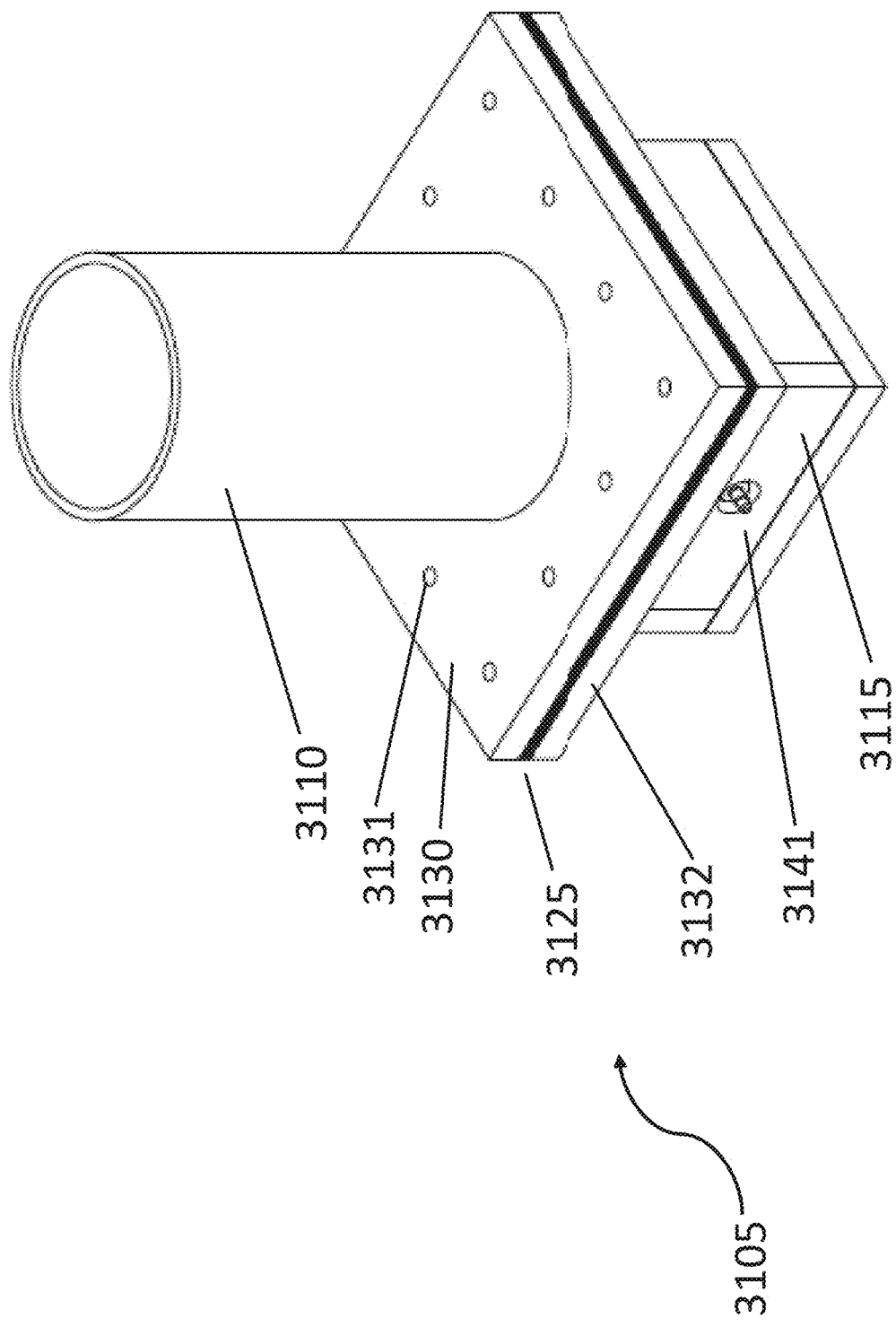
FIG. 9E is a perspective schematic view of the second configuration of the bioreactor of the present teachings.

Referring now to FIGS. 9D-9G, second configuration tissue enclosure 3105 can comprise at least two sections—an incoming chamber 3110 and an effluent chamber 3115—that can be separated by at least one filtration zone 3125. Incoming chamber 3110 can include a container made of, but not limited to a biologically inert material, that can include metal or non-metal, for example, but not limited to, an engineering plastic. In some configurations, incoming chamber 3110 can include a fluid inlet (not shown) through which a fluid can enter the incoming chamber 3110 and can flow substantially vertically through second configuration tissue enclosure 3105. In some configurations, incoming chamber 3110 can include a chamber open to the atmosphere and to incoming fluid. Incoming chamber 3110 can include an engagement means between incoming chamber 3110 and an effluent chamber 3115 with filtration zone 3125 disposed there-between. In some configurations, the engagement means can include first flange 3130 operably coupling incoming chamber 3110. First flange 3130 can include a plurality of engagement holes 3131 (FIG. 9E).

Continuing to refer to FIGS. 9D-9G, effluent chamber 3115, likewise can be constructed of a biologically inert material, which can be, but not limited to, a metal, or a non-metal including an engineering plastic. Effluent chamber 3115 can further comprise at least one fluid outlet 3140 (FIG. 9F) wherefrom the fluid can leave the effluent chamber 3115. Effluent chamber 3115 can include a vacuum outlet 3141 (FIG. 9E). The effluent chamber 3115 can further comprise a complementing engagement means to engage with incoming chamber 3110 with the filtration zone 3125 disposed there-between. The engagement means can include complementing flange 3132 operably coupled with effluent chamber 3115. Complementing flange 3132 can further comprise plurality of holes (not shown).

Continuing to refer to FIG. 9D-9G, a pressure differential can be created between the incoming chamber 3110 and effluent chamber 3115. In some configurations, incoming chamber 3110 can be open to the atmosphere while the effluent chamber 3115 can be maintained at a negative pressure by way of a vacuum pump (not shown) that can be disposed along a downstream of second configuration tissue enclosure 3105, thereby creating a negative pressure differential between incoming chamber 3110 and effluent chamber 3115. Vacuum outlet 3141 (FIG. 9E) can be used to create negative pressure differential. A water swellable polymer in a semi-solid form, therefore termed as a gel throughout this description, can partially or completely occupy a portion of incoming chamber 3110. Portion of incoming chamber 3110 that can comprise the gel, can be termed as gel layer 3120 of incoming chamber 3110. Gel layer 3120 can maintain the position of the cells or tissues in a controlled and hygienic environment in second configuration tissue enclosure 3105 for their sustenance and growth. Gel layer 3120 and all its constituents, such as but not limited to, tissues or cells and their excreta and soaked fluid, disassociation agents, can be supported by filtration zone 3125. A mass of the gel and all its constituents, namely tissues or cells their excreta and soaked fluid, etc. can be restricted within incoming chamber 3110 by filtration zone 3125 that can be in turn supported by support structure 3127.

Figure 9F:
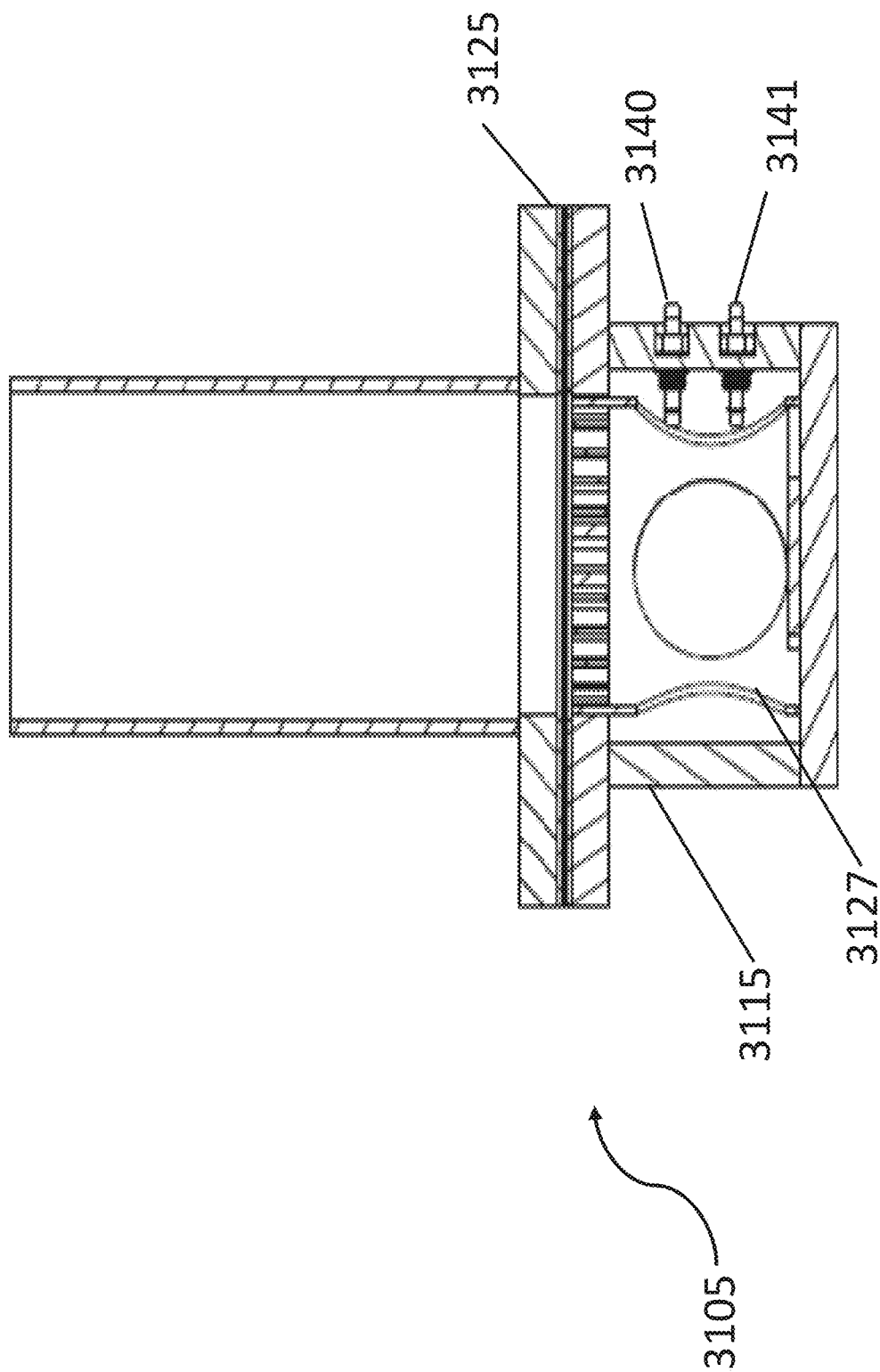
FIG. 9F is a schematic cross section view of the second configuration of the bioreactor of the present teachings.

Continuing to refer to FIG. 9D-9F, filtration zone 3125 in this configuration can comprise a plurality of filters 3145 of prescribed pore sizes. Filters 3145 can be sandwiched between supporting mesh 3140, disposed on either side and by sealing frame 3180. Thus, the filtration zone 3125 of current configuration can be a five layered assembly, comprising sealing frame 3180—supporting mesh 3140—plurality of filters 3145—supporting mesh 3140—sealing frame 3180. Such five-layered assembly can further comprise a plurality of holes around its periphery, consonant with a pre-defined pitch and size of the plurality of holes that can be provided on first flange 3130 of incoming chamber 3110 and second flange 3132 of effluent chamber 3115. The filtration zone 3125 can be disposed between incoming chamber 3110 and effluent chamber 3115, by providing fasteners through plurality of holes, or in any other manner. Presence of a differential pressure can cause the fluid to flow from incoming chamber 3110 via gel layer 3120 and through filtration zone 3125 and finally through thin walled tunnels 3160 of support structure 3127, to effluent chamber 3115.

Referring now to FIGS. 9F and 9G, support structure 3127 can include a plurality of thin walled tunnels 3160 (FIG. 9G) that can stretch along a length 3170 (FIG. 9G) of support structure 3127. In some configurations, the plurality of thinned walled tunnels 3160 (FIG. 9G) can occupy a part 3165 (FIG. 9G) of a height of the support structure 3127. Support structure 3127 can include a plurality of reinforcing ribs 3175 (FIG. 9G) that can span the diameter of support structure 3127. Support structure 3127 can be sized in height 3170 (FIG. 7D) to support, at first end 3190, filtration zone 3125 (FIG. 9G). An opening 3185 (FIG. 9G) of the first end 3190 can include a surface area that can exceed the surface area of plurality of filters 3145. Support structure 3127 can have a funnel construction (not shown) at first end 3190.

Figure 9H:
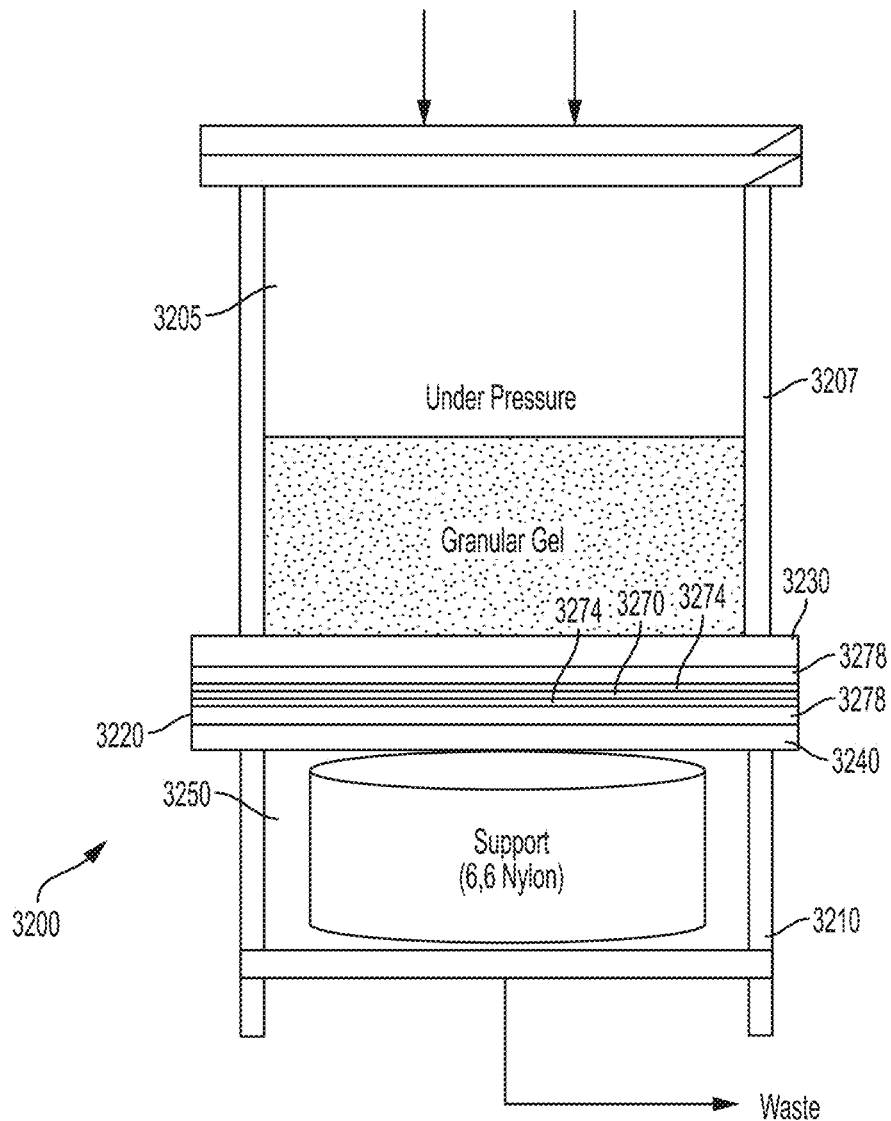
FIG. 9H is a pictorial representation of the third configuration of the bioreactor of the present teachings.
Figure 9I:
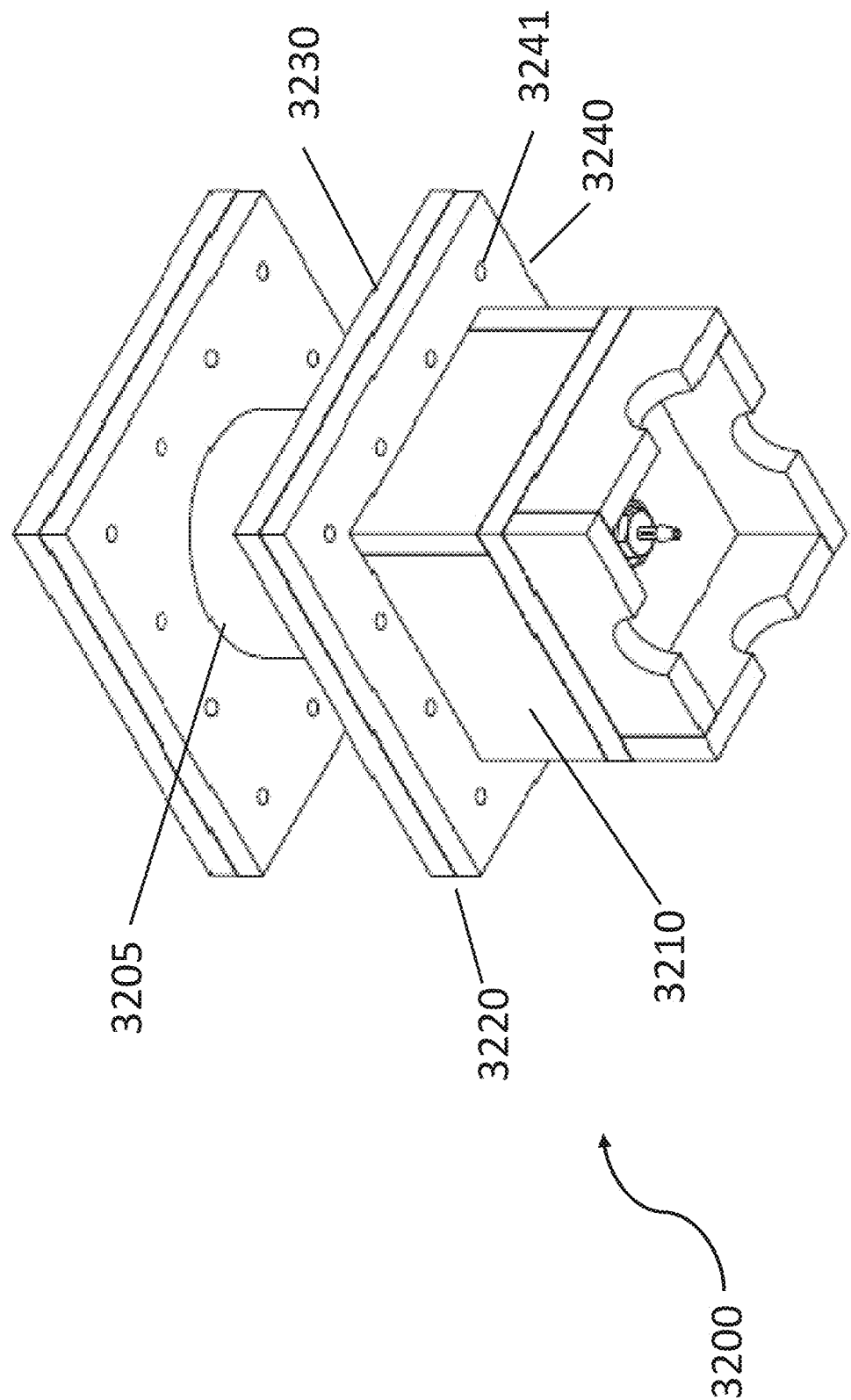
FIG. 9I is a perspective schematic view of the third configuration of the bioreactor of the present teachings.
Figure 9J:
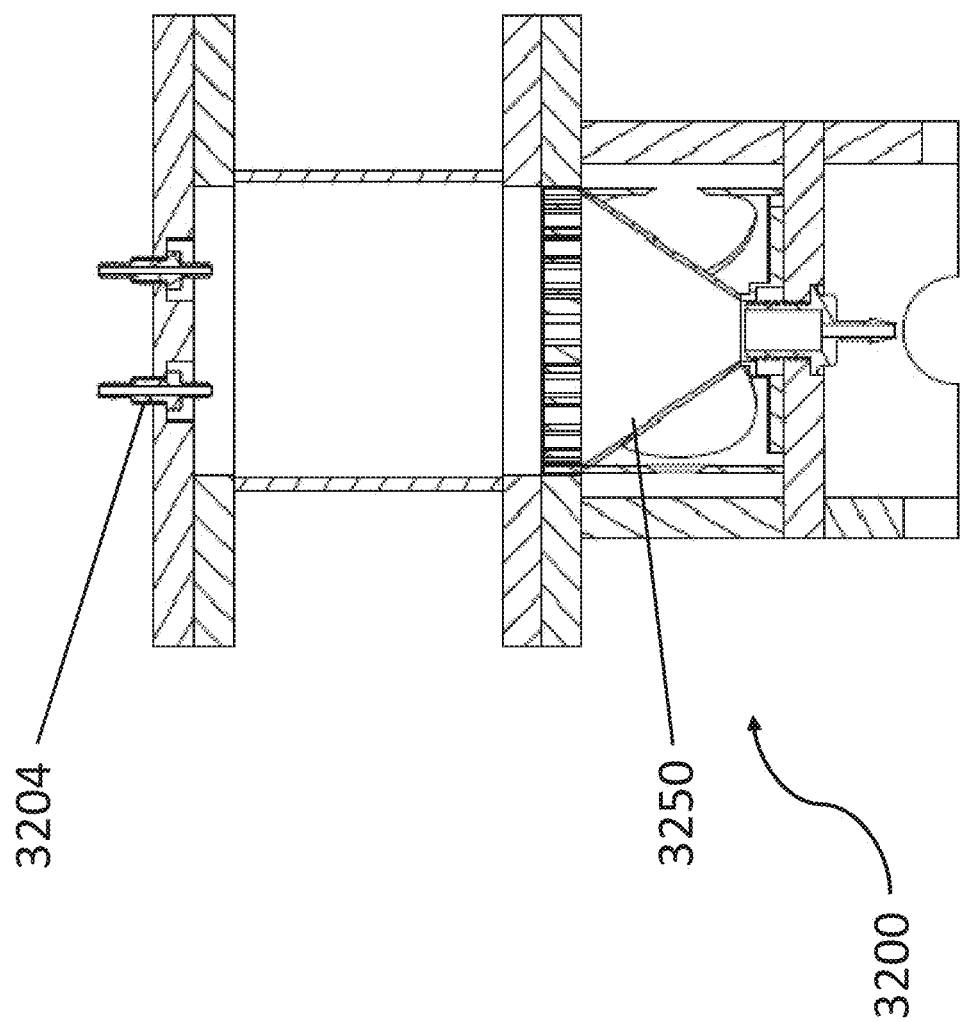
FIG. 9J is a schematic cross section view of the third configuration of the bioreactor of the present teachings.

Referring now to FIGS. 9H-9L, third configuration tissue enclosure 3200 can comprise at least two sections—an incoming chamber 3205 and an effluent chamber 3210 that can enable vertical fluid flow between them. The two chambers can be further separated by a filtration zone 3220. The incoming chamber 3205 can include a container that can include a biologically inert material, such as but not limited to, a metal or a non-metal including an engineering plastic. The incoming chamber 3205 can further comprise at least one fluid inlet (not shown) configured to serve as an entrance for fluid into incoming chamber 3205. Incoming chamber 3205 can include a pressure inlet 3204 (FIG. 9J). Incoming chamber 3205 can interface effluent chamber 3210 through filtration zone 3220 disposed there between through an engagement means. The engagement means in the present configuration can be a first flange 3230 operably coupled with incoming chamber 3205. First flange 3230 can further comprise a plurality of holes Continuing to refer to FIGS. 9H-9L, effluent chamber 3210, likewise can include a biologically inert material, that can include, but is not limited to including, a metal, or a non-metal including an engineering plastic. Effluent chamber 3210 can further comprise at least one fluid outlet that can allow fluid to exit effluent chamber 3210. Effluent chamber 3210 can further comprise a complementing engagement means to engage with incoming chamber 3205 with filtration zone 3220 disposed there between. This engagement means of present configuration can be a second flange 3240 disposed inseparably with effluent chamber 3210. Second flange 3240 can further comprise a plurality of holes 3241 (FIG. 9I). There can be further disposed a support structure 3250 in effluent chamber 3210.

Continuing to refer to FIGS. 9H-9L, a pressure difference can be created between incoming chamber 3205 and effluent chamber 3210. In some configurations, incoming chamber 3205 can be pressurized by a fluid pressure pump (not shown), using pressure inlet 3204 (FIG. 9J), along an upstream side of third configuration tissue enclosure 3200 while effluent chamber 3210 can remain at atmospheric pressure, or the effluent chamber 3210 can be at a negative pressure, thereby creating a positive pressure differential between incoming chamber 3205 and effluent chamber 3210, or both. A water swellable polymer in a semi-solid form can partially or completely occupy a portion of incoming chamber 3205. Portion of incoming chamber 3205 that can comprise above mentioned gel, can be termed as gel layer 3207 (FIG. 9H) of incoming chamber 3205. Gel layer 3207 (FIG. 9H) can maintain and aid in reproducing cells or tissues in a controlled and hygienic environment for their sustenance and growth. Gel layer 3207 and all its constituents, such as but not limited to, tissues or cells and their excreta and soaked fluid, disassociation agents, can be supported by filtration zone 3220. A mass of the gel and all its constituents, namely tissues or cells, their excreta and soaked fluid, etc. can be restricted into the incoming chamber 3205 by filtration zone 3220 and supported by support structure 3250. In some configurations, filtration zone 3220 can comprise a plurality of filters 3270 (FIG. 3) of pre-selected pore sizes. At least one filter 3270 (FIG. 9H) can be sandwiched between supporting meshes 3274 (FIG. 9H), disposed laterally upon at least one filter 3270 (FIG. 9H). Sealing frames 3278 (FIG. 9H) can sandwich supporting meshes 3274 (FIG. 9H), disposed laterally upon supporting meshes 3274 (FIG. 9H). In some configurations, filtration zone 3220 can include a five layered assembly, comprising sealing frame 3278 (FIG. 9H)—supporting mesh 3274 (FIG. 9H)—plurality of filters 3270 (FIG. 9H)—supporting mesh 3274 (FIG. 9H)—sealing frame 3278 (FIG. 9H). In some configurations, hydrogel can be laterally disposed between gel layer 3207 (FIG. 9H) and sealing frame 3278 (FIG. 9H). In some configurations, filtration zone 3220 (FIG. 9H) can include sealing frame 3278 (FIG. 9H)—supporting mesh 3274 (FIG. 9H)—sealing frame 3278 (FIG. 9H), with or without at least one filter 3270 (FIG. 9H).

Continuing to refer to FIGS. 9H-9L, supporting mesh 3274 (FIG. 9H), filter 3270 (FIG. 9H) and sealing frame 3278 (FIG. 9H) can comprise a plurality of holes, consonant with a pre-selected pitch and size of plurality of holes 3241 (FIG. 9I) that can be provided on first flange 3230 of incoming chamber 3205 and second flange 3240 of effluent chamber 3210. Filtration zone 3220 can be disposed between incoming chamber 3205 and effluent chamber 3210. When the differential pressure is created between the incoming chamber 3205 and the effluent chamber 3210, the fluid can follow a flow path from incoming chamber 3205 via gel layer 3207 and through filtration zone 3220 and finally through the thin walled tunnels of the support structure 3250, to the effluent chamber 3210 and thus exit the third configuration tissue enclosure 3200. Third configuration tissue enclosure 3200 can optionally include a dialysis system as described in '237.

Figure 9L:
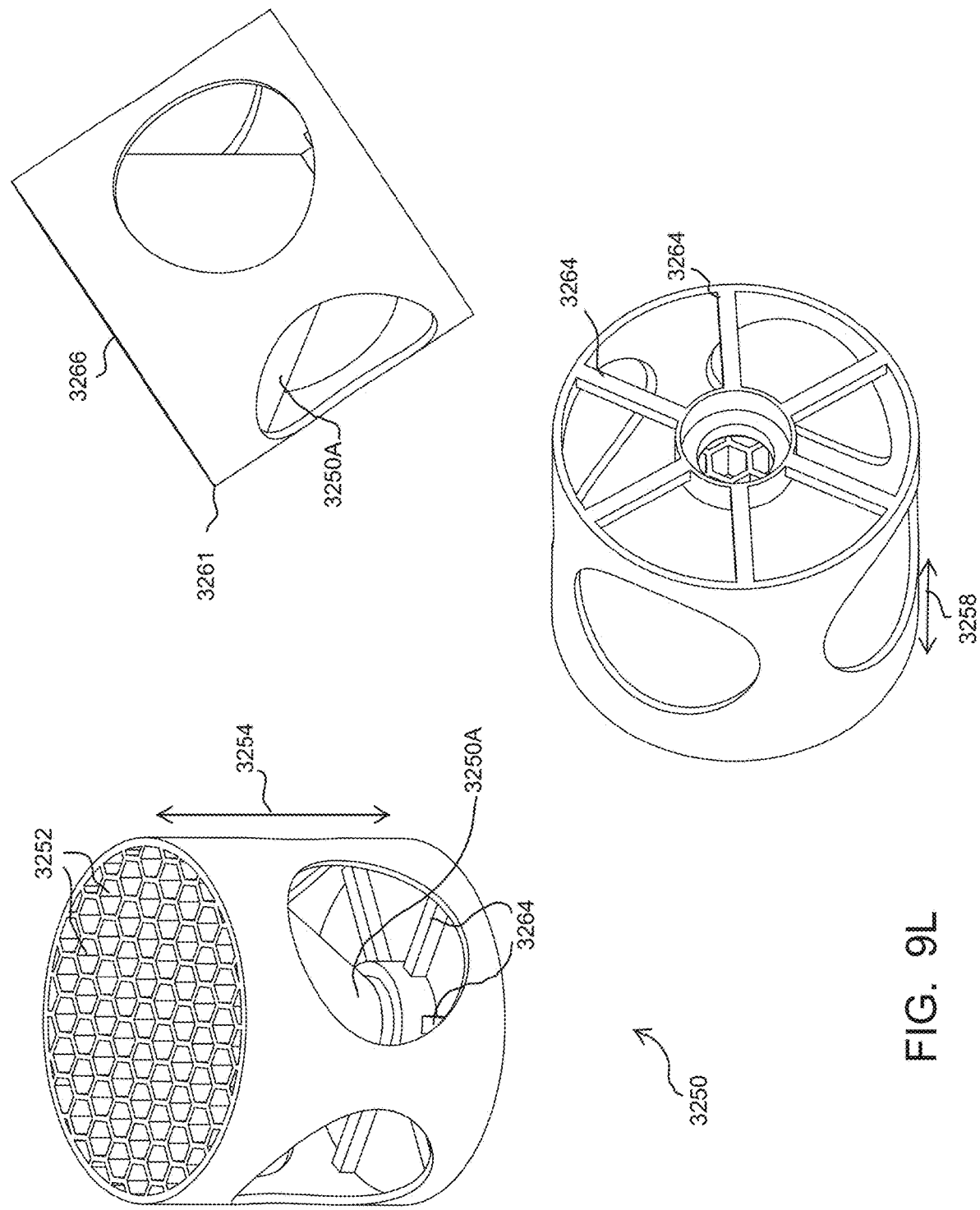
FIG. 9L is a perspective schematic view of the support structure of the third configuration of the bioreactor of the present teachings.

Referring to FIGS. 9K and 9L, support structure 3250 can be constructed of a biologically inert material, and can include a plurality of thin walled tunnels, stretching along a length 3254 of support structure 3250. In some configurations, the plurality of thinned walled tunnels can partially occupy length 3258 of support structure while a plurality of reinforcing ribs 3264 can span support structure 3250. Disposition of support structure 3250 can be on a surface of effluent chamber 3210 such that a first end 3261 of support structure 3250 can support filtration zone 3220 (FIG. 9I) from a surface of filtration zone that faces effluent chamber 3210 (FIG. 9I). Opening 3266 of first end 3261 of support structure 3250 can be a different size from a surface area of the plurality of filters through which fluid passes. Support structure 3250 can include funnel structure 3250A at first end 3261. Funnel structure 3250A can receive filtered contents through thin walled tunnels, and can emit filtered contents through a waste outlet.

Figure 9M:
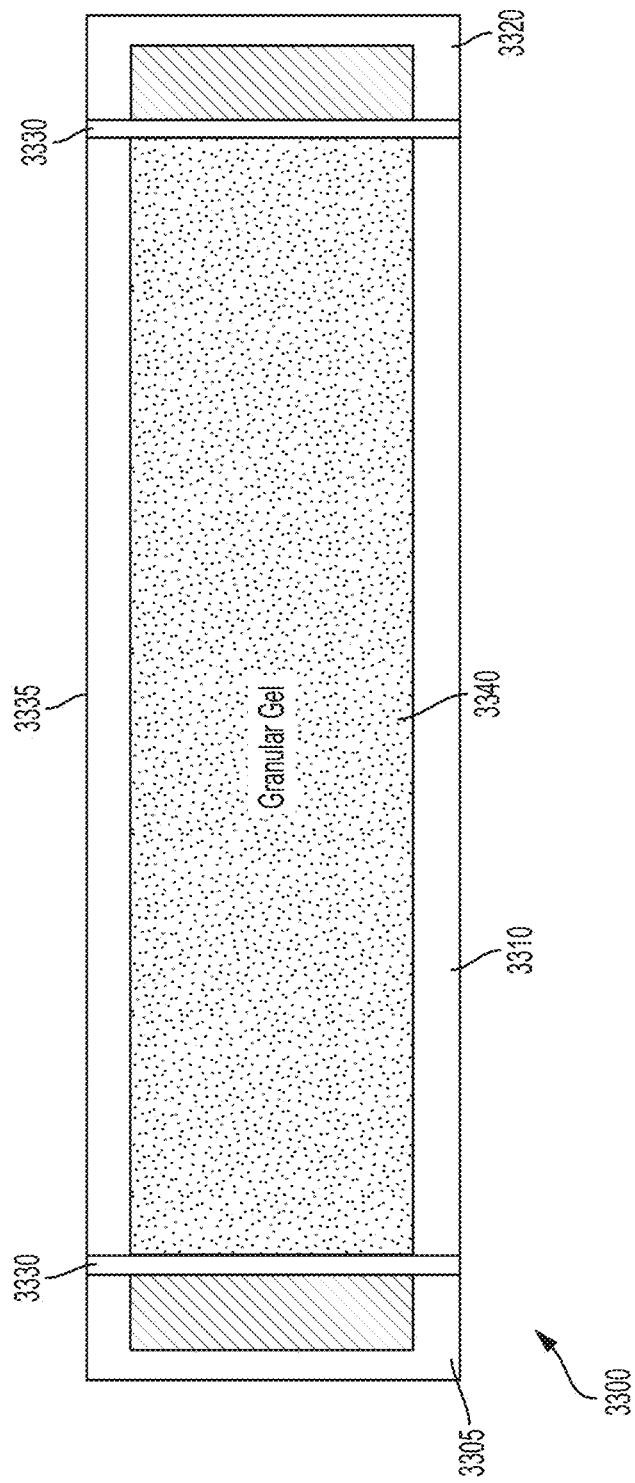
FIG. 9M is a pictorial representation of the fourth configuration of the bioreactor of the present teachings.
Figure 9N:
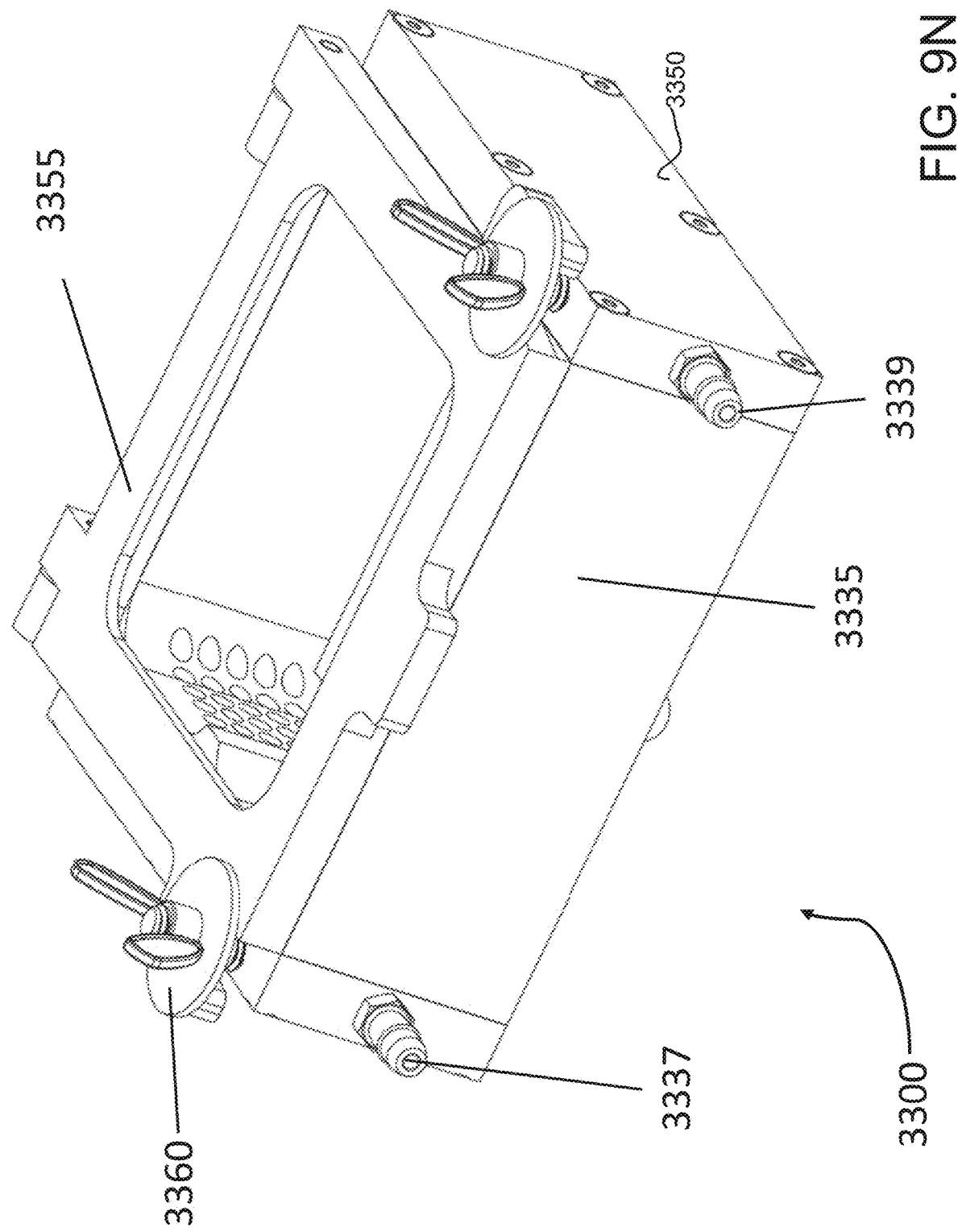
FIG. 9N is a perspective schematic view of the fourth configuration of the bioreactor of the present teachings.
Figure 90:
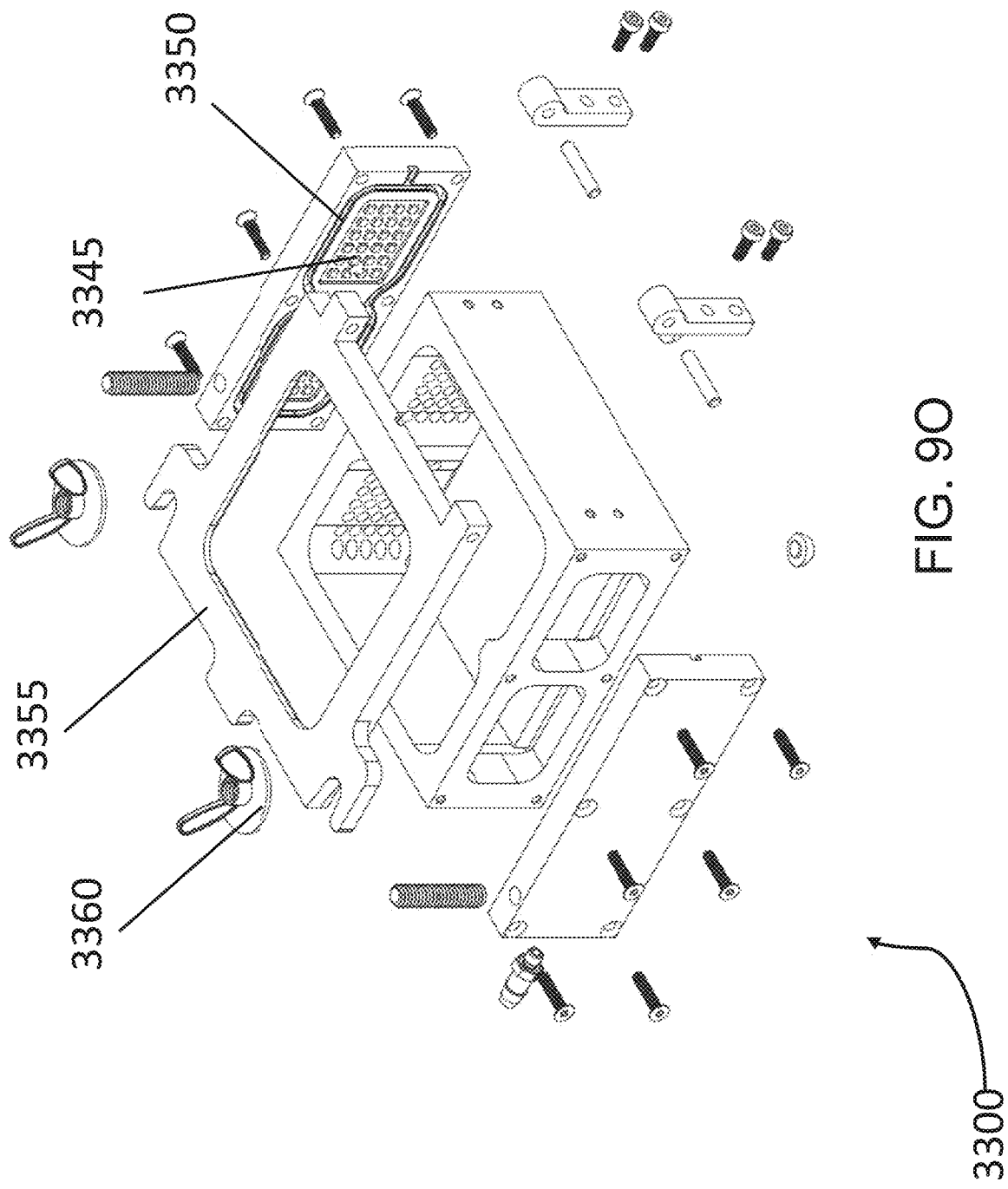

Referring to FIG. 9M, fourth configuration tissue enclosure 3300 can include three sections—incoming chamber 3305, gel chamber 3310, and effluent chamber 3320—each section separated from the other sections by filtration zone 3330, the three sections enabling fluid flow that may not rely on gravity. In some configurations, the three sections can be disposed within a single integral chamber 3335. In some configurations, each of the three chambers can be separate entities that can be operably coupled. A continuous exterior body, termed as integral chamber 3335 can be constructed of a biologically inert material, for example, but not limited to, a metal or a non-metal such as, for example, an engineering plastic. Integral chamber 3335 can be opened by a hinged door 3355 (FIG. 9N) or by a bolted door. Integral chamber 3335 can be closed using pressure equalizing assembly 3360. Incoming chamber 3305 (FIG. 9M) can include a fluid inlet from which a fluid can enter incoming chamber 3305, and a fluid outlet from which the fluid can exit effluent chamber 3320. Integral chamber 3335 can include a means to hold filtration zones 3330 between incoming chamber 3305 and gel chamber 3310, and between gel chamber 3310 and effluent chamber 3320. Integral chamber 3335 can include pressure inlet 3337 (FIG. 9N) and/or vacuum outlet 3339 (FIG. 9N). A pressure differential can be created between incoming chamber 3305 and effluent chamber 3320. The pressure differential can include providing a fluid pressure pump (not shown) on an upstream side of the fourth configuration tissue enclosure 3300 or by providing a fluid suction pump (not shown) on a downstream side of the fourth configuration tissue enclosure 3300, or both. A water swellable polymer in a semi-solid form, referred to as a gel herein, can be held in gel chamber 3310. Gel layer 3340 can maintain and aid in reproducing cells or tissues in a controlled and hygienic environment for their sustenance and growth. Gel layer 3340 and all its constituents, such as but not limited to, tissues or cells and their excreta and soaked fluid, disassociation agents, can be supported by gel chamber 3310.

Continuing to refer to FIG. 9M, a method for feeding printed structure can include, but is not limited to including, compressing the structures printed within gel 3340 (FIG. 9M) towards effluent chamber 3320 by the pressure driven nutrient flow, and decreasing the pressure by a pre-selected amount that can vary or remain constant over time. During the feeding cycle, the lower the compression compared to the volume of nutrients flowing through tissue enclosure 3300, the less likely it is that the structures are damaged while compressed. Simultaneously it is required to transfer a sufficient volume of nutrients to maintain the health of the cellular structures. When the pressure is decreased, the structures can begin to decompress and absorb fluids upstream and downstream of the compressed structures. Because the upstream volume of tissue enclosure 3300 can include fresh nutrient containing material, the decompression can allow the structures to continue to be fed while restoring their previous geometries and positions in tissue enclosure 3300. The method can optionally include pulsing the flow of nutrients to change the compression on the structure, for example, but not limited to, periodically. The structure can be minimally displaced during the optional pulsing, while adequate nutrient flow can be maintained. In some configurations, the pulsing rate can be governed by the amount of nutrient that must be replaced over time to maintain tissue viability. The pressure-driven nutrient flow and optional pulsing can stress the structure within the structure in a pre-selected amount that can result in increasing the robustness of the structure. Systems described herein can track the structures and control the pressure to both stress the structure to a desired amount and prevent damage to the structure due to excess compression. The method can optionally include setting a concentration gradient of the medium in which the structure resides. The structure can compress to an equilibrium state at some point after compression begins. The amount of time for the structure the reach the equilibrium state can be based at least on the size of tissue enclosure 3300, and the concentration of the medium in which the structure resides. Reducing the amount of time to reach the equilibrium state can reduce the compensation for compression while printing.

Referring to FIGS. 9M-9O, fourth configuration tissue enclosure 3300 can include three sections—an incoming chamber 3305, a gel chamber 3310 and an effluent chamber 3320—each section separated from the other sections by a filtration zone 3330, the three sections enabling fluid flow that may not rely on gravity. In some configurations, the three sections can be disposed within a single integral chamber 3335. In some configurations, each of the three chambers can be separate entities that can be operably coupled. A continuous exterior body, termed as integral chamber 3335 can include a biologically inert material, for example, but not limited to, a metal or a non-metal such as, for example, an engineering plastic. Integral chamber 3335 can be opened by a hinged door 3355 (FIG. 9N) or by a bolted door. Integral chamber 3335 can be closed using pressure equalizing assembly 3360. Incoming chamber 3305 can have a fluid inlet where from a fluid can enter incoming chamber 3305, and a fluid outlet wherefrom the fluid can exit effluent chamber 3320. Integral chamber 3335 can further comprise a means to hold filtration zones 3330 (FIG. 9M) between incoming chamber 3300 and gel chamber 3310, and between gel chamber 3310 and effluent chamber 3320. Integral chamber 3335 can further comprise a pressure inlet 3337 (FIG. 9N) and/or a vacuum outlet 3339 (FIG. 9N).

Continuing to refer to FIGS. 9M-9O, there can be created a pressure differential between incoming chamber 3305 and effluent chamber 3320. The pressure differential can be obtained either by providing a fluid pressure pump (not shown) on an upstream side of the fourth configuration tissue enclosure 3300 or by providing a fluid suction pump (not shown) on a downstream side of the fourth configuration tissue enclosure 3300, or both. A water swellable polymer in a semi-solid form, therefore termed as a gel throughout this description, can be held in the gel chamber 3310. Gel layer 3340 can maintain and aid in reproducing cells or tissues in a controlled and hygienic environment for their sustenance and growth. Gel layer 3340 and all its constituents, such as but not limited to, tissues or cells and their excreta and soaked fluid, disassociation agents, can be supported by gel chamber 3310.

Continuing to refer to FIGS. 9M-9O, in some configurations, filtration zone 3330 (FIG. 9M) can comprise a plurality of flow dividers 3345 (FIG. 9O) and filters (not shown) of pre-selected pore sizes. There can be provided a sealing frame 3350 (FIG. 9O) laterally disposed upon the plurality of flow dividers 3345 (FIG. 9O) and filters (not shown). In some configurations, the filtration zone 3330 (FIG. 9M) can include a three layered assembly, comprising sealing frame 3350 (FIG. 9O)—plurality of flow dividers 3345 (FIG. 9O) and filters (not shown)—sealing frame 3350 (FIG. 9O). In some configurations, filtration zone 3330 (FIG. 9M) can be a two layered assembly, comprising sealing frame 3350 (FIG. 9O) and plurality of flow dividers 3345 (FIG. 9O). Filtration zones 3330 (FIG. 9M) can be disposed between the incoming chamber 3305 (FIG. 9M) and gel chamber 3310 (FIG. 9M), and between the gel chamber 3310 (FIG. 9M) and the effluent chamber 3320 (FIG. 9M). Filtration zone 3330 (FIG. 4) between incoming chamber 3305 (FIG. 9M) and gel chamber 3310 (FIG. 9M) can have the same types of filters or different types of filters as filtration zone 3330 (FIG. 9M) between gel chamber 3310 (FIG. 9M) and effluent chamber 3320 (FIG. 9M). Creating a differential pressure between incoming chamber 3305 (FIG. 9M) and effluent chamber 3320 (FIG. 9M) can cause fluid, small monomers and/or soluble molecules to flow from incoming chamber 3305 (FIG. 9M) via gel chamber 3310 (FIG. 9M) and through respective filtration zones 3330 (FIG. 9M) to effluent chamber 3320 (FIG. 9M). First configuration tissue enclosure 3005, second configuration tissue enclosure, third configuration tissue enclosure, and fourth configuration tissue enclosure, and any of their variants, can include viewing windows for observation and provisions to dispose parameter measurement sensors. Filters 3060 (FIG. 9A), 3145 (FIG. 9D), 3270 (FIG. 9H), and 3330 (FIG. 9M) can include, for example, but not limited to, membrane filters and/or paper filters and/or hydrogel used as filter, or any combination thereof. Pressure differential can be created by, for example, but not limited to, a fluid pressure pump in upstream, and by a fluid vacuum pump in downstream, and a combination thereof.

Referring now primarily to FIG. 9O, in some configurations, filtration zone 3330 can include at least one filter 3345 of pre-selected pore sizes. There can be provided sealing frame 3350 laterally disposed upon at least one filter 3345. In some configurations, filtration zone 3330 can include a three layered assembly, comprising sealing frame 3368 (FIG. 9P), at least one filter 3345, and sealing frame 3350. In some configurations, filtration zone 3330 (FIG. 9M) can be a two layered assembly, comprising sealing frame 3350 and at least one filter 3345. Filtration zones 3330 (FIG. 9M) can be disposed between incoming chamber 3305 (FIG. 9M) and gel chamber 3310 (FIG. 9M), and between gel chamber 3310 (FIG. 9M) and effluent chamber 3320 (FIG. 9M). Filtration zones 3330 (FIG. 9M) between incoming chamber 3305 (FIG. 9M) and gel chamber 3310 (FIG. 9M) can include the same types of filters or different types of filters as filtration zone 3330 (FIG. 9M) between gel chamber 3310 (FIG. 9M) and effluent chamber 3320 (FIG. 9M). Creating a differential pressure between incoming chamber 3305 (FIG. 9M) and effluent chamber 3320 (FIG. 9M) can cause fluid, small monomers and/or soluble molecules to flow from incoming chamber 3305 (FIG. 9M) via gel chamber 3310 (FIG. 9M) and through respective filtration zones 3330 (FIG. 9M) to effluent chamber 3320 (FIG. 9M).

Figure 9P:
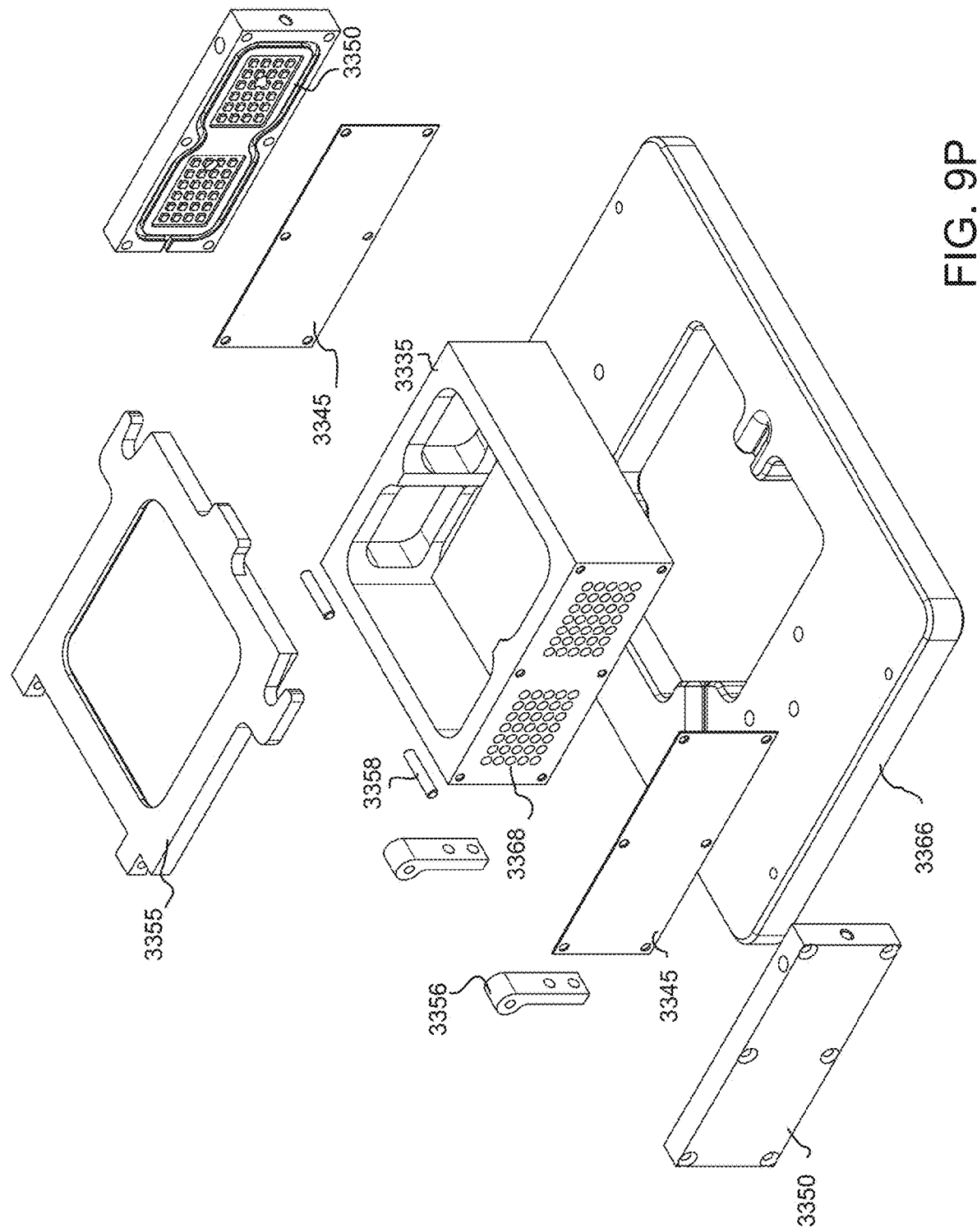

Referring now to FIGS. 9P-9Q, fourth configuration tissue enclosure 3300 (FIG. 9N) can include lid hinge connecting means that can include, but is not limited to including lid hinge 3356 that can include operable coupling with dowel pin 3358, integral chamber 3335, and hinged door 3355. Fourth configuration tissue enclosure 3300 can include base mount buttons 3335B (FIG. 9Q) that can enable kinematic mounting between fourth configuration tissue enclosure 3300 and tissue enclosure holder 3366. Base mount buttons 3335B (FIG. 9Q) can removably couple fourth configuration tissue enclosure 3300 (FIG. 9N) with tissue enclosure holder 3366 at mount wells 3335C (FIG. 9Q). The removable coupling in mount wells 3335C (FIG. 9Q) can insure substantially identical placement of fourth configuration tissue enclosure 3300 (FIG. 9N) between removal and replacement cycles. The identical placement can enable consistent x-y-z alignment for printing and imagery. Integral chamber 3335 can include lower plate 3335A (FIG. 9Q) that can be used to view the contents of integral chamber 3335 during printing and/or during tissue growth. An inverted microscope (not shown) mounted adjacent to lower plate 3335A (FIG. 9Q) can be used to examine cell growth, for example. In some configurations, lower plate 3335A (FIG. 9Q), as well as chamber sides, can be constructed of transparent material.

Referring again to FIGS. 9C, 9D, 9H, and 9M, first configuration tissue enclosure 3005 (FIG. 9C), second configuration tissue enclosure 3105 (FIG. 9D), third configuration tissue enclosure 3200 (FIG. 9H), and fourth configuration tissue enclosure 3300 (FIG. 9M), and any of their variants, can include viewing windows for observation and provisions to dispose parameter measurement sensors. Filters 3060 (FIG. 9C), 3145 (FIG. 9D), 3270 (FIG. 9H), and 3330 (FIG. 9M) can include, for example, but not limited to, membrane filters and/or paper filters. Vertically filtered tissue enclosures such as, for example, but not limited to third configuration tissue enclosure 3200 (FIG. 9L) can include, but are not limited to including, hydrogel used as filter in addition to membrane and/or paper filters.

Figure 9R:
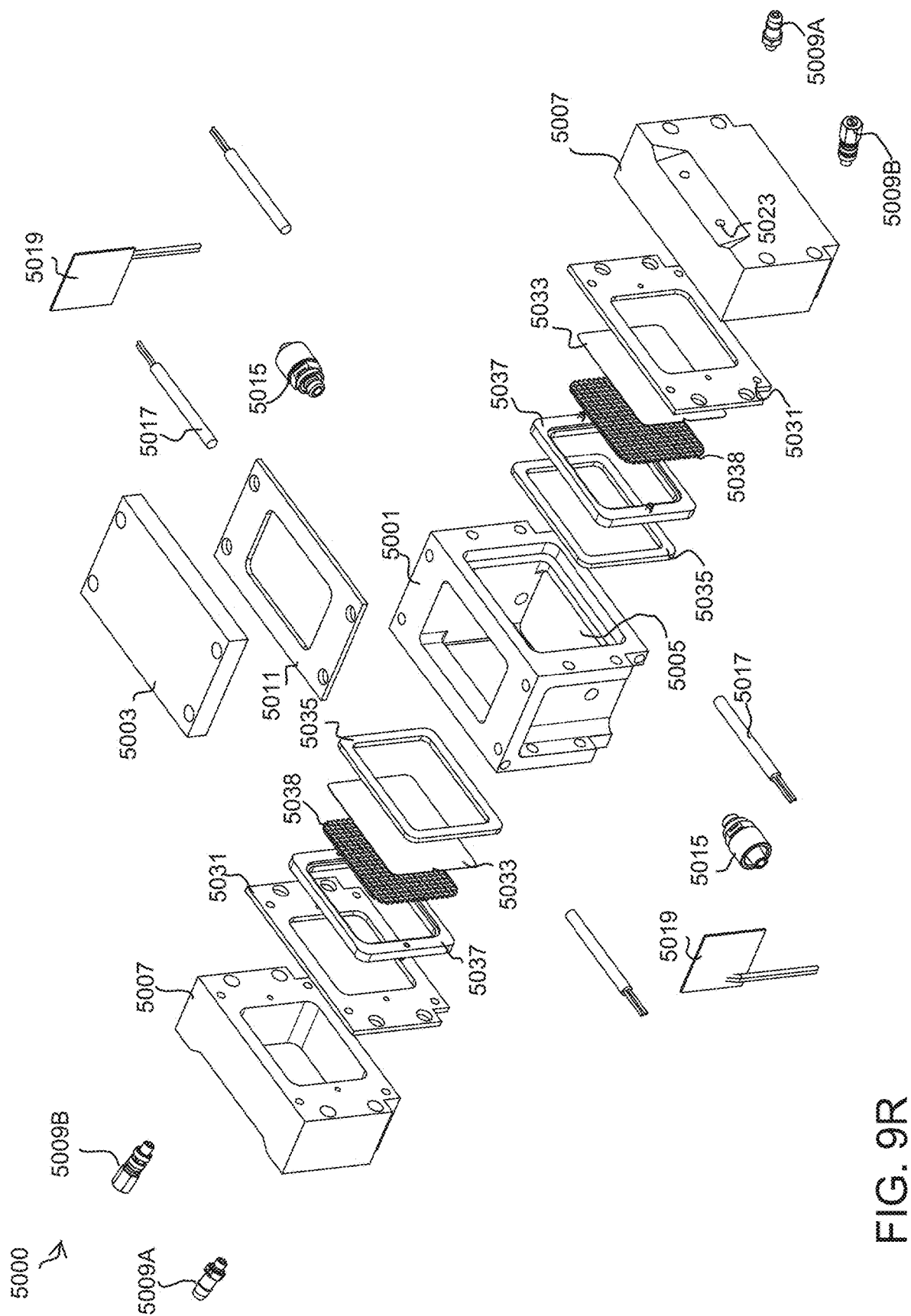
FIG. 9R is an exploded schematic perspective of the fifth configuration of the filter of tissue enclosure of the present teachings.
Figure 9S:
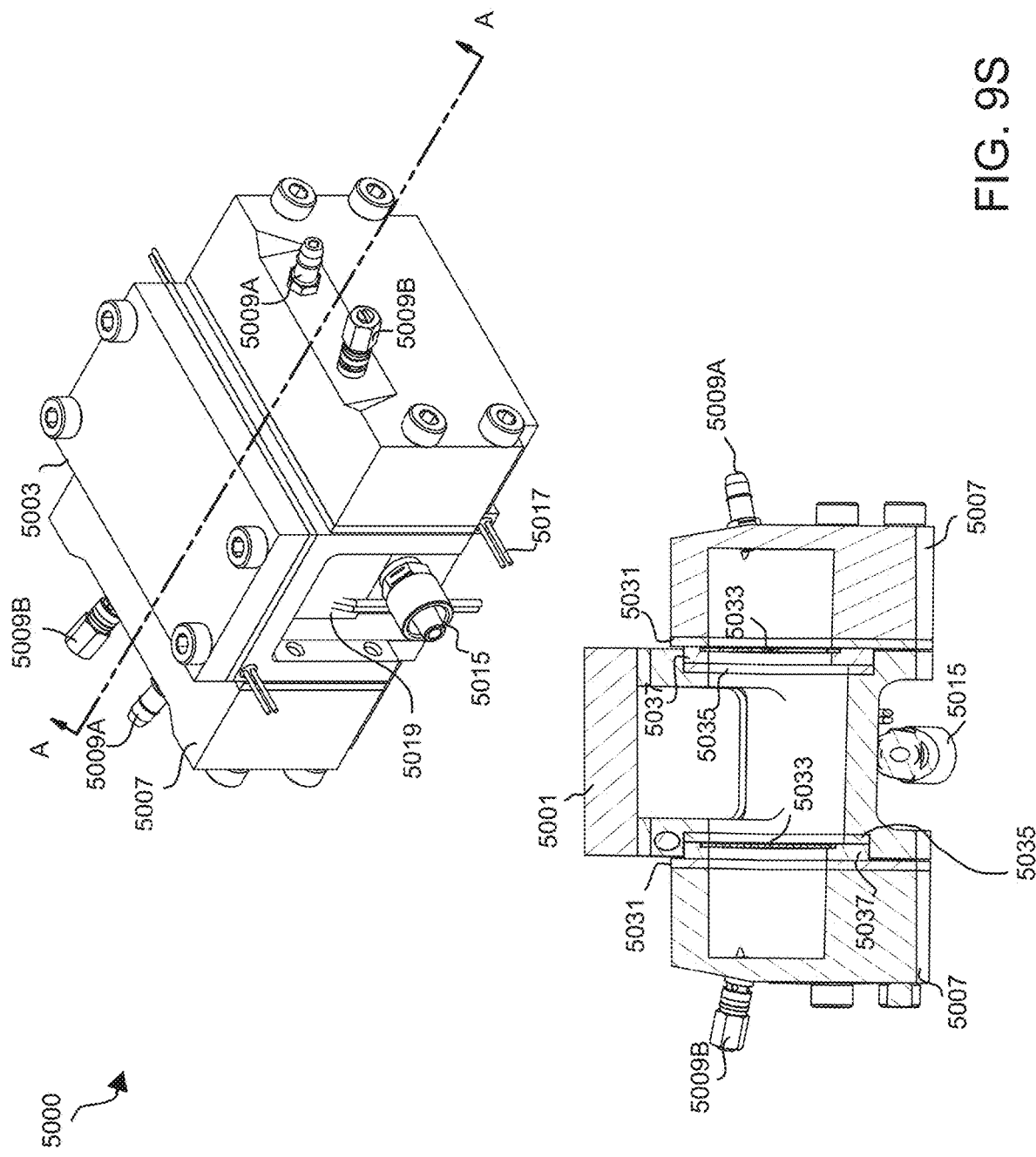
FIG. 9S is a cross section of the interior of the tissue enclosure of FIG. 9R.
Figure 9U:
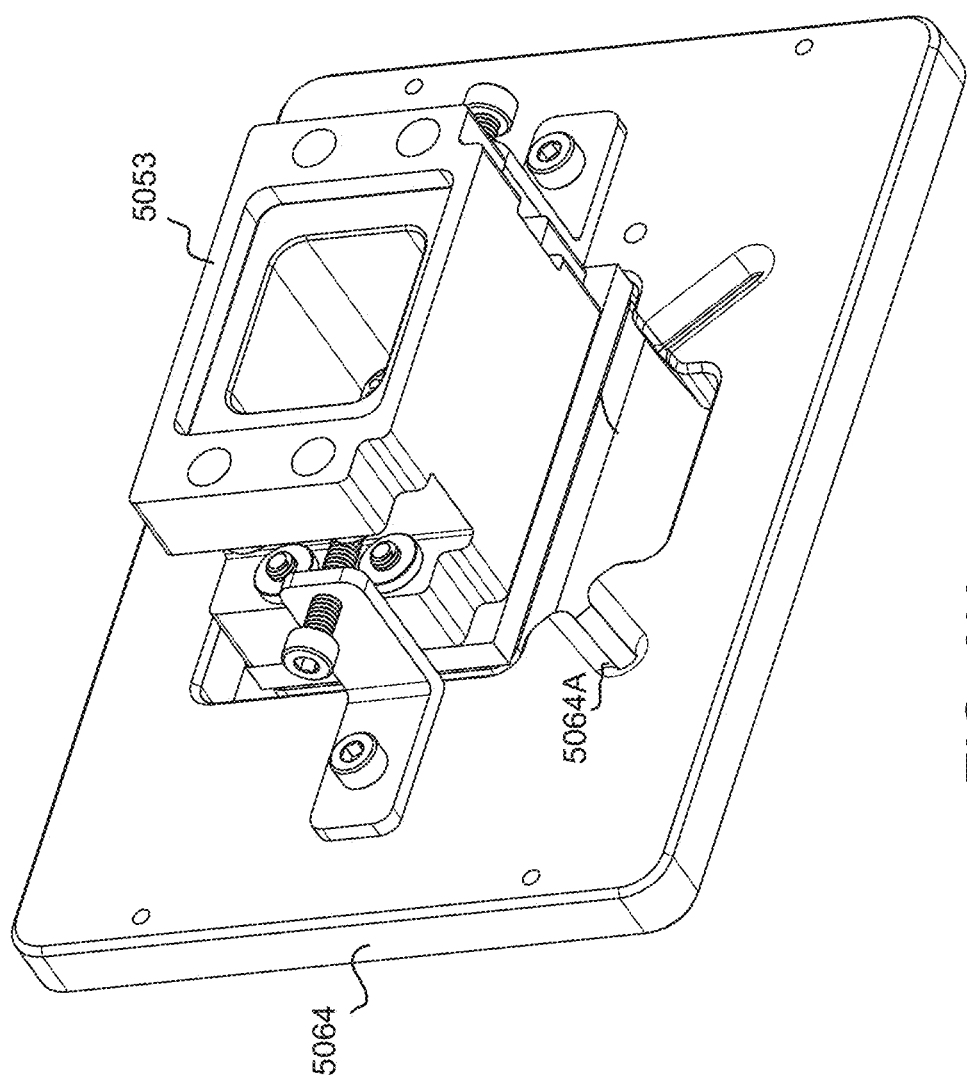
FIG. 9U is a schematic perspective of the tissue enclosure of FIG. 9T mounted on a printing mounting plate.
Figure 9V:
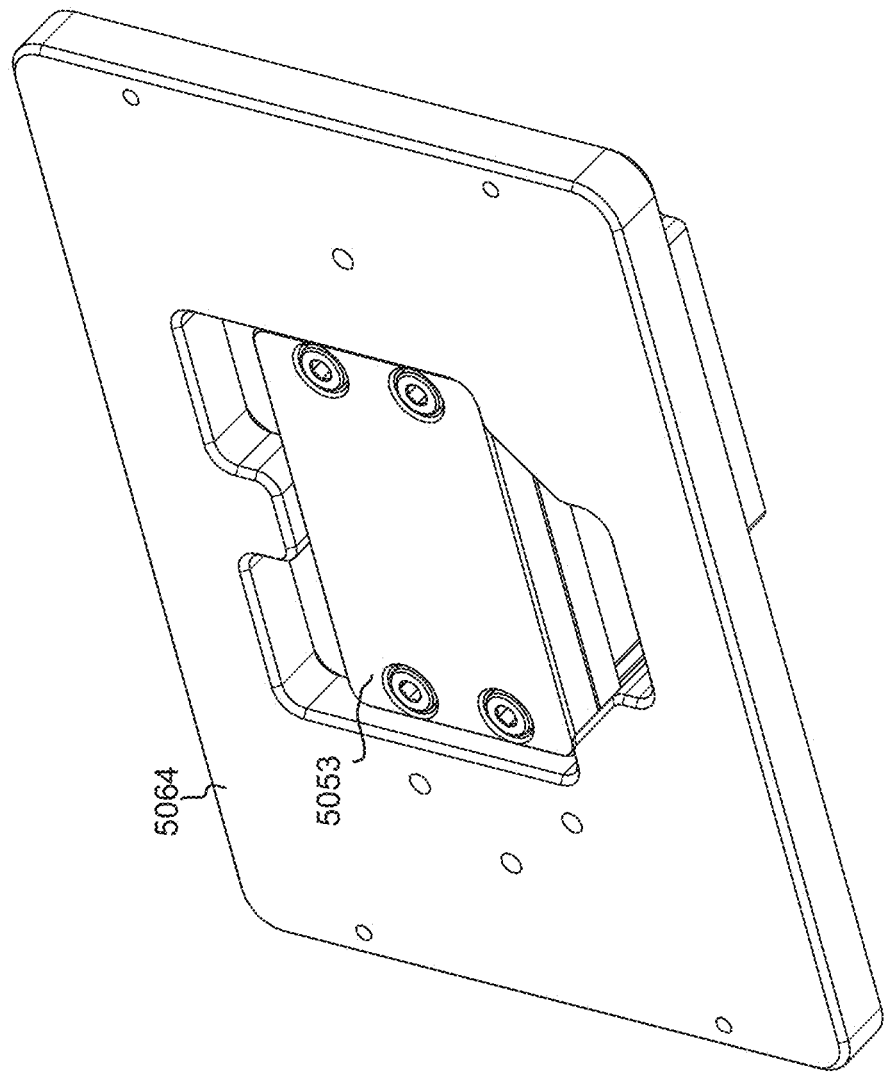
FIG. 9V is the opposite side of the tissue enclosure and mounting plate of FIG. 9U.

Referring now to FIGS. 9R-9S, fifth configuration tissue enclosure 5000 can optimize the diffusion distance required to reach the tissue and to exit fifth configuration tissue enclosure 5000. Pressure distribution of the inlet fluid can be normalized by the volume and depth of plena 5007. Fifth configuration tissue enclosure 5000 can include lid 5003, lid gasket 5011, window 5005, and heaters 5017/5019. Surfaces such as, for example, lid 5003 and window 5005, can include transparent material to enable monitoring of the contents of core 5001. Fifth configuration tissue enclosure 5000 can include relatively small overall dimensions to accommodate portability and to maintain relatively low medium requirements. Plena 5007 can enable distribution of flow throughout fifth configuration tissue enclosure 5000, and inlet/outlet tube 5023 can remove air from plena 5007. The depth of plena 5007 can be based on, for example, how dispersed the pressure is in tissue enclosure core 5001. Luer lock fittings 5015 can be included to enable needle injection of substances into and/or removal of substances from tissue enclosure core 5001, and/or sensor access to fifth configuration tissue enclosure 5000. In some configurations, a self-sealing membrane can enable access to the contents of fifth configuration tissue enclosure 5000. Heating elements 5017 can be, for example, but not limited to, 25 W and can be used to maintain the temperature of the contents of fifth configuration tissue enclosure 5000. Heating elements 5019 can be, for example, but not limited to, 10 W, and can be used alternatively or in addition to heating elements 5017 to maintain the temperature of the contents of fifth configuration tissue enclosure 5000.

Continuing to refer to FIGS. 9R-9S, interface gasket 5035 and plenum gasket 5031 can surround filter support 5037/5048. Interface gaskets 5035 can provide interfaces between the filter assembly and core 5001. Interface gaskets 5035 can be constructed of, for example, silicone. Filter 5033 can include materials such as, but not limited to, polypropylene, hydrophilic polyvinylidene fluoride, polycarbonate (PC), polyester, or other etched plastic with a pore size of, for example, but not limited to, approximately 0.65 µm-3.0 µm. Examples of filter 5033 can include, but are not limited to including, STERLITECH® 2.0 µm polycarbonate track etched, STERLITECH® 1.0 µm polyester track etched, and MILLIPORE® 1.2 µm polycarbonate. Filter 5033 can filter molecules smaller than a pre-selected size depending upon the application, and can maintain molecules larger than a pre-selected size depending upon the application. Metabolites, vitamins, growth factors, signaling factors, inorganic salts, pH buffers, and surfactants can be pumped through fifth configuration tissue enclosure 5000 at a rate that can maintain viable tissue. The contents of fifth configuration tissue enclosure 5000 can receive an inflow of various substances through inlet/outlet tube 5023, and the contents can be monitored through window 5005 among other ways such as, for example, but not limited to, sensors connected through luer locks 5015, outflow from inlet/outlet tube 5023, and visual monitoring means. There can be a vacuum/suction created in fifth configuration tissue enclosure 5000 having a negative pressure range of, for example, approximately −11 psi to 0 psi, a positive pressure range of, for example, 0 psi to 13 psi, or both. The pressure within fifth configuration tissue enclosure 5000 can encourage nutrients admitted to fifth configuration tissue enclosure 5000 to support the tissue being grown, and can encourage waste products generated by the tissue to exit fifth configuration tissue enclosure 5000. Fifth configuration tissue enclosure 5000 can be constructed of non-reactive metal such as, for example, but not limited to, titanium, or injection molded plastic. Needle valve 5009B can be used for priming and releasing air from plena 5007. Barb 5009A can be used to admit and release fluids from plena 5007.

Referring now to FIG. 9T, sixth configuration tissue enclosure 5050 can enable printing of tissue, monitoring of the tissue, and life support of the tissue within the same enclosure. Sixth configuration tissue enclosure 5050 can include, but is not limited to including, core 5053 and plena 5063. Core 5053 can include at least one printing cavity that can accommodate at least one end effector, such as, for example, but not limited to, at least one needle. The at least one needle can be directed by at least one printer to print at least one structure in core 5053. Core 5053 can contain a medium into which printing can proceed. The medium can include, for example, but not limited to, a carbomer gel. Plena 5063 can enable life support of the printed structure by enabling, through positive or negative pressure, routing of nutrients and wastes through the printed structure and the medium.

Figure 9W:
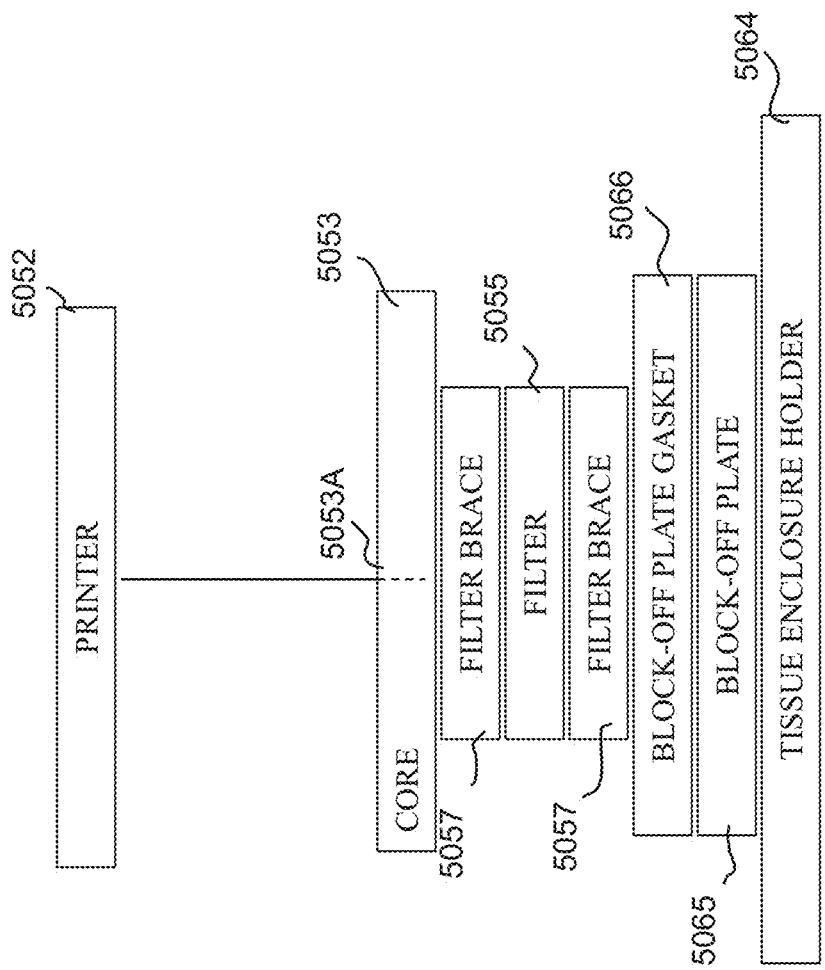
FIG. 9W is a schematic block diagram of the sixth configuration tissue enclosure in printing mode.
Figure 9A:
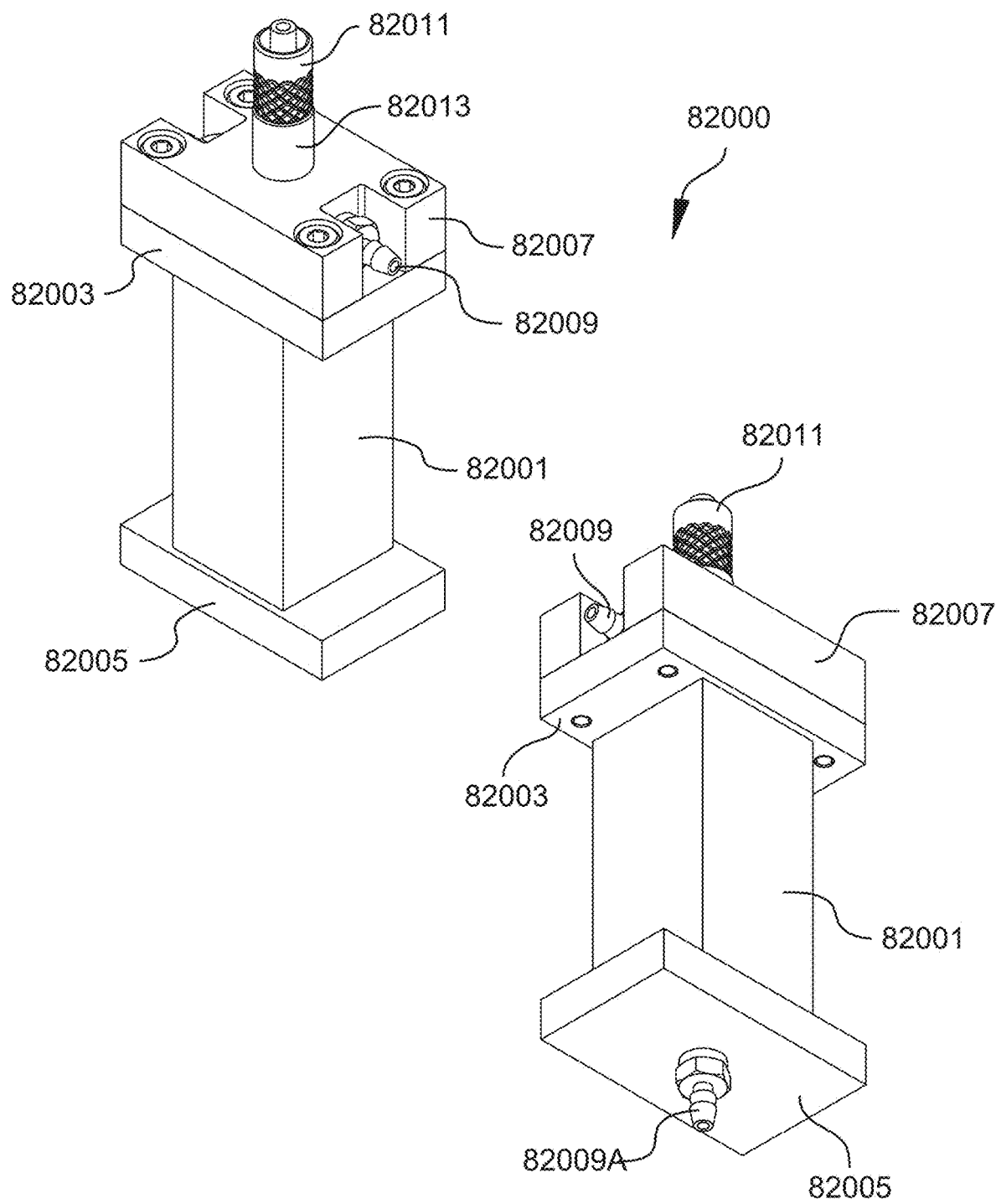
Figure 9A:
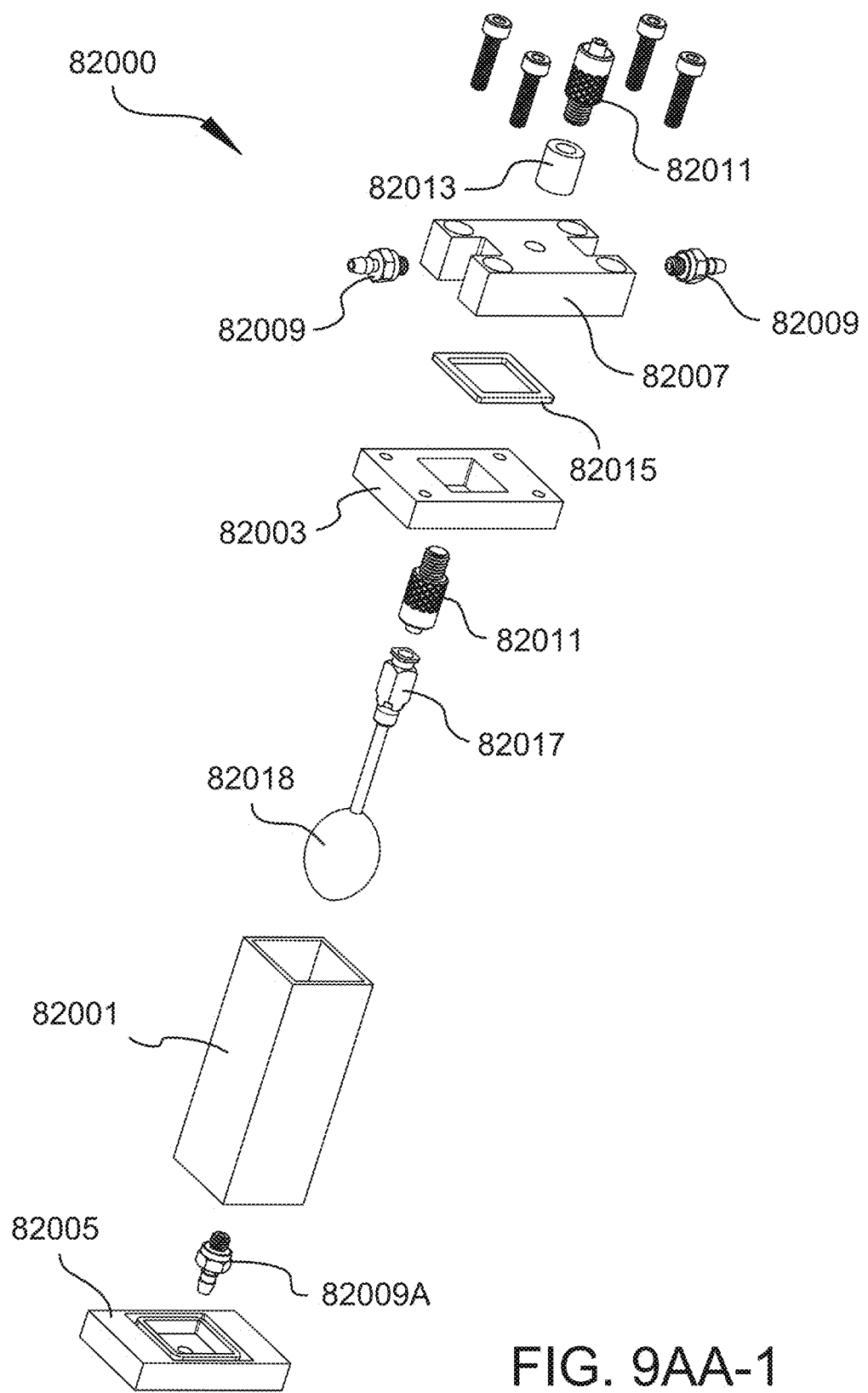
Figure 9B:
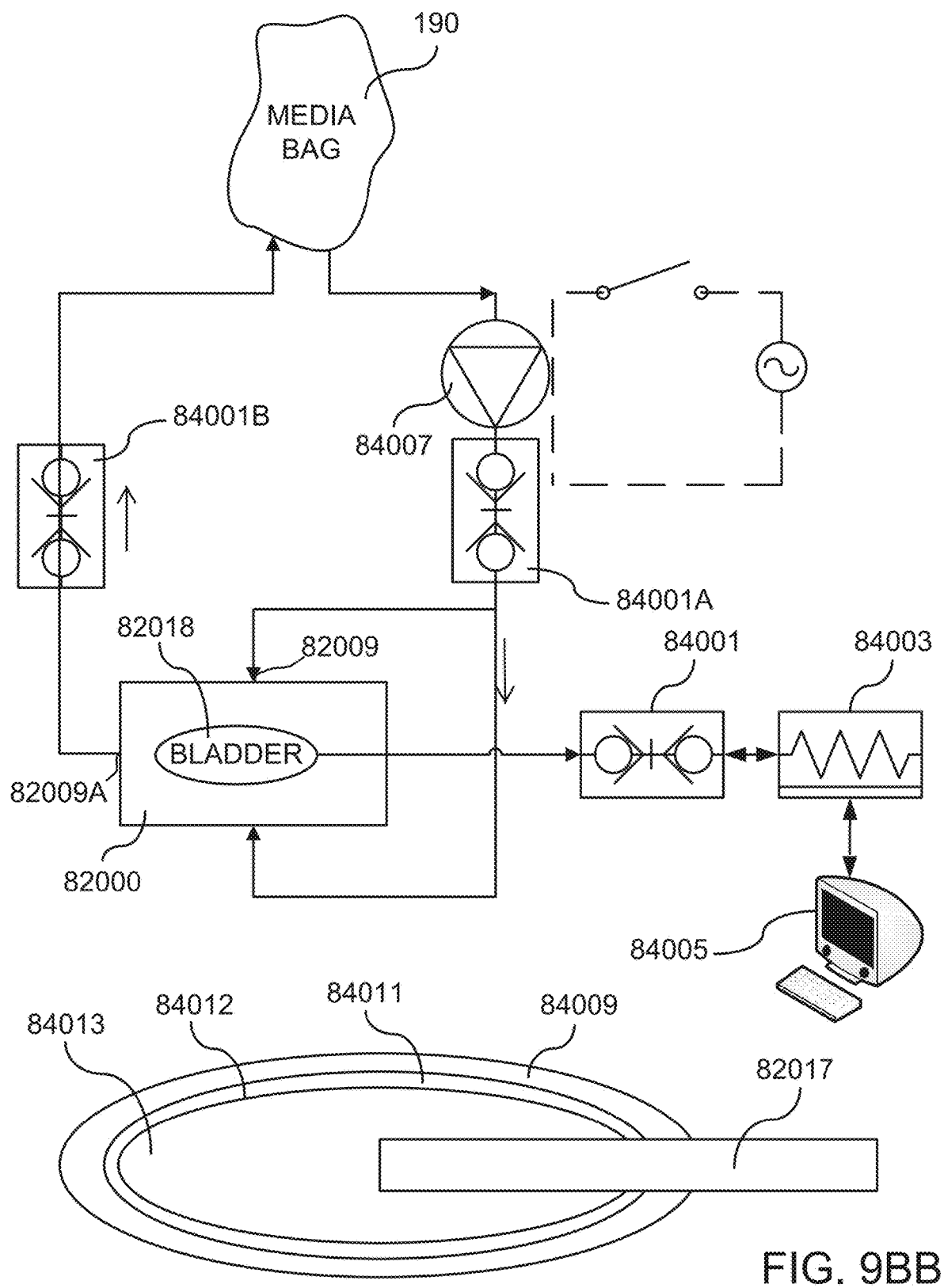

Referring now to FIGS. 9U-9X, sixth configuration tissue enclosure 5050 can include multiple configurations, depending on how it is being used. For example, if printer 5052 is printing tissue into core 5053, block-off plate 5065 can removably rest upon tissue enclosure holder 5064. Block-off plate gasket 5066 (FIG. 9W) can maintain an environmental seal for block-off plate 5065 (FIG. 9W). At least one filter brace 5057 (FIG. 9W) can support filter 5055 (FIG. 9W). At least one filter 5055 (FIG. 9W) can be used in a tissue engineering application to allow the removal of wastes while maintaining the structure growing in sixth configuration tissue enclosure 5050 (FIG. 9T) intact. Filter assemblies can include at least one filter support 5057 (FIG. 9W), and filter 5055 (FIG. 9W). Filter supports 5057 (FIG. 9Y) can provide structural integrity to filters 5055 (FIG. 9Y), assisting filters 5055 (FIG. 9Y) in remaining operational throughout exposure to the pressure from the contents of fifth configuration tissue enclosure 5050 (FIG. 9Y).

Referring now to FIG. 9Y, when a cycle of printing has completed, block-off plate 5065 (FIG. 9X) and gasket 5066

(FIG. 9X) can be removed, and plena 5063 and gasket 5061 can be installed to replace block-off plate 5065 (FIG. 9X) and gasket 5066 (FIG. 9X) on one side of core 5053, and can optionally be placed, along with filter 5055 and at least one brace 5057 on the opposite side of core 5053 to cover the cavity through which printing had occurred. Bi-directional filter supports can prevent injury to filters 5055 during setup. Sixth configuration tissue enclosure 5050 can be used to maintain tissue. Alternating pressure control can enable management of flow dead-zones, and can enable uniform laminar flow of fluid from the fluid inlet throughout the cross sectional area of core 5054. Uniform flow and pressure management can discourage leaks and excessive forcing on the tissue. Pulsed flow can enable adequate waste removal.

Referring now to FIG. 9Z, core 5053 can include sides 5054/5056, top 5058, and bottom 5052. At least one of sides 5054/5056, top 5058, and bottom 5052 can include transparent material through which the contents of tissue enclosure 5050 (FIG. 9Y) can be monitored. Operationally, tissue enclosure 5050 (FIG. 9Y) can be placed in a receiving space of a tissue printing means, and tissue can be printed directly into tissue enclosure 5050 (FIG. 9Y) through top 5058. Core 5053 can hold a medium such as, for example, but not limited to, a bio-friendly gel, into which printing can occur. Tissue enclosure 5050 (FIG. 9Y) can provide a secure transport means for the tissue.

Referring now to FIG. 9AA, bioreactor 82000 can flow media 190 (FIG. 9BB) around the outside of cellularized scaffold 82018 (FIG. 9AA-1) while exercising the cells upon scaffold 82018 (FIG. 9AA-1) by applying pressure from the center of scaffold 82018 (FIG. 9AA-1). Media 190 (FIG. 9BB) can be pumped into bioreactor 82000 by pump 84007 (FIG. 9BB), for example, but not limited to, a peristaltic pump, through coupling 84001A (FIG. 9BB), for example, but not limited to, a luer lock coupling, through inlets 82009 (FIG. 9AA-1). The pressure created by pump 84007 (FIG. 9BB), for example, but not limited to, a peristaltic pump, can force media 190 (FIG. 9BB) to exit bioreactor 82000 through outlet 82009A and coupling 84001B (FIG. 9BB) which can be, but is not limited to being, a luer lock coupling. The forced media 190 (FIG. 9BB) can return to the source of media 190 (FIG. 9BB), or can exit elsewhere. Scaffold 82018 (FIG. 9AA-1) can be shaped according to the geometry of the organ being constructed, for example, but not limited to, a bladder. Scaffold 82018 (FIG. 9AA-1) can be constructed of fibers 84009 (FIG. 9BB), for example, but not limited to, polymer fibers, that can be attached to the outside of removable mold 84012 (FIG. 9BB) coated in compliant material 84011 (FIG. 9BB) such as, for example, but not limited to, silicone. Removable mold 84012 (FIG. 9BB) can be constructed of, for example, wax, and can be removed, leaving scaffold 82018 (FIG. 9AA-1) as hollow shape 84013 (FIG. 9BB) such as, for example, an ellipsoid, having a "balloon" on the inside. Fibers 84009 (FIG. 9BB) can be seeded with cells and placed in bioreactor 82000. While in bioreactor 82000, balloon 84011 (FIG. 9BB) can be slowly inflated and deflated, for example, but not limited to, by syringe pump 84003 (FIG. 9BB) full of material, to simulate filling scaffold 82018 (FIG. 9AA-1) with, and evacuating scaffold 82018 (FIG. 9AA-1) of, the material. The fill/empty cycle time period can be adjusted based at least on, for example, mimicking the physiology of the organ being constructed and its typical operational environment.

Referring now to FIG. 9BB, syringe pump 84003 can be operably connected to needle 82017 through luer lock coupling 84001. Tube couplings 82011 (FIG. 9AA-1) and coupling interface 82013 (FIG. 9AA-1) can provide a fluid path through needle 82017 and into scaffold 82018. Controlling syringe pump 84003, processor 84005 can direct the degree of inflation to begin slowly, and gradually increase until a pre-selected exercise strain level is reached. The rate of the increase of the degree of inflation, the pre-selected exercise strain level, and a maximum exercise strain level can be adjusted based at least on, for example, but not limited to, a desired exercise environment for the organ being constructed. The inner diameter of needle 82017 can be adjusted to accommodate the flow rate, amount, and viscosity of the liquid expected to enter and exit scaffold 82018. If scaffold 82018 takes an elliptical shape, the major and minor axis radii of scaffold 82018 can be adjusted to substantially mimic the geometry of the organ being constructed. The volume of material to pump into scaffold 82018 can be calculated based at least on the geometry of the organ and the change in surface area equal to the strain increase. When an ellipse is the shape of scaffold 82018, the major and minor axis radii can stretch proportionately to their initial values. Using the stretched radii values, the volume of the inflated or strained balloon can be calculated. The initial volume can be subtracted from the inflated volume to determine the volume of material required to properly exercise scaffold 82018. Processor 84005 (FIG. 9BB) can calculate pumping commands destined for syringe pump 84003 (FIG. 9BB) based at least on the volume of material.

Figure 10:
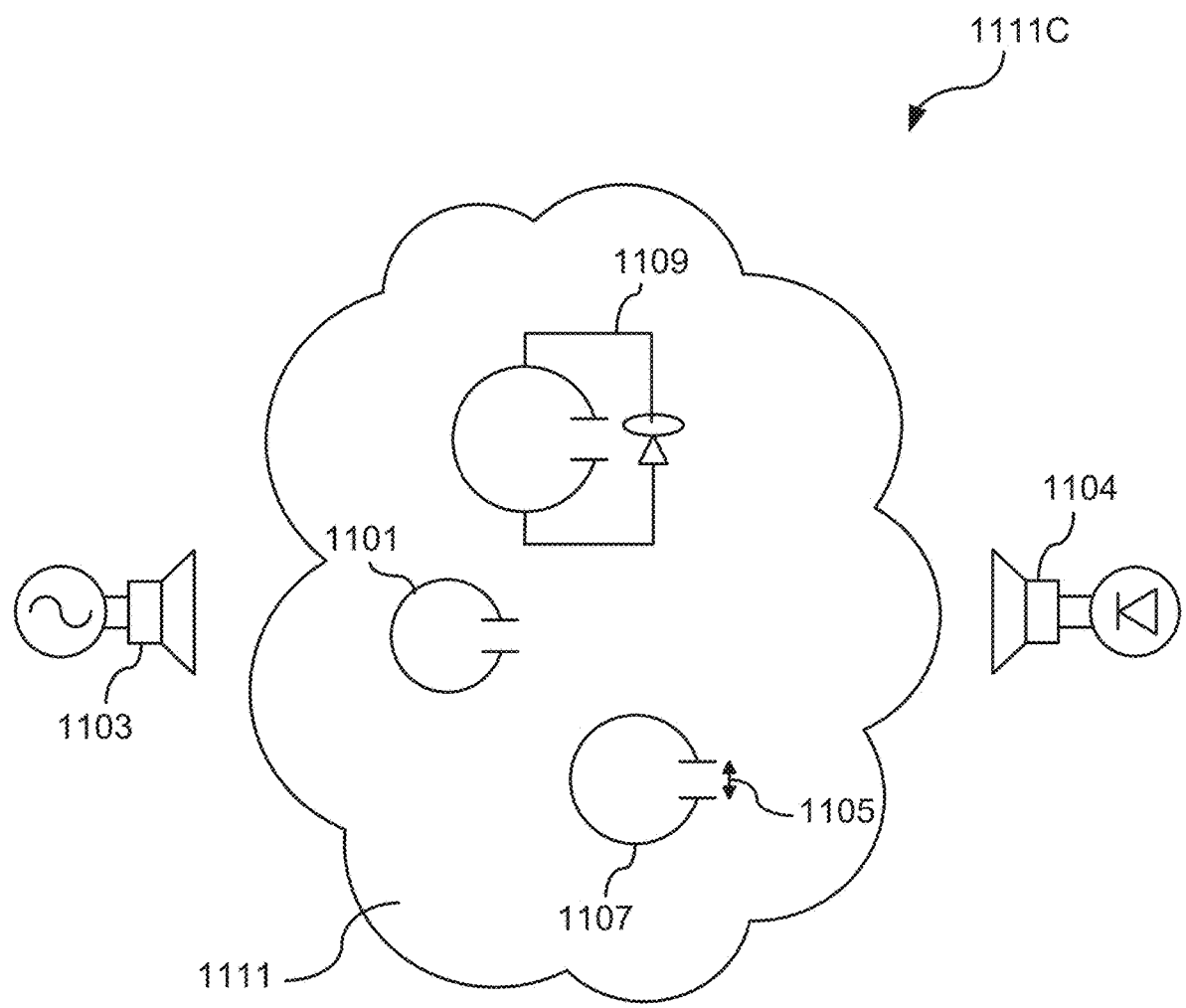
FIG. 10 is a pictorial representation of a system of the present teachings for monitoring tissue activity.

Referring now to FIG. 10, inducing electromagnetic energy in tissue or surrounding materials can be used to monitor tissue activity in situ, and to create action and injury potentials, as well as therapeutically dissipate heat. Metallic geometries can be fashioned to absorb specific frequencies and dissipate the energy absorbed in heat. Strategic placement of resonator 1101 in tissue can enable regular, non-invasive therapy. Resonator 1101 can include, but is not limited to including, a thermally sensitive material having absorption properties that can be stopped and/or reduced when the proper heat level is attained. When resonator 1101 is illuminated, for example, but not limited to, with a dipole antenna, resonator 1101 can absorb energy and can convert the energy into heat due to the resistive losses of the material of resonator 1101. Resonator 1101 can be constructed in any shape and with any complexity, and can include at least one inductive component 1107 and at least one capacitive component 1105. When resonator 1101 is periodically illuminated, resonator 1101 can remain charged between illuminations. When resonator 1101 is continuously illuminated, a current can flow in and charge inductor 1107, and inductor 1107 can store magnetic energy. When the illuminator signal reverses polarity, the stored energy can discharge from inductor 1107 and can charge capacitor 1105. As the stored energy in resonator 1101 continues to oscillate back and forth, the resistance of the material that is used to construct resonator 1101 can convert the energy into heat.

Continuing to refer to FIG. 10, by adding rectifier 1109, in the form of, for example, but not limited to, a diode, an approach similar to heating can be used to convert the energy absorbed by resonator 1101 into a lower frequency control pulse, or a DC voltage, or both. Microwave resonators can be illuminated from, for example, but not limited to, an external source and can create various voltage gradients. In some configurations, the external source can produce low frequency signals, for example, but not limited to, frequencies in the RF range, and low power signals, for example, but not limited to, ~10 mW. The lower frequency or DC voltage can enhance tissue creation. Complex electromagnetic signals can be used to perform several functions simultaneously, and complex geometries of resonator 1101 can be used to respond to multiple frequencies. The geometries of array 1111C of resonators 1101 can be adjusted to be resonant at various frequencies, and thus can produce a voltage gradient across a material, for example, but not limited to, the contents of bioreactor 700 (FIG. 7D). By illuminating, for example, workspace 1111 with a complex electromagnetic signal, DC voltages and pulses can be directed into specific areas of workspace 1111 to mimic normal bioelectrical potentials, for example, action and injury potentials, thermal gradients, and other electrical waveshapes. Array 1111C of resonators 1101 with selectively populated rectifiers 1109 can be used to produce a voltage gradient across workspace 1111. The geometry of each resonator 1101 can be adjusted to be resonant at different frequencies. The geometry of resonator 1101 can be used to create a concentrator, or a focusing agent, that can absorb specific frequencies and re-direct the frequencies into a target area. In biomedical sensor applications, flexible resonators can be positioned in strategic locations, for example, but not limited to, in circulatory and muscular regions, and observed as the resonant frequency changes from flexure. Resonators 1101 can be used to monitor biological activity based on the change of resonant frequency during interaction with biological material. In some configurations, resonator 1101 can include a compliant geometry that can be attached and/or adhered to the biological material to be monitored. For example, resonator 1101 can be placed in the vicinity of biological material that changes geometry during normal biological activity, for example, but not limited to, around the circumference of a growing or grown artery or vein, on the surface area of a growing or grown organ or muscle. Resonator 1101 can monitor the biological material at a relatively high resolution, for example, millions of samples/second. In some configurations, interrogation of the frequency of resonator 1101 can include, but is not limited to including, sweeping a constant amplitude over the range of frequencies that resonator 1101 may be resonant, radiating the area containing resonator 1101 with a transmitter 1103, capturing the change in amplitude of the swept signal in receiving antenna 1104, and converting the captured change in amplitude into a form for signal analysis.

Figure 11A:
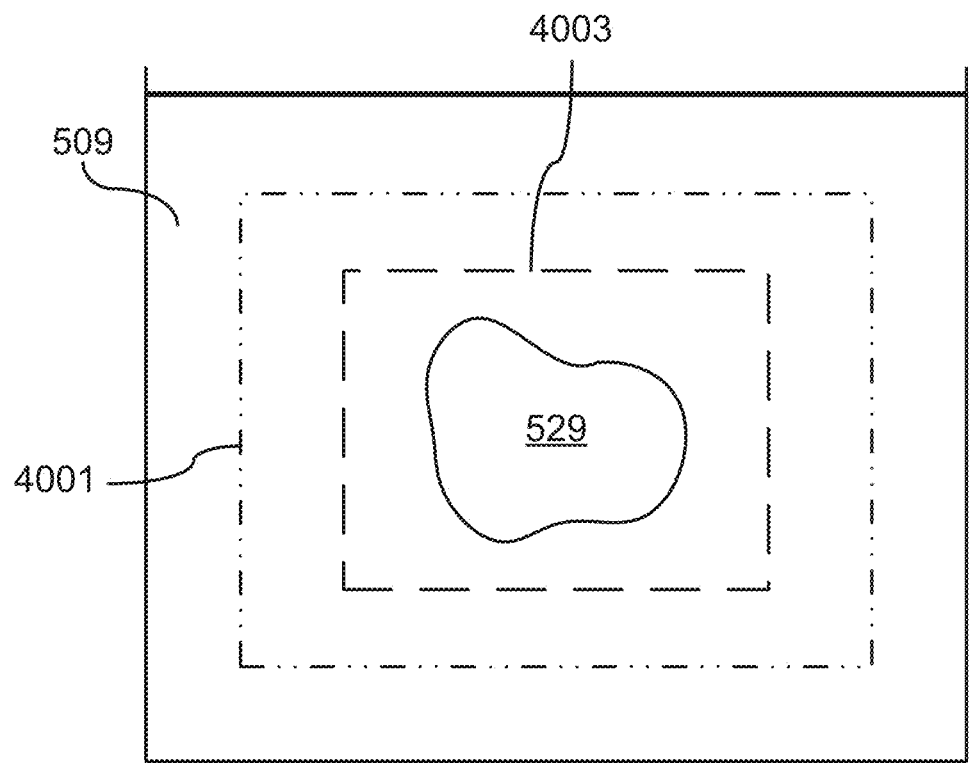
FIGS. 11A-11C are pictorial representations of the optics-based tissue monitoring system of the present teachings.

Referring now to FIG. 11A, emitted and incident radiation can be used to collect information about the tissue in the bioreactor. Growing tissue can emit radiation, tissue can be stimulated with radiation and tested for its response, and radiation can be used to characterize the environment around tissue 529. Oxidation reactions that can occur due to cells' metabolic activity can cause the emission of photons. These photons can require a photo multiplier and/or high sensitivity sensing devices, and might possibly require a suitable optical background, to detect. Structures can be printed within the gel that can allow the sensing of low signals, and can so isolate tissue 529 from the background radiation to lower the noise with respect to the emitted photons. Printed structures can include photonic pathways in tissue 529 that can sense the photon emission within tissue 529, for example, within a grown organ. In some configurations, a background EMF signal can be imposed upon the tissue to modulate tissue photonic emission. In some configurations, creating a suitable background for collecting photonic emissions can include printing material around the tissue that can absorb and/or reflect external radiation, and printing a set of elements that can amplify the signal emitted by the tissue. In some configurations, enhancing the sensitivity to photon emission from tissue 529, whether spontaneously emitted or externally excited, can be accomplished by shielding the sensing elements from unwanted external radiation and placing sensing elements close to tissue 529. Shielding layer 4001 can surround the tissue and sensing elements to isolate the interior from selected wavelengths of radiation. Shielding layer 4001 can be printed into gel 509 in the same fashion as printing tissue 529, or shielding layer 4001 can be a prefabricated structure which is placed within gel 509. The isolation could be through material selection, e.g., dyes or quantum dots which can absorb the desired wavelengths, or it could be through photonic structures. Sensing layer 4003 can be implemented as actual electronic structures, e.g., photo-detectors, deposited on electronic substrates isolated electrically from the surrounding material. Power to these electronic structures can be provided by wire leads that can exit gel 509, or it could be powered remotely using an inductive connection and RF energy. A photo-multiplier layer can be created using a system analogous to an RF-pumped or light-pumped laser. The material of sensing layer 4003 can be brought to an excited state by irradiating it with light or RF energy, and photons from tissue 529 can provide energy to cause the excited molecules to emit additional photons, or higher energy photons. Optical fibers printed into gel 509 can provide another method of sensing. Gel 509 can include a fluidic medium. The receiving end of the fiber can be situated in proximity tissue 529, and can direct the captured photons to an external sensor.

Continuing to refer primarily to FIG. 11A, printing biological material and supporting structures can include simultaneous printing of material, (b) precise printing of material, and (c) printing particular elements, for example, but not limited to, bio-ink. Methods to print biological material can include printing layers of cells, for example, in a holding container, shaping the tissue by etching fine details using laser and/or water jet. In some configurations, a mesh structure can underlie the etched tissue, and the method can including lifting the mesh and etched tissue into a tissue enclosure. In some configurations, gel 509 can be printed into the holding container, or gel 509 can be printed along with tissue 529. In some configurations, a printing method can include printing the biological material and supporting structures onto a drum-like structure, unrolling the drum-like structure into growth media, and optionally vibrating the drum-like structure to release the biological material and supporting structures from the drum-like structure. In some configurations, the method can optionally include scraping the drum-like structure to release the biological material and supporting structures with, for example, but not limited to, a wire. In some configurations, the method can include printing a layer of gel 509 onto the drum-like structure, printing a layer of biological material onto the drum-like structure, and scraping a layer of printed material from the drum-like structure. In some configurations, the method can include loading a holding container with fluid, printing a layer of cells on the fluid, dipping the tissue into the layer of cells, extracting the layer of cells that adhere to the tissue. In some configurations, the method can include loading the holding container with tissue, and lowering the layer of cells onto the tissue in the holding container where the layer of cells can adhere to the tissue in the holding container. Gel 509 can include a fluidic medium.

Figure 11B:
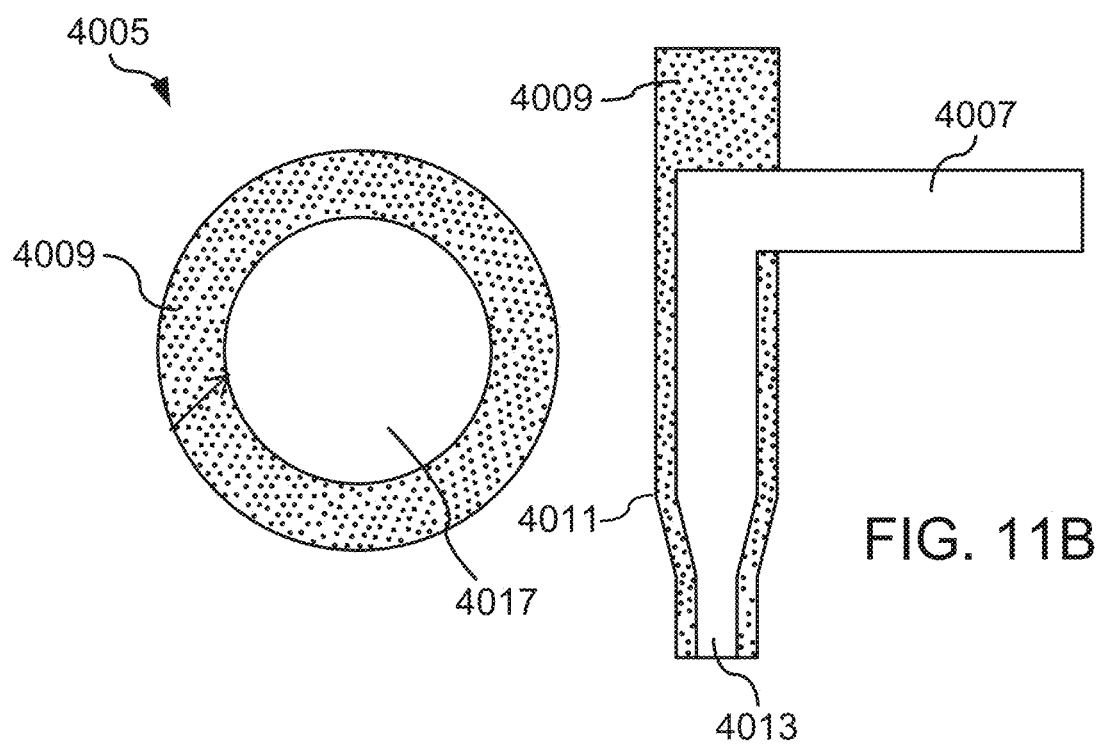

Referring now to FIG. 11B, printing fiber strands into gel 509 (FIG. 11A) can be an extension of printing tissue 529 (FIG. 11A). Fiber optic strand 4005 can include relatively high refraction index material 4007 surrounded by relatively lower refraction index material 4009. Printed fiber 4013 including fiber optic strand 4005 can be printed using the low speed and highly laminar flow from a printer to isolate high index material 4007 within lower index material 4009 as it passes through nozzle 4011. This same principle can be used in flow cytometry and in the drawing of conventional fiber optics. High index material 4007 can include, but is not limited to including, polymer beads or biocompatible oil or alcohol that can exceed the background index of refraction, nominally 1.33, of the water in gel 509 (FIG. 11A). In some configurations, low index material 4009 co-printed with high index material 4007 can be gel 509 (FIG. 11A). In some configurations, high index material 4007 can be printed using surrounding fluid instead of low index material 4009. In some configurations, a specific one of low index materials 4009 can be used with either gel 509 (FIG. 11A) or a specific one of high index materials 4007 as the center of fiber 4005. The specific of low index materials 4009 can include an alcohol or an aerated of gel 509 (FIG. 11A). The air bubbles within the aerated of gel 509 (FIG. 11A) can provide the required index change. In some configurations, bio-incompatible of printed fibers 4013 and tissues 529 (FIG. 11A) can be printed together in gel 509 (FIG. 11A), depending on the diffusion characteristics of gel 509 (FIG. 11A).

Figure 11C:
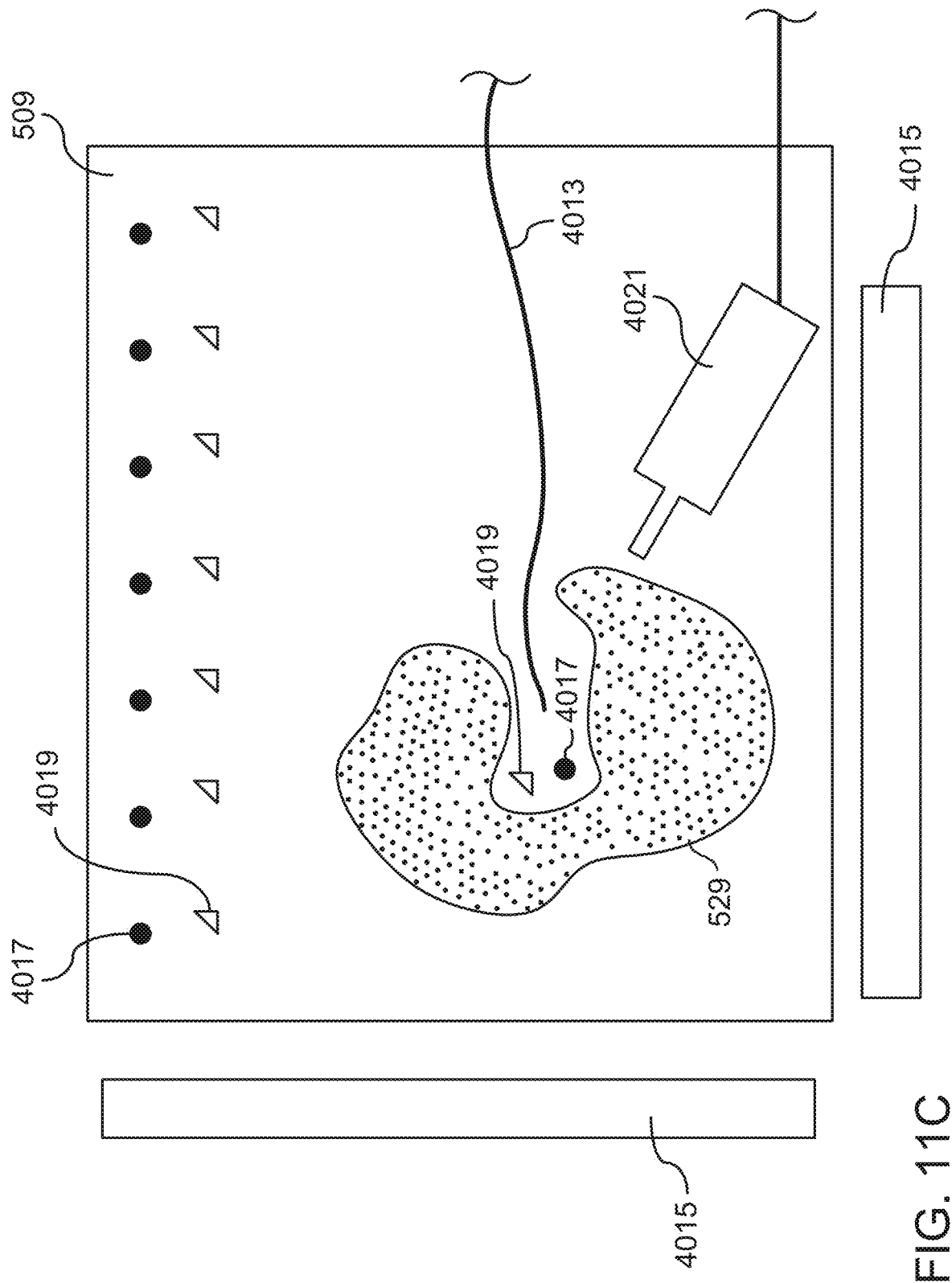

Referring now to FIG. 11C, several optical sensing techniques can be effective for monitoring tissue 529. Optical tomography, that can infer a structure from the pattern of received light from known sources, can have intimate access to tissue 529. The location of sources 4017 can be accurately known, can remain stable within gel 509, and can be sensed by sensors 4015. Raman spectroscopy and two-photon microscopy can benefit from access to tissue 529 and the well-characterized nature of gel 509 surrounding tissue 529. Creating sources 4017 for tomography can include, but is not limited to including, placing photon emitting sources 4017, for example, but not limited to, quantum dot emitters, within gel 509 using the same printing technology used to deposit tissue 529. Photon sources 4017 can be stimulated by a light or RF source external to the system. In some configurations, this external source may not need to be too carefully controlled in position. In some configurations, photon emitting sources 4017 can be printed relatively densely, and a finely controlled external laser can be used to excite them. The tomography source location can be specified by the laser orientation combined with the known orientation of the emitting source matrix. In some configurations, photon scattering structures 4019 can be created with tailored scattering patterns. This can allow the location and the orientation of the source to be characterized simultaneously, and the shape of the scattered beam can provide additional information for solving a tomographic inverse problem. In some configurations, light could be brought from the outside of the system to the interior of printed tissue 529 using fiber 4013. Fiber 4013 can act as a source of light for tomography and can allow an internally generated source to be used to characterize tissue 529. Fiber 4013 can be a source to illuminate emitting source 4017 and scattering sources 4019 located in tissue 529. A high-precision printing head used to deposit tissue 529 can be used as a system for positioning sensor/source head 4021. Sensor/source head 4021 can be replaced with an optical device which can provide a movable source for characterizing tissue 529 tomographically. Sensor/source head 4021 can be used as a source and sensor for multi-photon microscopy and for Raman spectroscopy. In some configurations, printed fiber optics 4013 can act as source/sensor fibers to support some types of optical measurements. In some configurations, as tissue 529 grows, the change in location of photon emitting sources 4017 and photon scattering structures 4019 can be used to characterize changes in gel 509 that accommodate the changes of tissue 529. This might also be accomplished by printing regular structures, for example, but not limited to, Moiré patterns, in gel 509. Small changes in the location or size of these structures can be detectable and translatable into descriptions of the size and shape of tissue 529. Gel 509 can include a fluidic medium.

Continuing to refer to FIG. 11C, various imaging techniques can monitor cell growth and tissue development. In some configurations, magnetic resonance imaging (MRI) can apply a magnetic field to the tissue in order to align the protons with that field. Subsequent use of a radiofrequency current can cause the protons to strain against the magnetic field. When the radiofrequency current is turned off, the protons can realign with the magnetic field, and a sensing device can detect the energy released. MRI can provide contrast between different soft tissues without using exogenous contrast agents. In some configurations, MRI has a spatial resolution of about 100 µm. Bioluminescence imaging can monitor light emitted in enzyme-catalyzed reactions using a specific enzyme and substrate pairing such as luciferase and luciferin. Bioluminescence imaging requires transfection of certain cells with a luciferase reporter gene. The enzyme luciferase can oxidize its substrate luciferin in the presence of oxygen and ATP to release photons. A sensing device can capture the photonic release and can determine the number of viable cells present in the sample. Raman spectroscopy can measure light scattering and molecular vibrations at a spatial resolution of about 1 µm. Raman spectroscopy focuses a laser on a sample, causing an energy exchange between the laser and the sample molecules. The energy exchange can lead to a shift in the laser's wavelength that can create a spectrum that is unique and identifiable as to the biochemical composition and cellular structure of the sample. Two-photon fluorescence light microscopy can enable three-dimensional imaging of a biological specimen by using two-photon excitation. Two-photon excitation includes exciting a fluorophore with near-infrared light while simultaneously absorbing two photons. Both the two photon absorption and near-infrared light help can suppress background signal. A phased array can utilize a plurality of radiating elements to electronically move a beam of radio waves in various directions. The movement of the beam of radio waves can enable the phased array to change directions without physically moving the antennas. The data obtained from the plurality of phased arrays can create an image that can include a slice perspective through the sample. Sensors embedded within the bioreactor can detect information that can be used to determine when growing cells need more or different nutrients.

Continuing to refer to FIG. 11C, precisely printing biological material can include providing laminar streams of bio-inks under conditions that inhibit mixing of the bio-inks. For example, a number of reasonably sized tubes can be placed in a nozzle that can be used to provide bio-ink to a printing device. The tubes can maintain laminar flow in the streams. The size of the tubes can be continually reduced so that a small nozzle at the termination of the printing device includes all the different bio-inks. Choosing appropriate bio-inks can include, for example, if optical sensing technology is being used, choosing materials that include indices of refraction that differ from the background in which the bio-ink is printed. In some configurations, air or any kind of gas can be appropriate, and multiple different types of gases can be printed to accommodate variations in fluorescence. Quantum dots and nanoparticle/fluorescent beads can be printed as probes/markers. Entire additional structures that may support tissue generation may be printed along with cells that can ultimately grow into tissue 529, or that can accompany tissue 529 to, for example, monitor and/or sustain tissue 529. The additional structures can be placed in a tissue enclosure after being printed, for example, but not limited to, any of the tissue enclosures described herein. The additional structures can include, but are not limited to including, photodetectors, silicon or other semi-conductors, electronics, and sensors that can be collocated with tissue 529. Feedback on growth and topology of tissue 529 can be accommodated by, for example, printing and/or placing grid patterns/optical gratings in the vicinity of the inside and/or outside of tissue 529 and monitoring the contours of tissue 529. Marker patterns can be placed around tissue 529 by depositing ink into media or by cutting out bits of gel. In some configurations, photodetectors can be placed in the gel and can be powered by connecting leads and/or inductive coupling that can power the photodetectors without leads.

Figure 12A:
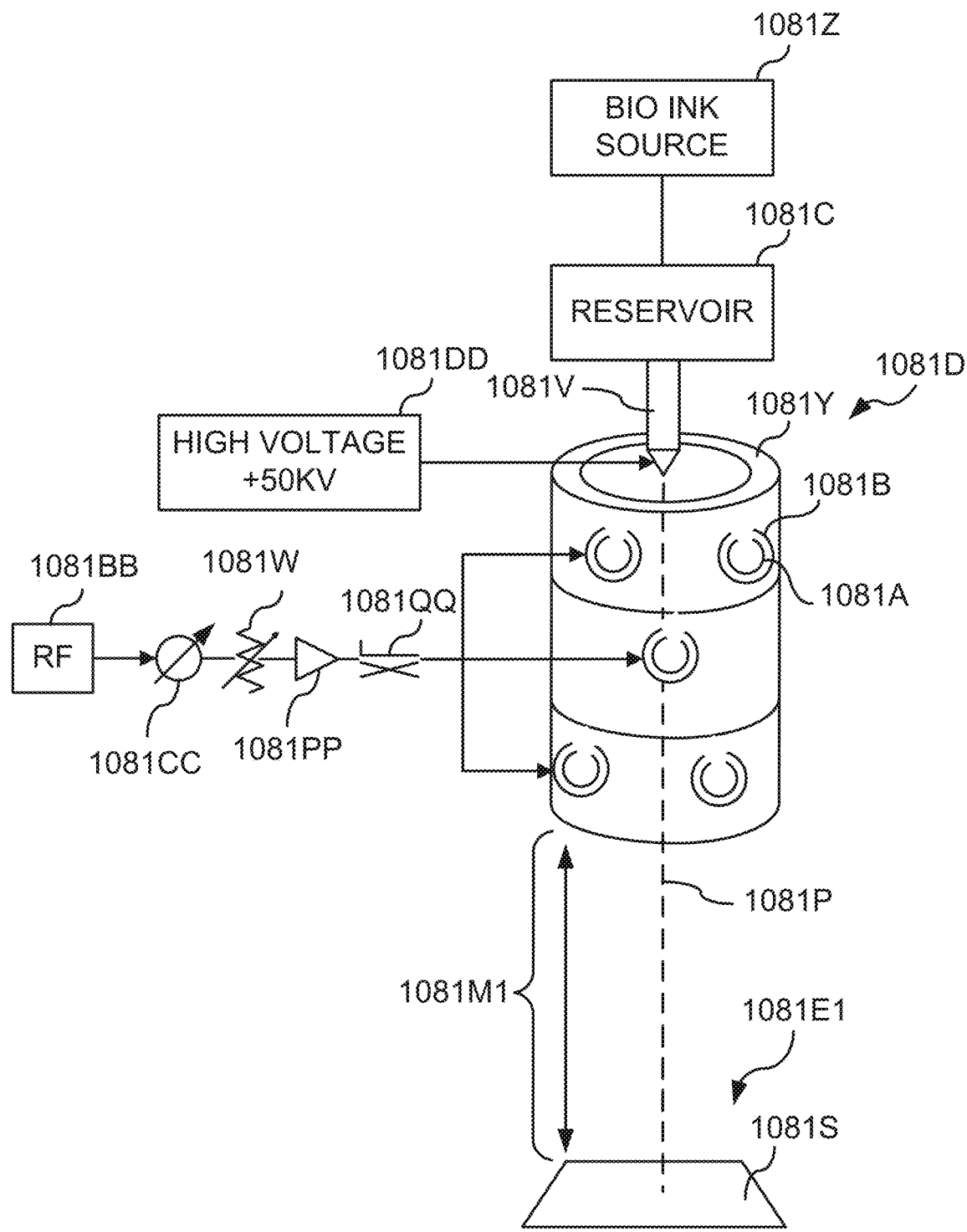
FIG. 12A is a pictorial representation of the first configuration of the precise printing apparatus of the present teachings.
Figure 12B:
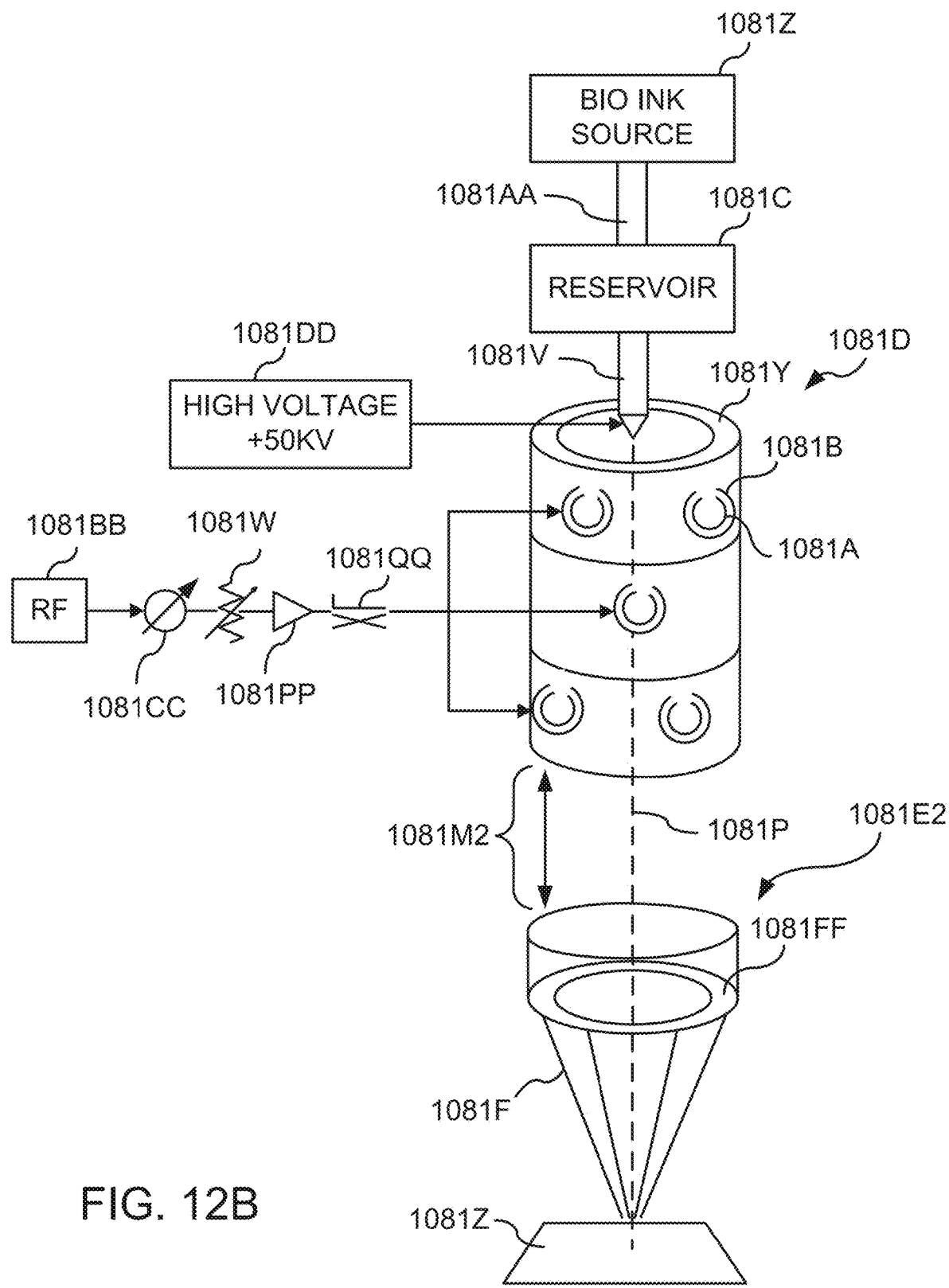
FIG. 12B is a pictorial representation of the second configuration of the precise printing apparatus of the present teachings.
Figure 12C:
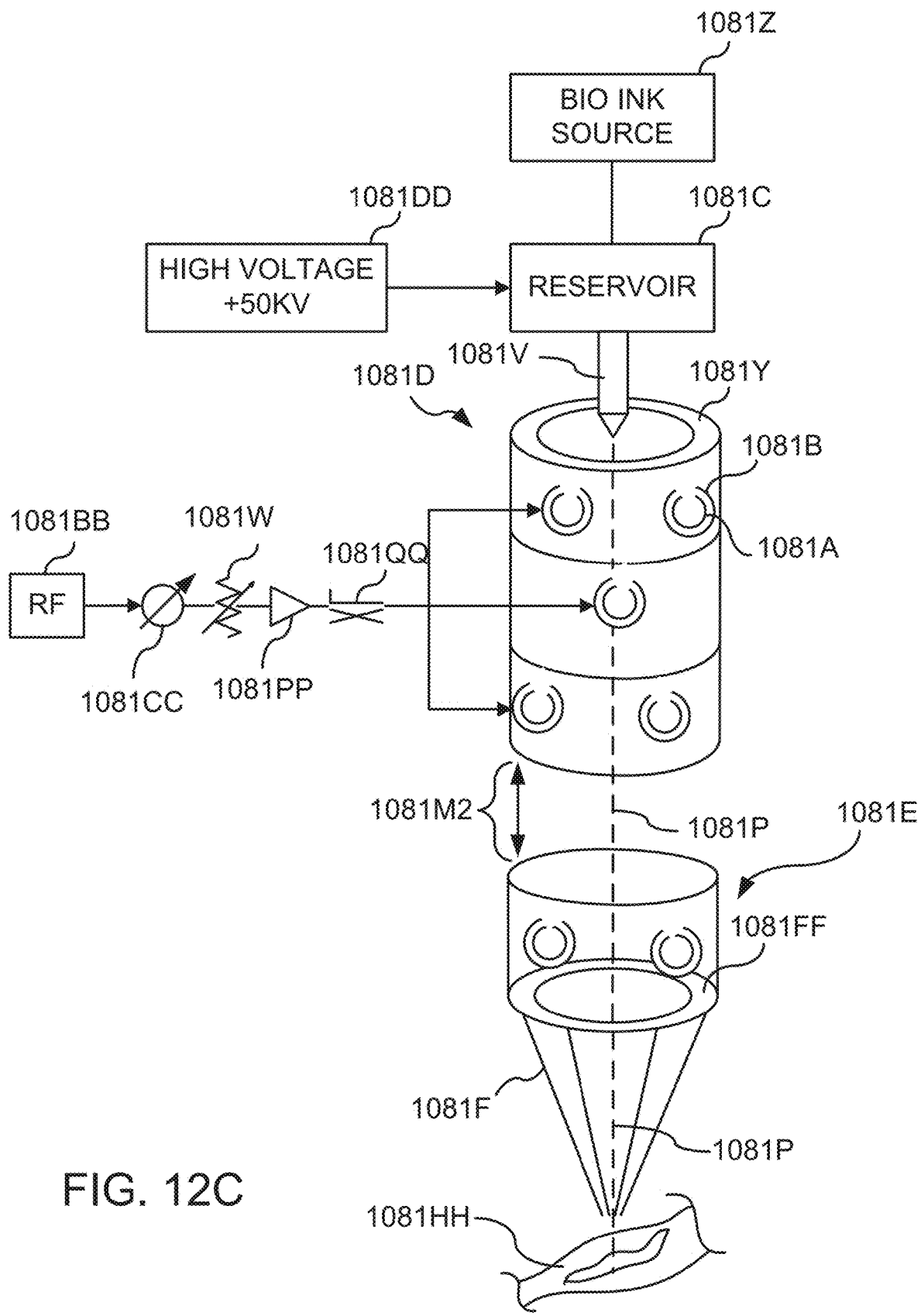
FIG. 12C is a pictorial representation of the third configuration of the precise printing apparatus of the present teachings.

Referring now to FIGS. 12A, 12B, and 12C, precisely printing biological material can include guiding the streams of biological material by various means, including, but not limited to including, electrospinning. Electrospinning is a technique in which high voltage is applied to droplets, the energized droplets being stretched into fiber 1081P, and fiber 1081P being shaped on a grounded flat surface such as collection plate 1081S (FIG. 12A), or onto a three-dimensional shape 1081HH (FIG. 12C). Split ring resonators, or tank circuits, can be used to receive and shape the charge applied to the droplets. Array 1081D of split ring resonators 1081A and antennas 1081B can be positioned around nozzle 1081V in which the electrospinning technique is employed. Array 1081D can be attached, for example, to a strip that can be mounted upon ring 1081Y. In some configurations, antennas 1081B and resonators 1081A can be attached to opposite sides of the strip. Nozzle 1081V can include an optional nipple that can modify the geometry of stream 1081P according to the geometry of the nipple. Nozzle 1081V can receive the biological material from material well 1081C. High voltage system 1081DD can supply voltage such as, for example, but not limited to, +10-50 kV to material well 1081C, and therefore to nozzle 1081V. Optional guides 1081F (FIG. 12B) can fine-tune the ultimate location of stream 1081P by focusing the energy into a specific area. Emitter array 1081D can include any number of resonators 1081A and antennas 1081B, and can direct/orient streams destined for collector array 1081E. The deposition locations of the streams of thin fiber of bio-ink source 1081Z can be based on the physical placement of resonators 1081A, and the feedback control of resonators 1081A. Collector array 1081E and guides 1081F can generate a raster-like deposition of stream 1081P. Collection ring 1081FF and collection array 1081E can optionally be replaced by collection plate 1081S. Distance 1081M1/1081M2, either between array 1081D and collection ring 1081FF, collection array 1081E, or between array 1081D and collection plate 1081S, can be chosen based on the desired characteristics of shaped fiber. In some configurations, guides 1081F, integral with collector ring 1081FF, can be used to direct stream 1081P into substantially preselected locations within, for example, tissue. Thus, guides 1081F can enable the electrospinning device to repair tissue 1081HH (FIG. 12C) in situ without an extra step of transferring the biological material from a collection plate to the ultimate destination of the biological material.

Continuing to refer to FIGS. 12A, 12B, and 12C, electrospinning can produce streams that can chaotically whip around. A high voltage, for example, but not limited to, +10 kV or greater, can be applied to the tip of needle 1081V as material such as polymer is being extruded from the tip of needle 1081V. As the material leaves the tip in a stream, for example, a 10 μm stream, the material can form a Taylor cone before it advances toward collector plate 1081S (FIG. 12A) or tissue 1081HH (FIG. 12C). Different kinds of materials can have different characteristics that can impact the resulting pattern on collector plate 1081S (FIG. 12A) or tissue 1081HH (FIG. 12C). To address the spin that the stream takes on after the extrusion, a torque generated by an electrostatic field can be applied to the stream. The torque can be applied by, for example, slowly adjusting the phase angle of RF signal 1081BB on each tank circuit 1081A. RF signal 1081BB transmitted across tank circuits 1081A can create voltage gradients. The voltage gradient magnitude and the physical geometry of tank circuit 1081A can, in combination, result in a torque that can overcome the natural whipping motion of the stream.

Figure 12D:
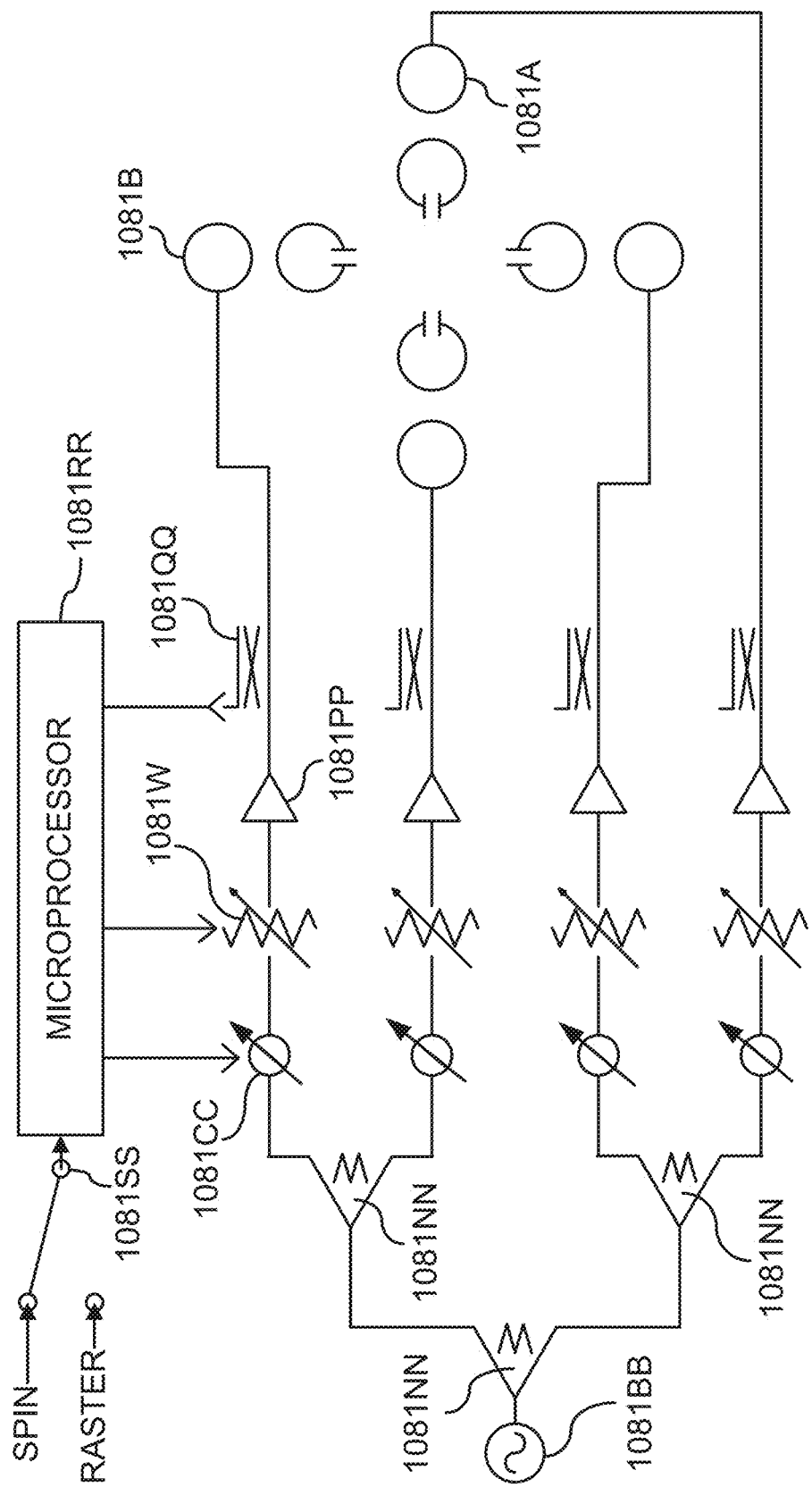
FIG. 12D is a pictorial representation of the signal treatment of the configurations of FIGS. 12A, 12B, and 12C of the present teachings.

Referring now to FIG. 12D, array 1081D can be controlled by processor 1081RR, and can execute in at least two modes selected by switch 1081SS: rotational stabilization/spinner and raster generation. As phase lock oscillator 1081BB provides a signal destined for array 1081D, the signal can be divided by, for example, in-phase power dividers 1081NN, to produce as many signals as there are loop antennas 1081B in array 1081D. Each signal can proceed through a path that can include voltage variable phase shifter 1081CC, voltage variable attenuator 1081W, power amplifier 1081PP, and power level measure 1081QQ until the filtered signal is picked up by loop antenna 1081B. In raster generation mode, the devices between phase lock oscillator 1081BB and loop antenna 1081B can focus the signal preparing it for rotational stabilization mode. In rotational stabilization mode, the phase angle of the signal can be slowly shifted to enable accurate placement of the stream of material onto surface 1081S or tissue 1081HH.

Configurations of the present teachings are directed to computer systems for accomplishing the methods discussed in the description herein, and to computer readable media containing programs for accomplishing these methods. The raw data and results can be stored for future retrieval and processing, printed, displayed, transferred to another computer, and/or transferred elsewhere. Communications links can be wired or wireless, for example, using cellular communication systems, military communications systems, and satellite communications systems. Parts of systems 500A (FIG. 1), 500 (FIG. 1A), 513 (FIG. 1B), 515 (FIG. 1C), 517 (FIG. 1D), and other systems of the present teachings, for example, can operate on a computer having a variable number of CPUs. Other alternative computer platforms can be used.

The present embodiment is also directed to software for accomplishing the methods discussed herein, and computer readable media storing software for accomplishing these methods. The various modules described herein can be accomplished on the same CPU, or can be accomplished on different CPUs. In compliance with the statute, the present embodiment has been described in language more or less specific as to structural and methodical features. It is to be understood, however, that the present embodiment is not limited to the specific features shown and described, since the means herein disclosed comprise preferred forms of putting the present embodiment into effect.

Method 6300 (FIGS. 6C-6E) and other methods of the present teachings, can be, in whole or in part, implemented electronically. Control and data information can be electronically executed and stored on at least one computer-readable medium. The systems can be implemented to execute on at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, an erasable programmable read only memory (EPROM), a Flash EPROM, or any other memory chip or cartridge, or any other medium from which a computer can read. Further, the at least one computer readable medium can contain graphs in any form, subject to appropriate licenses where necessary, including, but not limited to, Graphic Interchange Format (GIF), Joint Photographic Experts Group (JPEG), Portable Network Graphics (PNG), Scalable Vector Graphics (SVG), and Tagged Image File Format (TIFF).

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

The invention claimed is:

1. A method for automatically growing tissue using a system having a controller, the tissue having tissue characteristics, the method comprising the controller:
   selecting, from a tissue sample, cells associated with the tissue, based on the tissue characteristics;
   expanding the selected cells;
   creating at least one printable protein bio-ink;
   creating at least one protein from the at least one printable protein bio-ink;
   creating at least one tissue bio-ink including the expanded cells, the bio-ink, and the at least one protein;
   creating at least one tissue growth medium mixture including the at least one protein;
   printing the at least one tissue bio-ink in the at least one tissue growth medium mixture;
   growing the tissue from the printed at least one tissue bio-ink in the at least one tissue growth medium mixture; and
   maintaining viability of the tissue.

2. The method as in claim 1 wherein the tissue growth medium mixture further comprises:
   indicators, support materials, gel, and basal medium.

3. The method as in claim 1 wherein the tissue growth medium mixture further comprises:
   indicators, support materials, carbomer, and basal media.

4. The method as in claim 1 maintaining the viability comprises:
   evacuating wastes from metabolism of the tissue.

* * * * *